United States Patent
Mindrinos et al.

(10) Patent No.: US 8,795,968 B2
(45) Date of Patent: *Aug. 5, 2014

(54) METHOD TO PRODUCE DNA OF DEFINED LENGTH AND SEQUENCE AND DNA PROBES PRODUCED THEREBY

(75) Inventors: Michael Mindrinos, Menlo Park, CA (US); Sujatha Krishnakumar, Cupertino, CA (US); Ronald W. Davis, Palo Alto, CA (US); Peidong Shen, Union City, CA (US); Curt Scharfe, Oakland, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 452 days.

This patent is subject to a terminal disclaimer.

(21) Appl. No.: 12/972,377

(22) Filed: Dec. 17, 2010

(65) Prior Publication Data
US 2011/0086393 A1    Apr. 14, 2011

Related U.S. Application Data

(62) Division of application No. 11/805,676, filed on May 24, 2007, now Pat. No. 7,897,742.

(60) Provisional application No. 60/808,490, filed on May 25, 2006.

(51) Int. Cl.
*C12Q 1/68*    (2006.01)
*C12P 19/34*    (2006.01)

(52) U.S. Cl.
USPC ........................ 435/6.12; 435/91.2

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,883,750 A | 11/1989 | Whiteley et al. | |
| 4,965,188 A | 10/1990 | Mullis et al. | |
| 5,066,584 A | 11/1991 | Gyllensten et al. | |
| 5,130,238 A | 7/1992 | Malek et al. | |
| 5,455,166 A | 10/1995 | Walker | |
| 5,518,900 A | 5/1996 | Nikiforov et al. | |
| 5,854,033 A | 12/1998 | Lizardi | |
| 6,221,603 B1 | 4/2001 | Mahtani | |
| 6,235,472 B1 | 5/2001 | Landegren et al. | |
| 6,558,928 B1 | 5/2003 | Landegren et al. | |
| 6,812,005 B2 | 11/2004 | Fan et al. | |
| 6,815,167 B2 | 11/2004 | Crothers et al. | |
| 6,858,412 B2 | 2/2005 | Willis et al. | |
| 6,955,901 B2 | 10/2005 | Schouten | |
| 7,897,747 B2 * | 3/2011 | Mindrinos et al. | 536/24.3 |
| 2002/0012902 A1 | 1/2002 | Fuchs et al. | |
| 2004/0067511 A1 | 4/2004 | Thomas | |
| 2004/0171047 A1 | 9/2004 | Dahl et al. | |
| 2005/0026204 A1 | 2/2005 | Landegren | |
| 2005/0255477 A1 | 11/2005 | Carr et al. | |
| 2006/0166334 A1 * | 7/2006 | Yang | 435/91.2 |

OTHER PUBLICATIONS

Higuchi, et al., "Production of single-stranded DNA templates by exonuclease digestion following the polymerase chain reaction," Nucleic Acids Research, 1989, vol. 17, No. 14, 5865.
Johan Baner, et al., "Parallel gene analysis with allele-specific padlock probes and tag microarrays," Nuceic Acids Reseach, 2003, vol. 31, No. 17, e103.
Sanchez, et al., "Linear-After-The-Exponential (LATE)-PCR: an advanced method of asymmetric PCR and its uses in quantitative real-time analysis," PNAS, Feb. 17, 2004, vol. 101, No. 7, 1933-1938.
Binkowski, et al., "Correcting errors in synthetic DNA through consensus shuffling," Nucleic Acids Research, 2005, 33(6), e55.
Dahl, et al., "Multiplex amplification enabled by selective circularization of large sets of genomic DNA fragments," Nucleic Acids Research,2005, vol. 33, No. 8, e71.
Szemes, et al., "Diagnostic application of padlock probes-multiplex detection of plant pathogens using universal microarrays," Nucleic Acids Research, Apr. 28, 2005, vol. 33, No. 8, e70.
Sambrook, et al., "Ch. 10 Preparation of Radiolabeled DNA and RNA probes," (selected pages) in Molecular Cloning: A Laboratory Manual, Second Edition, Cold Spring Harbor Laboratory Press, 1989, pp. 10.4-10.5, and 10.29.
Padgett, et al., "Creating seamless junctions independent of restriction sites in PCR cloning," Gene, 1996, vol. 168, pp. 31-35.
Porreca, et al., "Multiplex amplification of large sets of human exons", Nature Methods, Nov. 2007, vol. 4, No. 11, pp. 931-936.
Krishnakumar, et al., "A comprehensive assay for targeted multiplex amplification of human DNA sequences," PNAS, Jul. 8, 2008, vol. 105, No. 27, pp. 9296-9301.

* cited by examiner

*Primary Examiner* — Kenneth R. Horlick
*Assistant Examiner* — David Thomas
(74) *Attorney, Agent, or Firm* — David J. Aston; Peters Verny, LLP

(57) ABSTRACT

A method for producing a single stranded DNA (ssDNA) molecule of a defined length and sequence is disclosed. This method enables the preparation of, inter alia, probes of greater length than can be chemically synthesized. The method starts with a double stranded molecule, such as genomic, double stranded DNA (dsDNA) from any organism. A fragment of the starting molecule (dsDNA) is amplified by specific primers engineered to introduce cleavage sites on either side of the desired sequence. Cleavage steps on the amplified, engineered fragment are combined with a phosphate removal step, thereby creating a construct that can be digested with an exonuclease without damage to the desired ssDNA. Probes, which hybridize with large gaps between the ends of the probes, are also disclosed.

9 Claims, 4 Drawing Sheets

SEQUENCE LISTING

```
<160> NUMBER OF SEQ ID NOS: 607

<210> SEQ ID NO 1
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 cctcagc                                                                   7

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 gaattc                                                                    6

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
```

<223> OTHER INFORMATION: a, c, g, t, unknown or other

<400> SEQUENCE: 3
gccnnnnngg c                                                           11

<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 ctgaag                                                                  6

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 5
cgannnnnnt gc                                                          12

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 ggtctc                                                                  6

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, g, t, unknown or other

<400> SEQUENCE: 7
ggtctcnnnn nn                                                          12

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, g, t, unknown or other -continued

```
<400> SEQUENCE: 8
nnnnnnnnnn gagacc                                               16

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(14)
<223> OTHER INFORMATION: a, c, g, t, unknown or other

<400> SEQUENCE: 9
gagtcnnnnn nnnn                                                 14

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, c, g, t, unknown or other

<400> SEQUENCE: 10
nnnnnnnnnc actc                                                 14

<210> SEQ ID NO 11
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 cacctgc                                                          7

<210> SEQ ID NO 12
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 acctgc                                                           6

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 cagctc                                                           6

<210> SEQ ID NO 14
```

```
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 ggatc                                                                    5

<210> SEQ ID NO 15
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 gtctc                                                                    5

<210> SEQ ID NO 16
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 gaagac                                                                   6

<210> SEQ ID NO 17
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 gcagc                                                                    5

<210> SEQ ID NO 18
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 gaagac                                                                   6

<210> SEQ ID NO 19
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 acggc                                                                    5

<210> SEQ ID NO 20
<211> LENGTH: 6
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 gaagac                                                                   6

<210> SEQ ID NO 21
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 ggtctc                                                                   6

<210> SEQ ID NO 22
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 cgtctc                                                                   6

<210> SEQ ID NO 23
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 gggac                                                                    5

<210> SEQ ID NO 24
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 cccgc                                                                    5

<210> SEQ ID NO 25
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25 ggatg                                                                    5

<210> SEQ ID NO 26
<211> LENGTH: 5
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 26 gacgc                                                                    5

<210> SEQ ID NO 27
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27 gcatc                                                                    5

<210> SEQ ID NO 28
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28 gagtc                                                                    5

<210> SEQ ID NO 29
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 gctcttc                                                                  7

<210> SEQ ID NO 30
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 ctgaag                                                                   6

<210> SEQ ID NO 31
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31 ggtga                                                                    5

<210> SEQ ID NO 32
<211> LENGTH: 6
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 32 gtatcc                                                                   6

<210> SEQ ID NO 33
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 actggg                                                                   6

<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34 ctggag                                                                   6

<210> SEQ ID NO 35
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 gcaatg                                                                   6

<210> SEQ ID NO 36
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36 ggatg                                                                    5

<210> SEQ ID NO 37
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37 ctcag                                                                    5

<210> SEQ ID NO 38
<211> LENGTH: 6
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 38 gaggag                                                                    6

<210> SEQ ID NO 39
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39 gcaatg                                                                    6

<210> SEQ ID NO 40
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40 ggatg                                                                     5

<210> SEQ ID NO 41
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41 ggcgga                                                                    6

<210> SEQ ID NO 42
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42 ctgaag                                                                    6

<210> SEQ ID NO 43
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43 ctgrag                                                                    6

<210> SEQ ID NO 44
<211> LENGTH: 6
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 44 tccrac                                                                  6

<210> SEQ ID NO 45
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 cccaca                                                                  6

<210> SEQ ID NO 46
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46 atgaa                                                                   5

<210> SEQ ID NO 47
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 caarca                                                                  6

<210> SEQ ID NO 48
<211> LENGTH: 298
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 48
ttgttttctc cgtcgccgta tcccttttagt gagggttaat agtacgctta cttccgcgaa      60
acgtcagcgg aagcaccact atctggcgat caaaaggatg gtcatcggtc acggtgacag     120
tacgggtacc tgacggccag tccacactgc tttcacgctg gcgcggaaaa gccgcgctcg     180
ccgcctttac aatgtccccg acgattttttt ccgccctcag cgtaccgttt atcgtacagt    240
tttcagctat cgtcacatta tttaggtgac actatagcca caaatcaaga tccgaatt      298

<210> SEQ ID NO 49
<211> LENGTH: 298
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 49
ttgttttctc cgtcgccgta tcccttttagt gagggttaat agtacgctta cttccgcgaa      60

```
acgtcagcgg aagcaccact atctggcgat caaaaggatg gtcatcggtc acggtgacag    120
tacgggtacc tgacggccag tccacactgc tttcacgctg gcgcggaaaa gccgcgctcg    180
ccgcctttac aatgtccccg acgattttt ccgccctcag cgtaccgttt atcgtacagt    240
tttcagctat cgtcacatta tttaggtgac actatagcca caaatcaaga tccgaatt     298
```

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 50

```
catcgtgagt cactcgaatt cggatcttga tttgtgg                              37
```

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 51

```
gtacgaggtc tcacttgttt tctccgtcgc cgta                                 34
```

<210> SEQ ID NO 52
<211> LENGTH: 326
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 52

```
gtacgaggtc tcattgtttt ctccgtcgcc gtatcccttt agtgagggtt aatagtacgc     60
ttacttccgc gaaacgtcag cggaagcacc actatctggc gatcaaaagg atggtcatcg    120
gtcacggtga cagtacgggt acctgacggc cagtccacac tgctttcacg ctggcgcgga    180
aaagccgcgc tcgccgcctt tacaatgtcc ccgacgattt tttccgccct cagcgtaccg    240
tttatcgtac agttttcagc tatcgtcaca ttatttaggt gacactatag ccacaaatca    300
agatccgaat tgagtgactc acgatg                                         326
```

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 53

```
tgtctatagt gtcacctaaa ttaatgtgac gatagctg                             38
```

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 54 tgtccctta gtgagggtta atagtacgct tacttccgcg                    40

<210> SEQ ID NO 55
<211> LENGTH: 263
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 55
tgtctatagt gtcacctaaa ttaatgtgac gatagctgaa aactgtacga taaacggtac    60
gctgagggcg gaaaaaatcg tcggggacat tgtaaaggcg gcgagcgcgg cttttccgcg   120
ccagcgtgaa agcagtgtgg actggccgtc aggtacccgt actgtcaccg tgaccgatga   180
ccatcctttt gatcgccaga tagtggtgct tccgctgacg tttcgcggaa gtaagcgtac   240
tattaaccct cactaaaggg aca                                          263

<210> SEQ ID NO 56
<211> LENGTH: 62
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
gtacgaggtc tcagaaatga caaatataga tggcaaaagc catcccttta gtgagggtta    60
at                                                                  62

<210> SEQ ID NO 57
<211> LENGTH: 62
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
catcgtgagt cactcgtcac agataggcat ggtgtcaaag tcatctatag tgtcacctaa    60
at                                                                  62

<210> SEQ ID NO 58
<211> LENGTH: 344
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 58
catcgtgagt cactcgtcac agataggcat ggtgtcaaag tcatctatag tgtcacctaa    60
attaatgtga cgatagctga aaactgtacg ataaacggta cgctgagggc ggaaaaaatc   120
gtcggggaca ttgtaaaggc ggcgagcgcg gcttttccgc gccagcgtga aagcagtgtg   180
gactggccgt caggtacccg tactgtcacc gtgaccgatg accatccttt tgatcgccag   240
atagtggtgc ttccgctgac gtttcgcgga agtaagcgta ctattaaccc tcactaaagg   300
gatggctttt gccatctata tttgtcattt ctgagacctc gtac                   344

<210> SEQ ID NO 59
<211> LENGTH: 301
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 59

| | |
|---|---|
| atgactttga caccatgcct atctgtgagg aagctggcaa catgtcacac ctggaaatcc | 60 |
| taggtttgag tggggcaaaa atacaaaaat cagatttcca gaaaattgct catctgcatc | 120 |
| taaatactgt cttcttagga ttcagaactc ttcctcatta tgaagaaggt agcctgccca | 180 |
| tcttaaacac aacaaaactg cacattgttt taccaatgga cacaaatttc tgggttcttt | 240 |
| tgcgtgatgg aatcaagact tcaaaaatat tagaaatgac aaatatagat ggcaaaagcc | 300 |
| a | 301 |

<210> SEQ ID NO 60
<211> LENGTH: 390
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 60

| | |
|---|---|
| ttctagacat gcccttcatg tgattcttat gagaaaaaac cacccaaaga attcctagaa | 60 |
| agattcaaat cacttctcca aaaggtatct accttaagtt tcatttgatt ttctgcttta | 120 |
| tctttaccta tccagatttg cttcttagtt actcacggta tactatttcc acagatgatt | 180 |
| catcagcatc tgtcctctag aacacacgga agtgaagatt cctgaggatc taacttgcag | 240 |
| ttggacacta tgttacatac tctaatatag tagtgaaagt catttctttg tattccaagt | 300 |
| ggaggagtac aatatattag cgatgggaaa aaaaaactca taagtgtgca aagtcaggat | 360 |
| tatttcccca taatcactat acaatagtct | 390 |

<210> SEQ ID NO 61
<211> LENGTH: 66
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61

| | |
|---|---|
| catcgtgagt cactcgtagg catggtgtca aagtcattaa aagaaagact atagtgtcac | 60 |
| ctaaat | 66 |

<210> SEQ ID NO 62
<211> LENGTH: 65
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62

| | |
|---|---|
| gtacgaggtc tcagaaatga caaatataga tggcaaaagc caatttccct ttagtgaggg | 60 |
| ttaat | 65 |

<210> SEQ ID NO 63

-continued

<211> LENGTH: 315
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 63
tctttctttt aatgactttg acaccatgcc tatctgtgag gaagctggca acatgtcaca      60
cctggaaatc ctaggtttga gtggggcaaa aatacaaaaa tcagatttcc agaaaattgc    120
tcatctgcat ctaaatactg tcttcttagg attcagaact cttcctcatt atgaagaagg    180
tagcctgccc atcttaaaca caacaaaact gcacattgtt ttaccaatgg acacaaattt    240
ctgggttctt ttgcgtgatg gaatcaagac ttcaaaaata ttagaaatga caaatataga    300
tggcaaaagc caatt                                                     315

<210> SEQ ID NO 64
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggggcgcgcc ctatagtgtc acctaaatta atgtgacgat agctg                     45

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccatcgatcc ctttagtgag ggttaatagt acgcttactt ccgcg                     45

<210> SEQ ID NO 66
<211> LENGTH: 275
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 66
ggggcgcgcc ctatagtgtc acctaaatta atgtgacgat agctgaaaac tgtacgataa     60
acggtacgct gagggcggaa aaatcgtcg gggacattgt aaaggcggcg agcgcggctt    120
ttccgcgcca gcgtgaaagc agtgtggact ggccgtcagg tacccgtact gtcaccgtga   180
ccgatgacca tccttttgat cgccagatag tggtgcttcc gctgacgttt cgcggaagta   240
agcgtactat taaccctcac taaagggatc gatgg                               275

<210> SEQ ID NO 67
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

```
gtacgaggtc tcactgtaag ccctgcaatt tcccccatc gattccctt ag         52
```

<210> SEQ ID NO 68
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

```
catcgtgagt cactcgtcat ggggtaagac gatcatagag gggcgcgccc tatagtgt    58
```

<210> SEQ ID NO 69
<211> LENGTH: 346
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 69

```
gtacgaggtc tcactgtaag ccctgcaatt tcccccatc gattccctt agggttaata    60 gtacgcttac ttccgcgaaa cgtcagcgga agcaccacta tctggcgatc aaaaggatgg   120
tcatcggtca cggtgacagt acgggtacct gacggccagt ccacactgct ttcacgctgg   180
cgcggaaaag ccgcgctcgc cgcctttaca atgtccccga cgatttttc cgccctcagc   240 gtaccgttta tcgtacagtt ttcagctatc gtcacattaa tttaggtgac actatagggc   300
gcgcccctct atgatcgtct taccccatga cgagtgactc acgatg              346
```

<210> SEQ ID NO 70
<211> LENGTH: 235
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 70

```
atcttttttgc aggtcatcat cagatttgaa atatttaaag tggatacaaa actatttcag    60
caatgcagac aattaagtgt gttgttgtgg gcgatggtgc tgttggtaaa acatgtctcc   120
tgatatccta cacaacaaac aaatttccat cggaatatgt accgactgta agtataaagg   180
cttccttctg ttagtaaaat gttgtaaaat ttgatatcct tttgaaaacg ctttc          235
```

<210> SEQ ID NO 71
<211> LENGTH: 287
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 71

```
aaaacgcttt ctctatgtgt actgaatttt tttctgttgt ctgcctttgt ttcctgtttt    60
taaagatctt gacttctcat gggtaaatta tatacacttt aaacagctga aaatcagtg    120 gaaagtcaga aggggtgaca cagggtttgc aagaagtgct gggaggcaaa actccagtag   180
acaagattct aacgagtggt ggtctcaatt tggtgaagta tgccctacat cttggaatga   240
ggtgactttt tttttttttt ttttgatatt ttggccaatt attgatc                287
```

```
<210> SEQ ID NO 72
<211> LENGTH: 177
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 72
tttaactctc tccttgcaca ctaacagtgt tgtattttt tgttttagg tttttgacaa      60 ctatgcagtc acagttatga ttggtggaga accatatact cttggacttt ttgatactgc    120
aggtgaaaac ttaatgtctt ttatactgtt ttgatcttta acagttgcta gttgtct       177

<210> SEQ ID NO 73
<211> LENGTH: 209
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 73
tgaggacacc aagattcagt tgctgaattc tctccaatat ttttcttttt tctagggcaa    60
gaggattatg acagattacg accgctgagt tatccacaaa cagatgtatt tctagtctgt    120
ttttcagtgg tctctccatc ttcatttgaa aacgtgaaag aaaaggtaag ctgatcagat    180
actcttgccc taagaagatc atctcagaa                                      209

<210> SEQ ID NO 74
<211> LENGTH: 186
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 74
ctaatcctct aacctggctg ctattctctc tcctcccctc tgtcttgtag agaggtctga    60
agaatgtgtt tgatgaggct atcctagctg ccctcgagcc tccggaaact caacccaaaa    120
ggaagtgctg tatattctaa actgttttct ccttcccttc tttgctgctg cttcctgtcc    180
cactac                                                              186

<210> SEQ ID NO 75
<211> LENGTH: 184
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 75
actgaaaatc agaccgccca ttttttcttt ctaccccttt tcagaaaggc ctaaagaatg    60
tatttgacga agcaatattg gctgccctgg agcctccaga accgaagaag agccgcaggt    120
gtgtgctgct atgaacatct ctccagagcc ctttctgcac agctggtgtc ggcatcatac    180
taaa                                                                184

<210> SEQ ID NO 76
<211> LENGTH: 425
<212> TYPE: DNA
<213> ORGANISM: Artificial Sequence
<220> FEATURE:
```

<223> OTHER INFORMATION: Description of Artificial Sequence: Synthetic
      nucleotide construct

<400> SEQUENCE: 76
cgattcctac cccctcgcct tccccggcg ccgacggcca caccgccgga cgatgcgcgc      60
ccgcggccgc ccgggaggct gagcccagct tcccgctccg ccttccccgc gcagctgccc    120
ccatggcttt gcggggcgcc gcgggagcga ccgacacccc ggtgtcctcg gccggggag    180 cccccggcgg ctcagcgtcc tcgtcgtcca cctcctcggg cggctcggcc tcggcgggcg    240
cggggctgtg ggccgcgctc tatgactacg aggctcgcgg cgaggacgag ctgagcctgc    300
ggcgcggcca gctggtggag gtgctgtcgc aggacgccgc cgtgtcgggc gacgagggct    360
ggtgggcagg ccaggtgcag cggcgcctcg gcatcttccc cgccaactac gtggctccct    420
gccgc                                                                425

<210> SEQ ID NO 77
<211> LENGTH: 278
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 77
ttgtgacaga aaaattaaaa gaatatgcaa atgtctcact tttgattttt ctttagtttt      60
gctacttgag aagatagaac atgatgacat ctgcaataaa actttgaaga ttacagattt    120
tgggttggcg agggaatggc acaggaccac caaaatgagc acagcaggca cctatgcctg    180
gatggccccc gaagtgatca agtcttcctt gttttctaag ggaagcgaca tctggaggtg    240
agcctttcct tttgcaaaca tcggcagaaa ctgcttgc                            278

<210> SEQ ID NO 78
<211> LENGTH: 232
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 78
acactgttta gcccattgag catatgaaat ccttgctttc tagctatgga gtgctgctgt      60
gggaactgct caccggagaa gtcccctatc ggggcattga tggcctcgcc gtggcttatg    120
gggtagcagt caataaactc actttgccca ttccatccac ctgccctgag ccgtttgcca    180
agctcatgaa aggtattgtg tgtgtgtgtg tgtgtctttg tgggggcaag aa             232

<210> SEQ ID NO 79
<211> LENGTH: 285
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 79
tctaaactgc gttgagagat ggtattaatg tgattttttgt ttattttaga atgctggcaa     60
caagaccctc atattcgtcc atcgtttgcc ttaattctcg aacagttgac tgctattgaa    120
ggggcagtga tgactgagat gcctcaagaa tcttttcatt ccatgcaaga tgactggaaa    180
ctagaaattc aacaaatgtt tgatgagttg agaacaaagg aaaaggtgag agaaattttt    240
aaacagcata atgtactcaa atttatgaaa actatggaaa atatg            285

<210> SEQ ID NO 80
<211> LENGTH: 344
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 80
ccttcttcct gctgggaatg attccggtgg gtgtgaatct gtgtcgcagg agctgcgatc            60
ccgggaagag gagctgactc gggcggctct gcagcagaag tctcaggagg agctgctaaa           120
gcggcgtgag cagcagctgg cagagcgcga gatcgacgtg ctggagcggg aacttaacat           180
tctgatattc cagctaaacc aggagaagcc caaggtaaag aagaggaagg gcaagtttaa           240
gagaagtcgt ttaaagctca agatggaca tcgaatcagt ttaccttcag gtatgatctt            300 gttttatgt ttttgaaaga tttttgtgtg tcctcctttt aatc                             344

<210> SEQ ID NO 81
<211> LENGTH: 216
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 81
taaaggaaaa ccatgaaata ccagttctcc cttttttgcct ccaacagatt tccagcacaa          60
gataaccgtg caggcctctc ccaacttgga caaacggcgg agcctgaaca gcagcagttc          120
cagtcccccg agcagcccca caatgatgcc ccgactccga gccatacagt gtgagctttc          180
tgcactgcca cgggggctcc tgtgttgact tctctc                                     216

<210> SEQ ID NO 82
<211> LENGTH: 252
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 82
atattggtta atatgattgt tgtggttaat atggttaata atgttctttt tagtgacttc           60
agatgaaagc aataaaactt ggggaaggaa cacagtcttt cgacaagaag aatttgagga          120
tgtaaaaagg aatttttaaga aaaaggttg tacctgggga ccaaattcca ttcaaatgaa          180
agatagaaca gattgcaaag aaaggtacgt gtgtggtatc tggtggtatt cattgtgtaa          240
tatgacaaat cc                                                               252

<210> SEQ ID NO 83
<211> LENGTH: 197
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 83
ctaattggtg tgttgtgtgc ttctatctta tgaaaagaaa cattttctc ttgtaggata            60

```
agacctctct ccgatggcaa cagtccttgg tcaactatct aataaaaaa tcagaaaacc        120 atgcccttgg cttcattgtt tgtggaccag ccaggtaaat gtgtttcagg aggtaggatt       180
tgcttgagca gtccttg                                                      197
```

```
<210> SEQ ID NO 84
<211> LENGTH: 355
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 84
caatcttgtt taaatgactt ttgctgtaaa atgatactac agtgtatgta cttatacctt        60
tatttagggt cctgtgaaga gccaaaactt tcccctgatg gattagaaca cagaaaacca       120
aaacaaataa aattgcctag tcaggcctac attgatctac ctcttgggaa agatgctcag       180
agagagaatc ctgcagaagc tgaaagctgg gaggaggcag cctctgcgaa tgctgccaca       240
gtctccattg agatgactcc tacgaatagt ctgagtagat cccccagag aaagaaaacg        300 gagtcagctc tgtatgggtg caccgtcctt ctggcatcgg tggctctggg actgg           355
```

```
<210> SEQ ID NO 85
<211> LENGTH: 336
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 85
tctttctcca caaagtgcct gctgcagatg gacagtgaag atccactggt ggacagtgca        60
cctgtcactt gtgactctga gatgctcact ccggattttt gtcccactgc cccaggaagt       120
ggtcgtgagc cagccctcat gccaagactt gacactgatt gtagtgtatc aagaaacttg       180
ccgtcttcct tcctacagca gacatgtggg aatgtacctt actgtgcttc ttcaaaacat       240
agaccgtcac atcacagacg gaccatgtct gatggaaatc cgaccccaag taggttgcat       300
taattaggta aaagcataaa acactgctgt agagat                                 336
```

```
<210> SEQ ID NO 86
<211> LENGTH: 286
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 86
tttagaactc attttctttc taactgcata ctgttttggc tttctcaacc agctggtgca        60
actattatct cagccactgg agcctctgca ctgccactct gccccctcacc tgctcctcac      120 agtcatctgc caagggaggt ctcacccaag aagcacagca ctgtccacat cgtgcctcag       180
cgtcgccctg cctccctgag aagccgctca gatctgcctc aggcttaccc acagacagca      240
gtgtctcagc tggcacagac tgcctgtgta gtgggtcgcc caggac                      286
```

```
<210> SEQ ID NO 87
<211> LENGTH: 307
<212> TYPE: DNA
<213> ORGANISM: Artificial Sequence
<220> FEATURE:
```

<223> OTHER INFORMATION: Description of Artificial Sequence: Synthetic
nucleotide construct

<400> SEQUENCE: 87

| ctgcctcagg | cttacccaca | gacagcagtg | tctcagctgg | cacagactgc | ctgtgtagtg | 60 |
| ggtcgcccag | gaccacatcc | cacccaattc | ctcgctgcca | aggagagaac | taaatcccat | 120 |
| gtgccttcat | tactggatgc | tgacgtggaa | ggtcagagca | gggactacac | tgtgccactg | 180 |
| tgcagaatga | ggagcaaaac | cagccggcca | tctatatatg | aactggagaa | agaattcctg | 240 |
| tcttaaacta | agtgccttac | tgttgtttaa | gcattttttt | aaggtgaaca | aatgaacaca | 300 |
| atgtatc | | | | | | 307 |

<210> SEQ ID NO 88
<211> LENGTH: 224
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 88

| tacaaaaatt | accacttgta | ctagtatgcc | ttaagaaaaa | agtacaaatt | gtatttacat | 60 |
| aattacacac | tttgtctttg | acttcttttt | cttcttttta | ccatctttgc | tcatcttttc | 120 |
| tttatgtttt | cgaatttctc | gaactaatgt | atagaaggca | tcatcaacac | cctgaaatac | 180 |
| ataaaaagta | ttaaaatgtg | aatatatacg | atggcttcat | gtgt | | 224 |

<210> SEQ ID NO 89
<211> LENGTH: 225
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 89

| aaaagacatc | tgctttctgc | caaaattaat | gtgctgaact | taaacttacc | agattacatt | 60 |
| ataatgcatt | ttttaatttt | cacacagcca | ggagtctttt | cttctttgct | gattttttttc | 120 |
| aatctgtatt | gtcggatctc | cctcaccaat | gtataaaaag | catcctccac | tctctgcatt | 180 |
| gtaaaacaca | acttctttaa | agtctgttgc | attggtaaga | gtaat | | 225 |

<210> SEQ ID NO 90
<211> LENGTH: 356
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 90

| gccctctcaa | gagacaaaaa | catttactaa | atattgtttt | atttcctagt | atagcataat | 60 |
| tgagagaaaa | actgatatat | taaatgacat | aacagttatg | attttgcaga | aaacagatct | 120 |
| gtatttattt | cagtgttact | tacctgtctt | gtctttgctg | atgtttcaat | aaaaggaatt | 180 |
| ccataacttc | ttgctaagtc | ctgagcctgt | tttgtgtcta | ctgttctaga | aggcaaatca | 240 |
| catttatttc | ctactaggac | cataggtaca | tcttcagagt | ccttaactct | tttaatttgt | 300 |
| tctctgggaa | agaaaaaaaa | gttatagcac | agtcattagt | aacacaaata | tctttc | 356 |

```
<210> SEQ ID NO 91
<211> LENGTH: 231
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 91
caaagaatgg tcctgcacca gtaatatgca tattaaaaca agatttacct ctattgttgg      60
atcatattcg tccacaaaat gattctgaat tagctgtatc gtcaaggcac tcttgcctac     120
gccaccagct ccaactacca caagtttata ttcagtcatt ttcagcaggc cttataataa     180
aaataatgaa aatgtgacta tattagaaca tgtcacacat aaggttaata c              231

<210> SEQ ID NO 92
<211> LENGTH: 225
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 92
ccttctgcag ggttcccagg cccccgctcc agggccgggc tgacccgact cgctggcgct      60
tcatggagaa cttccaaaag gtggaaaaga tcggagaggg cacgtacgga gttgtgtaca     120
aagccagaaa caagttgacg ggagaggtgg tggcgcttaa gaaaatccgc ctggacacgt     180
gagtggcctc tgtacccggg actcctaact ggggacctcc ttgat                     225

<210> SEQ ID NO 93
<211> LENGTH: 405
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 93
ggaatatttg taaccatatt cccatctctg ctttcccaac ctctccaagt gagactgagg      60
gtgtgcccag tactgccatc cgagagatct ctctgcttaa ggagcttaac catcctaata     120
ttgtcaagta agtatgcgtc tgagaggtga tccagctgga aaggaggata agttctgtct     180
gtacagtgtg ggcatttctc tctctcacac acctccattt cctcaaactt tccttctcta     240
ggctgctgga tgtcattcac acagaaaata aactctacct ggtttttgaa tttctgcacc     300
aagatctcaa gaaattcatg gatgcctctg ctctcactgg cattcctctt ccccctcatca    360 aggtaatgct tctcatcagc tcctctcatc atgggcatgt cttgg                     405

<210> SEQ ID NO 94
<211> LENGTH: 266
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 94
gtctgctcac tgtaatggag aaacacagtc ctctctttct cctttgtcag agctatctgt      60
tccagctgct ccagggccta gctttctgcc attctcatcg ggtcctccac cgagacctta    120
aacctcagaa tctgccttat taacacagagg gggccatcaa gctagcagac tttggactag    180
```

```
ccagagcttt tggagtccct gttcgtactt acacccatga ggtgagtccc tttatgtctt    240 tttctctga gcttcccaag aggtgt                                          266
```

<210> SEQ ID NO 95
<211> LENGTH: 205
<212> TYPE: DNA
<213> ORGANISM: Artificial Sequence
<220> FEATURE:
<223> OTHER INFORMATION: Description of Artificial Sequence: Synthetic
      nucleotide construct <400> SEQUENCE: 95

```
ccataccta taaaccaccc cgcccctccc tattcccgtc cctcaggtgg tgaccctgtg     60
gtaccgagct cctgaaatcc tcctgggctg caaatattat tccacagctg tggacatctg  120
gagcctgggc tgcatctttg ctgagatggt atggaggctt gcccaagttc cacccagccc  180
cctccctctc ctccccacat ccaag                                        205
```

<210> SEQ ID NO 96
<211> LENGTH: 294
<212> TYPE: DNA
<213> ORGANISM: Artificial Sequence
<220> FEATURE:
<223> OTHER INFORMATION: Description of Artificial Sequence: Synthetic
      nucleotide construct <400> SEQUENCE: 96

```
gactgacgtc aacgtgggtc ttggtatttc ctctttcccc attttcaggt gactcgccgg    60
gccctattcc ctggagattc tgagattgac cagctcttcc ggatctttcg gactctgggg  120
accccagatg aggtggtgtg gccaggagtt acttctatgc ctgattacaa gccaagtttc  180
cccaagtggg cccggcaaga ttttagtaaa gttgtacctc ccctggatga agatggacgg  240
agcttgttat cggtgagagt gggcacctgt tttccctcat tcatttctcc cagg         294
```

<210> SEQ ID NO 97
<211> LENGTH: 205
<212> TYPE: DNA
<213> ORGANISM: Artificial Sequence
<220> FEATURE:
<223> OTHER INFORMATION: Description of Artificial Sequence: Synthetic
      nucleotide construct <400> SEQUENCE: 97

```
gctgcccatt tagtccacta tcacatcatt gaagtcaaca tgcatctctc cctctagcaa    60
atgctgcact acgaccctaa caagcggatt tcggccaagg cagccctggc tcacccttc   120 ttccaggatg tgaccaagcc agtaccccat cttcgactct gatagccttc ttgaagcccc  180
cagccctaat ctcaccctct cctcc                                        205
```

<210> SEQ ID NO 98
<211> LENGTH: 244
<212> TYPE: DNA
<213> ORGANISM: Artificial Sequence
<220> FEATURE:
<223> OTHER INFORMATION: Description of Artificial Sequence: Synthetic
      nucleotide construct <400> SEQUENCE: 98

```
tgagaatttg tgtccagccc tcagccactc ttccctctgc tttgaacagt gtgtcctggg    60
actctgaatg gcctgagtgt gaccggcgat gctgagaacc aataccagac actgtacaag  120
ctctacgaga ggtgtgaggt ggtgatgggg aaccttgaga ttgtgctcac gggacacaat  180
```

```
gccgacctct ccttcctgca ggttagtgag cccaccctcc ttcctcaacc tgctcctctt    240
tatt                                                                 244

<210> SEQ ID NO 99
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 99
attattttgc cctgttgtct ctctcattta cataatctgc tctgtcacag tggattcgag    60
aagtgacagg ctatgtcctc gtggccatga atgaattctc tactctacca ttgcccaacc   120
tccgcgtggt gcgagggacc caggtctacg atgggaagtt tgccatcttc gtcatgttga   180
actataacac caactccagc cacgctctgc gccagctccg cttgactcag ctcaccggtc   240
agttcccgat ggttccttct ggcctcaccc ctcagc                             276

<210> SEQ ID NO 100
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 100
atgggtggag aggtaaggaa gaggcgttcc gctgcggccc ttaaccctgt cacttctttc    60
cctacctcag agattctgtc aggggggtgtt tatattgaga agaacgataa gctttgtcac   120
atggacacaa ttgactggag ggacatcgtg agggaccgag atgctgagat agtggtgaag   180
gacaatggca gaagctgtaa gtggccgtga tcaagattgc tccccagtcc caccaa       236

<210> SEQ ID NO 101
<211> LENGTH: 165
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 101
caagcctttc ttagccctga tggccccttg tgttgccttc cttcccaacc aggtcccccc    60
tgtcatgagg tttgcaaggg gcgatgctgg ggtcctggat cagaagactg ccagacatgt   120
gggtttgaaa ttccctccaa aaacttcact catacgcttt catat                   165

<210> SEQ ID NO 102
<211> LENGTH: 206
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 102
cagtcctagg agccctaaca gccatgcttt ctctccttcc atagtgacca agaccatctg    60
tgctcctcag tgtaatggtc actgctttgg gcccaacccc aaccagtgct gcatgatga    120 gtgtgccggg ggctgctcag gccctcagga cacagactgc tttgtatgta ccctttccat   180
```

```
tgcctgggtt ctgaaattgg gatgtg                                          206
```

<210> SEQ ID NO 103
<211> LENGTH: 265
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 103

```
ggaggaggta ggggtacaca cgtaacataa atctgatgag cctccttttt tcccaggcct     60
gccggcactt caatgacagt ggagcctgtg tacctcgctg tccacagcct cttgtctaca   120
acaagctaac tttccagctg aacccaatc cccacaccaa gtatcagtat ggaggagttt     180
gtgtagccag ctgtccccgt aagtgtctga ggggaaggaa caatgatcaa caatagtaga   240
tccaagattt tagacaaaat tgtgg                                         265
```

<210> SEQ ID NO 104
<211> LENGTH: 412
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 104

```
gatgttcctc cctcatctct aatggtgtcc tcctcctctt ccctagataa ctttgtggtg    60
gatcaaacat cctgtgtcag ggcctgtcct cctgacaaga tggaagtaga taaaaatggg   120
ctcaagatgt gtgagccttg tgggggacta tgtcccaaag gtgggtagga gatggtaaga   180
agttgtaaag agacagcctt tcctctgagc ctgcgcagac cacccccact gaacctctct   240
tacatttgca gcctgtgagg gaacaggctc tgggagccgc ttccagactg tggactcgag   300
caacattgat ggatttgtga actgcaccaa gatcctgggc aacctggact ttctgatcac   360
cggcctcaat gggttagaga tcctgccttc cctccttaga ccccagccca cg           412
```

<210> SEQ ID NO 105
<211> LENGTH: 433
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 105

```
gctcattgcc attgagttat acctttacct tattgactgg tttctactgt tctattcaga    60
gacccctggc acaagatccc tgccctggac ccagagaagc tcaatgtctt ccggacagta   120
cgggagatca caggtgagtg gcagagagtt tgcccttttct agaagaatag gtgaaccact   180
ggcataaatt gcggtataac tacttgagaa aatcacgtcc caagttatag gggaggagcc   240
aggagaaccc aagaaagaag aaggctccct gcccatatgc ctctctccaa cccctcaggt   300
tacctgaaca tccagtcctg gccgccccac atgcacaact tcagtgtttt ttccaatttg   360
acaaccattg gaggcagaag cctctacaag tgagtaaagg gtatggagga aatggcatct   420
tcaggcaatg aag                                                      433
```

<210> SEQ ID NO 106
<211> LENGTH: 256
<212> TYPE: DNA

<213> ORGANISM: Artificial Sequence
<220> FEATURE:
<223> OTHER INFORMATION: Description of Artificial Sequence: Synthetic
      nucleotide construct

<400> SEQUENCE: 106
gaagagaggg cttgctggga gtcctcagac tcctctccta acccaccct tcctttccag      60 tggcagaggg caaagtgtgt gacccactgt gctcctctgg gggatgctgg ggcccaggcc    120
ctggtcagtg cttgtcctgt cgaaattata gccgaggagg tgtctgtgtg acccactgca    180
actttctgaa tgggtacagt aaggggagcc agtcaaggat gggtgggggt ggggccctgc    240
aatggaactg ttcagg                                                    256

<210> SEQ ID NO 107
<211> LENGTH: 183
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 107
ggtcaggact tggaagtgac ccccccctcc ctttattccc cactacaggg agcctcgaga     60
atttgcccat gaggccgaat gcttctcctg ccacccggaa tgccaaccca tggagggcac   120
tgccacatgc aatggctcgg tatactagta gcaccaggat ctccaaggga gacagagaag   180
ggg                                                                 183

<210> SEQ ID NO 108
<211> LENGTH: 245
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 108
gaattgacct tgggatctga ttcttcctga ccttctctct tccactcagg gctctgatac     60
ttgtgctcaa tgtgcccatt ttcgagatgg gccccactgt gtgagcagct gccccatgg    120 agtcctaggt gccaagggcc caatctacaa gtacccagat gttcagaatg aatgtcggcc   180
ctgccatgag aactgcaccc aggggtcagt gatgggataa taaggagagg gggtcaggtg   240
gaagg                                                               245

<210> SEQ ID NO 109
<211> LENGTH: 165
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 109
gcctctgctg tccaagctct catttaaggt ggtgactttc ttccctaggt gtaaaggacc     60
agagcttcaa gactgtttag gacaaacact ggtgctgatc gggtatgatg gggttggaga   120
ttctggaaac tggggatatt tgggagttgg gagagaggtg gttac                   165

<210> SEQ ID NO 110
<211> LENGTH: 244
<212> TYPE: DNA
<213> ORGANISM: Artificial Sequence

```
<220> FEATURE:
<223> OTHER INFORMATION: Description of Artificial Sequence: Synthetic
      nucleotide construct

<400> SEQUENCE: 110
agatgcaaac ccaggataat gttgggtttc tatatatccc atagcaaaac ccatctgaca      60
atggctttga cagtgatagc aggattggta gtgattttca tgatgctggg cggcactttt     120
ctctactggc gtgggcgccg gattcagaat aaaagggcta tgaggcgata cttggaacgg     180
ggtgaggtga gtacttagct tactttgtt ttttctttc ttttttgca tgtcctggaa        240 gtct                                                                  244

<210> SEQ ID NO 111
<211> LENGTH: 205
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 111
gggaatggcc tttcctgagt aactccttcc catttgctcc tcagagcata gagcctctgg      60
accccagtga aaggctaac aaagtcttgg ccagaatctt caaagagaca gagctaagga     120
agcttaaagt gcttggctcg ggtgtctttg gaactgtgca caaagtgagt gacccatagg     180
aattctggag aggtggggaa ggcat                                           205

<210> SEQ ID NO 112
<211> LENGTH: 186
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 112
ctagggagaa tgaccttatg ccaactcctg ccccaaactt cccagggagt gtggatccct      60
gagggtgaat caatcaagat tccagtctgc attaaagtca ttgaggacaa gagtggacgg     120
cagagttttc aagctgtgac agatgtaagt gaaggaaatt ctgtatgccg ctaggagaga     180
ggacaa                                                                186

<210> SEQ ID NO 113
<211> LENGTH: 284
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 113
gtatgtgaac ctgttggttt cctagataat acctttgtg tctcttagca tatgctggcc       60
attggcagcc tggaccatgc ccacattgta aggctgctgg gactatgccc agggtcatct     120
ctgcagcttg tcactcaata tttgcctctg ggttctctgc tggatcatgt gagacaacac     180
cggggggcac tggggccaca gctgctgctc aactggggag tacaaattgc caaggtgaga     240
gaagcctgga ggaattctgt gataagaact gcttgtctgg gggc                      284

<210> SEQ ID NO 114
<211> LENGTH: 250
<212> TYPE: DNA
```

<213> ORGANISM: Artificial Sequence
<220> FEATURE:
<223> OTHER INFORMATION: Description of Artificial Sequence: Synthetic nucleotide construct

<400> SEQUENCE: 114

```
actgattccc ccaaccttaa gaatactttc ttcccctata cctacaggga atgtactacc      60
ttgaggaaca tggtatggtg catagaaacc tggctgcccg aaacgtgcta ctcaagtcac     120
ccagtcaggt tcaggtggca gattttggtg tggctgacct gctgcctcct gatgataagc     180
agctgctata cagtgaggcc aaggtgagga gacacaaagg gtaaggaggc ggggtggag      240
tgaagcatgg                                                            250
```

<210> SEQ ID NO 115
<211> LENGTH: 170
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 115

```
ctaagaaaat ttgtggaaat aaacttgtga tacctctatc tttaatccgc agactccaat      60
taagtggatg ccccttgaga gtatccactt tgggaaatac acacaccaga gtgatgtctg     120
gagctatggt cagtgcatct ggatgccctc tctaccatca ctggccccag                170
```

<210> SEQ ID NO 116
<211> LENGTH: 194
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 116

```
ccatggaatg tattctcttt tatgtctcta cctcctacat cttatctcca ggttggatga      60
ttgatgagaa cattcgccca acctttaaag aactagccaa tgagttcacc aggatggccc     120
gagacccacc acggtatctg gtcataaagg tgagtaggga gtaggaggtg ctaaggaaat     180
ttagaaaaag gagg                                                       194
```

<210> SEQ ID NO 117
<211> LENGTH: 245
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 117

```
ctatcgatat agagagagag tgggcctgga atagccctg ggccagagcc ccatggtctg       60
acaaacaaga agctagagga agtagagctg gagccagaac tagacctaga cctagacttg     120
gaagcagagg aggacaacct ggcaaccacc acactgggct ccgccctcag cctaccagtt     180
ggaacactta atcggccacg tggggtaaga caacttctaa ttacccaaca ctttgcaccc     240
tgagc                                                                 245
```

<210> SEQ ID NO 118
<211> LENGTH: 162
<212> TYPE: DNA
<213> ORGANISM: Artificial Sequence

```
<220> FEATURE:
<223> OTHER INFORMATION: Description of Artificial Sequence: Synthetic
      nucleotide construct

<400> SEQUENCE: 118
gtagatttct cccttcatct taaccttttc cttattttt catcctagag ccagagcctt      60
ttaagtccat catctggata catgcccatg aaccagggta atcttgggga gtcttgccag    120
gtaagttctg ttgctgagag gctgggtttt aggatcagat tg                      162

<210> SEQ ID NO 119
<211> LENGTH: 425
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 119
taaacaaatc tctcttcttt cctcatcatg taaatttcct tgcattattt tctgtttatt     60
ttcttcctta ggagtctgca gtttctggga gcagtgaacg gtgccccgt ccagtctctc    120 tacacccaat gccacgggga tgcctggcat cagagtcatc agagggcat gtaacaggct    180 ctgaggctga gctccaggag aaagtgtcaa tgtgtaggag ccggagcagg agccggagcc    240
cacggccacg cggagatagc gcctaccatt cccagcgcca cagtctgctg actcctgtta    300
ccccactctc cccacccggg ttagaggaag aggatgtcaa cggttatgtc atgccagata    360
cacacctcaa aggtgcctga ctcttcctag ggctttcctc aatttttcct cgaattcttt    420
ccccg                                                                425

<210> SEQ ID NO 120
<211> LENGTH: 356
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 120
ctaccctcat gaagttcttc acatacctag cctttcttct caaccccccag gtactccctc     60 ctcccgggaa ggcacccttt cttcagtggg tctcagttct gtcctgggta ctgaagaaga    120
agatgaagat gaggagtatg aatacatgaa ccggaggaga aggcacagtc cacctcatcc    180
ccctaggcca agttccctt g aggagctggg ttatgagtac atggatgtgg ggtcagacct    240
cagtgcctct ctgggcagca cacagagttg cccactccac cctgtaccca tcatgcccac    300
tgcaggcaca actccagatg aagactatga atatatgaat cggcaacgag atggag        356

<210> SEQ ID NO 121
<211> LENGTH: 344
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 121
ctccaccctg tacccatcat gcccactgca ggcacaactc cagatgaaga ctatgaatat     60
atgaatcggc aacgagatgg aggtggtcct gggggtgatt atgcagccat ggggcctgc    120 ccagcatctg agcaagggta tgaagagatg agagcttttc aggggcctgg acatcaggcc    180
```

```
ccccatgtcc attatgcccg cctaaaaact ctacgtagct tagaggctac agactctgcc    240
tttgataacc ctgattactg gcatagcagg cttttcccca aggctaatgc ccagagaacg    300
taactcctgc tccctgtggc actcagggag catttaatgg cagc                    344
```

<210> SEQ ID NO 122
<211> LENGTH: 186
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 122

```
agaagggaaa tggcagcttt tcttccttcc atggcagcca ctccattgct cactccggat    60
taccttcatc cttatgtaga taagagtgct gcagagctcg aaaggcagag attcgcttgt    120
gtgggttaaa agtcagcatt tcctgagggg agaggcaaag gtcagaaaac catgaagaaa    180
acagac                                                              186
```

<210> SEQ ID NO 123
<211> LENGTH: 417
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 123

```
ttccccagtc tctatttctt tccctgtgcc cacagccatc tccagtacca gcagcagctg    60
tgctcccgac tcctccatct caggtaccac cgactgcact gggcggggcc ctctgggggg    120
aaaggctcca cggggcaggg atacatctcg aggccagtca tcctctggag gcagcccaat    180
caggctgtgg gggacaggag aactctggtc aggagggtcc tccagttccc atccccatgg    240
gcagagccag ttgccatcct gggttcagca gaaagaggac tcagaataga aaatcttttt    300
ctcccatgtt ggtcacttac tcaaagattt tgcccaactg gtcggcttca gagtttccac    360
agaagagagg cctaaggtga gaagggatat aaggtagcag tcattttcaa agatatc      417
```

<210> SEQ ID NO 124
<211> LENGTH: 223
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 124

```
aagcgatttg gggaattcaa ggtagtccag ggtatgtggg tcccatactt tcgacgaaac    60
atctctgcaa agatacagcc aacactccac atgtccacag gtgttgcata tgtggactgc    120
agaagaactt cgggagctcg gtaccagagt gtaacaacct aaagggaata ggaagaatgg    180
atggggaccc catgggttac catgaaacac aacttgcttg act                     223
```

<210> SEQ ID NO 125
<211> LENGTH: 263
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 125

```
ctcctactcc caaccagaac ccattttggt accatctttc tactgaccac gggtgtaagt    60
gccatctggt agctgtagat tctggccagg ccaaagtcag ccagcttgac tgttccacca   120
cttgtcacca gaatgttctc tggcttcaga tctcggtgaa cgatgcaatt ggcatgaagg   180
aaatctaggc ctcttagaaa ctggcgcatc agatcctagt ttcaaagggg aggtacagat   240
gcactggaaa ctaggcacca tac                                          263
```

<210> SEQ ID NO 126
<211> LENGTH: 225
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 126

```
acaaaggtcc caatccacct ctcaatgcct accaacccca ctcaccttga tcgtttcggc    60
tggcaagcct ggtgggggtg ccttgtccag atatgtcctt aggtcctggt ctacatgctc   120
aaacaccagg gttaccttga tctcccggtc agttcgggat gtggcacaga cgtccatcag   180
cctgaccaga gtaaatgctc acttttcaat cccctttaac ccaac                  225
```

<210> SEQ ID NO 127
<211> LENGTH: 346
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 127

```
gtttcctggg ggtataaata cacatgtgct tctagaaata aggcttcgtg tcaaactcta    60
gatgggtggg gtggagtaca ggaccaccga gttgtagtct gggggcgggg agcagcacgc   120
gattttcctt tccagctcag cgtggtcgta ggtgaacctg cgcttgcctt cgctgacgtg   180
cccacagctg gaatggcaga aactgggcct gctgacatca gacagccccg actccttact   240
tttactggtt actctcaagc taagaaaga aggaaagaa atcaaatatt caaaattggt   300
tttttagaaa acaaagacac taaaatctac tctttctgag tgggtc                 346
```

<210> SEQ ID NO 128
<211> LENGTH: 183
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 128

```
taccctcca tcaactgatc acagaaaaga tacccaattc ttactcaatc ttgagcgagg     60
ccttgggttt gctgtcagtc caggtgaagc gcttcagcat gggagaggcc aacagagtgc   120
tgctgtcgcc ctggtagtcc taggggaga aggagaaagg ttatactctt gcctggccca   180
gcg                                                                 183
```

<210> SEQ ID NO 129
<211> LENGTH: 175
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 129
gggtctatcg gggtgcacta ggtaccttaa cttcacgact tacatcaaac atggaggtgg     60
cattcggtaa aagttcttca aaggttttga ttctttccag gctcatgaac ttgaaagcat    120
ttacgtatct aatgaagaaa cagaaagaat tatcaagaca ggaaaaggca tccag         175

<210> SEQ ID NO 130
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 130
cttttttttg ttggaaaatt ctgtgatata aagtttgaga agaaatcttt acctgacatc     60
atcagagctt cctgaattaa acttcggagc tgaaatactt tccttgaaga agtcctcaga    120
gaaggcagga gttgagtatg taaacccact atttcctgtc agtatggcat tgattgggat    180
gtagtcttta ccatcctaaa ataccaaagg tagagctctc gttgcaccaa ttctga        236

<210> SEQ ID NO 131
<211> LENGTH: 204
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 131
gcccccctga cgtacattca aaggcatttt gatgtaaata aatttagttt tacctgttgt     60
acatttgctt gaagcaaatc acctagtttt tccacaagtt ctgcaaatct tggccttttct   120 tttgggtctc tgtgccagca gtccagcatg atctgatagc tggtggggaa aacagcaaca    180
gaaatagttg gagagcagtg atca                                           204

<210> SEQ ID NO 132
<211> LENGTH: 195
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 132
gaaaagcgag ctgtcagatg gggagcagag ggcaccaagg gctcacattt caggagtaga     60
gtactcagga gctctcatcc tcatgccttc cctcaggcga ctgcaaaagt cctcatccat    120
ttgtactcct gggtatggag acccacctgc gggagacaat gtggaaaaca cagggcctgt    180
tatggcttaa gggta                                                     195

<210> SEQ ID NO 133
<211> LENGTH: 207
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 133
agacatttat ttctgggctg tttgatttct tccttctccc aaatttacct aaggagaaga     60

```
tttcccacag caatactccg taagaccaca cgtcgctctt ggtgctgtag attttgtcaa      120
agatagattc aggagccatc catttcagag gaagtcgagt ctagaagagg gcaaggggc       180 cttgagcaga agggcatgaa aacaaag                                          207
```

```
<210> SEQ ID NO 134
<211> LENGTH: 197
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 134
ccagccctgg cagagaagaa aaacagtaaa cagcaagact gacctttctg gaagacagga      60
actccatgcc tctggccact tgaaaactgt aagaaatcag atcttccata gtgatgggct     120
ccttgtagaa accgtcagaa tctggaaagc attagaaccg taactgtttg taatggctct    180
tgttatccca ccaaatc                                                    197
```

```
<210> SEQ ID NO 135
<211> LENGTH: 243
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 135
gtaaaaatat ctcagcgcgt aggacaggaa ggaattaata cctaccctcc tcttcctcaa      60
catcactcag acttttatct tcctgaaagc cggagctcgc aaagctttcg ctgctggtga    120
cgctatctag tcttggtttc ttgccttgtt ccaggcctgg ctccatttt tctttcttag    180 gctccatgtg tagtgctgca tcctttgaag agaccgaaaa ggacccaggt gaaaaggagc    240
tcc                                                                   243
```

```
<210> SEQ ID NO 136
<211> LENGTH: 184
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 136
aaatgaaaac tcattgctat ctttaaaaac ctccaacttt tgaaatcctt accttgttga      60
gaaaaaataa gtcacgtttg ctcttgaggt agttggagag atttccatat ttgcagtatt    120
caacaatcac catcagaggc cctgcagcca aaacagcaca tgctcatgct cagccacacc    180
aagc                                                                  184
```

```
<210> SEQ ID NO 137
<211> LENGTH: 194
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 137
aaaatggtga tgggtcagtt gaaagccaaa ctacagcata catacctttc agcattttca      60
```

```
cagccacagt ccggcacgta ggtgatttct taatgccaaa tgctgatgct tgaaccactt      120
ttccaaaagc ccctcttcca agtgatttgc ctgtaatgaa gagaagacac tggtttgttt      180
gccgaggcaa tagg                                                         194

<210> SEQ ID NO 138
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 138
gtttttcatg taatatgtgc tcagtatagg tttatgaatc tgttgaacaa atatcttacc       60
cagtttaagt ctctcccggg caaactccca cttgctggca tcataaggga gccgctcaca      120
ctgctcatcc aaaggaactt catctgggtc cattataatt gataggtagt cagtctttat      180
ttcagaagaa gactgagaaa taaagagatc tcaaagtcat cgagaagaaa acaact         236

<210> SEQ ID NO 139
<211> LENGTH: 226
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 139
ctagacatca gatcgggctt tttagaatat atgtaaaaag gagcatagaa catcacctat       60
gttcttaccc ttttcatttt tcggataaag agggttaata ggagccagaa gagagtcgca      120
gccacacagg tgcatgttag agtgatcagc tccagattag acttgtccga ggttcctgga      180
gagaaaaaaa atcacaatag tggtgcaaca aagaaattcc caaact                    226

<210> SEQ ID NO 140
<211> LENGTH: 225
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 140
aatagatgtc tgaccaattt cttgttgctt tcttaagcag ctgtttacct tgaacagtga       60
ggtatgctga actttccaca gagcccttct ggttggtggc tttgcagtga tagacacctt      120
catcctcttc tgtgactctt tcaataaaca gcgtgctgct tcctggtcct aaaataattc      180
ctgaggggtg agagatgttt agattagtgg gcctggatga caaac                     225

<210> SEQ ID NO 141
<211> LENGTH: 250
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 141 gggggctga tgaaagatga gaaataataa atggaagaaa aaaaagtctc ttaccaggct       60
cttgttgtat tttgtggttg tttttaaacc aagtgatctg aggctcgggg acaccattag      120
catgacagtc taaagtggtg gaactgctga tggccactgt gtgatcactg aggtttcgca     180
```

```
ggaggtatgg tgcttcctga tctagtgaag aaagaaaggg agctgtgatt actcgtcaac    240
tttattcttg                                                          250
```

<210> SEQ ID NO 142
<211> LENGTH: 417
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 142

```
tgtgctttta aatttggaga tccgagagaa aacagccttt ttgttgcagt gctcacctct     60
gattgtaatt tctttcttct ggaggatttc ttcccctgtg tatacattcc tggctctgca    120
ggcataggtg cctgaatctt gcagggaaac attcatgatg gtaagattaa gagtgatgga    180
gtgctcctta gtgatggcca tttttttgctt gctaatactg tagtgcattg ttctgttatt    240
aactgtccgc agtaaaatcc aagtaacgtc tctgtataag aacttgttaa ctgtgcaaga    300
cagtttcagg tcctctcctt ccgtcggcat ttttttccaag ttaacatgaa acccatttgg    360
cacatctata aataagaat aaagaacttc agttcacaga aaaatcagtg tctttta        417
```

<210> SEQ ID NO 143
<211> LENGTH: 217
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 143

```
gaatgaagtc accaggctgt ctctggttat aggatgtgtg gcttacctgt gatataaaag     60
cttatgtttc ttcccacagt cccaacttta ttggaagcta tgcaaatgta gattccagaa    120
attctagagt cagccacaac caaggtgcta gccatctgca aaagaaaagg aaactttagc    180
tagcaacagg acaaataact aattgaacac cccaagc                             217
```

<210> SEQ ID NO 144
<211> LENGTH: 227
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 144

```
gaattgggag ctgagagtgt atttgtggaa taaatatccc agtgcgcatt tttacaaaca     60
ataccttatt ctttccttct attattgcca tgcgctgagt gatgctctca attctgtttc    120
ccatgttgct gtcagcatcc aggataaagg actcttcatt attggaacaa aagtcacacc    180
tattaaaaaa aaaagttgtc acaatgtggc tttacagcat ggttcag                  227
```

<210> SEQ ID NO 145
<211> LENGTH: 265
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 145

```
aaaatcttaa ttccaggtgt caaaaagtat ttgaaagtta gtaaaaaaac tgactgtccc      60
taccttgctt cggaatgatt atggttacag gggtgccaga accacttgat tgtaggttga     120
gggataccat atgcggtaca agtcaggatt tgtctgctgc ccagtgggta gagagccggg     180
tctggaaacg atgacacggc cttttcgtaa atctggggtt tcactggaaa ggagatgaag     240
aacgggacag aagtcaagag cagtt                                           265
```

<210> SEQ ID NO 146
<211> LENGTH: 266
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 146

```
ctaatttgtt gcctaccaga accagaagaa agtatgaaca gcaaacttac cattgacaat      60
tagagtggca gtgaggtttt taaacacatt tgactgtttt atgctcagca agattgtata    120
attccctgca tcctcttcag ttacgtcctt gataattaac gagtagccac gagtcaaata    180
gcgagcagat ttctcagtcg caggtaaccc atcttttaac ctgtggttaa aaacatgatc    240
agtaagtcat ttcacacggc ctctca                                          266
```

<210> SEQ ID NO 147
<211> LENGTH: 237
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 147

```
gcagcttccc acttacaaag tatgtcttaa actgttatgg aaataaggat ggtcctacca      60
tacaacttcc ggcgagggaa atgccttcac tttcatagag agccggtaag accgcttgcc    120
agctacggtt tcaagcacct gctgttttcg atgtttcaca gtgatgaatg ctttatcttt    180
gaaaggagaa gtgatacata cattagaaaa gaataatttc cataaacaaa accttag       237
```

<210> SEQ ID NO 148
<211> LENGTH: 277
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 148

```
caatgattag aaagcatagc atgagttggc aacgctgaac tatgcttacc atatatatgc      60
actgaggtgt taacagattt gaatgatggt ccactcctta cacgacaagt ataaagtcct    120
ttgtctttgt tctgcatttt gtcaatagta agaacactgt agaatatgtt ggcatgggaa    180
ttgctttggt caattcgtcg ccttacggaa gctctcttat ttttctagaa agaaaatgta    240
taacaaatgt agaaggagtg agtgttcatg cttaaag                             277
```

<210> SEQ ID NO 149
<211> LENGTH: 267
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 149

```
atttcacttg cttaaaatac tgtcctgcag aagaaataga aaaatgggtc actcacttca      60
tcagggtaac tccaggtcat ttgaactctc gtgttcaagg gagtggtagc agtacaattg     120
aggacaagag tatggcctct aagtaatttg actgggcgtg gtgtgcttat ttggacatct    180
atgattgtat tggctgcaag cataagagag aaattttta aaattaagat ttcattacac     240
agataaaaat acagagcact tcggctt                                         267
```

<210> SEQ ID NO 150
<211> LENGTH: 256
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 150

```
acagagcact tcggcttatg ttcatgcctt tgaagcatca cttactttgt cgatgtgtga      60
gatagtttgt cttatacaaa tgcccattga ctgttgcttc acaggtcaga agccctattt    120
ctttgtacgt tgcatttgat atgatgaagc cctttctact gtcccagatt atgcgttttc    180
catcagggat caaagtgtca agtggaaact gaaaggaag aggcatgcat taacaaggtc    240
ctattagcac tggttg                                                     256
```

<210> SEQ ID NO 151
<211> LENGTH: 229
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 151

```
cttatttgca gtgaaagtat gctgagaata gcggtgttca aatttacctt ttttaaagta     60
acagtgatgt taggtgacgt aacccggcag ggaatgacga gctcccttcc ttcagtcatg    120
tgtataattt cggggatttc actgtacatc tctacgaaag gtctacctgt atctgaatga    180
gaagaaaatg aaaaaaatat atacataaat gattgacatg caagcatct                229
```

<210> SEQ ID NO 152
<211> LENGTH: 323
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 152

```
atttgcaaag caaaagcaaa cagaatgtag aaaatggaag tcttaccact aataaatata     60
tagattgcag attctgtttc cttcttcttt gaagtaggta cagctagata tttgcagctg    120
tagaagccag tgtggttgc ttgagctgtg ttcaaggtta aagtactgca gaattgtttg    180
ccatttcttc cacaggcaga tttagttatg ctcagccttt cgctttcctt actcaccatt    240
tcaggcaaag accatttatg ggctgcttcc cccctgcaat cacagataag aaaacaaaac    300
atatttatgg ctgggcccta ggc                                            323
```

<210> SEQ ID NO 153
<211> LENGTH: 226

<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 153
cttaggcatg gcaactagat tattcccaaa ccaacacagc cacttacctg cattggagat     60
gcagtgtctg gcctgcttgc atgatgtgct gggtgccttt taaactcagt tcaggatctt    120
ttaattttga acctgaacta gatcctgaaa aacaaatttt taaaatgtat tatttgtaaa    180
ttgtcttctt acctttttt aagttatctt tccatgaagg tgagtt                    226

<210> SEQ ID NO 154
<211> LENGTH: 259
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 154
ggctacagcc tcgtctcccc gcgtgcaccc cgccctggcc tcggaggctc tgccctccgg     60 ccgcccatc gcagcccgcc tcaggccccg gccccagcc gcgcctcacc tgtgagaagc      120
agacagctga gcagcgcgca cagcaggacc ccggtgtccc agtagctgac catggtgagc    180
gcgacgcggc ctgctcgccc ggtgcccgcg ctccccgcgg ccaacgaccc ggccgccaga    240
gtccgtcctc tcgttcgcc                                                 259

<210> SEQ ID NO 155
<211> LENGTH: 195
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 155
ctccatccct ccaagctatc gtccagcgca gtccaccgcc gcctcaggcc gtgccgctgg     60
ccgagtagga gaactgggg aagtggggcc tgcgctcgct gtccacacac tccatgctgt    120
catctgtggg tgtagacagc tcagaccccg gtgccccacc tccctgccac ctccacccac    180
ccacagctcc agtag                                                     195

<210> SEQ ID NO 156
<211> LENGTH: 201
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 156
tgagtgtgga gagaaaaggg agtgggcggg ggcaggcagt ggcccctcac cttggtcagg     60
tggtgtgatg gtgatcatct gggccgtgaa ctcctcatca aaatacctgg tgtcagtctc    120
cgacgtgacc tggggcttga agggtgggct gagctgcaga ggtgggcaga cgggacagtc    180
atgagcttcg ctccccactc c                                              201

<210> SEQ ID NO 157
<211> LENGTH: 234
<212> TYPE: DNA

<213> ORGANISM: Artificial Sequence
<220> FEATURE:
<223> OTHER INFORMATION: Description of Artificial Sequence: Synthetic
nucleotide construct

<400> SEQUENCE: 157

```
atgcgtgagt gtggatatgt ggggagcatg cgtgcgcgtg aatatgcggg gagcagccgc      60
accttcttct cgtacacgtg ctgccacacg ataccggcaa agaagcgatg ctgcatgatc     120
tccttggcgt cctcggagcc cccgccaagc ctgcaggcag gaaacaaggc cacagtgtcg     180
gtaccgccac ctgcccaggc cctgggttca ggcccttcc tcctgtgatg tagg            234
```

<210> SEQ ID NO 158
<211> LENGTH: 262
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 158

```
ccgtctggtg ccatggagag tagccgaggc tccgggaagg accggcccca ccatgggcgg      60
cccacaggcc gcgaagtcca tcccccgcag ccccagcccc tacctcgccc ccgttggcgt     120
actccatgac aaagcagagg cggtcgtggg tctggaaaga gtacttcagg gcctgcaagg     180
aagggggagct ggaactgcgg ccccacaggc aggacggcag ccccgcacca cgctgcccga   240
caccacgctg cttgatacca cg                                              262
```

<210> SEQ ID NO 159
<211> LENGTH: 252
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 159

```
ccctccacag tccaaggcag ccccaggcac aggcagaagt ggggacaggc ctcaccacgc      60
ggtgcttggg cttggccagg gacacctcca tctcttcagc ccctgagttg tcactgggtg     120
agcccgaccg gaagtccatc tcctcctcct cctgcttctt gaggccgtca gccacagtct     180
ggatggcggt tgtccactcc tccctgcagg aggtcaggtg aggctgcagg cctgtaccag     240
atcaggagct cc                                                         252
```

<210> SEQ ID NO 160
<211> LENGTH: 289
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 160

```
ccatccccgt gtccctccta agcgctgggg ctgcccaagt gcctggcctg ccgccacag      60
cccacgtacc gctcctcagg agtctccaca tggaaggtgc gttcgatgac agtggtccac    120
tgcaggcagc ggatgatgaa ggtgttgggc cggggccgct ccgtcttcat cagctggcac    180
tctgcgggca ggcagagcct ctgtctgcgt gcatccccct gccctccca gggccctcac    240
cacagccccc gctgcaccag ccagctcccc ttgcatacca cccaccagg                 289
```

<210> SEQ ID NO 161
<211> LENGTH: 212
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 161

```
cccccccaaat ctgaatcccg agaggccaag gggatactta cgcgccacag agaagttgtt      60
gaggggagcc tcacgttggt ccacatcctg cggccgctcc ttgtagccaa tgaaggtgcc     120
atcattcttg aggaggaagt agcgtggccg ccaggtcttg atgtactccc ctacagacgt     180
gcgggtggtg agagccacgc acactctacc cg                                   212
```

<210> SEQ ID NO 162
<211> LENGTH: 235
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 162

```
ggaggaagcg agaggtgctg ccctccccccc ggagttggaa gcgcgttacc cgggtccaaa     60
atgcccaaga gaagccgac gcccatccag ctgaacccgg ccccgacgg ctctgcagtt      120 aacgggacca gctctgcgga gtaagtatgg ggcgggcggt gaacctcggg gcccggctgg    180
ggaggcccga gccggggagc aggagcgcgc gccaggctcc gatctggttt gtcac         235
```

<210> SEQ ID NO 163
<211> LENGTH: 314
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 163

```
ctttgggttg acttctctgg tgacagtatt gacttgtgct ccccactttg aacaggacc      60 aacttggagg ccttgcagaa gaagctggag gagctagagc ttgatgagca gcagcgaaag    120
cgccttgagg cctttcttac ccagaagcag aaggtgggag aactgaagga tgacgacttt    180
gagaagatca gtgagctggg ggctggcaat ggcggtgtgg tgttcaaggt ctcccacaag    240
ccttctggcc tggtcatggc cagaaaggtg agtttgcctt gattaacagg taattggatt    300
atttctcagg gtac                                                       314
```

<210> SEQ ID NO 164
<211> LENGTH: 248
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 164

```
ctttcatccc ttcctccctc tttctttcat aaaacctctc tttcttccac ctttctccag     60
ctaattcatc tggagatcaa acccgcaatc cggaaccaga tcataaggga gctgcaggtt    120
ctgcatgagt gcaactctcc gtacatcgtg ggcttctatg gtgcgttcta cagcgatggc    180
gagatcagta tctgcatgga gcacatggta tgtgacaccc tctcagcctc tggagcaatg    240
```

```
gccttaag                                                                       248

<210> SEQ ID NO 165
<211> LENGTH: 186
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 165
tcacttgaaa gaatagttag aacattgtca ctaactggtc tggtattctc gatcttagga             60
tggaggttct ctggatcaag tcctgaagaa agctggaaga attcctgaac aaattttagg            120
aaaagttagc attgctgtga gtatgttatg aagtttttct tctaagttcc tcattgataa            180
gttaat                                                                       186

<210> SEQ ID NO 166
<211> LENGTH: 158
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 166
gtatttttct tatcaccagt attttctttt cttttacatt cccttcctc taggtaataa              60 aaggcctgac atatctgagg gagaagcaca agatcatgca cagaggtaag aagttatttg            120
ctagttattt tgctttgaat tttagatata atccaaag                                    158

<210> SEQ ID NO 167
<211> LENGTH: 213
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 167
ctacctgtgt cagttccctc cttttctatt ttctcttccc tgcagatgtc aagccctcca             60
acatcctagt caactcccgt ggggagatca agctctgtga ctttgggtc agcgggcagc             120 tcatcgactc catggccaac tccttcgtgg gcacaaggtc ctacatgtcg gtatgaacag            180
aagtttccat tgcttgagct tcttgtacgg tca                                         213

<210> SEQ ID NO 168
<211> LENGTH: 294
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 168 ccagggtcc aagttaggtt aggtgattat cactgtctgt ctctcctgca gccagaaaga              60
ctccagggga ctcattactc tgtgcagtca gacatctgga gcatgggact gtctctggta            120
gagatggcgg ttgggaggta tcccatccct cctccagatg ccaaggagct ggagctgatg            180
tttgggtgcc aggtggaagg agatgcggct gagaccccac ccaggccaag gaccccgggg            240
aggcccctta gctgtgagta gcctggtgtg tccccatctt ggactgttgg aggg                  294
```

```
<210> SEQ ID NO 169
<211> LENGTH: 176
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 169
cttgcctcat attaacaagt aatctgtttc tgagaagtat ttttctttt tataaatttt      60 gtagcatacg gaatggacag ccgacctccc atggcaattt ttgagttgtt ggattacata    120
gtcaacgagg taagtactgc ctggtttcct tcaccttgga atttacttgc tcatct        176

<210> SEQ ID NO 170
<211> LENGTH: 164
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 170
gagcaaggag ccaggcattt ttcttatctc aacatgtgtt tgcagcctcc tccaaaactg     60
cccagtggag tgttcagtct ggaatttcaa gattttgtga ataaatggta agttggctcc   120
ttgttctctg gaagcgtata ctctggattt gtcaggctcc ccac                    164

<210> SEQ ID NO 171
<211> LENGTH: 165
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 171
ccagtgccag gcaacagctc ttaccttgtc tttcttcctt taagcttaat aaaaaacccc     60
gcagagagag cagatttgaa gcaactcatg gtgagtctat ttattccgga ttcttacagt   120
acctgtttat tcatttgttc ttctctgtca gtcatctgtg cagta                   165

<210> SEQ ID NO 172
<211> LENGTH: 224
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 172 ttttttgtt tcttttaac accacgtcct ctcgtttcct tacatgcagg ttcatgcttt       60
tatcaagaga tctgatgctg aggaagtgga ttttgcaggt tggctctgct ccaccatcgg   120
ccttaaccag cccagcacac caacccatgc tgctggcgtc taagtgtttg ggaagcaaca   180
aagagcgagt cccctgcccg gtggtttgcc atgtcgcttt tggg                   224

<210> SEQ ID NO 173
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 173
```

```
gacttgtttc ctttcatttc cttttttttct ttttcttttct tttttttttt tttttttttt      60
tttgagaaag gggaatttca tcccaaataa aaggaatgaa gtctggctcc ggaggagggt     120
ccccgacctc gctgtggggg ctcctgtttc tctccgccgc gctctcgctc tggccgacga     180
gtggagaaag tgagtatgtg cccgccgccc gcggccactg cgggaacttt tcctcc        236

<210> SEQ ID NO 174
<211> LENGTH: 357
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 174
taaaaattat ttccttctaa ctgagacgtt taccctcttg tctcccttca gtctgcgggc      60
caggcatcga catccgcaac gactatcagc agctgaagcg cctggagaac tgcacggtga    120
tcgagggcta cctccacatc ctgctcatct ccaaggccga ggactaccgc agctaccgct    180
tccccaagct cacggtcatt accgagtact tgctgctgtt ccgagtggct ggcctcgaga    240
gcctcggaga cctcttcccc aacctcacgg tcatccgcgg ctggaaactc ttctacaact    300
acgccctggt catcttcgag atgaccaatc tcaaggatat tgggctttac aacctga       357

<210> SEQ ID NO 175
<211> LENGTH: 352
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 175
cttctacaac tacgccctgg tcatcttcga gatgaccaat ctcaaggata ttgggcttta      60
caacctgagg aacattactc gggggggccat caggattgag aaaaatgctg acctctgtta    120
cctctccact gtggactggt ccctgatcct ggatgcggtg tccaataact acattgtggg    180
gaataagccc ccaaaggaat gtggggacct gtgtccaggg accatggagg agaagccgat    240
gtgtgagaag accaccatca acaatgagta caactaccgc tgctggacca caaaccgctg    300
ccagaaaagt aagaatgatg ctgactgctg ctttctctct gcctctctct ct            352

<210> SEQ ID NO 176
<211> LENGTH: 245
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 176
cttacaccaa gtgagcacac agtgacacaa tcccctttca atgtagataa cattgcttca      60
gagctggaga acttcatggg gctcatcgag gtggtgacgg gctacgtgaa gatccgccat    120
tctcatgcct tggtctcctt gtccttccta aaaaaccttc gcctcatcct aggagaggag    180
cagctagaag ggtaagtgcc ccaaatttca tgagctgacg ttctattaca aaataagcag    240
cgtgc                                                                 245

<210> SEQ ID NO 177
<211> LENGTH: 215
```

```
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 177
agagacacat gaatctctgt cactcacgga tgtactcttt gccccaggtg aaagtgacgt    60
cctgcatttc acctccacca ccacgtcgaa gaatcgcatc atcataacct ggcaccggta   120
ccggccccct gactacaggg atctcatcag cttcaccgtt tactacaagg aagcgtgagt   180
ttctgctttg ggtgatgcca ttctgttgac agggc                              215

<210> SEQ ID NO 178
<211> LENGTH: 324
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 178
gatgtcagag ccccgaactt tctctgaact taattgtctt tcagacccct taagaatgtc    60
acagagtatg atgggcagga tgcctgcggc tccaacagct ggaacatggt ggacgtggac   120
ctcccgccca acaaggacgt ggagcccggc atcttactac atgggctgaa gccctggact   180
cagtacgccg tttacgtcaa ggctgtgacc ctcaccatgg tggagaacga ccatatccgt   240
ggggccaaga gtgagatctt gtacattcgc accaatgctt caggtatcca tgcctagaca   300
agcccccagc atccacactt cttc                                          324

<210> SEQ ID NO 179
<211> LENGTH: 294
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 179
aacggctttc attcccactc ttgttttggc ttttcttttc cgagaagaca aaatccccat    60
caggaagtat gccgacggca ccatcgacat tgaggaggtc acagagaacc ccaagactga   120
ggtgtgtggt ggggagaaag ggccttgctg cgcctgcccc aaaactgaag ccgagaagca   180
ggccgagaag gaggaggctg aataccgcaa agtctttgag aatttcctgc acaactccat   240
cttcgtgccc aggtacccag ctcatgtgaa atttcagttg gcaaaaccca ctgc         294

<210> SEQ ID NO 180
<211> LENGTH: 259
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 180
agacaaaaga ggtaaaagta cttaaaagcc acatttctct cctccttgca gacctgaaag    60
gaagcggaga gatgtcatgc aagtggccaa caccaccatg tccagccgaa gcaggaacac   120
cacggccgca gacacctaca acatcaccga cccggaagag ctggacacag agtacccttt   180
ctttgagagc agagtggata acaaggagag aactgtcatt tctaaccttc ggcctttcac   240
```

```
attgtaccgc atcgatatc                                              259

<210> SEQ ID NO 181
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 181
gcatcgatat ccacagctgc aaccacgagg ctgagaagct gggctgcagc gcctccaact    60
tcgtctttgc aaggactatg cccgcaggta tggtatgatc cagctggccc cattgccacc   120
ttcctcacaa cctagtggag aagatgtgtt ttatggacac agggtc                  166

<210> SEQ ID NO 182
<211> LENGTH: 223
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 182
cctgggaacc caaatccaac tttgtcacct gtttaaattg tacagaagga gcagatgaca    60
ttcctgggcc agtgacctgg gagccaaggc ctgaaaactc catcttttta aagtggccgg   120
aacctgagaa tcccaatgga ttgattctaa tgtatgaaat aaaatacgga tcacaagttg   180
aggtaggact ggggcagtgg cccgtgcctg catgtacttc cat                     223

<210> SEQ ID NO 183
<211> LENGTH: 255
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 183
cctgcattca tgggaaattg acatgtatgt tttatttccc caggatcagc gagaatgtgt    60
gtccagacag gaatacagga agtatggagg ggccaagcta aaccggctaa acccggggaa   120
ctacacagcc cggattcagg ccacatctct ctctgggaat gggtcgtgga cagatcctgt   180
gttcttctat gtccaggcca aaagtaaggc ttgtggaggg agaagaaacg tggtaaaact   240
gaaagcaggg tggtc                                                    255

<210> SEQ ID NO 184
<211> LENGTH: 217
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 184
gtgaagaaat gaaatgagca aattgttcac ctggtgatat tttatcattt cctcctcttt    60
gctgcagcag gatatgaaaa cttcatccat ctgatcatcg ctctgcccgt cgctgtcctg   120
ttgatcgtgg gagggttggt gattatgctg tacgtcttcc atagaaagag gtcagtgatg   180
tgcaaagtta tgacactttc tgtggctgag tggtttg                            217
```

```
<210> SEQ ID NO 185
<211> LENGTH: 172
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 185
gaatgtatgg aggtggggtt ttgttaacgt gaatttaatc ttttgacag aaataacagc      60 aggctgggga atggagtgct gtatgcctct gtgaacccgg agtacttcag cgctgctgat    120
ggtaagagtc cgggccacca gcactgccag cgtgcagggc aggtagatcg gg            172

<210> SEQ ID NO 186
<211> LENGTH: 316
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 186
ctaagggctt gtttctgtac ctgctttaat tacggtttct tctccagtgt acgttcctga     60
tgagtgggag gtggctcggg agaagatcac catgagccgg gaacttgggc aggggtcgtt   120
tgggatggtc tatgaaggag ttgccaaggg tgtggtgaaa gatgaacctg aaaccagagt   180
ggccattaaa acagtgaacg aggccgcaag catgcgtgag aggattgagt ttctcaacga   240
agcttctgtg atgaaggagt tcaattgtca ccatgtggta agagaaagtt cctgaaaagc   300
caaaatgcag cacagg                                                   316

<210> SEQ ID NO 187
<211> LENGTH: 200
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 187
aagggccacc tgaccctctg agtctttctc tttttgattc ctcccaggtg cgattgctgg     60
gtgtggtgtc ccaaggccag ccaacactgg tcatcatgga actgatgaca cggggcgatc   120
tcaaaagtta tctccggtct ctgaggccag aaatggaggt cagttttcat ttccaccggt   180
attgcatgtt gcctggcctg                                               200

<210> SEQ ID NO 188
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 188
ctcgaaagaa attggcatgg aaaaaaaaaa tccaaaattc tcatgtgaat ttttttaaat     60
ctccaacaga ataatccagt cctagcacct ccaagcctga gcaagatgat tcagatggcc   120
ggagagattg cagacggcat ggcataccte aacgccaata agttcgtcca cagagacctt   180
gctgcccgga attgcatggt agccgaagat ttcacagtca aaatcggagg tgtgtcctta   240
gctttccagg tctgggcaag aactaaactc aggtgt                             276
```

<210> SEQ ID NO 189
<211> LENGTH: 226
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 189
ttcagtccat ccctttccaa gctcctcaca gttttttct ccctgtaggt ccttcggggt    60
cgtcctctgg gagatcgcca cactggccga gcagccctac cagggcttgt ccaacgagca   120
agtccttcgc ttcgtcatgg agggcggcct tctggacaag ccagacaact gtcctgacat   180
gctgtacgta cttcctgggc cctccgtgct cttctgagtt ctcttc                  226

<210> SEQ ID NO 190
<211> LENGTH: 326
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 190
tacgcttgta tgcgggaaac cactgcaggc ggcccatgaa gcctcctggc catgtgcgcc    60
ctcccggttt ggacccctc ccgtgtgtct tggctgcagg tttgaactga tgcgcatgtg    120
ctggcagtat aaccccaaga tgaggccttc cttcctggag atcatcagca gcatcaaaga   180
ggagatggag cctggcttcc gggaggtctc cttctactac agcgaggaga acaagctgcc   240
cgagccggag gagctggacc tggagccaga gaacatggag agcgtccccc tggacccctc   300
ggcctcctcg tcctccctgc cactgc                                        326

<210> SEQ ID NO 191
<211> LENGTH: 272
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 191
ctggacctgg agccagagaa catggagagc gtccccctgg acccctcggc ctcctcgtcc    60
tccctgccac tgcccgacag acactcagga cacaaggccg agaacggccc cggccctggg   120
gtgctggtcc tccgcgccag cttcgacgag agacagcctt acgcccacat gaacgggggc   180
cgcaagaacg agcgggcctt gccgctgccc cagtcttcga cctgctgatc cttggatcct   240
gaatctgtgc aaacagtaac gtgtgcgcac gc                                 272

<210> SEQ ID NO 192
<211> LENGTH: 320
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 192
tgtgaagctg agattcccct ccattgggac cggagaaacc aggggagccc cccgggcagc    60
cgcgcgcccc ttcccacggg gcccttact gcgccgcgcg cccggccccc acccctcgca   120
gcaccccgcg ccccgcgccc tcccagccgg gtccagccgg agccatgggg ccggagccgc   180

```
agtgagcacc atggagctgg cggccttgtg ccgctggggg ctcctcctcg ccctcttgcc    240 cccggagcc gcgagcaccc aaggtgggtc tggtgtgggg aggggacgga gcagcggcgg     300
gaccctgccc tgtggatgcc                                                320
```

<210> SEQ ID NO 193
<211> LENGTH: 280
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 193

```
ggccaggtct gagaaggtcc cccgccagtg tcctctgacc catctgctct ctcctgccag    60
tgtgcaccgg cacagacatg aagctgcggc tccctgccag tcccgagacc cacctggaca    120
tgctccgcca cctctaccag ggctgccagg tggtgcaggg aaacctggaa ctcacctacc    180
tgcccaccaa tgccagcctg tccttcctgc aggtgaggcc cgtgggcaac ccagccaggc    240
cctgcctcca gctgggctga gccctctgtt tacaggtggg                         280
```

<210> SEQ ID NO 194
<211> LENGTH: 306
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 194

```
gtggcagtgt tcctatttca gccccactct gcttccccct cccaggatat ccaggaggtg    60
cagggctacg tgctcatcgc tcacaaccaa gtgaggcagg tcccactgca gaggctgcgg    120
attgtgcgag gcacccagct ctttgaggac aactatgccc tggccgtgct agacaatgga    180
gacccgctga caataccac ccctgtcaca ggggcctccc caggaggcct gcgggagctg    240
cagcttcgaa gcctcacagg tggccttcac cgtcattgaa accttctctt ggttattcag    300
agctga                                                               306
```

<210> SEQ ID NO 195
<211> LENGTH: 222
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 195

```
gtgacagaag gggaaagggt cctctgatca ttgctcaccc cacagagatc ttgaaaggag    60
gggtcttgat ccagcggaac ccccagctct gctaccagga cacgattttg tggaaggaca    120
tcttccacaa gaacaaccag ctggctctca cactgataga caccaaccgc tctcgggcct    180
gtaagccatg cccctccctg ctgcctcttc tctcagacag cc                       222
```

<210> SEQ ID NO 196
<211> LENGTH: 230
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 196

```
tagaaggtga tgctgatgag ggtctggtgc ccagggcgcc actcagccct catcctgccc      60
tttgcccaac agtgacgcgc actgtctgtg ccggtggctg tgcccgctgc aaggggccac     120
tgcccactga ctgctgccat gagcagtgtg ctgccggctg cacgggcccc aagcactctg     180
actgcctggt atgtgcctct gctttgtgcc caatgtgctc tacccccag                 230
```

<210> SEQ ID NO 197
<211> LENGTH: 234
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 197

```
caccagggca aaacagcaca gtgaaagcca gccacctgtc cccccaggcc tgcctccact      60
tcaaccacag tggcatctgt gagctgcact gcccagccct ggtcacctac aacacagaca    120
cgtttgagtc catgcccaat cccgagggcc ggtatacatt cggcgccagc tgtgtgactg    180
cctgtccctg tgagtgccag ggagaaacac agttttctca ttttggtggg gagg          234
```

<210> SEQ ID NO 198
<211> LENGTH: 237
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 198

```
ggtaatgctg ctcatggtgg tgcacgaagg gccagggtat gtggctacat gttcctgatc      60
tccttagaca actacctttc tacggacgtg ggatcctgca ccctcgtctg ccccctgcac    120
aaccaagagg tgcacagaga ggatggaaca cagcggtgtg agaagtgcag caagccctgt    180
gcccgaggta cccactcact gcccccgagg ccagctgcag ttcctgtccc tctgcgc        237
```

<210> SEQ ID NO 199
<211> LENGTH: 313
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 199

```
gaatagcctt tgctgaccgg gaaggggtcc gtggtaaggt gcccacccttt ctcccatagt      60 ggcgcctact cgctgaccct gcaagggctg gcatcagct ggctggggct gcgctcactg      120
agggaactgg gcagtggact ggccctcatc caccataaca cccacctctg cttcgtgcac     180
acggtgccct gggaccagct ctttcggaac ccgcaccaag ctctgctcca cactgccaac     240
cggccagagg acgagtgtgg taagacaggg agcccagtgt gcgcactccc catctgccag     300
cacacagcag tgc                                                        313
```

<210> SEQ ID NO 200
<211> LENGTH: 445
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 200

```
ggcctcccct aaaagtcccc tgcggtccct tcctcctcac tgcagtgggc gagggcctgg    60
cctgccacca gctgtgcgcc cgagggcact gctggggtcc agggcccacc cagtgtgtca   120
actgcagcca gttccttcgg ggccaggagt gcgtggagga atgccgagta ctgcaggggt   180
atgaggggcg gaggagaggg tggctggagg ggtgcatggg gctcctctca gaccccctca   240
ccactgtccc ttctctcagg ctccccaggg agtatgtgaa tgccaggcac tgtttgccgt   300
gccaccctga gtgtcagccc cagaatggct cagtgacctg ttttggaccg gtgagctgct   360
ggcgggctca gagctgggtg gagggggggca gcgagggggga ttgccaggga cttggcagga   420
tggcgagatg cagtagggtg tgcta                                         445
```

<210> SEQ ID NO 201
<211> LENGTH: 277
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 201

```
ctaagggcct gatcctactg ccctgggggt gtcagtgcca gccccccaca aatcttttct    60
gccccccca ggaggctgac cagtgtgtgg cctgtgccca ctataaggac cctcccttct   120
gcgtggcccg ctgccccagc ggtgtgaaac ctgacctctc ctacatgccc atctggaagt   180
ttccagatga ggagggcgca tgccagcctt gccccatcaa ctgcacccac tcgtgagtcc   240
aacggtcttt tctgcagaaa ggaggacttt cctttca                            277
```

<210> SEQ ID NO 202
<211> LENGTH: 164
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 202

```
ttgttgtgag gctggaaagg tggttcccaa gagggtggtt cccagaattg ttgatgagac    60
tgtttctcct gcagctgtgt ggacctggat gacaagggct gccccgccga gcagagagcc   120
aggttggcct ggaccccagg atgtaccctt cattgccctt cact                    164
```

<210> SEQ ID NO 203
<211> LENGTH: 295
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 203

```
cacccccaaac tagccctcaa tccctgaccc tggcttccgc ccccagccct ctgacgtcca    60
tcatctctgc ggtggttggc attctgctgg tcgtggtctt gggggtggtc tttgggatcc   120
tcatcaagcg acggcagcag aagatccgga agtacacgat gcggagactg ctgcaggaaa   180
cggaggtgag gcggggtgaa gtcctcccag cccgcgtggg gtctgcaccg gcccccggca   240
ctgacccacc ccccctcac cccagctggt ggagccgctg acacctagcg gagcg         295
```

```
<210> SEQ ID NO 204
<211> LENGTH: 299
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 204
gctgcaggaa acggaggtga ggcggggtga agtcctccca gcccgcgtgg ggtctgcacc      60
ggcccccggc actgacccac cacccccctca ccccagctgg tggagccgct gacacctagc    120
ggagcgatgc ccaaccaggc gcagatgcgg atcctgaaag agacggagct gaggaaggtg    180
aaggtgcttg gatctggcgc ttttggcaca gtctacaagg tcagggccag gtcctggggt    240
gggcggcccc agaggatggg ggcggtgcct ggaggggtgt ggtcggcagt tctgatggg     299

<210> SEQ ID NO 205
<211> LENGTH: 192
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 205
ccagcccacg ctcttctcac tcatatcctc ctctttctgc ccagggcatc tggatccctg      60
atggggagaa tgtgaaaatt ccagtggcca tcaaagtgtt gagggaaaac acatccccca    120
aagccaacaa agaaatctta gacgtaagcc cctccaccct ctcctgctag gaggacagga    180
aggaccccat gg                                                          192

<210> SEQ ID NO 206
<211> LENGTH: 242
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 206
cccaggccct cccagaaggt ctacatgggt gcttcccatt ccaggggatg agctacctgg      60
aggatgtgcg gctcgtacac agggacttgg ccgctcggaa cgtgctggtc aagagtccca    120
accatgtcaa aattacagac ttcgggctgg ctcggctgct ggacattgac gagacagagt    180
accatgcaga tgggggcaag gttaggtgaa ggaccaagga gcagaggagg ctgggtggag    240
tg                                                                     242

<210> SEQ ID NO 207
<211> LENGTH: 191
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 207
ccacctcccc acaacacaca gttggaggac ttcctcttct gccctcccag gtgcccatca      60
agtggatggc gctggagtcc attctccgcc ggcggttcac ccaccagagt gatgtgtgga    120
gttatggtgt gtgatggggg gtgttgggag gggtgggtga ggagccatgg ctggagggag    180
gatgagagct g                                                          191
```

<210> SEQ ID NO 208
<211> LENGTH: 252
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 208
cagtacacta aagctccctc tggccctccc actcctgacc ctgtctctgc cttaggtgtg      60
actgtgtggg agctgatgac ttttggggcc aaaccttacg atgggatccc agcccgggag     120
atccctgacc tgctggaaaa gggggagcgg ctgccccagc cccccatctg caccattgat     180
gtctacatga tcatggtcaa atgtgcgtgg ctgagctgtg ctggctgcct ggaggagggt     240
gggaggtcct gg                                                        252

<210> SEQ ID NO 209
<211> LENGTH: 185
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 209
cacagggcct gggactagca tgctgacctc cctcctgccc caggttggat gattgactct      60
gaatgtcggc caagattccg ggagttggtg tctgaattct cccgcatggc cagggacccc     120
cagcgctttg tggtcatcca ggtactgggc ctctgtgccc catccctgcc tgtggctaag     180
agcac                                                                185

<210> SEQ ID NO 210
<211> LENGTH: 298
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 210
cccctcacgg aaggctgcat gctgggctgg ggaggggcca ccatcctgcc tctccttcct      60
ccacagaatg aggacttggg cccagccagt cccttggaca gcaccttcta ccgctcactg     120
ctggaggacg atgacatggg ggacctggtg gatgctgagg agtatctggt accccagcag     180
ggcttcttct gtccagaccc tgcccggggc gctggggca tggtccacca caggcaccgc     240
agctcatcta ccagggtcag tgccctcggt cacactgtgt ggctgtctgc ttacctcc      298

<210> SEQ ID NO 211
<211> LENGTH: 342
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 211
cccagatccg tgagtgaccc ccatcatgac tttctttctt gtcccagag tggcggtggg       60 gacctgacac tagggctgga gccctctgaa gaggaggccc ccaggtctcc actggcaccc     120
tccgaagggg ctggctccga tgtatttgat ggtgacctgg aatgggggc agccaagggg     180 ctgcaaagcc tccccacaca tgaccccagc cctctacagc ggtacagtga ggaccccaca     240

```
gtacccctgc cctctgagac tgatggctac gttgccccc  tgacctgcag ccccagcct       300 ggtatggagt ccagtctaag cagagagact gatgggcagg gg                         342

<210> SEQ ID NO 212
<211> LENGTH: 296
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 212
agagacaccg gggttccttc ccctaatggg tcaccttctc ttgacctttc agaatatgtg       60
aaccagccag atgttcggcc ccagccccct tcgccccgag agggccctct gcctgctgcc     120
cgacctgctg gtgccactct ggaaaggccc aagactctct ccccagggaa gaatgggtc      180 gtcaaagacg tttttgcctt tgggggtgcc gtggagaacc ccgagtactt gacaccccag     240
ggaggagctg cccctcagcc ccaccctcct cctgccttca gccagccttc gacaa           296

<210> SEQ ID NO 213
<211> LENGTH: 399
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 213 gacgttttg cctttggggg tgccgtggag aaccccgagt acttgacacc ccagggagga       60
gctgcccctc agccccaccc tcctcctgcc ttcagcccag ccttcgacaa cctctattac     120
tgggaccagg acccaccaga gcgggggct ccacccagca ccttcaaagg acacctacg      180 gcagagaacc cagagtacct gggtctggac gtgccagtgt gaaccagaag gccaagtccg     240
cagaagccct gatgtgtcct cagggagcag ggaaggcctg acttctgctg gcatcaagag     300
gtgggagggc cctccgacca cttccagggg aacctgccat gccaggaacc tgtcctaagg     360
aaccttcctt cctgcttgag ttcccagatg gctggaagg                            399

<210> SEQ ID NO 214
<211> LENGTH: 174
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 214
ccagcagcct tatttcctgg ggcctgggtg gcagcctgca ccctcccggt cccagaaccc       60
gctggcatca ctcactgtga gcatcttcag gtccgcccgc tccgctgggt tcttgatgag     120
gctgggggtt ccaagaggca ggaccgggag gcggtggagg agacaagaca gggc             174

<210> SEQ ID NO 215
<211> LENGTH: 176
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 215
```

```
ggaaggagtg gcacatctgg gtcccggcca ggggtgtggg cagcccggct ccacctacca    60
tttattgaca aactcctgga agtcgggggt gaacacaccg ttgggcagct taggaggtgg   120
ctgtggagga gaacagaggg tggggtcagc cctgggcatc gtcagggacc ctcggc       176
```

<210> SEQ ID NO 216
<211> LENGTH: 177
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 216

```
aagaagaaag aaaaggaaaa gaaaagccaa aaggcatcaa gcacaaacct cgttcacaat    60
atagtccagg agttcaaaga tggccatggc aggccggcta tccatcccgt gacctgcaca   120
gggagagaga tggaggtgag atgggccgat ggccacctca cttctgctgg gggttgg      177
```

<210> SEQ ID NO 217
<211> LENGTH: 403
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 217

```
ggaggcagct gctgaccctg gcacagcagg ccccgcgcag ggcactgcgc gtccagaccg    60
gaagttgcag attcaggccg taccgctgac ggggcgcccg gggggcctcg gccgaggcga   120
gatgctgtga ggctctcctt cttccccgtc gaccacgggc cggccaaaga tggcctccag   180
ctctttggcg tcgggcgggg ggatggggta ccttccgacg gccagctcca ccagggacag   240
gcccatgctc cagatgtccg actgcaccga gtaatgtgtg ccctgcaacc gctccggctg   300
cagcagagcc agggaggaaa gagcccagag gggcgaggat ggcagctgga acccgggagg   360
cttgccccgt tacagccccc gtcaccctct ccatggctaa tga                     403
```

<210> SEQ ID NO 218
<211> LENGTH: 442
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 218

```
ggagacatgg gggtgagagc tgaggggag agctggctgg cagagctggg tggggagagc    60
ttgggggaga gcagcaggga ggagagctgg aggggagagc cagcggggac tcacagccat   120
gtaggagcgc gtgcccacga aggagttggc catggagtcg atgagctggc cgctcacccc   180
gaagtcacac agcttgatct cccctctaga gttcacgagg atgttggagg cttcacatc    240 tggaggcggc aggctgcggg tgaggggcgc ccaacagttg cctgccggcc cccggggctc   300
tggggagggc gggctggcc ttacctcggt gcatgatctg gtgcttctct cggaggtacg    360
ccaagccccg gagaacctgc aggggagcgc ggagggagtc acgggacaag gccaccaggg   420
cttagctcct gaccgagccc gg                                            442
```

<210> SEQ ID NO 219
<211> LENGTH: 304
<212> TYPE: DNA

<213> ORGANISM: Artificial Sequence
<220> FEATURE:
<223> OTHER INFORMATION: Description of Artificial Sequence: Synthetic
nucleotide construct

<400> SEQUENCE: 219

| gtggaagagg tccgtgcaga gtgcggtggg ggcgcgatgt gggtctgcgg tggactcacc | 60 |
| gcgatgctga ctttccccag gatctcctcg ggaatcctct tggcctcttt cagcacctgg | 120 |
| tccagggagc cgccgtccta gagggcacac aaggagtgag tgcaggctct cgcaggtgg | 180 |
| ccgggaagcc acggatgcgt ccccccactc ccggcgaggg ggtggtctgc ctcctgacgg | 240 |
| gaagcagggg ccggagccca actccaccca cgggccaagg gcagggcgtc ttctgacagt | 300 |
| tctg | 304 |

<210> SEQ ID NO 220
<211> LENGTH: 266
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 220

| ccaacatgct ctgttccgtg gaggccctgc ccctgcccct gccccggacg cactcaccat | 60 |
| gtgttccatg caaatgctga tctccccgtc actgtagaag gccccgtaga agcccacgat | 120 |
| gtacggcgag ttgcattcgt gcaggacctg cagctcgcgg atgatctggt tccggatggc | 180 |
| cggcttgatc tcaaggtgga tcagctgcaa ggggagaggg gcgagactgg cttgggggt | 240 |
| gcccgaaaac gggatgaagg catttg | 266 |

<210> SEQ ID NO 221
<211> LENGTH: 243
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 221

| ctcgtgcact cctcgcgaac ccccgtcccc tcgccccgtc cttccccgag ggctccctgc | 60 |
| cccgtgcacc ccaagcctcc ggctgacccc tgcccactca ctcggaggcg ccctcgctgg | 120 |
| taggggatgg gccctcggcg atggtagggt tgatggtgag cgccggcagc accggcttcc | 180 |
| tccgggccag catcggggct ccgcgggccg gcggcggcgg cgcctctagc cggggcccat | 240 |
| agg | 243 |

<210> SEQ ID NO 222
<211> LENGTH: 237
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 222

| gttattccca aatgaatgaa tgaatgagtg agtgaatgga tgcattcctc tcattttaca | 60 |
| gatgagtaac ccgaagcccc tagaggagtg gtcacctgcc tgagggcact tctgtcccac | 120 |
| cagcatcaga ccaggtgtgt gcaggtgtgt gcgactccag ggcccaggcc cggggcagct | 180 |
| ggggtggggc cttaggggg agcaggacct gggcccctcc tcccacaggc actgtgg | 237 |

<210> SEQ ID NO 223
<211> LENGTH: 353
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 223
agagacatgg gcaggctctc actcacccac cgtgattccc tcccgcaggc cgcaccgagt      60
ccccggcacc atgtttggga agaggaagaa gcgggtggag atctccgcgc cgtccaactt     120
cgagcaccgc gtgcacacgg gcttcgacca gcacgagcag aagttcacgg ggctgccccg     180
ccagtggcag agcctgatcg aggagtcggc tcgccggccc aagcccctcg tcgacccgc      240 ctgcatcacc tccatccagc ccggggcccc caaggtatgt ggcacccacc accacctccc     300
ccagcccacc caacccccg agtggccctg ccctcaacc ccacactcga ccc              353

<210> SEQ ID NO 224
<211> LENGTH: 337
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 224
tgtgtgcccc actccttgct gggcccccac ccaccattgc ctgggacccc agaccatcgt      60
gcggggcagc aaaggtgcca agatggggc cctcacgctg ctgctggacg agtttgagaa     120
catgtcggtg acacgctcca actccctgcg gagagacagc ccgccgccgc cgcccgtgc     180 ccgccaggaa aatgggatgc cagaggagcc ggccaccacg gccagagggg gcccaggaa     240 ggcaggcagc cgaggccggt tcgccggtca cagcgaggcg ggtggcggca gtggtgacag     300
gcgacgggcg gggccagaga agaggcccaa gtcttcc                              337

<210> SEQ ID NO 225
<211> LENGTH: 428
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 225
ggaaaatggg atgccagagg agccggccac cacggccaga gggggcccag ggaaggcagg      60
cagccgaggc cggttcgccg gtcacagcga ggcgggtggc ggcagtggtg acaggcgacg     120
ggcggggcca gagaagaggc ccaagtcttc cagggagggc tcaggggtc cccaggagtc     180 ctcccgggac aaacgccccc tctccggggcc tgatgtcggc accccccagc ctgctggtct     240
ggccagtggg gcgaaactgg cagctggccg gcccttaac acctacccga gggctgacac     300
ggaccaccca tcccggggtg cccaggtaac ccatcccccg cccagggcc cccactgtcc     360 cctgcccgtt gctcctctgt ccccaccttc agccccgcc ccaccaccgt gcatctcatc     420
ctgaccac                                                             428

<210> SEQ ID NO 226
<211> LENGTH: 292
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 226

```
ccctggcacc catcactgac agctacctct cttctgtttc aggggggagcc tcatgacgtg    60
gccctaacg ggccatcagc gggggggcctg gccatccccc agtcctcctc ctcctcctcc    120
cggcctccca cccgagcccg aggtgccccc agccctggag tgctgggacc ccacgcctca    180
gagcccagc tggcccctcc agcctgcacc cccgccgccc ctgctgttcc tgggcccct     240
ggccccgct caccacagcg ggagccacag cgagtatccc atgagcagtt cc             292
```

<210> SEQ ID NO 227
<211> LENGTH: 504
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 227

```
cccctaacgg gccatcagcg ggggcctgg ccatccccca gtcctcctcc tcctcctccc    60
ggcctcccac ccgagcccga ggtgccccca gccctggagt gctgggaccc cacgcctcag   120
agccccagct ggcccctcca gcctgcaccc ccgccgcccc tgctgttcct gggcccctg   180
gccccgctc accacagcgg gagccacagc gagtatccca tgagcagttc cgggctgccc   240
tgcagctggt ggtggaccca ggcgacccc gctcctacct ggacaacttc atcaagattg   300
gcgagggctc cacgggcatc gtgtgcatcg ccaccgtgcg cagctcgggc aagctggtgg   360
ccgtcaagaa gatggacctg cgcaagcagc agaggcgcga gctgctcttc aacgaggtgc   420
gggcgctgct gccctgccgc cctgctggtc ctcccacccc tccctcccac cctccctccc   480
ctcctccctc ctctccctgc actc                                         504
```

<210> SEQ ID NO 228
<211> LENGTH: 256
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 228

```
cggtggctgg gtctggcact ggcagccctc ccgcctccct ccaccactga cccagcccct    60
gcacaggtgg taatcatgag ggactaccag cacgagaatg tggtggagat gtacaacagc   120
tacctggtgg gggacgagct ctgggtggtc atggagttcc tggaaggagg cgccctcacc   180
gacatcgtca cccacaccag gtatttctgg ggcctcagac ccctcctgtg acacgaccaa   240
gtcccctcca gaccac                                                   256
```

<210> SEQ ID NO 229
<211> LENGTH: 287
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 229

```
cattgtgtct gaagccaagg aatgacgcag gcagacgccc ctgctcgccc tcctgctgtg    60
```

```
ccagctcctc tgaccccact gcctctgccc tgtcccaggt gaagctgtca gactttgggt    120
tctgcgccca ggtgagcaag gaagtgcccc gaaggaagtc gctggtcggc acgccctact    180
ggatggcccc agagctcatc tcccgccttc cctacgggcc agaggtgagc cccggggtgg    240
cttggttgtc ccgccgtgga cagcgtacgc tgccattttc cagctgc                  287
```

<210> SEQ ID NO 230
<211> LENGTH: 343
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 230

```
ccaccatccc caacagctc agccctgctg tcccttctcc cgccccaggt agacatctgg     60
tcgctgggga taatggtgat tgagatggtg gacggagagc cccctactt caacgagcca    120 cccctcaaag ccatgaagat gattcggac aacctgccac cccgactgaa gaacctgcac    180
aaggtaggcc cctccctggc tgggaaactg tgcgccagct ggcgggtggc agggctccag    240
gtggagcatg gggtgtggat gggatgggga caatgatggc gcctgggatg gcgcttactg    300
tgtgctgggc cccccacccc cgggcctcat gtgtctgtgc aga                     343
```

<210> SEQ ID NO 231
<211> LENGTH: 295
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 231

```
cactgcagcc ctacagcaaa tgaacagtgg ggagcctcgc cccctgaccc tcccctcctt     60
ctcgacaggt gtcgccatcc ctgaagggct tcctggaccg cctgctggtg cgagaccctg    120
cccagcgggc cacggcagcc gagctgctga agcacccatt cctggccaag gcagggccgc    180
ctgccagcat cgtgccccte atgcgccaga accgcaccag atgaggccca gcgcccttcc    240
cctcaaccaa agagcccccc gggtcacccc cgccccactg aggccagtag ggggc         295
```

<210> SEQ ID NO 232
<211> LENGTH: 246
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 232

```
gagcgacaga gacatttatt gttatttgtt ttttggtggc aaaaagggaa aatggcgaac     60
gactcccctg caaaaagtct ggtggacatc gacctctcct ccctgcggt gagtgggccc    120 gcgagcgggc gcgcggggag cgggcagccg gcagccggca gccggggccg cgcccaggtc    180
ggccgggcgc tcgggcgccg ccgtgggcag agccgcgggg gcgggcggccc ctttgtctt    240 cctgtg                                                               246
```

<210> SEQ ID NO 233
<211> LENGTH: 166
<212> TYPE: DNA
<213> ORGANISM: Artificial Sequence
<220> FEATURE:

<223> OTHER INFORMATION: Description of Artificial Sequence: Synthetic
nucleotide construct

<400> SEQUENCE: 233

```
caaaaaaatt ggtgctgatt tttgatctat tttttctgtt tttcagggtc gacatgttaa    60
aacgggtcag ttggcagcca tcaaagttat ggatgtcact gaggtaagat tgagtcacac   120 acattttttaa ataatgttag atggaagaca aagattcccc caacaa                 166
```

<210> SEQ ID NO 234
<211> LENGTH: 215
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 234

```
ttcacatcgt tcagtagcca cacattttat ttttattttt tcataaggat gaagaggaag    60
aaatcaaact ggagataaat atgctaaaga aatactctca tcacagaaac attgcaacat   120
attatggtgc tttcatcaaa aagagccctc caggacatga tgaccaactc tgggtaggtg   180
gatgtttcct gagcatttgt gggcattcca tttgc                              215
```

<210> SEQ ID NO 235
<211> LENGTH: 203
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 235

```
aatttctcca agatatgttg ctcaccttgt gtcttgtctg ccctatagct tgttatggag    60
ttctgtgggg ctgggtccat tacagaccctt gtgaagaaca ccaaagggaa cacactcaaa  120
gaagactgga tcgcttacat ctccagagaa atcctgaggg taaggaaagt gggtggctac   180
agtgctccaa ctcatgatcc tgt                                           203
```

<210> SEQ ID NO 236
<211> LENGTH: 193
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 236

```
cctggctgtt tacttatagt cacagaaaac taaaattcag gtctgtcttt cctattcagg    60
gactggcaca tcttcacatt catcatgtga ttcaccggga tatcaagggc cagaatgtgt   120
tgctgactga gaatgcagag gtgaaacttg gtatgtaatg gatgtgcggc gtgatctcat   180
aattgcacct ggc                                                      193
```

<210> SEQ ID NO 237
<211> LENGTH: 244
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 237

```
atctggtttg tagttgtgtt tatctttctt tatctgcctt tttcttcctc ccacagttga      60
ctttggtgtg agtgctcagc tggacaggac tgtggggcgg agaaatacgt tcataggcac     120
tccctactgg atggctcctg aggtcatcgc ctgtgatgag aacccagatg ccacctatga     180
ttacagagta agaggcacct gctccgtagg ccttttgcagg gccactggca tacccgaggg    240
atgg                                                                  244

<210> SEQ ID NO 238
<211> LENGTH: 176
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 238
tgtaagttag tggctttgta tctactccag tatctgtaac gtactgtttt atttttgcag      60
agtgatcttt ggtcttgtgg cattacagcc attgagatgg cagaaggtgc tccccgtaag    120
taactttctt ttcttttag ctcacttgtt acatgtgact taaacccctc ccaaga         176

<210> SEQ ID NO 239
<211> LENGTH: 204
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 239
gaatgagtga ataagtgcc atactgacac gaccgtctcc tctccccagc tctctgtgac      60
atgcatccaa tgagagcact gtttctcatt cccagaaacc ctcctcccg gctgaagtca     120 aaaaaatggt aagctatata tggttttttg ttgttctttt ccctttttt taaattgctt     180 cttttagtt atactttcct ctga                                             204

<210> SEQ ID NO 240
<211> LENGTH: 284
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 240
tttactcttt gtggtggaaa tttgatgatc tttttcactt cttacaggtc gaagaagttt     60
tttagtttta tagaagggtg cctggtgaag aattacatgc agcggccctc tacagagcag    120
cttttgaaac atccttttat aagggatcag ccaaatgaaa ggcaagttag aatccagctt    180
aaggatcata tagatcgtac caggaagaag agaggcgaga aggtactaa gcctgttttt     240 gttttcatcc tttaaaattt ttatgtttag tttcttgcca acta                      284

<210> SEQ ID NO 241
<211> LENGTH: 172
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 241
gtgtcaggac ttgtgaactg tcccatttat cttgtccttt tcttcataga tgaaactgag     60
```

```
tatgagtaca gtgggagtga ggaagaagag gaggaagtgc ctgaacagga aggagagcca      120
aggtaaccac aaagccactg ttcagtatcc tgctttatga agggattaag tt              172
```

<210> SEQ ID NO 242
<211> LENGTH: 317
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 242

```
cttataggac agtgtgatcg gtgcacaccc tgaaagccc tgcttttcc aacagttcca        60 ttgtgaacgt gcctggtgag tctactcttc gccgagattt cctgagactg cagcaggaga     120
acaaggaacg ttccgaggct cttcggagac aacagttact acaggagcaa cagctccggg     180
agcaggaaga atataaaagg caactgctgg cagagagaca gaagcggatt gagcagcaga     240
aagaacagag gcgacggcta aagaggtag caaaaggaaa atgtccaagt tggttggtct      300
tttctctttc tgcattt                                                    317
```

<210> SEQ ID NO 243
<211> LENGTH: 249
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 243

```
ggcgggaaga tccctggtaa ttatacattt ttacttacgt agcaacaaag gagagagcgg      60
gaagctagaa ggcagcagga acgtgaacag cgaaggagag aacaagaaga aaagaggcgt    120
ctagaggagt tggagagaag gcgcaaagaa gaagaggaga ggagacgggc agaagaagaa    180
aagaggagag ttgaaagaga acaggttagt tcacagataa catagcaggc atacacttgt    240
gaagtttgt                                                            249
```

<210> SEQ ID NO 244
<211> LENGTH: 175
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 244

```
cttttctttg ggataatttg attgctgggt gatttctgtg tgacaggagt atatcaggcg      60
acagctagaa gaggagcagc ggcacttgga agtccttcag cagcagctgc tccaggagca    120
ggccatgtta ctggtaaagc cccgcctctg tttcattctg tagcatcagg gctcc          175
```

<210> SEQ ID NO 245
<211> LENGTH: 315
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 245

```
cgagctctcc agtgtcccat agatttagtg ttatcctctc cctctccaag gagtgccgat      60
```

```
ggcgggagat ggaggagcac cggcaggcag agaggctcca gaggcagttg caacaagaac      120
aagcatatct cctgtctcta cagcatgacc ataggaggcc gcacccgcag cactcgcagc      180
agccgccacc accgcagcag gaaaggagca agccaagctt ccatgctccc gagcccaaag      240
cccactacga gcctgctgac cgagcgcgag aggtatcctc tttcctttgt cacttagaca      300
ttgccctgga aagtc                                                       315

<210> SEQ ID NO 246
<211> LENGTH: 378
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 246
tttatgcaga acgcattgaa tgttttgtgt tttgttttct tgtaaggtac agtggtccca       60
cctggcatct ctcaagaaca atgtttcccc tgtctcgcga tcccattcct tcagtgaccc      120
ttctcccaaa tttgcacacc accatcttcg ttctcaggac ccatgtccac cttcccgcag      180
tgaggtgctc agtcagagct ctgactctaa gtcagaggcg cctgacccta cccaaaaggc      240
ttggtctaga tcagacagtg acgaggtgcc tccaagggta aggagcagaa agacagatgt      300
gtgctgcttt tttccttttt gttatttttt tttaaagatt atttatttta attatgggta      360
tgcaacttga ccaaattt                                                    378

<210> SEQ ID NO 247
<211> LENGTH: 207
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 247 tttttttcc ttttcatgtt ttcaataatt taattgctat attttctact taaaggttcc        60
tgtgagaaca acatctcgct cccctgttct gtcccgtcga gattccccac tgcagggcag      120
tgggcagcag aatagccagg caggacagag aaactccacc aggtaaaaga caagtgagca      180
ctgagaacag gccttctgtg cagtcta                                          207

<210> SEQ ID NO 248
<211> LENGTH: 245
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 248
gcatctagag atgacacatt agctgttctc tcttcttctt ttctaacagc agtattgagc       60
ccaggcttct gtgggagaga gtggagaagc tggtgcccag acctggcagt ggcagctcct      120
cagggtccag caactcagga tcccagcccg ggtctcaccc tgggtctcag agtggctccg      180
gggaacgctt cagagtgaga tgtaagctgc ctttcctttc cttttccct gctaatgttt       240 tgagc                                                                  245

<210> SEQ ID NO 249
<211> LENGTH: 205
<212> TYPE: DNA
```

<213> ORGANISM: Artificial Sequence
<220> FEATURE:
<223> OTHER INFORMATION: Description of Artificial Sequence: Synthetic nucleotide construct

<400> SEQUENCE: 249

```
catatgttga tatgtgtctg tccatcttgt ccctttttgaa cccaacagca tcatccaagt    60
ctgaaggctc tccatctcag cgcctggaaa atgcagtgaa aaacctgaa gataaaagg     120
aagttttcag acccctcaag cctgctgtaa ggattgtgca ggatcagttt tacttatttc   180
agacttgaat gagatctttc tatta                                         205
```

<210> SEQ ID NO 250
<211> LENGTH: 285
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 250

```
gtccctgctc ctgcttgcct tactctctct tttctgtcct ttgctttagg atctgaccgc    60
actggccaaa gagcttcgag cagtggaaga tgtacggcca cctcacaaag taacggacta  120
ctcctcatcc agtgaggagt cggggacgac ggatgaggag gacgacgatg tggagcagga  180
aggggctgac gagtccacct caggaccaga ggacaccaga gcagcgtcag tccccggtct  240
cttttagagc ggatgagagt attctctcag agcctgcttt ccact                  285
```

<210> SEQ ID NO 251
<211> LENGTH: 244
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 251

```
agaagtgaat tgaaatgtgt attttttaatg ttcattttta aaatgccagt tgtattaata   60
acattgaaat ttacattgca gactcagtcc gctagtagca cactccagaa acacaaatct  120
tcctcctcct ttacaccttt tatagacccc agattactac agatttctcc atctagcgga  180
acaacagtga catctgtggg taagtacagt agcaacaaga aagcagctga caaatgggac  240
ttta                                                                244
```

<210> SEQ ID NO 252
<211> LENGTH: 275
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 252

```
ggaggcaggc atagtgtgtg tgtgtacaga aaataatttc aaatatattg tgtttcagtg    60
ggattttcct gtgatgggat gagaccagaa gccataaggc aagatcctac ccggaaaggc  120
tcagtggtca atgtgaatcc taccaacact aggccacaga gtgacacccc ggagattcgt  180
aaatacaaga agaggtttaa ctctgagatt ctgtgtgctg ccttatgggg taggtgtcta  240
gccactactc caaactttc attttttgttc tgagt                              275
```

```
<210> SEQ ID NO 253
<211> LENGTH: 235
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 253
gccaagcaca gcataaaatt gaggcctttc tgtgtccctg aaacaggagt gaatttgcta      60
gtgggtacag agagtggcct gatgctgctg gacagaagtg gccaagggaa ggtctatcct     120
cttatcaacc gaagacgatt tcaacaaatg gacgtacttg agggcttgaa tgtcttggtg     180
acaatatctg gtgagtgttt gttttgtaaa ccagaatatg tgacaccatc ttaac          235

<210> SEQ ID NO 254
<211> LENGTH: 195
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 254
tactgacctg tgcttctctt gctttttat ttgctgcttt tcagtaaaat atgaaagaat       60
caaatttctg gtgattgctt tgaagagttc tgtggaagtc tatgcgtggg caccaaagcc    120
atatcacaaa tttatggcct ttaaggtaac aacatcaagt gaatttaaaa gtagtattgg    180
ccattcaagc tgcaa                                                      195

<210> SEQ ID NO 255
<211> LENGTH: 277
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 255
aaaaaaaaat gttctccttc atcttctcac ttctcttatg gcttctttgc agtcatttgg     60
agaattggta cataagccat tactggtgga tctcactgtt gaggaaggcc agaggttgaa    120
agtgatctat ggatcctgtg ctggattcca tgctgttgat gtggattcag gatcagtcta    180
tgacatttat ctaccaacac atgtaagaaa gaacccacac tctatggttg gttgactggc    240
ttcattttgt tttgactttc ttctttactc tgcttag                             277

<210> SEQ ID NO 256
<211> LENGTH: 247
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 256
aataaccaca gacgttcttc cctgtacttt gttcctgttc tctagatcca gtgtagcatc     60
aaaccccatg caatcatcat cctccccaat acagatggaa tggagcttct ggtgtgctat   120
gaagatgagg gggtttatgt aaacacatat ggaaggatca ccaaggatgt agttctacag   180
tggggagaga tgcctacatc agtaggtatg gagaacttgg ggaaaggcag catttgtgaa   240
aatggag                                                              247
```

<210> SEQ ID NO 257
<211> LENGTH: 245
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 257
gggctgtttc ctcatctttta acggtttgca attttttccct ccccaaaagc atatattcga      60
tccaatcaga caatgggctg gggagagaag gccatagaga tccgatctgt ggaaactggt     120
cacttggatg gtgtgttcat gcacaaaagg gctcaaagac taaaattctt gtgtgaacgc     180
aatgacaagg taatagttcc cttatggatt ctttttagtt gctctatctt taataatgg      240 cttgt                                                                 245

<210> SEQ ID NO 258
<211> LENGTH: 398
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 258
ggaaacctgg cgtactggct gtggcttctc tagcgggact cggcatgagg ctggcgcggc      60
tgcttcgcgg agccgccttg gccggcccgg gcccggggct gcgcgccgcc ggcttcagcc     120
gcagcttcag ctcggactcg ggctccagcc cggcgtccga gcgcggcgtt ccgggccagg     180
tggacttcta cgcgcgcttc tcgccgtccc cgctctccat gaagcagttc ctggacttcg     240
gtgagtgcgg cccgggacct tgggcctttt tgcgcggtcc cggcgcggga gctgcggccg     300
ctgccccagg ccgggtcggc gccggccagc tctcgcctga ggcgcacccc tcctcctcag     360
cgtttccgcc cccagcgcct taggtgcttc cttcctcc                             398

<210> SEQ ID NO 259
<211> LENGTH: 237
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 259
gtttccttat ggcttttact tactgcttta cccatcatgt ttggtttcag gatcagtgaa      60
tgcttgtgaa aagacctcat ttatgtttct gcggcaagag ttgcctgtca gactggcaaa     120
tataatgaaa gaaataagtc tccttccaga taatcttctc aggacaccat ccgttcaatt     180
ggtacaaagc tggtaagatt ctcatcttgt gtttgcaatt tgatggagtt gtggact        237

<210> SEQ ID NO 260
<211> LENGTH: 188
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 260
atattgaact ttcagaatat aaaagaacaa acttatccta ttgatctgca ttttaggtat      60
atccagagtc ttcaggagct tcttgattt aaggacaaaa gtgctgagga tgctaaagct     120

```
atttatgagt aagttcacta ttttgaccct attcttaaac ctattattag gtcacttggg    180
ggaaattg                                                              188

<210> SEQ ID NO 261
<211> LENGTH: 192
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 261
aagtttactt gtcaaaatat ttggctgttt tgacagatgg gtttgtttag ctttacagat    60
actgtgatac ggatcagaaa ccgacacaat gatgtcattc ccacaatggc ccagggtgtg   120
attgaataca aggagagctt tggggtggat cctgtcacca gccagaatgt tcagtacttt   180
ttggatcgat tc                                                        192

<210> SEQ ID NO 262
<211> LENGTH: 265
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 262
agagcattag gtggtttagc ttattttgtt ggtttttttc cttttggat agctttattg     60 tttggtggaa aaggcaaagg aagtccatct catcgaaaac acattggaag cataaatcca   120
aactgcaatg tacttgaagt tattaaaggt aaatactgac atttctcctt gcaaaaaaag   180
atacaaaaat caaattatt gttatttctt actattaaaa catctatttg tatcatgaga    240
taaaatggta ggcacaaatg catgg                                          265

<210> SEQ ID NO 263
<211> LENGTH: 215
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 263
taccattgcc atcttaatgc gtgaaagaga agtatattta ttaaatcctt ttttgttttg   60
ttttgattca cactagatgg ctatgaaaat gctaggcgtc tgtgtgattt gtattatatt   120
aactctcccg aactagaact tgaagaacta aatggtaagc ctgatgttgt cttttctca    180 ataattagtg ctttgattac ttgataaggg ataag                              215

<210> SEQ ID NO 264
<211> LENGTH: 184
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 264
gctttaagca catctctctg tactttcata tttttctctt ctgctctgta gcaaaatcac   60
caggacagcc aatacaagtg gtttatgtac catcccatct ctatcacatg gtgtttgaac  120
```

```
ttttcaaggt tgtaaaata gtattacata acctttacca gtactttct gaggttagga      180 atct                                                                184

<210> SEQ ID NO 265
<211> LENGTH: 287
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 265
gattctttgg catatttcca tcaaatttta aaacttcaaa tagtgcatat gtacttgaaa      60 attacactt ctcttttcta aaagctgta tttttaatac aaccctaatg tatttcagaa       120
tgcaatgaga gccactatgg aacaccatgc aacagaggt gtttacccc ctattcaagt      180 tcatgtcacg ctgggtaatg aggatttgac tgtgaaggta aatgtgttta atggtttgtt    240
ttcttttttt ttttttgta attgatgaac agacatgcaa aggtaac                   287

<210> SEQ ID NO 266
<211> LENGTH: 207
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 266
gttttgagga tttgggcata gagcacgatc ctttcttac cttagatgag tgaccgagga      60
ggtggcgttc ctttgaggaa aattgacaga cttttcaact acatgtattc aactgcacca   120
agacctcgtg ttgagacctc ccgcgcagtg cctctggtat gttatcaaga ataatgaag    180 tgtgtttctg tgaattgcct tccacat                                      207

<210> SEQ ID NO 267
<211> LENGTH: 233
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 267
agaaaagtat ttcagtgtgt gtcttctga atagaatttt gttttctca tcaaacaggc      60 tggttttggt tatggattgc ccatatcacg tctttacgca caatacttcc aaggagacct  120
gaagctgtat tccctagagg gttacgggac agatgcagtt atctacatta aggtaatagc   180
tgtagtcttc ttgatttaat atttcttttg atgataagaa cagatgtcca tac            233

<210> SEQ ID NO 268
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 268 cttttttgcca ttgtctattt tctcaaataa tgaattctaa aaaatgccag acttaatagg    60
tcttaggttt ttcttttca ggctctgtca acagactcaa tagaaagact cccagtgtat    120
aacaaagctg cctggaagca ttacaacacc aaccacgagg ctgatgactg gtgcgtcccc   180
```

```
agcagagaac ccaaagacat gacgacgttc cgcagtgcct agacacactt gggacatcgg    240
aaaatccaaa tgtggctttt gtattaaatt tggaag                              276

<210> SEQ ID NO 269
<211> LENGTH: 305
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 269
aaattggagc aggtgtgtct ctccacctaa aaaaccacaa ctgagcttac accacagtat    60
tccggtgtct gtaaggtgga ggcggcagca cagtgcctgg cttcagggag aactcagaga   120
ggtattcagg attctctgcc acaataggcc ggatccgccc attctgttta taaaaatatt   180
ttgtgctgta ctcctgcagg tagtctgggt gctgaagggt gctccgaggt ggcaggctgt   240
ggttccagta gtcagggttg tcaaacgctt tcttggcctt tctggcattg acagtatgt    300 tgttc                                                               305

<210> SEQ ID NO 270
<211> LENGTH: 306
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 270
gctgtggttc cagtagtcag ggttgtcaaa cgctttcttg gccttctctg gcattgacag    60
tatgttgttc ttcaggtact cagcttttcc caaggtgttg gcaaggtgt tgaggtacag    120 tggctcattc acatactcat cctcggcctt gggtggacca ttggatgcat tgtgatattc    180
gggattatcc aatgcttgaa ggtctccatt ttttctccga gaaacaaaag ggttctcctc    240
cactggattc aggtattcta aaggaataaa aaaatatcag ctaacctcta gtttctggaa    300
aatatt                                                              306

<210> SEQ ID NO 271
<211> LENGTH: 387
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 271
ggaagtgaac ttcgaatggc gatcgtttct gaataatcag ttcatacctt gtttgggttt    60
gtctcgcata ggagtcatgt aaccttcctc atccagctct cctcgtgggc tccgttctgg   120
ggcaaacacg gtggggtcag cactgtacct ctgggtgcta ctgtcctctt ggacatgggg   180
tgccactggc ttgcgtaggg tgccattaca gcaggagtca tcaaaaatct cagcagtagc   240
accctgtgcc acaggagctt ctggaattgt gctagttggg gctctgtagg cacagacac    300 tccttgttca gcagcaaaac ctccatctcg gtatacaaac tggttctgtt aataagagaa   360
acatatgtgg agagaaggcg ttgttag                                       387

<210> SEQ ID NO 272
<211> LENGTH: 158
```

```
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 272
ggaaacatgg taagcaaaga ccgaaaatcc taaaagatga aggttgattg tgaaatactt      60
actcctgaca tgggggtgta ggcaggagga gggctgtgtc caatttcact ctaataggaa     120
agaaaaatgg aatgatggat ataataagag gcaatatg                             158

<210> SEQ ID NO 273
<211> LENGTH: 196
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 273
gtttgccatt ggcctagtct taaaggcata agtcaaatgt actcacctga ataactaggt      60
atctttgagg gtctcgagcc atccttgaaa actcagcagc cagttcctta aatttaggtc     120
tactgtcagc atcaatcatc caacctggaa atttacacag tgaaaatgtc actatattcg     180
taactagaaa ggagtt                                                     196

<210> SEQ ID NO 274
<211> LENGTH: 271
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 274
ctattacttt actaagaatg atgatggtga taacattatt ttgcagtctt acatttgacc      60
atgaccatgt aaacgtcaat agtgcagatg ggaggctgag gcaaacgttc tcctttctct     120
aataaatcag ggatttctcg cgttggaatt ccatcatagg gttttcctcc aaaggtcatc     180
agttcccata tagtaactcc tatattggag aaaaaattct tacttaagca tattaacaac     240
atatgttgaa caaaccagca ctataccagt a                                    271

<210> SEQ ID NO 275
<211> LENGTH: 306
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 275
ctaagcttca ggcttattgg tttcttgtat aaaatataag gagataaaag gatattatac      60
tatattttca agcaagattg ctctcaaaaa gatacccacc tttcctccat cagcattgta     120 ctcttttca tctccttcca agagtctggc tagcccaaaa tctgtgattt tcacatggtt     180
tggagatttc actaagacat tacgggctgc caaatcccga tgaacgagtc gtctttcttc     240
caggtacatc attccctgaa aaatatcaag ttccttaatg atattcagtt aatgcccagg     300
tttttcc                                                               306

<210> SEQ ID NO 276
```

```
<211> LENGTH: 308
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 276
aatatgaaaa ctgttccagg ttaggaaata ttaacctaaa aatgtaattt ccatagaaat     60
tgacaggcac ttaccttagc tatctggaca caccagttaa gcagcagttg tgatccaatg    120
ttatccttgt gctcgtggac atactccaac aggcagccat ggggcataag ttgagtaacc    180
agctggatgg ttgggctcag acacacaccc agcaaccgga ctaggtgtgg atgatccata    240
cttgccatga tcagagcttc ctgtaagaaa aaatgcaat accatgattt caactcaaat     300
tttcttag                                                             308

<210> SEQ ID NO 277
<211> LENGTH: 275
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 277
gcaggctatt tgataatgga gaaaaatgtg attgcctggg tgtctgtact tacatccatg     60
aactccacat ttgccttggg accagttgtc tcattaagaa tcttaatagc cacaggaatc    120
ttcacagttt ctccttcagg tacccaaata ccctttgggg aaaaaatttt acattaaata    180
tgacatctca acctattaag ttcttacaaa gtaacttaga agtttgatat tataacattc    240
aatcaacaaa tgtttattta gcacctgtta catgt                               275

<210> SEQ ID NO 278
<211> LENGTH: 244
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 278
aactccattg gctattattt tctaaacatc taaaacaaaa cttaactaac gatatgcgtt     60 gtttttact tactttataa accgttccaa aagcacctga gccaaggact tttaccctct    120
tcagctcagt ttctttcaaa atacgaagtt gagcttgatt gggtgctgtg ccactgggag    180
ttaatggttc caccaactgc aaagcggaaa gaagaaggtt atactttcag tccgatagtc    240
agtc                                                                 244

<210> SEQ ID NO 279
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 279
cctgatgaaa atccccaaac acatgaagag gagaaagaaa tacctcacct ctgtttccaa     60
gaatcttctc aaggctcttt tcttttgat gctcttcctt ctaacataaa cagcaaatgt    120 cagaccccaca atgaccagaa tgaagagccc accaattact ccagctgcaa tcaggggagt    180
```

```
tctgacaacc agaatgagaa aaaaaaaaat aaaaagtatg aagagagaga agacagagga      240
agagaa                                                                246
```

<210> SEQ ID NO 280
<211> LENGTH: 415
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 280

```
ggaaaggatt tgagcgacaa aatggaaaca tggtagatgt tacctagcat gttgtggtaa       60
agtggaatgg cccgtccatg ggtagtaaat gcagtcatga ctagtgggac cgttacacct      120
gcaggcaatt acagaacaga aaacatcatt ctccatccac agtgacatgc acacacatgc      180
accagtgctc acacatggag ccttggagga agaacatggg aagcaagcac accaagtacc      240
tatccatcag gccgatgcag tcttcaatac ttgagcctat gcacctgcag aaaatgcaaa      300
tttaaaaaaa tacaagggga aaaaattagt catttaaaaa atcagtaaaa taaatattga      360
ttgtctcgaa ttcttataac tattagacta ttttggaaca caatgaattt caagc          415
```

<210> SEQ ID NO 281
<211> LENGTH: 255
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 281

```
gataacacat accaggtgag cccttggcca gcaagaatgc ttacccttgg gtgcagtttg       60
gatggcatgg gtggcactcc cgatctggat cagcatactt gaaaatgaaa ctgtttgccc      120
cctgtaagcc atctggacat ttttccacac agtttgggcc atctttaaaa tgagagcact      180
ttgtacagtt gtcaggaccc tgaaatgtga aaacgaaaaa aaaagaaaaa agaaaagtgg      240
tgtcatttcc tctgg                                                      255
```

<210> SEQ ID NO 282
<211> LENGTH: 191
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 282

```
catacatgat actaaataag ccaacacacc acagatgtct tcaggcttac cggtccatgg       60
catgtgagga ggccatcttc catcttctca cactgggggt cacactccac acagatggag      120
ccattctcaa actcccgaaa ttcactgtga aacatcagc cacatgagga ggtgtaagca       180
aacaagcgtc a                                                          191
```

<210> SEQ ID NO 283
<211> LENGTH: 223
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 283
ccttcaaagc tcatgaggtg aaggcaaccc tagaagaagc cttacccatc atagaggtta    60
caagactcta tgcagatcct tcctctactg aagcggcgac acgacagaca ttggtctggc   120
ccaggtcccc aacagccatc actgaacac agatggttgc acaccattcc ttcagcagct   180
gtgaaacacc aaaatcaagg ggaaataaaa cagaggattg tgt                      223

<210> SEQ ID NO 284
<211> LENGTH: 313
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 284
tgtttggtcc aaagaagaat gggaaaaaat ttaagtttct atgttttaaa tgtctgagta    60
atgtacttac tacaattttc agcttttctg ttgtcccgga ttactattct ctggttgatt   120
gtgctgaaga gtgttgtcca gttaatggta tgataataac acaggttgct gttgtcagta   180
atatagatgt ttcctgcgct gatttccttc agggactgga actgtagaga ggtgatgccc   240
tgttgcttga ggataagcaa ggacaggcca ctaaggaggg ggaagtgaga aaacggaacc   300
atgaaacgca ttc                                                       313

<210> SEQ ID NO 285
<211> LENGTH: 200
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 285
tcttgaaatc tgtgagccct gcagctttaa acatatccac ttacctatag agtactcttc    60
caccaatggt caccaggtta gaaaaaacac tgaagtcagt catgtttggt ggccatgact   120
gtatgttcag gaaacctaca agtgaagagt agaaaaaata aatcagaata tcattgtctt   180
agtattagtg ctgattttc                                                 200

<210> SEQ ID NO 286
<211> LENGTH: 197
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 286
ttaaaaaaat tatattgttc atagcgcaac agttgcagtt taaaaaatta cctgttatct    60
ctctgactgt ccgaaagacg ttcagtttct ctgggtctat ggcttcaatt gcattgtaag   120
ggtccctaga aaatcaagaa gagatgtagc caaatttaaa ttttactaaa ggattgaaaa   180
tatgagaaat gtgacaa                                                   197

<210> SEQ ID NO 287
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 287

```
gaatctcttc agttttgtct acactttgta aataacttg cacaaaaatt taatactgac    60
ccatgaatac cagtgactag aaagatcaaa ttcccattga tcttggtaca gtttatgaat   120
ttgtcaatgt tactgaatc cacagtctga gctgacatca atgatcctgt gccaatgcca   180
tcacaagctg tagaaacaag actcagagtt aggggattga gaaacttatt tttggc      236
```

<210> SEQ ID NO 288
<211> LENGTH: 237
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 288

```
taaaaacctt gttatatagg cccagttcta actaaataat ctgagctacc actcaccttt    60
tgggcaaatg tcagtgcaag gtttacacat tttaatccca ttttcttcta cttccatctt   120
ggaactaggg caggcacgca cacaagaact ggaatctacc acaaagttat ctgattaaaa   180
aaaaaaaaaa ggtaaaataa gcattaatgt taacattcag caaacaagct caaaaca     237
```

<210> SEQ ID NO 289
<211> LENGTH: 276
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 289

```
aaaattcttt tgatttcaaa taatgaccta attaatttgg ttattcttat tctgttactt    60
acgtggacat ttcttgacac agaatgctcc atatgtgtac tttgcattga aattgtgctc   120
cagttgaaag gtggttggat tgtagacaaa ggtttgggga cactgagtaa cacatgctcc   180
actgtcattg aaattcatgc aggcctgcaa cacagcaaat attactttca tttacaaata   240
aactcataat acttgttaat gaaacgctgc caaaac                             276
```

<210> SEQ ID NO 290
<211> LENGTH: 215
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 290

```
gaaggaaagg agagcaggat aataaaagag agaaatcaca gacatacaaa gcagtctgtg    60
tccttaggtc ctgagcagcc tccagcacat tctcgatggc agcagtcact gacgtaaggt   120
ccgtagcatc tgccgtcaca ttgttctgca cacaccgtcc ttgtcactgc agaagacaga   180
gataggacca tgatcaaagt ctgccaccag gagaa                              215
```

<210> SEQ ID NO 291
<211> LENGTH: 166
<212> TYPE: DNA
<213> ORGANISM: Artificial Sequence
<220> FEATURE:
<223> OTHER INFORMATION: Description of Artificial Sequence: Synthetic nucleotide construct

```
<400> SEQUENCE: 291
aattccttga ccacatcaaa cctgtgtgct ctcactgatg aacacttaca agtctggcaa      60
tgattttctg tgggtcccca gcaacggcca gtacaggact tatggcaacg tccacctgca     120
gaacacgaaa agggaaaaag gacatgcacg ttataatctt tcactc                    166

<210> SEQ ID NO 292
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 292
tcatcgccac atagggtaga acattttgag aaattaaaaa gaataattct acttacatcc      60
tgaactacca tttgttgaca caagagtcaa gttggaaggc catgggttcc gaacaatatc     120
ttgccaatga atggtgtctg cataacaaag gaatttgttc tggtctacat agactccacc     180
atttaggatt tctgtattaa aaaacaaata aacaaatttt ttgtcaaact gcttgttgat     240
gaaaag                                                                246

<210> SEQ ID NO 293
<211> LENGTH: 162
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 293
tgacagtaac cctacatata caattgcctt atattgataa tgaaagcata tttgccattt      60
tggatatatt ccttacctgt caagttcttt aatccaagtt cttgaagtcc aaagtttcca     120
tcttttctgt agtttaaaaa tattgccaag gcatatcgat cc                        162

<210> SEQ ID NO 294
<211> LENGTH: 158
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 294
catatcgatc ctcataaagt tttgtcccac gaataatgcg taaattctcc agaggcaggt      60
aacgaaactg attaagagcc actaacacgt agcctgtgac ttctcgaaca gactgaaaag    120
acacaaacag ttgcctgtgt tataaaacga atttgtca                             158

<210> SEQ ID NO 295
<211> LENGTH: 263
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 295
gacgccactg tccattcaca aagaagagaa agaaagccac agctttaccc gcaggaagga      60
gaggtcccgg ttgtgctcaa tgctggttat ctccaggttg cccatgacaa cctcacagtt     120
ttcatagtac ttgcgcaagg ctcggtactg ctgttccagg tcagagagag agctcagttt     180
```

```
attctccgtt cctgcacaca ctgcaaagac aagaagatac acgtgaaatt acataacctt    240
tatatgatat gcgcaatgat aat                                            263
```

<210> SEQ ID NO 296
<211> LENGTH: 215
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 296

```
gggatgggtg aagagggcag gggagccact cgaggcagcc ccgccggcgg ctgcaggttc    60
ggcgaccgga gtgccagaag gaacccacct gactgagaat cgctgggctg acggtcccc    120 gccgccacga aaggctcac ccagacccaa agtcctgtcg ccggcttcat tttttggaag    180
tctcagatcc cgtgctgaca attacatgtc caaat                              215
```

<210> SEQ ID NO 297
<211> LENGTH: 178
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 297

```
gaacaagaat ctacaggaat agccacatac agaatgccaa tttcttacct ttataagaca    60
gtcctcttct tgagatgaca gtaaaacatt ctctggcttt aagtcacggt gtataatacc    120
gttttcatga aggtactaca cagaaaggca ggcatgaccc tcagattcat gcagtaga     178
```

<210> SEQ ID NO 298
<211> LENGTH: 185
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 298

```
aactaaaaga aaggcagctg tcaaaagaat tgagggcttc ttttacctgc acagccaaga    60
gcatctggta aaatagagc ttgcaggtag cttctttcag gcgtttattc cccaccactt     120
tgtcaaacag ctctccccct tccatcctga aacacaaagg caaggcaagg ggttcattcc    180
tgggg                                                                185
```

<210> SEQ ID NO 299
<211> LENGTH: 167
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 299

```
ataaagcatt tgaatggaaa cagaaatttt taaaaagttt actacttaca attccaaaac    60
aatataataa tcttctgcat caaaaaagtt tttaatcttg atgatgcaag gctaagaaga    120
gggggagaaa aaagggaaag tagtgagaaa ctcccaagag gaaaacc                  167
```

<210> SEQ ID NO 300

```
<211> LENGTH: 205
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 300
gaaaccacca atcacaaatg tatagtgaaa aaattaagtg catttatata agaaaataat      60
ttaccttcca agagttttg acatgatgta ttcatctctt aatgccttag gataaactga     120
ctgatcatct acagtcagat caaaaaagac aaaaactaag gaagaaaaga gtagaaatgg    180
gtttcattaa tttattcaca agagg                                          205

<210> SEQ ID NO 301
<211> LENGTH: 257
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 301
attttcctcc tatgagagag tggaaaaaaa aaattccagt aaccataaga taataatatt     60
acctttattt ctgcttagtg acagtgcaat ttcagaattg ttattcaaag gacggcgttt    120
tcctttccct acaagctctg tatttacaaa ggttccattg ccactgtgat cttctatgta    180
tgcaatgtaa gagttttag gacccacttc ctaaaataga gaacattttg tttcagactt     240
tgaatagcag agattta                                                  257

<210> SEQ ID NO 302
<211> LENGTH: 216
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 302
tgaccaaatt accagctctc ctagatacat gggtattcat tacctaccct gaaaatccga     60
aagtgtttct tgctgtatgt tcggtattta tctgttcttt tcagcagtgg ttcatcaaag    120
caatattcac agcttttgtc cctcccaaac cagtagttgt cattcacaca ttctgtaata    180
taaaagcatg catcagaggg ctgttgaatt tcatgt                              216

<210> SEQ ID NO 303
<211> LENGTH: 414
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 303
aagtgttttt ctgaacaaaa cgtgatacta tacaacaaag ggtcttacca agattggcaa     60
atccatcctg aagggcccat aatcgagccc aggggcagg ggtaggctcc tcaggttctt     120
ggtcctcagg ttcttggtcc tcaggaatag aatagagttc ctgagtggac actgtctcta    180
aggagctcag tgtcccagag ctggagtgag aggactggct ggagtttggc atcgtgctgg    240
tagaggagct ggatatgccc tgggactgtg aggaggagcc ttgggactgg gtaacgctgc    300
catggggctg tgaacaggca ctgctgccat gagactgctg agcctcaaca tccgactccc    360
```

```
gagacatcac gacctcaaaa agaaagtgtc caacaacaaa ggtgagtttc aagg        414
```

<210> SEQ ID NO 304
<211> LENGTH: 349
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 304

```
ttggggttag ctcaaggcag ctaagcaggt ccagcccaag aactaagtca agtgggccga    60
ggaggctctg agagtggccg gggccggcgt acattccctg gcatgggtga gaactgcggc   120
tgttctggac gcacattcat ctcatgcgag gtgctggggc ccaagttcat gtaggttgct   180
ggcagctgca cataatggtc cccaagcagt gcagacacta tctgctccac ctcccccact   240
agtactctga aggtgggtcg cactgctggg tctgcctccc agcattgctg catcacttgg   300
tacctgttgg gggaaaggga tgtcaggtta aggcaatttc cacccaagg              349
```

<210> SEQ ID NO 305
<211> LENGTH: 250
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 305

```
ggtgccaaag ccatgtggac tgtagggcag gtggggcctc accacatcag acttggtggt    60
aaatctatag gtctgcaggc tctccagcgc catccacttc acaggtaggc gagcgtggcg   120
atgctgttga acactatagt actccctgtc caggatgtcg cgggccaaac caaagtcagc   180
caccttgact gtgaatgact cgtccagcct taggggtagg gagaggatca cacttaggac   240
tggcccttac                                                          250
```

<210> SEQ ID NO 306
<211> LENGTH: 207
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 306

```
catgccctgt cctttgtctt cacccagct actctggact ctcacatgca gttccgcgca    60
gccaggtccc tgtgcacaaa cttctgctct gccaggtact ccatgctgcg ggctacctgc   120
aggccaaagc tgatgaggtc cttcacggtg gggttctggg ggcacaggtg ggttggtggg   180
caagggcaca gcagctcctt ctccagc                                       207
```

<210> SEQ ID NO 307
<211> LENGTH: 295
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 307

```
gggcacagca gctccttctc cagctgctgc ccagccccca acccagagcc agatgaacac    60
```

```
tgacccgctg aggtgagcgg atgaactgga gcaggtcacc gtggcacata tagggcagca      120
gcacatgggg caggccctca ggtggcaaca tgataccaat gagagccagc acattcgggt      180
ggttcaggcc acgcatgagc agccctctc gcaggaaggc ctccacctgc tgcatctctg       240
tgatgcctgc agagcagcgc aagtcaggca cagggcaggg cgtcccttta taagg           295

<210> SEQ ID NO 308
<211> LENGTH: 204
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 308
ggagcttgta gggacagggg gtggctttag cttctcatgc ctccactatc tcaccaaggc      60
cacttctgta gtcagagccc gagtacagaa taggcagggg tgtggctcca gcagtctggt     120
ccagggatgc caggtcattc aggttgggag gaagaactgt ggaaagagaa tccttggtgg     180
cttggctttc caagctccta gggg                                            204

<210> SEQ ID NO 309
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 309
gttgggggta gggctgatt aaaggtagga gcagagaact cacctagctg cttcctccgc       60
caccagtagc tgaagaccag tgcagtcgcc agtgcagcca caagcagcag caaaggcagc     120
aggataccaa ggagcgtgct ctgtgggacc ccatctggcc ctggccgcac cactctaccc     180
aggatatgac attccaccatc tacgcagacc tgggggcagg tggcaactca ggcccagcct    240
gtaggccctc tgcccgtgtt tcccagggag gtccag                               276

<210> SEQ ID NO 310
<211> LENGTH: 259
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 310
cccagcctgt aggccctctg cccgtgtttc cagggaggt ccagctgggc tgcctacctg       60
caatggggca ccatcctggc caagctgcag ggatgggggc aggggcagga caaccatgtc     120
cccccggaac tcgtgctggc agctctcacc acccacggtc acgttgatac ccacacagtc     180
agccacagcg cccagcccaa tatactgcag agagggtcat gaggaccagc cagtaggctg     240 gccccctactt tcagatccc                                                 259

<210> SEQ ID NO 311
<211> LENGTH: 303
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 311
```

```
gccctactt tcagatcccc aactgtccct gccctatcc cttacactta cctcaaactt    60
aatggcatgc tcctcaggct tcagtggaac taggttggca ctgggtggat ggggtggggg   120
taggaagcga agccaggca gtgtaaagcc agcagctcca tccctcggg cactcagatt   180 ccctgccacc catccctggg ggtctcggac cacatattca ggaaggcggc acagctgctg   240
ctctggaagc tgcctctcac actgctggga ccaatatgag agtgattagc caggaacccc   300
acc                                                                  303
```

<210> SEQ ID NO 312
<211> LENGTH: 185
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 312

```
ggaactcatc cagccttcct ccctcctggc cagcactcac tcaccctgct ttccactgcc    60
ctaagcccgt catggaatga cagcactaag tgccatgctg aagttagatg ctggccacag   120
atggtgatgt gggagttgct gtggaagagg gtagggtggt aggctttggg tgttctccaa   180
agctg                                                                185
```

<210> SEQ ID NO 313
<211> LENGTH: 254
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 313

```
ggctctctca ttccccagag gccagagtgg gcaaagaggc agtgcttaca tgtagccaca    60 gttgggctg atgcttagca cgacagggtc ttctctgtac tggaaggtcc aggaaccagg   120
tacctgggca ccccccacct gcaggctaag ggggacactg ccaccgtgg ccccaggggg   180 tgtggcacat aaaagctgcc cctcactgac cctacaggaa caagagattg ggctcaaggt   240
taccctcttt gtga                                                     254
```

<210> SEQ ID NO 314
<211> LENGTH: 235
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 314

```
ggtccccacc tggatagaac cctgcggcct cccatgcctg cctggtggta cttaccgtgc    60
tagcagacac tcagtcccat tgaccagcac agcccggctg gtgcctacag acagactctg   120
gccttcaaga gtgagacagg tgcctcctgc ccgtgggcca agagggggtt gcactgctat   180
cagcactggc tcctaagagg acatagaggt ggcttaggca ggtcctccac tccaa         235
```

<210> SEQ ID NO 315
<211> LENGTH: 275
<212> TYPE: DNA
<213> ORGANISM: Artificial Sequence
<220> FEATURE:
<223> OTHER INFORMATION: Description of Artificial Sequence: Synthetic -continued nucleotide construct

<400> SEQUENCE: 315

```
cccctcccctt cccgtaccat gcactggcca agggcacaga cagggcaagg tagcctcacc    60
atgaaagaga agcctctcag cacggagctg ccgtctaccc ggaagtgctt gcccggtggc   120
atgttagtca cggtgaggct gacgttggta ggccccactg cctgggtgcc caagggctcc   180
agttcacact caaactcctc tacaaagtct ttccggggca ctggtctggg gcaccagggg   240
aaccctgag gtcagccagg aattacacag gccta                                275
```

<210> SEQ ID NO 316
<211> LENGTH: 291
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 316

```
ggctgcttgg tttccccctt cagggaaagg gaggggaggg accagattgt acctgagttt    60
tgagctgtcc ttgggcagtg gccggcaggg actttggccc acagtgacct gatgggttcc   120
ctcaggcacc agaccagaag ggtgaaggta gaagttggag ccacacaggg tcagccttgt   180
actgccccctt agaggtccac tgtggggtg gaactgaaat gggggaaaca gcctgagtcc   240
tcatgtgggg ttgggctctc tcagccccac ctgcttcccc aaagtctcct g            291
```

<210> SEQ ID NO 317
<211> LENGTH: 222
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 317

```
gtctgtgatc ccacaaccct ggccccaggc cctgccctg cccacctcac ctggtcccca    60
gaggcaaaga gtaggtggtc cccaagacga ctgacatccc gctgcacggg ctgcccactg   120
tcacccagtg agaagttgga cacatacagc aagtagttta gtgacctgac cagctccacc   180
taggacaggt cagatgtgag caaaatgggg atggagacaa gg                       222
```

<210> SEQ ID NO 318
<211> LENGTH: 286
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 318

```
ggatggagac aaggacccag ggctagggga ctgtggggat gaggacccac ctgcaggata    60
cgcccatcca ttgtgcccat gtgtgccact gtgacgttgt caaggcgtgt cacatacaat   120
gcagtgacct gtactggtcc caacagccca ttgaataggt ccacacgtga aagctgcta   180
ctgaccagca gagggaagtg gcggcagctg gtgttgggc tgagggcttc caggccaggc   240
tgggaaaggt cagggaaggg aaggagtcag ggttcagcct tgtgcc                   286
```

<210> SEQ ID NO 319
<211> LENGTH: 386
<212> TYPE: DNA

<213> ORGANISM: Artificial Sequence
<220> FEATURE:
<223> OTHER INFORMATION: Description of Artificial Sequence: Synthetic
       nucleotide construct

<400> SEQUENCE: 319

| | | | | | |
|---|---|---|---|---|---|
| atgtgcatgc | agctcacaag | taagggcccc | ttctttcagc | ttaccgggtt | ggggcaaaaa | 60 |
| ctgggcgact | ggaagaagtc | gaggcctcgc | cggaggcctg | gatggactgg | ggattcacaa | 120 |
| cagcgctcca | caccctcatc | aattagtgtg | tccagcaggt | caatgggaa | ggcacagacg | 180 |
| acagagttgg | ggcccacgcc | aggaccacca | tccttgccag | tcacaaagac | cccaaatagt | 240 |
| acttcctggc | cctcggcgat | gctcagctca | gtggcaagtt | gggcacccac | tggagcggag | 300 |
| tgggccaccc | gcagcacagg | gtagggctgt | ccgccttctg | ggcccccg | gcgcctgcgt | 360 |
| tttggagcaa | atctgcagtc | gaggac | | | | 386 |

<210> SEQ ID NO 320
<211> LENGTH: 384
<212> TYPE: DNA
<213> ORGANISM: Artificial Sequence
<220> FEATURE:
<223> OTHER INFORMATION: Description of Artificial Sequence: Synthetic
       nucleotide construct

<400> SEQUENCE: 320

| | | | | | |
|---|---|---|---|---|---|
| gcagcacagg | gtagggctgt | ccgccttctg | ggcccccg | gcgcctgcgt | tttggagcaa | 60 |
| atctgcagtc | gaggaccagc | tcccgatagt | cacccaactc | tggctcagtg | gcgctaagcc | 120 |
| gtgccaggcg | tgtgtgcagg | gcactaggat | catctgtcac | gctggccggc | tgtacagtca | 180 |
| ggaagtatac | gaaggctccc | gtgtggaagc | tgtgcacgta | ttcaatactg | taggagacaa | 240 |
| gatgcttggg | cagcactgac | aacgccacaa | agcccggtgc | gaatcccgag | gcgtcagcct | 300 |
| tgagacgcct | gatagacact | gagcgtgggc | tgaagctggc | agccacggct | gcgtccagtg | 360 |
| aggatgccac | gtagaaatag | gagg | | | | 384 |

<210> SEQ ID NO 321
<211> LENGTH: 404
<212> TYPE: DNA
<213> ORGANISM: Artificial Sequence
<220> FEATURE:
<223> OTHER INFORMATION: Description of Artificial Sequence: Synthetic
       nucleotide construct

<400> SEQUENCE: 321

| | | | | | |
|---|---|---|---|---|---|
| agacactgag | cgtgggctga | agctggcagc | cacggctgcg | tccagtgagg | atgccacgta | 60 |
| gaaataggag | gcctggcctt | gctcaaccac | agttacacgg | gtgcccaatg | ggctggccac | 120 |
| acagtcgggg | cagtcatcgg | gccggttatg | gtgggctgag | aagaggcagg | ctggcgctgc | 180 |
| cagatgcacg | gctgtccctt | ggggctctag | gtcatgcagg | aagcagcggc | cctgcaggct | 240 |
| ggagccacaa | ctgaccagcg | caggcagcgc | gggatccagc | accagcacct | ttgtgtctgt | 300 |
| gtcaccggga | gggccgtggg | gtcctgggcc | acaggctgca | cacgtctggc | agccagggtc | 360 |
| tccagcaggg | cccgtggcca | ggctctggac | agacttcagg | tcag | | 404 |

<210> SEQ ID NO 322
<211> LENGTH: 466
<212> TYPE: DNA
<213> ORGANISM: Artificial Sequence
<220> FEATURE:
<223> OTHER INFORMATION: Description of Artificial Sequence: Synthetic
       nucleotide construct

<400> SEQUENCE: 322

```
ttgtgtctgt gtcaccggga gggccgtggg gtcctgggcc acaggctgca cacgtctggc      60
agccagggtc tccagcaggg cccgtggcca ggctctggac agacttcagg tcaggcccaa     120
gcacatgcag gcgattgcgt atggctacaa acacagcact ctcatttctg tcgccctcgt     180
aggtcaccat ggcctgtacc aggcctccgg cggagaagct gggcaccacg tacttcacgt     240
caaagtcgcg agaggccgcg taggggtgc gcgggcactg ccagtcctcg cccgccgcgg      300
gcttggcagg caacagcagc agcaacagga aggactgagg cagcggcggg aggagctcca     360
tcgaggcgag ctgggaccct agaggatccc taccggcctg gcctggacc tgggcgtggg      420 cctggctggg ggcccgactc gaggtctgga ctgggccaaa tttaag                    466
```

<210> SEQ ID NO 323
<211> LENGTH: 313
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 323

```
gcacctctca tgtgatgtcc aggagttggg ggtgtggatg cttcctttta aacaggagga      60
gagctcagtg tggtccccga gtcaggctgg agaatctggg ctgtgctacc ggtttgcact     120
ccaatctcta tcagctttaa aagttctgct tcctcactgg agtacacggt ggtgtctgtg     180
tcatcggagt gatatccgga ctggtagccg cttgtctggt ttgagccttc agatgccaca     240
gactccctgc ttttgctggg caccattcca ctgcagaaga aatggcaaac aaaggagttg     300
gcagagagaa gac                                                        313
```

<210> SEQ ID NO 324
<211> LENGTH: 213
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 324

```
ctagctagtg tttcatcctt tgtattattt ctaagactat ttttaaaaga cgtacttaca      60
tctgggatta cttttacttc tggttcttct aacgggatat cttcaaatgt ttttacactc     120
acaggccggc tctttcgctt actgttctgc agatactgac tgcaaaagaa caaatattta     180
tattttagtg gtggtatatt tgactgcaga tcg                                  213
```

<210> SEQ ID NO 325
<211> LENGTH: 245
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 325

```
gccttgaagt caccctcccc cggggatgt taggccatat acagtacctg attcctgctg       60
tgttgtcata atggaatttg ggtcacata cttcctcctc ctccatacag gaaacaggtg      120
aggtaggcag agagagtcca gaatcctctt ccatgctcaa agtctctgat atcggaagaa     180
caatgtagtc tttgccatcc tgaaacaata aacacagaag actgttgtta tggcttcagt     240
``` tcttc 245

<210> SEQ ID NO 326
<211> LENGTH: 212
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 326
ccttgacatc taagtactct ttgtaggtgc ttcttggatg gaggtgacaa acctgctgag    60
cattagcttg caagagattt cccaaatgtt ccaccaactc tgaaaacgtg ggtctctgac   120
tgggctcccc gtgccagcag tccagcatgg tctggtacct agagaagcaa aacactgatt   180
tcattaaatg cctctttctt cctgaatgct ga                                 212

<210> SEQ ID NO 327
<211> LENGTH: 198
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 327
atttgcgagc aaagaaagag aacacaggaa tacttcttaa agtcttacat ttctggtgta    60
gtataatcag gggccctcat tctagttcct tctttcaatc gcctacaaaa ttcttcatca   120
atctttaccc caggatatgg agaagcacct agaataaaac agggaggaga cattctttga   180
tttgattttc tcttatag                                                 198

<210> SEQ ID NO 328
<211> LENGTH: 207
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 328
atttccaaac ctgtgatctg aaaagatagc tgatttcccc tcaacctttc ttaccttcg    60 cgatgccaag aactccatgc ccttagccac ttggaagctg taacagatga gatgctccaa   120
ggtcaggaag tccttataca gatcttcagg agctgtccaa agaggcagga ggatggagat   180
cagtatttcc atgagttagt gtgatgt                                       207

<210> SEQ ID NO 329
<211> LENGTH: 266
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 329
acaccctatc accctgtctg ctctgacaag agcatgccat agcatgcagg aagcactagc    60
cagtaccttc ctcttcttct acatcactga gggacttctc ctccacaaat ccagagctgg   120
ctgagctctg gctactggtg atgctgtcca agcgccgttt cagatccaca gggattgctc   180
caacgtagtc tttcccttga cggaatcgtg cccctttggt ctataaaaaa gcaaggaac   240 aaacaaactc cttgaataca aaatga                                              266

<210> SEQ ID NO 330
<211> LENGTH: 195
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 330
gtaccatttt gagtttccct tcattttata acatggccag agcaggatta ggagatgaca     60
taccttgtag gggacaaatt catttctctt gctcctcagg taagtggaca ggtttccaaa    120
tttgcagaat tccacaatca ccatgagtgg ccctgcaggc agcatgtcca ggaaggaaaa    180
tgggttttca ctcat                                                     195

<210> SEQ ID NO 331
<211> LENGTH: 206
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 331
agaggcatgt taaaattggg tgaccaaaac cacccacagt tactcacctc ctggcttggt     60
acaggcacct agaaggttga ccacattgag atggtgacca atatgaatga ggatcttgag    120
ttcagacatg agagctcgat gctcactgtg tgttgctcct tctacaaata cagtacaaag    180
agggaaatca taggtatgga catttc                                         206

<210> SEQ ID NO 332
<211> LENGTH: 226
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 332
actgatacaa gccttgcaac atatttaaag actagataaa acagaaagat agatcaccac     60
ataattttgc ttttaccttt caacattttg actgctactg tcctgcaagt tgctgtcttg    120
tcaattccaa aggcatctgc ttcaatcact tggccaaagg caccacggcc aagaggctta    180
cctagagtca acaacaacag caacaagaaa acagacttgg attact                   226

<210> SEQ ID NO 333
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 333
atggcctggt aaacacaata tcaaattaat agcaattgaa aatgcaccta gcttcagccg     60
gtctctgggg aattcccatt tgctggcatc ataaggcagt cgttcacaat gttcatccaa    120
tgggagttca tctggatcca tgacgatgga caagtagcct gtcttcagtt cccctccatt    180
ggcctggaaa gcatcaatcc ttccagtcat aaacacactg ttgtttggct gttgtt        236

```
<210> SEQ ID NO 334
<211> LENGTH: 214
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 334
tcattaatca tgaaaaccaa tgtgcatggg cagaagggaa attatttttt tacccgctta      60
acggtccgta ggatgatgac aagaagtagc cagaagaaca tggcaatcac cgccgtgcct    120
actagaataa tgatttccaa gttcgtcttt tcctgggcac ctggaaagac acaattgaat    180
gagtatcaac agttggaaac ttatactttt tgtt                                214

<210> SEQ ID NO 335
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 335
gctgcatagc attccatggt gtatatgtac cacatttttt tttatcccac tgaccttcta      60
ttatgaaaaa tgcctccact tttgcacagc caagaacact gcatgcctgg caggtgtaga    120
ggccttcgtc ctccttcctc actctgcgga tagtgaggtt ccggttccca tccttcaata    180
caatgcctaa cagaggaaga aaacgatcat tctcatttat gatgatgtag tctgtgaagt    240
ttttca                                                               246

<210> SEQ ID NO 336
<211> LENGTH: 244
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 336
ctgggaaagt tctgcaaccc aagagtgata gccaaattct atttacctga gtcttctaca      60
agggtctcat tatctttaaa ccacatgatc tgtggagggg gattcccaga tgccgtgcat    120
gagacttcga tgctttcccc aatacttgtc gtctgattct ccaggtttcc tgtgatcgtg    180
ggtgccacac gctctagaca cacaaaaaga aaatcacaga acatggaatt ataacttttg    240
aaat                                                                 244

<210> SEQ ID NO 337
<211> LENGTH: 247
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 337
cattccaact gcctctgcac aatgatccag aattgtctcc ctacctagga ctgtgagctg      60
cctgaccacg caatgtcttt tcttggtctt cctgtcttga gcaaggcaga catagtctcc    120
ttggtcctgc aaggatgcat tcttaagctc catgatcaaa atgtcatttg tgctattaga    180
gaacatggtg gcattcaatt tccaaagagt atccaagttc ttgcaaacag gtgtgggcaa    240
```

```
ctctccc                                                            247
```

<210> SEQ ID NO 338
<211> LENGTH: 262
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 338

```
gaacatggtg gcattcaatt tccaaagagt atccaagttc ttgcaaacag gtgtgggcaa    60
ctctcccaca tggattggca gaggctgtgg gccaagcttg taccatgtga ggttctcaaa   120
cgtagatctg tctgcagtgc accacaaaga cacgctctcc tgctcagtgg gctgcatgtc   180
aggttgcaaa gtaatttcag gaccccctaa aatgaagagg ccatagttat tgaatggtga   240
tttaacttgg tacagctcac ta                                           262
```

<210> SEQ ID NO 339
<211> LENGTH: 194
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 339

```
ctgtgtgagt gatccaaccc aaacctccag agaagagtac ttactggtca cgtggaagga    60
gatcaccctc tctcctctcc cgactttgtt gaccgcttca catttgtaca aagctgacac   120
atttgccgct tggataacaa gggtacttac agtctgtgcg gggaaaaaac aaatcccagg   180
ccataaacaa cgcg                                                    194
```

<210> SEQ ID NO 340
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 340

```
atgcaagatg gcaggaaagc aaagagcatg tggccttact cacctgggct cgttggcgca    60
ctcttcctcc aactgccaat accagtggat gtgatgcggg ggaggaatgg catagaccgt   120
acatgtcagc gtttgagtgg tgccgtactg gtaggaatcc acaggagaga ttagagattt   180
ctcaccaatc tggggtggga ctgaagatgg gaaaaacaac ttttgaattg tcagtcagct   240
ttgaag                                                             246
```

<210> SEQ ID NO 341
<211> LENGTH: 262
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 341

```
caatgtatca taataaatct tgggcagaga ggaaaattga atggactcac catacacaac    60
cagagagacc acatggctct gcttctcctt tgaaatggga ttggtaagga tgacagtgta   120
atttcctgtg tctctttcac tcacttccat aatcgtcagt acatgccccg ctttaattgt   180
```

```
gtgattggac tcaaggggta ttccattttt atacctatga aaaaaaattc tcaggaatta    240
gtatagtcaa aggatttgct ct                                             262
```

<210> SEQ ID NO 342
<211> LENGTH: 215
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 342

```
atttgctctc acacgaaatg atgctttgca tttatttcca gtagttacca ttttatttct    60
gggggtgggt aaccaaggta cttcgcaggg attctgacac gctcccccac cgtggcttcc   120
accagagatt ccatgccact tccaaaagca acaaaaggtt tttctggaag aaaataaaaa   180
aaaaaaaagg tcaacttact gtaaatggtc atttg                              215
```

<210> SEQ ID NO 343
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 343

```
tttaaattat ctcacttgtc aaggcacaga ataatttcca agaccatagc ttaccatgga    60
ccctgacaaa tgtgctgttc ttcttggtca tcagcccact ggatgctgca caggtgtaca   120
atccttggtc actccgggtt acaccatcta tagttaaggt gctcaaaaat ttcttcatct   180
cactcccaga ctgggttttt aggtctcggt ttacaagttt cttatgctga tgctgaaaaa   240
aagagttgac tgaacttcca aagcacagca tataacatta cccaataa                288
```

<210> SEQ ID NO 344
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 344

```
ctggggctta ttatctaagt atttggaggt ctggctttga atcattagcg ttaccttcga    60
agaagggtat tcccagttga agtcaatccc cacatttagt tcagttcttg ctgtacaatt   120
taagacaagc ttttctccaa cagatagttc aattccatga gacggactca gaaccacatc   180
ataaatccta taccctagag caagtaaatt gaaaaaacag aacatgagag agcaaataag   240
cctata                                                              246
```

<210> SEQ ID NO 345
<211> LENGTH: 284
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 345

```
atctccaaga tcttaataca aggatatgtt attaatgata tggaaggaa atgtcctctt     60
```

```
acctacaacg acaactatgt acataataga ctggtaactt tcatcattaa ttttgcttc      120 acagaagacc atgccagcat agctgatcat gtagctggga atagtaaagc ccttcttgct      180
gtcccaggaa attctgttac catcaggaac aaatctcttt tctgggtatc tctgggtaat      240
aaaaagacat atcaaatatt taatccagta ccaaaaatga gagc                      284
```

<210> SEQ ID NO 346
<211> LENGTH: 297
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 346

```
tcattgtgaa tattataaac aggttaccca tcttaatatt agcttaaaat tataaaaact      60
taagagacga ttggaggaga tgcaacttac tgcacaaagt gacacgttga gatttgaaat      120
ggacccgaga catggaatca ccacagtttt gtttttgttc tcagtaatgt acacgactcc      180
atgttggtca ctaacagaag caataaatgg agatctgtaa tctagaagaa aatttagttt      240
tattaatgag ttaatagtat ttactagaaa agttggtcat ttttcaggtt cctaaac        297
```

<210> SEQ ID NO 347
<211> LENGTH: 296
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 347

```
aactggtaaa gagacgtggg aaatgaattt tatttcacca cttaccttga acatagacat      60
aaatgaccga ggccaagtca gtttcccggt agaagcactt gtaggctcca gtgtcatttc      120
cgatcacttt tggaattgtg agtgtcttac agaagaggcc atcgctgcac tcagtcacct      180 ccacccttg ctcactgcca ctctgattat tgggccaaag ccagtccaag tccctctgtc      240
ccctgaaaaa ttaatttcag ggaggtatta atatgaagtg ccagactgtg aggcta         296
```

<210> SEQ ID NO 348
<211> LENGTH: 207
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 348

```
aattatttcc actcaataaa caatcagtta cttaacacaa gaaatctaga tctagaatga      60
atccttacct gcaagtaatt tgaagagttg tattagcctt aattgtaagt atgtcttttt      120
gtatgctgag cctgggcaga tcaagagaaa cactaggcaa acctagaaac aaattaaata      180
aatgaatgta gttgccactg agttaga                                         207
```

<210> SEQ ID NO 349
<211> LENGTH: 181
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 349

```
agatctggct ttcaggtcct ctccgccctc acccgacctg tctgccttcc tcctccagag    60
tgggctcctt acccacagag gcggcccggg tctccacgca gagccacagg gcgacggcca   120
gcagcacctt gctctgcatc ctgcacctcg agccgggcga aatgcccaga actcgggagc   180
c                                                                  181
```

<210> SEQ ID NO 350
<211> LENGTH: 290
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 350

```
ggcctgaacc cccaagtgct gggggtcttg tccgatgctg cttagtagct gttgtctgtg    60
aagaaagtca cgcgggcaga cggggagcag tggtcctcct cgcttggctc cgacagctcc   120
ccatactcgc tgttgtaaaa cacctggcct cctcgggccc ccgctcagg ccgccgccgc    180 ctcccttggg agtcagggtg tgccctggtc acagccacat tctggccagg tcctttacag   240
ctgccaagac agggaaggtg gtgttagtaa gagaagaagg ctgggtggcg              290
```

<210> SEQ ID NO 351
<211> LENGTH: 265
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 351

```
ccttacgaat tcctgacgct gcctccctg aggcggcccc agccctgagc cgagagcgca    60
gccccacccc ttcatgtgaa gtaccacaga gcctttgtag gtcgttgggg tcatggggaa   120
ttcctcaaat gtcttcatcc tggaggaacc acgggtctca gccctctgg ccaggcaccc    180 gggaaaggac acccagttgt aatacctgtg gggagaaatc agaaggtgct gaggaacgcg   240
ctgcagcaac cctcctcgaa cttct                                        265
```

<210> SEQ ID NO 352
<211> LENGTH: 245
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 352

```
acatggcttt ctcccaccct actcctggac ctgcaggaca gctgacctgg cggccaggct    60
gtggcgctgc aggcttggcg ggctgtcctc agcgtcagcc tgggcgatgt gtagggccat   120
ggtggacacc tgcgagaagc tgccctcttc tgagctctga gagctgcgcg gggccatgca   180
gacctcctct tcctcctggc gggaacagga gaggcagcca ggccagaaac caccagccac   240
tgccc                                                              245
```

<210> SEQ ID NO 353
<211> LENGTH: 212
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 353

```
ggggccaaag gccatagtag aacagggtgg ggaaggggct cacttgcagg ccccctgccct      60
ggagcaggtc cccaggatc tccaccagct ccgagaatgc aggtctcgcc ttggggtctc       120
cggaccagca gttcagcatg atgcggcgtc tgcaggatca cgtgggctgc tggactgcat      180
gcaccccacc cccgtcccag gaccttcagt gc                                    212
```

<210> SEQ ID NO 354
<211> LENGTH: 243
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 354

```
gacgcttgct gtccccaaaa cctgcagggc catggggagg ctcacatggc gggagtggcc      60
agctccgggg ccctcatcct tgtgccgtct ctcagccgct ggcagaactc ctcattgatc     120
tgcaccccag ggtacgggga ggcccctgac aacaggaagg ggaggtgggt ggggagcaag     180
cctcctgcgg ctcagcccag ccccccaagt caccccatcc tgtcccttcc ccatcaagtc     240
acc                                                                    243
```

<210> SEQ ID NO 355
<211> LENGTH: 293
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 355

```
ttcagaacga cctggcacac acctccaggt gcccagtccc ttactccagc aggggcggtc      60
atgtaacctg ccgccagtga cctcgcctcc tctccccacc ggcacccat cctgcactca     120
cccagagaga agatctccca gagaagcacc caaaggacc acacgtcact ctgcgtggtg      180
tacaccttgt cgaagatgct ttcaggggcc atccacttca ggggcagccg ggcctgggga     240
gacagaggga agcttgtccc gtggtggatg gggagacgga gggaagcgtg tcc             293
```

<210> SEQ ID NO 356
<211> LENGTH: 252
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 356

```
ccacccccttc acctgttccg ccccacgttc cctctcctca atggcctgca ctcacactgc     60
ccttgcggac gtagtcgggg tctttgtaga tgtcccgggc aaggccaaag tcacagatct     120
tcaccacgtc gctttccgac agcagaatgt tccgagcagc caggtctctg tggatgcact     180
ggggtgcggg gaggcggcag gggggctgtc agtgcaggcc cctggggtaa tacccacacc     240
cgaaactcca gg                                                          252
```

<210> SEQ ID NO 357
<211> LENGTH: 223
<212> TYPE: DNA

<213> ORGANISM: Artificial Sequence
<220> FEATURE:
<223> OTHER INFORMATION: Description of Artificial Sequence: Synthetic
      nucleotide construct

<400> SEQUENCE: 357
atgcaccctt tcccgtctg aagggccttc gggggaagct cacctttcgg gaagccagga    60
actccatccc tctggccacc tggaagctgt agcagacaag atcttccatg gtcagcgggc   120
tcagccacag gtcctcagct acacagtgga gccaggtggg ctcaggaggc gcctcctccg   180
cggcctccat ctacccagcc ccagggaaca gctaacaagc atg                    223

<210> SEQ ID NO 358
<211> LENGTH: 353
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 358
gcccgtcagg cactaggaaa agggaagagg ccaggctctc accttcttgg tctggagaag    60
cccgcctcgc tccgccctcg gtcttcgaga accgcgcgaa gaggaccctg tcgctgctcc   120
ccggccgcct ccgatccagc ctggcgagct ccaccatggc gcggaagcgt ccgcgctgct   180
cgggagactt ctcctgcgga tgcacgaagc tggctcgagg gcgcccagtc gtccgccgca   240
gaggcgcctc cattccccg ccgcccgcgg cgccccgcag gccgcccgct caccgcgcag    300
gggctgaagg cgtcccgctt ggcgcgcagg aagttggaga ggttgccgta ctt          353

<210> SEQ ID NO 359
<211> LENGTH: 371
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 359
cggatgcacg aagctggctc gagggcgccc agtcgtccgc cgcagaggcg cctccattcc    60
cccgccgccc gcggcgcccc gcaggccgcc cgctcaccgc gcaggggctg aaggcgtccc   120
gcttggcgcg caggaagttg gagaggttgc cgtacttgca gaactccacg atcaccatga   180 ggggggcctgc ggcgggaccg ggcggcggcc gtgcgttcgg aacccggggc gcgctgcggg   240
cgcgctccgc gtttgcaccc gcgccccctc ccgcccgcgg cgccccgcgc ccggggtctc   300
gccgtcccag cgggccgccc gctccgtacc ctgcggcttg gtgcacgccc cgaggaggtt   360
gaccacgttg a                                                       371

<210> SEQ ID NO 360
<211> LENGTH: 375
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 360
gaactccacg atcaccatga gggggcctgc ggcgggaccg ggcggcggcc gtgcgttcgg    60
aacccggggc gcgctgcggg cgcgctccgc gtttgcaccc gcgccccctc ccgcccgcgg   120
cgccccgcgc ccggggtctc gccgtcccag cgggccgccc gctccgtacc ctgcggcttg   180

```
gtgcacgccc cgaggaggtt gaccacgttg aggtggttgc cgatgtgaat gaggatcttg    240
agctccgaca tcagcgcgcg gtgctcgctg gccgtggcgc cctctggagg ggacacgggc    300
ctcacaccgg ccccgaccct ggcaggtccc cgttccccgc acccggcgc ttttgggagg     360 gggagggtta ctaag                                                     375
```

<210> SEQ ID NO 361
<211> LENGTH: 194
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 361

```
gctgctcctc accagctagg ctgccccttc cgcccgctga ccccacacct ttcagcattt     60
tcacggccac ggtgtcacag ctgctgccct tgtggatgcc gaaagcggag gcttccacca   120
ccttcccgaa ggcgccgtag ccgagcactc tccctgtcgg gcaggggc cagttgcagg     180 tgagctgtac gggg                                                     194
```

<210> SEQ ID NO 362
<211> LENGTH: 229
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 362

```
gggcaggagg tgtgggttgg gcaggctggt gctggcctca cccaggtgca gccgctctcg     60
ggggaattcc cactggctgg catcgtagga caggtattcg cattgctcct ccagaggcac   120
ctccccgggg tccatgatga tggacaggta gcccgtcttg atgtctgcgt gggccggctg   180
cggggagggg acagggagga gtggggcagc tcactgattt ggccatacc               229
```

<210> SEQ ID NO 363
<211> LENGTH: 228
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 363

```
ctggggacgg gaagggagtt gagggtgca gcctgaggcc agaccttcca cggccacgct      60
ggcggaggag ttgacgcagc ccttggcgtt gcacacgctg cacagatagc gtcccgcatc   120
ctcctcgcgc acgcgctgga tgctcagctt ctggttggag tccgccaagt cgactcctgc   180
agggggtggg gtggaggtgc gggtccacct gggtttggga tcgtcggc                228
```

<210> SEQ ID NO 364
<211> LENGTH: 263
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 364

```
gggtccacct gggtttggga tcgtcggcct cgcgggcctc cggacctgcc cttcgccagg     60
```

```
gccaccctcc ctaccagact tttcctccag cagcctctcg tctttgtacc acacgatgct      120
gggcgcgtgc gctccggcca ccaagcactg catctccagc gagtcgctca cgttcaccag      180
gaggtcggtc aagttctgcg tgagccgagg ggcttccagg gctggggca ggggtcgaga       240 gggagctaag tggagctgca ctt                                              263
```

<210> SEQ ID NO 365
<211> LENGTH: 205
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 365

```
cccctcctg accctgtacc caggcctccc cgccctggtc tggtcactca ctggtcacat       60
agaagtagat gagccgctca tcctggccca ccttgttgga gaccacacac ttgtacatgg     120
cagacacgtt ggcattctgg atcaccagct tgctcacagt ctgggagagc acaggcacaa     180
ggatccattt cctgcccaag ttctc                                           205
```

<210> SEQ ID NO 366
<211> LENGTH: 222
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 366

```
ccttctcctt ctccctgggc actcagcagc gcggctggcc tgtaccttat tctttccctc      60
cacaaactcg gtccaggtgt ccaggctctc gatggggttc acggcatcct gcgtggtcac     120
cgccctccag tcacggcact gtggcatgag gtcttgctgc tgccgccgcc ggctgccagg     180
accagaagag gcaagggcag gtcagggata caggcaggaa gg                       222
```

<210> SEQ ID NO 367
<211> LENGTH: 309
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 367

```
ttcctcatgg ctgaggctgg gggctgtggc tgtgcagggg acctgaggct ggagctgtac      60
tcacagacta cgctgggcaa acatcttgca gggtgtccag ggccgccagt gccactggat     120
gctgagaggc aggggcaccc cgtaggccgt gcaggtgagg gctggcggc tgtgacgcga      180 gtagatgctg gggaggagg cctccttctc atgtatctgg gggggcactg tgggcacaca     240
gatggccggt cagctggcct ccaatgccag gccgcccacc cgtgcgctct cccgtccctg     300
acctaccat                                                             309
```

<210> SEQ ID NO 368
<211> LENGTH: 294
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 368

```
cactgtgggc acacagatgg ccggtcagct ggcctccaat gccaggccgc ccacccgtgc    60
gctctcccgt ccctgaccta ccattcacca ccagctccag gctgatgttg cgcctcaggc   120
cagcagcgga gttccacagg gcgagggtgt aggtgcctgt gctggcctct gtcacctcct   180
tgagcaccag ggcatgtgga ctgtggcgcc cggacagtgc ctttccatcc ttgtacctgg   240
ccagggaagg gaggtcaggg cccatacaga tcccaccaca gccccaacct catg          294
```

<210> SEQ ID NO 369  
<211> LENGTH: 215  
<212> TYPE: DNA  
<213> ORGANISM: Artificial Sequence  
<220> FEATURE:  
<223> OTHER INFORMATION: Description of Artificial Sequence: Synthetic nucleotide construct

<400> SEQUENCE: 369

```
ctggacttgg aagggtatcg gcggggtcgg tggggagcca gggctgttac cactggaact    60
cgggcggggg gtacgctgcc agcttcacgg gcagcttcac cagctcgtct cctgccgtgg   120
cctccaggat gggtcctttg agccactcga cgctgatgaa gggattttct gccggacagg   180
agaagtcact gtaaatccag gactgacccg tcgtg                               215
```

<210> SEQ ID NO 370  
<211> LENGTH: 384  
<212> TYPE: DNA  
<213> ORGANISM: Artificial Sequence  
<220> FEATURE:  
<223> OTHER INFORMATION: Description of Artificial Sequence: Synthetic nucleotide construct

<400> SEQUENCE: 370

```
ctgagtgctc aagggcaccg tgagctctgg gcccaggccc acagggcaca aggaccctgg    60
tttcccaggc cataccatgc acaatgacct cggtgctctc ccgaaatcgc tggatgccgt   120
tgttggcctt gcacacatac gagcccaggt cgtgctggct gacgttgtgg atggtcagga   180
tgctggagag ttctgtgtgg gtctgctggg agcgtcgctc gggcacccac ttacccgct    240 ctgcctgccc gcacccaggg aagccccgcg tcagcaggcg ggctcctgca cagctacccc   300
accgaaggca cacctcccag cccagccagc ggtggctccg gaagccctgg acccaggccc   360
tgagttttct ttgggtggaa cact                                           384
```

<210> SEQ ID NO 371  
<211> LENGTH: 374  
<212> TYPE: DNA  
<213> ORGANISM: Artificial Sequence  
<220> FEATURE:  
<223> OTHER INFORMATION: Description of Artificial Sequence: Synthetic nucleotide construct

<400> SEQUENCE: 371

```
ggtcatccca caccacctcc tgcccgtctg gccacagcac cgagctttgc tggagggaca    60
aggccaccat cattgcccag ctgcccctttg ctcctggcca gacaggcggc cgcctttccc   120
aggggtggga tggagggtc ggatgctggg gttggggtgg ggccgtaccg agcgcagcgt   180
gacattgagg ccggggatgg acaccagaca gggcacccac atggcgtcct tcctgttgac   240
caagagcgtg tcaggcttgt tgatgaatgg ctgctcaaag tctatggaga gggagcaagc   300
tgttggggaa gggacgtggc ggccaggctg ggggagggct ccacggggct gggtggtgct   360
ggtcctgaac cagc                                                      374
```

<210> SEQ ID NO 372
<211> LENGTH: 451
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 372
gccccgttct ctcctcctgc cagcccaggg tccacaggct gggggcggtg tgggcccag      60 ctgcccggga ccctgctcca gcctggcccg cctccaagtc tcacctctca cgaacacgta    120
ggagctggcg gccgtggtgc cctcgatgcg tgccttgatg tacttgtagt agcagacgta    180
gctgcctgtg tcgttggcat gtacctcgtg cagcagcaac accttgcagt agggcctggc    240
gtctgtgccc tcgcagtctc gcaccacccc cgtgtcctcg ctgtccttgt ctccggtggc    300
tggcgcctcc tgagctcctg gccaagccca ctcgaggggg tgctgtcccc tggcagagga    360
caggagtggt caggtgggcc ccagggcagc ccatggggac tgtccctgag aagcctccct    420
caggccgagc ctcaccaggt ttgtcttacc c                                   451

<210> SEQ ID NO 373
<211> LENGTH: 201
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 373
gggcttgtgc agcctctctg gcctgccagt gggagaggga cccagtacct gcaggagatg     60
gacaggctgt caccggtgtc gatgacgtgt gactcctccg tgatgttcaa ggtcgggggg    120
gtcatggagt agccactcac caggcctggg gtgggagaca gggtcagcgt ggtgctgggc    180
tgtgacttgg cacgacgttg a                                              201

<210> SEQ ID NO 374
<211> LENGTH: 301
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 374 cccctteccte atcccgaggt cccgcgcccc aagcgccgtg ctcccctcag gcgtccgcgc     60
accagggcca ccgtgtcccc cgcccgtacc cggcggagcg gtctcagcgc ccgccccagg    120
tgcgcggtac cccctccccg gccagcccca cgctcgggcg ggtggcccgt tcgccgcgct    180
caccgtccag gagtcccagg cagagccaca gtcgcaggca cagcgcggcg ccccgctgca    240
tctccggccg ctgcgcgtgg gtccgacccg agcggccgcg gctcggggct gaaagtgtcc    300
g                                                                    301

<210> SEQ ID NO 375
<211> LENGTH: 313
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 375

```
ccagtattga tcgggagagc cggagcgagc tcttcgggga gcagcgatgc gaccctccgg    60
gacggccggg gcagcgctcc tggcgctgct ggctgcgctc tgcccggcga gtcgggctct   120
ggaggaaaag aaaggtaagg gcgtgtctcg ccggctcccg cgccgccccc ggatcgcgcc   180
ccggaccccg cagcccgccc aaccgcgcac cggcgcaccg gctcggcgcc cgcgccccg    240 cccgtccttt cctgtttcct tgagatcagc tgcgccgccg accgggaccg cgggaggaac   300
gggacgtttc gtt                                                      313
```

<210> SEQ ID NO 376
<211> LENGTH: 255
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 376

```
ttctgcattt ctcagtattt catgtgatat ctgtcttttt cttccagttt gccaaggcac    60
gagtaacaag ctcacgcagt tgggcacttt tgaagatcat tttctcagcc tccagaggat   120
gttcaataac tgtgaggtgg tccttgggaa tttggaaatt acctatgtgc agaggaatta   180
tgatctttcc ttcttaaagg ttggtgactt tgattttcct acacaaataa aattggagaa   240
aatctaagtg gagaa                                                    255
```

<210> SEQ ID NO 377
<211> LENGTH: 274
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 377

```
agttcctcaa aagagaaatc acgcatttat gttttctctt cttagaccat ccaggaggtg    60
gctggttatg tcctcattgc cctcaacaca gtggagcgaa ttcctttgga aaacctgcag   120
atcatcagag gaaatatgta ctacgaaaat tcctatgcct tagcagtctt atctaactat   180
gatgcaaata aaaccggact gaaggagctg cccatgagaa atttacaggg tgagaggctg   240
ggatgccaag gctgggggtt cataaatgca gaca                               274
```

<210> SEQ ID NO 378
<211> LENGTH: 225
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 378

```
taaaggagct ggaaagagtg ctcaccgcag ttccattctc ccgcagaaat cctgcatggc    60
gccgtgcggt tcagcaacaa ccctgccctg tgcaacgtgg agagcatcca gtggcgggac   120
atagtcagca gtgactttct cagcaacatg tcgatggact tccagaacca cctgggcagc   180
tgtaagtgtc gcatacacac tatctctgcc tccagctcct atggg                   225
```

<210> SEQ ID NO 379
<211> LENGTH: 172
<212> TYPE: DNA

<213> ORGANISM: Artificial Sequence
<220> FEATURE:
<223> OTHER INFORMATION: Description of Artificial Sequence: Synthetic nucleotide construct

<400> SEQUENCE: 379

| | | | | |
|---|---|---|---|---|
| gaaagggcgt catcagtttc tcatcatttc actgagatat gcatctatta cttttacatt | | | | 60 |
| tcaggccaaa agtgtgatcc aagctgtccc aatgggagct gctggggtgc aggagaggag | | | | 120 |
| aactgccaga aacgtaagtc agtgaacagc ctcagaccca tgtgtgaccg cc | | | | 172 |

<210> SEQ ID NO 380
<211> LENGTH: 241
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 380

| | | | | |
|---|---|---|---|---|
| ctaccctcac tcttcagctc acagggaacc tttgctcttt ttcagtgacc aaaatcatct | | | | 60 |
| gtgcccagca gtgctccggg cgctgccgtg gcaagtcccc cagtgactgc tgccacaacc | | | | 120 |
| agtgtgctgc aggctgcaca ggccccgggg agagcgactg cctggtaaga tgcccctcca | | | | 180 |
| gcagcctccc tggagcaggc tggggctgca cccgccccac ccacaccagg acagaagact | | | | 240 |
| t | | | | 241 |

<210> SEQ ID NO 381
<211> LENGTH: 235
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 381

| | | | | |
|---|---|---|---|---|
| gagtgtactt acctcacttg cccagcgtgt cctctctcct ccataggtct gccgcaaatt | | | | 60 |
| ccgagacgaa gccacgtgca aggacacctg ccccccactc atgctctaca accccaccac | | | | 120 |
| gtaccagatg gatgtgaacc ccgagggcaa atacagcttt ggtgccacct gcgtgaagaa | | | | 180 |
| gtgtccccgt gagtcctcct ctgtgggccc tctaactggt caggcatcct tgtcc | | | | 235 |

<210> SEQ ID NO 382
<211> LENGTH: 254
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 382

| | | | | |
|---|---|---|---|---|
| ttccatcacc cctcaagagg acctggaccg cctgtgtgag gcccgagcac ctggtgccac | | | | 60 |
| cgtcatcacc ttcctttcat gctctcttcc ccaggtaatt atgtggtgac agatcacggc | | | | 120 |
| tcgtgcgtcc gagcctgtgg ggccgacagc tatgagatgg aggaagacgg cgtccgcaag | | | | 180 |
| tgtaagaagt gcgaagggcc ttgccgcaaa ggtaggaagc ccgccggtgt gcggacgagg | | | | 240 |
| cttgttctcg gctg | | | | 254 |

<210> SEQ ID NO 383
<211> LENGTH: 397
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 383
ttaatccaac aaatgtgaac ggaatacacg tctctcttat ctctgcagtg tgtaacggaa      60
taggtattgg tgaatttaaa gactcactct ccataaatgc tacgaatatt aaacacttca     120
aaaactgcac ctccatcagt ggcgatctcc acatcctgcc ggtggcattt aggggtgag      180 tcacaggttc agttgcttgt ataaagaaaa acaaaatctg ccttttttaac tggtagagat    240 tggtgatcaa taatcaccct gttgtttgtt tcagtgactc cttcacacat actcctcctc    300
tggatccaca ggaactggat attctgaaaa ccgtaaagga aatcacaggt ttgagctgaa    360
ttatcacatg aatataaatg ggaaatcagt gttttag                              397

<210> SEQ ID NO 384
<211> LENGTH: 181
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 384
aactcctacg tggtgtgtgt ctgaagtctt tcatctgcct tacagggttt ttgctgattc      60
aggcttggcc tgaaaacagg acggacctcc atgcctttga gaacctagaa atcatacgcg     120
gcaggaccaa gcaacagtaa gttgaccaca gccaaagcct ggtagattac atttgccttt    180
t                                                                     181

<210> SEQ ID NO 385
<211> LENGTH: 304
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 385
acattgtttt tataattttt caccacatga tttttcttct ctccaatgta gtggtcagtt      60
ttctcttgca gtcgtcagcc tgaacataac atccttggga ttacgctccc tcaaggagat    120
aagtgatgga gatgtgataa tttcaggaaa caaaaatttg tgctatgcaa atacaataaa    180
ctggaaaaaa ctgtttggga cctccggtca gaaaaccaaa attataagca acagaggtga    240
aaacagctgc agtaagtcac cgctttctgt ttagtttatg gagttggttc taatgggtcc    300
ttta                                                                  304

<210> SEQ ID NO 386
<211> LENGTH: 222
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 386
ccctgctctg tcactgactg ctgtgaccca ctctgtctcc gcagaggcca caggccaggt     60
ctgccatgcc ttgtgctccc ccagggggctg ctggggcccg agcccaggg actgcgtctc    120 ttgccggaat gtcagccgag gcagggaatg cgtggacaag tgcaaccttc tggagggggta   180

```
ggaggttatt tctttaatcc ccttgcgttg atcaaaaata ag                         222
```

<210> SEQ ID NO 387
<211> LENGTH: 176
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 387

```
atgtctcagg ggtgggctga cgggtttcct cttcctcctc tcagtgagcc aagggagttt      60
gtggagaact ctgagtgcat acagtgccac ccagagtgcc tgcctcaggc catgaacatc     120
acctgcacag gacgggtaag agccccttgc tgctatccac gtccatttca tgggaa         176
```

<210> SEQ ID NO 388
<211> LENGTH: 256
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 388

```
gaaaagaaag agacatgcat gaacattttt ctccaccttg gtgcagggac cagacaactg      60
tatccagtgt gcccactaca ttgacggccc ccactgcgtc aagacctgcc cggcaggagt     120
catgggagaa acaacaccc tggtctggaa gtacgcagac gccggccatg tgtgccacct     180
gtgccatcca aactgcacct acgggtgagt ggaaagtgaa ggagaacaga acatttcctc     240
tcttgcaaat tcagag                                                     256
```

<210> SEQ ID NO 389
<211> LENGTH: 163
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 389

```
gtttgccaaa tatagaaaga ggggatttag tcaagattta aattaaaaat gttagtggtc      60
atttttctaa tgtctttcta ttttttccca ggtcctaata aatcttcact gtctgactttt    120
agtctcccac taaaactgca tttcctttct acaatttcaa ttt                       163
```

<210> SEQ ID NO 390
<211> LENGTH: 356
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 390

```
tgttacacca gggctcccca ggcctctcac atattgaaat gtacttgtcc atctttctcc      60
aggccaggaa atgagagtct caaagccatg ttattctgcc ttttttaaact atcatcctgt   120
aatcaaagta atgatggcag cgtgtcccac cagagcggga gcccagctgc tcaggagtca    180
tgcttaggat ggatcccttc tcttctgccg tcagagtttc agctgggttg ggtggatgc     240
agccacctcc atgcctggcc ttctgcatct gtgatcatca cggcctcctc ctgccactga    300
gcctcatgcc ttcacgtgtc tgttcccccc gcttttcctt tctgccaccc ctgcac        356
```

<210> SEQ ID NO 391
<211> LENGTH: 161
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 391
aaaatctcca aaatatatgc caaagaagta gaatgagaaa aatgtatatt tctctttcac      60
ttcctacaga tgcactgggc caggtcttga aggctgtcca acgaatgggt aagtgttcac     120
agctctgtgt cacatggacc tcgtcaagaa tgaccacact g                        161

<210> SEQ ID NO 392
<211> LENGTH: 252
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 392
gaatctgtca gcaacctcac ccttccttgt tcctccacct cattccaggc ctaagatccc      60
gtccatcgcc actgggatgg tgggggccct cctcttgctg ctggtggtgg ccctggggat     120
cggcctcttc atgcgaaggc gccacatcgt tcggaagcgc acgctgcgga ggctgctgca     180
ggagagggag gtgagtgcca gtcctgggtg ggctcaggag ccctcgcacc ccgacaggaa     240
caagggccag cc                                                        252

<210> SEQ ID NO 393
<211> LENGTH: 231
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 393
gagggctgag gtgacccttg tctctgtgtt cttgtccccc ccagcttgtg gagcctctta      60
cacccagtgg agaagctccc aaccaagctc tcttgaggat cttgaaggaa actgaattca     120
aaaagatcaa agtgctgggc tccggtgcgt tcggcacggt gtataaggta aggtccctgg     180
cacaggcctc tgggctgggc cgcagggcct ctcatggtct ggtggggagc c              231

<210> SEQ ID NO 394
<211> LENGTH: 203
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 394
cagcatgtgg caccatctca caattgccag ttaacgtctt ccttctctct ctgtcatagg      60
gactctggat cccagaaggt gagaaagtta aaattcccgt cgctatcaag gaattaagag     120
aagcaacatc tccgaaagcc aacaaggaaa tcctcgatgt gagtttctgc tttgctgtgt     180
gggggtccat ggctctgaac ctc                                            203

<210> SEQ ID NO 395

```
<211> LENGTH: 305
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 395
gggtccatgt gcccctcctt ctggccacca tgcgaagcca cactgacgtg cctctccctc      60
cctccaggaa gcctacgtga tggccagcgt ggacaacccc cacgtgtgcc gcctgctggg     120
catctgcctc acctccaccg tgcagctcat cacgcagctc atgcccttcg gctgcctcct     180
ggactatgtc cgggaacaca agacaatat tggctcccag tacctgctca actggtgtgt      240
gcagatcgca aaggtaatca gggaagggag atacggggag gggagataag gagccaggat     300
cctca                                                                 305

<210> SEQ ID NO 396
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 396
ttcccatgat gatctgtccc tcacagcagg gtcttctctg tttcagggca tgaactactt      60
ggaggaccgt cgcttggtgc accgcgacct ggcagccagg aacgtactgg tgaaaacacc     120
gcagcatgtc aagatcacag attttgggct ggccaaactg ctgggtgcgg aagagaaaga     180
ataccatgca gaaggaggca agtaaggag gtggctttag gtcagccagc attttcctga     240
caccag                                                                246

<210> SEQ ID NO 397
<211> LENGTH: 186
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 397
aactttttcc aacagaggga aactaatagt tgtctcactg cctcatctct caccatccca      60
aggtgcctat caagtggatg gcattggaat caattttaca cagaatctat acccaccaga     120
gtgatgtctg gagctacggt gagtcataat cctgatgcta atgagtttgt actgaggcca     180
agctgg                                                                186

<210> SEQ ID NO 398
<211> LENGTH: 176
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 398
ttgttcattc atgatcccac tgccttcttt tcttgcttca tcctctcagg ggtgactgtt      60
tgggagttga tgacctttgg atccaagcca tatgacggaa tccctgccag cgagatctcc     120
tccatcctgg agaaaggaga acgcctccct cagccaccca tatgtaccat cgatgt         176
```

```
<210> SEQ ID NO 399
<211> LENGTH: 165
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 399
ccatcgatgt ctacatgatc atggtcaagt gtgagtgact ggtgggtctg tccacactgc    60
ctagctgagc cttggtggct gctcttagcc aaacagctga ggcctttgca tccctggaga   120
aatgtcatca cattacttaa ggcaggcaca caaatccaga aacat                   165

<210> SEQ ID NO 400
<211> LENGTH: 267
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 400
gaatagcatc tctacgggcc attctaatag cctcaaaatc tctgcaccag ggggatgaaa    60
gaatgcattt gccaagtcct acagactcca acttctaccg tgccctgatg gatgaagaag   120
acatggacga cgtggtggat gccgacgagt acctcatccc acagcagggc ttcttcagca   180
gcccctccac gtcacggact cccctcctga gctctctggt atgaaatctc tgtctctctc   240
tctctctcaa gctgtgtcta ctcattt                                       267

<210> SEQ ID NO 401
<211> LENGTH: 164
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 401
cctgcattca ggaaaagtgg atgagatgtg gtacaagcat tccatgggca acttctctgt    60 ttcttttca gagtgcaacc agcaacaatt ccaccgtggc ttgcattgat agaaatgggg    120
tatgtatgaa caccttataa gccagaattt acagctctcc acta                    164

<210> SEQ ID NO 402
<211> LENGTH: 193
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 402
ggcagccctg accggagtaa ccttccctca tttcctcctg cagctgcaaa gctgtcccat    60
caaggaagac agcttcttgc agcgatacag ctcagacccc acaggcgcct tgactgagga   120
cagcatagac gacaccttcc tcccagtgcc tggtgagtgg cttgtctgga aacagtcctg   180
ctcctcaacc tcc                                                      193

<210> SEQ ID NO 403
<211> LENGTH: 272
<212> TYPE: DNA
<213> ORGANISM: Artificial Sequence
<220> FEATURE:
```

<223> OTHER INFORMATION: Description of Artificial Sequence: Synthetic
      nucleotide construct

<400> SEQUENCE: 403
ggtgctttgc tgattacttc acctctgatt tctttccact ttcagaatac ataaaccagt    60
ccgttcccaa aaggcccgct ggctctgtgc agaatcctgt ctatcacaat cagcctctga   120
accccgcgcc cagcagagac ccacactacc aggacccca cagcactgca gtgggcaacc    180
ccgagtatct caacactgtc cagcccacct gtgtcaacag cacattcgac agccctgccc   240
actgggccca gaaaggcagc caccaaatta gc                                 272

<210> SEQ ID NO 404
<211> LENGTH: 275
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 404
ggtgttctcc gcaggatcag cttaaggcgg ctgctgaggc ctcaggctgt attcagctcc    60
gaggtgttct ggctgggcgg caggtgggaa tccaggtttt ctttgcacct ttccaggtcc   120
tggaagtatg ggtgagacag ggcactgtag gcagatattc ttttggctgg gttaaatgtc   180
aaacacttct gtaataaaga aaaaaataat tggttgatat acaatacatc aatgtaaata   240
atgtacttac agagttatcc ctttattcac tgtca                              275

<210> SEQ ID NO 405
<211> LENGTH: 160
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 405
ccatgtggct gtggcatgtg atgcctatag cagctactga actgatattt gtgcccacca    60
cccagtctgg gtagagcagg tgtctcactg gcacagtgca gacgagcttg acatcagaaa   120
aacttaccag aagtaggtct ttgcctagtt catcgatatc                         160

<210> SEQ ID NO 406
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 406
tcatcgatat ctgttacaaa cttctcaatt ggttgggcag attttgaatg aaaagcctgc    60
ctgggaaggg caacatctct aggccagtct tcttctcctg ggagtccaat cacgctacaa   120
aagaaccaca catggacata agcattagct actatgcaga agctgt                  166

<210> SEQ ID NO 407
<211> LENGTH: 173
<212> TYPE: DNA
<213> ORGANISM: Artificial Sequence
<220> FEATURE:
<223> OTHER INFORMATION: Description of Artificial Sequence: Synthetic
      nucleotide construct

```
<400> SEQUENCE: 407
taaatgtttt aatgctatgg acactggtgt aaaattataa ttattactta ctccaagatt    60
tttcctagtt gatcaacatc tgaacttcca cgaaaaagag gcctaaaaga ataaagatac   120
attttaaata agaaatgttc tcagattaca tttcaatcat atttgccatt atc          173

<210> SEQ ID NO 408
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 408
gactgtcatt caaaatagga aaataagtt taataaaagg acagcactct ctcactcacc     60
actgaggtta gagccatctg gaaactatag atgcgggcaa ggccgaagtc agcgagtttt   120
atttgtccgc tgctggtcac cagaatgttc tgtggtttta gatcgcgatg cactactcgg   180
tgtgaatgaa gaaagtccag acctcggaga agctgaaaca tcatatccta ataaaattaa   240
aaaaagaaaa tcagtaaaca ctcaaaacgg aagttg                             276

<210> SEQ ID NO 409
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 409
agactataat agtcgactgc ctgataagac atgaagatga ttcttgatac ctttatggtt    60
tcagtgggca ctccaggctc tggaactta tccaagtaag tggtcaagtc ttgatcgaca    120
tgttcaaaca ctaaagttag tttggtttct ctgtctgttc gtgacactgt gcacacatca   180
aacaacctag aagaaaaaac aaagaggtta agtaggtggc aataagcaaa gaagta       236

<210> SEQ ID NO 410
<211> LENGTH: 381
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 410
cctttctggg cctgaggatt cccggctcgg ccctccccgc gcgcgcgagg ccccagatgg    60
cgagggcgca gctccctggc tcacctgacc acgttgggt gctcgaaggt ctccaggtgc    120
ctcagcaccg ccacctcgcg gatggtggag agcggcatgc cctcctcgcc ggtctgcacc   180
cgcacgcgct tcaacgccac gaaacggcct ccgttcttca gtcgcgggc cttgaacacc    240 ttcccatagg cgccctcccc gatctccgcc acgcattcgt actgctggtc agcgcggcac   300
aggccgtcct tctccatgcc gcctggacgc cgcccgccgc ggcgccgctg ggcgggcgg    360 ggggtgcgct caactagctg g                                             381

<210> SEQ ID NO 411
<211> LENGTH: 373
<212> TYPE: DNA
<213> ORGANISM: Artificial Sequence
<220> FEATURE:
```

<223> OTHER INFORMATION: Description of Artificial Sequence: Synthetic
      nucleotide construct

<400> SEQUENCE: 411
tgaactgctc tcgccttgaa cctgttttgg cagataaacc tctcataatg aaggcccccg      60
ctgtgcttgc acctggcatc ctcgtgctcc tgtttacctt ggtgcagagg agcaatgggg     120
agtgtaaaga ggcactagca aagtccgaga tgaatgtgaa tatgaagtat cagcttccca     180
acttcaccgc ggaaacaccc atccagaatg tcattctaca tgagcatcac attttccttg     240
gtgccactaa ctacatttat gttttaaatg aggaagacct tcagaaggtt gctgagtaca     300
agactgggcc tgtgctggaa cacccagatt gtttcccatg tcaggactgc agcagcaaag     360
ccaatttatc agg                                                        373

<210> SEQ ID NO 412
<211> LENGTH: 377
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 412
cctgtgctgg aacacccaga ttgtttccca tgtcaggact gcagcagcaa agccaattta      60
tcaggaggtg tttggaaaga taacatcaac atggctctag ttgtcgacac ctactatgat     120
gatcaactca ttagctgtgg cagcgtcaac agagggacct gccagcgaca tgtctttccc     180
cacaatcata ctgctgacat acagtcggag gttcactgca tattctcccc acagatagaa     240
gagcccagcc agtgtcctga ctgtgtggtg agcgccctgg agccaaagt cctttcatct     300 gtaaaggacc ggttcatcaa cttctttgta ggcaatacca taaattcttc ttatttccca     360
gatcatccat tgcattc                                                    377

<210> SEQ ID NO 413
<211> LENGTH: 377
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 413
ggaccggttc atcaacttct ttgtaggcaa taccataaat tcttcttatt tcccagatca      60
tccattgcat tcgatatcag tgagaaggct aaaggaaacg aaagatggtt ttatgttttt     120
gacggaccag tcctacattg atgttttacc tgagttcaga gattcttacc ccattaagta     180
tgtccatgcc tttgaaagca acaatttat ttacttcttg acggtccaaa gggaaactct     240
agatgctcag acttttcaca caagaataat caggttctgt tccataaact ctggattgca     300
ttcctacatg gaaatgcctc tggagtgtat tctcacagaa aagagaaaaa agagatccac     360
aaagaaggaa gtgttta                                                    377

<210> SEQ ID NO 414
<211> LENGTH: 210
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 414

```
tacatggaaa tgcctctgga gtgtattctc acagaaaaga gaaaaaagag atccacaaag    60
aaggaagtgt ttaatatact tcaggctgcg tatgtcagca agcctggggc ccagcttgct   120
agacaaatag gagccagcct gaatgatgac attcttttcg gggtgttcgc acaaagcaag   180
ccagattctg ccgaaccaat ggatcgatct                                    210
```

<210> SEQ ID NO 415
<211> LENGTH: 206
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 415

```
ggatcgatct gccatgtgtg cattccctat caaatatgtc aacgacttct tcaacaagat    60
cgtcaacaaa aacaatgtga gatgtctcca gcatttttac ggacccaatc atgagcactg   120
ctttaatagg gtaagtcaca tcagttcccc acttataaac tgtgaggtat aaattagaaa   180
taagtatcag tctcaaaaag aatatc                                        206
```

<210> SEQ ID NO 416
<211> LENGTH: 295
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 416

```
ttgttcatgt ctggattcac attaactcta tgaccatatt ttattccaga cacttctgag    60
aaattcatca ggctgtgaag cgcgccgtga tgaatatcga acagagttta ccacagcttt   120
gcagcgcgtt gacttattca tgggtcaatt cagcgaagtc ctcttaacat ctatatccac   180
cttcattaaa ggagacctca ccatagctaa tcttgggaca tcagagggtc gcttcatgca   240
ggtaagtgct ttctgagagt agctgtgtct gttctatctg gtattgtgca attaa         295
```

<210> SEQ ID NO 417
<211> LENGTH: 225
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 417

```
actgagcttg ttggaataag gatgttataa ctttttttgct gtttaggttg tggtttctcg    60
atcaggacca tcaacccctc atgtgaattt tctcctggac tcccatccag tgtctccaga   120
agtgattgtg gagcatacat taaaccaaaa tggctacaca ctggttatca ctgggaagaa   180
ggtaagctgt tcccacaggg aatttccata gacgtggttt tcccc                   225
```

<210> SEQ ID NO 418
<211> LENGTH: 262
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 418

```
actagatacc cctctggaag ctctttccac cccttctctt cacagatcac gaagatccca    60
ttgaatggct tgggctgcag acatttccag tcctgcagtc aatgcctctc tgccccaccc   120
tttgttcagt gtggctggtg ccacgacaaa tgtgtgcgat cggaggaatg cctgagcggg   180
acatggactc aacagatctg tctgcctgca atctacaagg taggaatctc taacagctgg   240
catacatgtt tttgtttggt gt                                            262
```

<210> SEQ ID NO 419
<211> LENGTH: 295
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 419

```
tatacatttt gtttgttcgt tttccatata tgtgaaaaat tataatatat tgggttttt     60 taaaagttct atgttgtcct tgtaggtttt cccaaatagt gcacccttg aaggagggac   120 aaggctgacc atatgtggct gggactttgg atttcggagg aataataaat ttgatttaaa   180
gaaaactaga gttctccttg gaaatgagag ctgcaccttg actttaagtg agagcacgat   240
gaatacgtaa ggatcttaaa atgctttgct ggggtgtgct tggaaaatag gtttt        295
```

<210> SEQ ID NO 420
<211> LENGTH: 256
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 420

```
cagaaaattc cttggatttg tcatgtatta aactttgggt ttttttttcca gattgaaatg    60 cacagttggt cctgccatga ataagcattt caatatgtcc ataattattt caaatggcca   120
cgggacaaca caatacagta cattctccta tgtggtaagg aagattctat cctatcatgt   180 ttgatttta cttaatctat ttaaattata agatgaacaa gttactttgt tttgttttta   240
tctcccctcc aggatc                                                    256
```

<210> SEQ ID NO 421
<211> LENGTH: 277
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 421

```
aaggaagatt ctatcctatc atgtttgatt tttacttaat ctatttaaat tataagatga    60
acaagttact ttgttttgtt tttatctccc ctccaggatc ctgtaataac aagtatttcg   120
ccgaaatacg gtcctatggc tggtggcact ttacttactt taactggaaa ttacctaaac   180
agtgggaatt ctagacacat ttcaattggt ggaaaaacat gtactttaaa aaggtgttgt   240
aaatttattt tttgttgcat ctgtcaattt gaattaa                             277
```

<210> SEQ ID NO 422
<211> LENGTH: 296
<212> TYPE: DNA
<213> ORGANISM: Artificial Sequence
<220> FEATURE:

```
<223> OTHER INFORMATION: Description of Artificial Sequence: Synthetic
      nucleotide construct

<400> SEQUENCE: 422
tatatccttt tgatttgtgg atataattct aaaatatgtg tatctctaat agctaaaatt      60
cacttcctta attttttttg ttcagtgtgt caaacagtat tcttgaatgt tatacccag     120 cccaaaccat ttcaactgag tttgctgtta aattgaaaat tgacttagcc aaccgagaga    180
caagcatctt cagttaccgt gaagatccca ttgtctatga aattcatcca accaaatctt    240
ttattaggta agtagaagct tctgatgggt ataagaaaac aatgaataca aggatg        296

<210> SEQ ID NO 423
<211> LENGTH: 266
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 423
gactgtgcct ctgacctgta atcagtgcag gtgattaaat tgaatccctc tcttacagta     60
cttggtggaa agaacctctc aacattgtca gtttctatt ttgctttgcc agtggtggga    120
gcacaataac aggtgttggg aaaaacctga attcagttag tgtcccgaga atggtcataa    180
atgtgcatga agcaggaagg aactttacag tggtaagtcc tttgagcaat ggttctactc    240
agagctctgc atctttgcct ctaacc                                          266

<210> SEQ ID NO 424
<211> LENGTH: 316
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 424
ttgccaagct gtattctgtt tacagtggat aattgtgtct ttctctaggc atgtcaacat     60
cgctctaatt cagagataat ctgttgtacc actccttccc tgcaacagct gaatctgcaa    120 ctcccctga aaccaaagc ctttttcatg ttagatggga tcctttccaa atactttgat    180
ctcatttatg tacataatcc tgtgtttaag ccttttgaaa agccagtgat gatctcaatg    240
ggcaatgaaa atgtactgga aattaaggta agaaatgctt taaacactgt cttaaatcat    300
cagctcaaac ttaatt                                                    316

<210> SEQ ID NO 425
<211> LENGTH: 257
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 425
gttagcattc ctgcagaact gtgaagtgtt aacaacctt ttttttttt ttcctttcag      60 ggaaatgata ttgaccctga agcagttaaa ggtgaagtgt taaaagttgg aaataagagc    120
tgtgagaata tacacttaca ttctgaagcc gttttatgca cggtcccaa tgacctgctg    180 aaattgaaca gcgagctaaa tatagaggtg ggattcctgc attcctctca tgatgtaaat    240
aaggaagcca gtgtaat                                                   257
```

<210> SEQ ID NO 426
<211> LENGTH: 262
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 426
aatatctatc atggctaaat gctgactttt ctttatttgt cattttagt ggaagcaagc      60 aatttcttca accgtccttg gaaaagtaat agttcaacca gatcagaatt tcacaggatt     120
gattgctggt gttgtctcaa tatcaacagc actgttatta ctacttgggt ttttcctgtg    180
gctgaaaaag agaaagcaaa ttaaaggtgc attttgtta ctgttcattt ttagaagtta     240
ccttaagaac acagtcatta ca                                              262

<210> SEQ ID NO 427
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 427
ccatgatagc cgtcttaac aagctctttc tttctctctg ttttaagatc tgggcagtga      60
attagttcgc tacgatgcaa gagtacacac tcctcatttg gataggcttg taagtgcccg    120
aagtgtaagc ccaactacag aaatggtttc aaatgaatct gtagactacc gagctacttt    180
tccagaaggt atatttcagt ttattgttct gagaaatacc tatacatata cctcagtggg    240
ttgtga                                                                246

<210> SEQ ID NO 428
<211> LENGTH: 335
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 428
cattaaatga ggttttactg ttgttcttta ataattttcc ttcatcttac agatcagttt      60
cctaattcat ctcagaacgg ttcatgccga caagtgcagt atcctctgac agacatgtcc    120
cccatcctaa ctagtgggga ctctgatata tccagtccat tactgcaaaa tactgtccac    180
attgacctca gtgctctaaa tccagagctg gtccaggcag tgcagcatgt agtgattggg    240
cccagtagcc tgattgtgca tttcaatgaa gtcataggaa gaggtaagta tttccactca    300 gcttttgtt aaatacgatt ttccagtaag cattt                                335

<210> SEQ ID NO 429
<211> LENGTH: 188
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 429
atttcataat taaatgttac gcagtgctaa ccaagttctt tctttgcac agggcatttt      60

```
ggttgtgtat atcatgggac tttgttggac aatgatggca agaaaattca ctgtgctgtg    120
aaatccttga acagtaagtg gcattttatt taaccatgga gtatacttttt gtggttttgca   180 acctaata                                                             188
```

<210> SEQ ID NO 430
<211> LENGTH: 282
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 430

```
gtattcactg ttccataatg aagttaatgt ctccaccact ggatttctca ggaatcactg     60
acataggaga agtttcccaa tttctgaccg agggaatcat catgaaagat tttagtcatc    120
ccaatgtcct ctcgctcctg ggaatctgcc tgcgaagtga agggtctccg ctggtggtcc    180
taccatacat gaaacatgga gatcttcgaa atttcattcg aaatgagact catgtaagtt    240
gactgccaag cttactaact ggcaaactag ctgtaagcca gc                       282
```

<210> SEQ ID NO 431
<211> LENGTH: 206
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 431

```
attagaacag tagatgctta gtttatgctt ttctaactct ctttgactgc agaatccaac     60
tgtaaaagat cttattggct ttggtcttca agtagccaaa ggcatgaaat atcttgcaag    120
caaaaagttt gtccacagag acttggctgc aagaaactgt atgtaagtat cagaatctct    180
gtgccacaat ccaaattaag tgacaa                                         206
```

<210> SEQ ID NO 432
<211> LENGTH: 265
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 432

```
attattctat ttcagccacg ggtaataatt tttgtccttt ctgtaggctg gatgaaaaat     60
tcacagtcaa ggttgctgat tttggtcttg ccagagacat gtatgataaa gaatactata    120
gtgtacacaa caaacaggt gcaaagctgc cagtgaagtg gatggctttg gaaagtctgc    180
aaactcaaaa gttaccacc aagtcagatg tggtaatgta ttggttatct ctgagtttct    240
cctcttttac tttcatatcc aactt                                          265
```

<210> SEQ ID NO 433
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 433

```
atggtcacat ctctcaccctc atctgtcctg tttcttgttt tactagtggt cctttggcgt     60
```

```
gctcctctgg gagctgatga caagaggagc cccaccttat cctgacgtaa acacctttga    120
tataactgtt tacttgttgc aagggagaag actcctacaa cccgaatact gcccagaccc    180
cttgtaagta gtctttctgt acctcttacg ttctttactt ttacagaaat gcctgc        236
```

<210> SEQ ID NO 434
<211> LENGTH: 328
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 434

```
tttattttcc ttttgttgct actctcctga actctctcac tcatttgttt cagtggacag    60
gaaacgcacc atatccccct gcctggatgg gtgttttgg agaagcacaa gcatatagac     120
taaaatcctc tgtttggaaa ccagcccgat tcaaggaggg ttctgatgca ctgcggtgaa    180
tttttggcaa tgagcgggcc agcagctcaa tagaggcgaa atctacaaa aaaaaaaaga    240 aaaaaaaag aaaaaaaaag aaaaagaaa aaaaagaaa gaaagaaaaa gaaaaaacag      300
aaagaagaat gaaaatctgg gtggtata                                       328
```

<210> SEQ ID NO 435
<211> LENGTH: 267
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 435

```
ctatgaatgt tagtctgttc ttttggatag catgaagctt ttacttactt ggggaaagag    60
tggtctctca tctcttttct ttttgaggca ctctgccatt aatctcttca tggcttttgg    120
acagttactc cgtaccttac tgagatctgg agacaggtat cctcgtccca ccataaaaat    180
tatctggaga gagaaaaaaa agggaaataa ttcaaccttg tagataagtt gaaaaatata    240
cttcacactc attgaaaaca caataag                                        267
```

<210> SEQ ID NO 436
<211> LENGTH: 267
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 436

```
cttattttct acaactggag ccttgtatat agacggtaaa ataaacacca agacgtggta    60
aatatttacc tggtccctgt tgttgatgtt tgaataaggt aactgtccag tcatcaattc    120
atacagaaca attccaaatg catatacatc tgactgaaag ctgtatggat ttttatcttg    180
cattctgatg acttctggtg cctgttagaa catacaaaga aaaatattct tcacttcaat    240
tgaataaaga ctgaaaaaca acctact                                        267
```

<210> SEQ ID NO 437
<211> LENGTH: 226
<212> TYPE: DNA
<213> ORGANISM: Artificial Sequence
<220> FEATURE:
<223> OTHER INFORMATION: Description of Artificial Sequence: Synthetic -continued nucleotide construct

<400> SEQUENCE: 437
tcagggccaa aaatttaatc agtggaaaaa tagcctcaat tcttaccatc cacaaaatgg    60
atccagacaa ctgttcaaac tgatgggacc cactccatcg agatttcact gtagctagac   120
caaaatcacc tattttact gtgaggtctt catgaagaaa tatatctgag gtgtagtaag   180
taaaggaaaa cagtagatct cattttccta tcagagcaag cattat              226

<210> SEQ ID NO 438
<211> LENGTH: 159
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 438
tcaggatgtt ttcaaacttc gcagacaaat ttcaggaagg atactattac tcttgaggtc    60
tctgtggatg attgacttgg cgtgtaagta actgaaaaac aaaacatcat tttaacctga   120
gtagggctaa aggactctgg cctcgaaatc tacagaaca                      159

<210> SEQ ID NO 439
<211> LENGTH: 294
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 439
aaaacatcct caatggtctt caaaaataat ttacaagaca tttaacgaat ggaacttact    60
ccatgccctg tgcagtctgt cgtgcaatat ctataagttt gatcatctca aatttggtct   120
caatgatatg gagatggtga tacaagctgg agccctcaca ccactgggta acaatagcca   180
gttgtggctt tgtggaatag cccatgaaga gtaggatatt cacatgtcgt gttttcctgt   240
acaaagaaat gtgacagtaa acattaaatg tcgacaaact ttagcaattc ttac        294

<210> SEQ ID NO 440
<211> LENGTH: 197
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 440
ctgggaacca ggagctaata aaataactt ctttctctgg aaaagagtaa ttcacacaag     60
ctcacctgag tactcctact tcattttga aggcttgtaa ctgctgaggt gtaggtgctg    120
tcacattcaa cattttcact gccacatcac ctaaaaggca attgttactc caagtgtcat   180
ttcaattttt aaaattt                                              197

<210> SEQ ID NO 441
<211> LENGTH: 267
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 441

```
atgcgaacag tgaatatttc ctttgatgat attttttaca aaataaaagt tgttaaacat    60
atcctattat gacttgtcac aatgtcacca cattacatac ttaccatgcc actttccctt   120
gtagactgtt ccaaatgatc cagatccaat tctttgtccc actgtaatct gcccatcagg   180
aatctcccaa tcatcactcg agtcccgtct accaagtgtt ttcttgataa aaacagtaaa   240
aaagtcaagt caagccaaac agaaaaa                                       267
```

<210> SEQ ID NO 442
<211> LENGTH: 242
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 442

```
gacttctaag aagaaagaat tcagagaaaa aaagatatca tatactctta ccattcgatt    60
cctgtcttct gaggatgaag atgacttcct ttctcgctga ggtcctggag atttctgtaa   120
ggctttcacg ttagttagtg agccaggtaa tgaggcaggg ggggtagcag acaaacctgt   180
ggttgatcct aaattagtga aagaaaaat gtatacatta aggaggagca agtatgttaa   240
tt                                                                  242
```

<210> SEQ ID NO 443
<211> LENGTH: 162
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 443

```
tataaggaa ataagcagca aagcaattgc agtttccttg agttttttaaa aaaacctgaa    60 atcactactt acctccatca ccacgaaatc cttggtctct aatcaagtcc tacaaataaa   120
tagtaatgta tatttattcc aagcaagcat ataatcagag ag                      162
```

<210> SEQ ID NO 444
<211> LENGTH: 333
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 444

```
ttatagcaga aaaataaaga tacatacttg gttttttttt agttctagca atgctggata    60
cttacatcaa tattgacagg ttctattgtg tttatatgca cattgggagc tgatgaggat   120
cggtctcgtt gcccaaattg atttcgatga tcttcatctg ctggtcggaa gggctgtgga   180
attggaatgg attttgaagg agacggactg gtgagaattt ggggcctgga aaaatgaagt   240
cattggaaga taagattcag agtaacgata taaaggtaat aatatttaaa aggaagata   300 aaaggatttt cttgtttta tattctcaaa atc                                333
```

<210> SEQ ID NO 445
<211> LENGTH: 206
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 445
gttcaagtag catgtcgccc aagagcagaa gtcaaaccat acccaataga gtccgaggcg    60
ggtgcggaag gggatgatcc agatgttagg gcagtctctg ctaaggacgc ctcttcctgt   120
ggtattgggt ggtgttcaaa gaacttggag acaaacagca aactgtgagg caaacaaaa    180 caaacctaac ttgtgcaaaa cccaga                                        206

<210> SEQ ID NO 446
<211> LENGTH: 275
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 446
catcgtagct tcacattaag aaaatttaag tgtaaaatgg taggtagaaa agagatattt    60
ttggattact tactcaagtt ggtcataatt aacacacatc agtggaactt ctgtactaca   120
acgctggtga aatttataac cacatgtttg acagcggaaa ccctggaaaa gcagctttcg   180
acaaaagtca caaatgcta aggtgaaaaa cgttttcgt acctgcaaag taaaaaatca     240
cagagatttc aaaaactcac aagaaaactt tctag                              275

<210> SEQ ID NO 447
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 447
catatttcac attccctaaa taaaaattca ttcattaaaa tctaaacatt tttgacattt    60
caaaaaaaaa tgtaaagata catacaaagt tgtgtgttgt aagtggaaca ttctccaaca   120
cttccacatg caattcttct ccagtaagcc aggaaatatc agtgtcccaa ccaattggtt   180
tcttctctct gaaaaatgta gacacaagcc tttcttggtt attacaccta aaaata       236

<210> SEQ ID NO 448
<211> LENGTH: 214
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 448
acttcaaagt ttaatgtgtg attttctttt taaacaaaat ttcacgtcac atacaaacca    60
tacccatcct gaattctgta aacagcacag cactctggga ttagacctct catcatcagt   120 gctttctta gactgtctcg gactgtaact ccacaccttg caggtaccta tggtatcata   180
aatatattga taagaggtaa agggagcaaa ttac                               214

<210> SEQ ID NO 449
<211> LENGTH: 363
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 449

```
ctgtctgaaa aatacaaaga aacagcaaaa tggtgatatt aaaactgact caccactgtc      60
ctctgtttgt tgggcaggaa gactctaacg ataggttttt gtggtgactt ggggttgctc     120
cgtgccacat ctgtgggatt ttgaaaaact gaaagagatg aaggtagcac tgaaaggcta     180
gaagaggaag aagatgtaac ggtatccatt gatgcagagc tagaaacaga aaaatcagtt     240
ccgttcccca gagattccaa taactgttgt tctctttgtt ggagtgcatc tagccttgctg    300
gtgtattctt cataggccta taaaataaag cagacttata ttcaatccgg actttgtcct     360
gac                                                                   363
```

<210> SEQ ID NO 450
<211> LENGTH: 307
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 450

```
taatcccacc tcctaaaata atcaagatta tcagtacaaa tgtttttata agttcatttt      60
ttttcttttc aaaattacta gatatgatac tcaaaagctt acctccagat atattgatgg     120
tggattatgc tccccaccaa atttgtccaa tagggcctct atatgttcct gtgtcaactt     180
aatcatttgt ttgatattcc acacctaaaa aatatttcaa aagaatttaa ataaaaatca     240
cttagtatat gaattagaaa tattttaaca tagacaacta catcacagta actgccagtg     300
ttcctca                                                               307
```

<210> SEQ ID NO 451
<211> LENGTH: 289
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 451

```
cgccgcctct ttccaaaata aacaccagcc agccgccgag cccggagtcg ggagggcggc      60
agggtggcgc cagcactcac ctcctccgga atggcagggt ccgcagccga agaggccgcg     120
gcgccggcgc cggcgccggc ctcgggctcc atgtccccgt tgaacagagc ctggcccggc     180
tccgcgccgc caccaccgcc accgctcagc gccgccatct tataaccgag agccggggcc     240
cgagcggccg ctgtcgggcg gggaggggga agggaggcgg agagctggg                 289
```

<210> SEQ ID NO 452
<211> LENGTH: 307
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 452

```
gaacatcttc aaaagagggt agcaagacgt gctcctaggg gaggctcagt gtggtctcgt      60
ctgcccaagc attttcagtc ttgcttggtc aatgacatcg agtaagtttt tggcatccac     120
agccagggcg tgagcagcag tcagcatttg cttttttgtac tcttgctgga ggctggtcat    180
gacatactgc tgggccagtt tcatcttgtt gatgagctca cccaggtcag agttcaatag    240
```

```
cttctgtgcc atctcaatct gaaagacaag agataggtca ggagaactgt tttcagtgat    300
tttttt                                                               307

<210> SEQ ID NO 453
<211> LENGTH: 176
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 453
agtgctgtca cagagggctg caaggggaag attgtgccct acctctcggt gggtgctggc     60
tggtaggagg ggaatggtct catccacagt ggccaataat gtcctcaggg ccaagccgac    120
ttcctaacag acaagaatca caaccaatat tagaacacac acaaaggatt tttatg       176

<210> SEQ ID NO 454
<211> LENGTH: 245
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 454
ggaaacaaga acatttttgc cagtacacaa aatgactcta ttttaccttc accataggga     60
catactcctc tggtggggct ggctggattt tactggacat ctcgatgaca gctttcacca    120
ggcccgtcac attctcgtac accttatcat tcgaccggtc caggttggca gtaggagggg    180
ggctgatttc ctggggctga agctgacaac acagaagcca gtcatttttc tgctctccag    240
cagat                                                                245

<210> SEQ ID NO 455
<211> LENGTH: 196
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 455
aaatcctgca agcagaaggt gctgcacagg ctcagatgcc caccttgaca ccctcgttgt     60
agctgtcagc agggctgctg aggctggcaa ggcttccag atgaccggga ctccagggc    120 gaggcggttt ctttggtgga gctgcaggat ctggtgagag agaatgattc ccattaagtc    180
atgtgcgtta agaaag                                                   196

<210> SEQ ID NO 456
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 456
tcaaaacctg ctttcatcaa attaaactaa cttctttccg cccaattctt ttcttcttta     60
cctggtttac ccacaggctg atatatatgt tggtttccaa tctgtgggaa aagaaaagtt    120
cagtcaatgc actggtatat acacttgggc aatgacctct ctcacc                  166
```

<210> SEQ ID NO 457
<211> LENGTH: 175
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 457

```
cgcacaggag aactggaaat caaatcctgc tgaaaactca ggcttaccgg accctgaaga      60
cttccatcct ccctgtcaat actgcctcga gagagtctca catcaggttt ctgaagaaat     120
taaaacaaaa tcaaaacaat ttcatttttg atttgaaaat ttttgacaga ttctg          175
```

<210> SEQ ID NO 458
<211> LENGTH: 235
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 458

```
ctaacagggc ttaaaaagtc aaagaagcct ttcagaaaca caattaccag aaatctttcc      60 tcttttttcca gccagcgctg atcttcttcc atttcctgtt gctgtcggat tagacgctct    120
tccatcagat gggttggcaa cacttgccca atccctcgca ggtccaatac tgtagagtcc    180
tggaagaagg gttgaaaaca gcatattcag tctcataagt ctattcctat gctct         235
```

<210> SEQ ID NO 459
<211> LENGTH: 255
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 459

```
gcccagcttt gccatgcttt ataagttaac aaactgaagc ccaagacacc cgatttacct      60
ccacattggg ctgccacatt gctatctcct gaggtctatg attccatgaa tctgtttggt    120
ccaaaagaga tgcctgacct ggatagatgc tgccagccat ggctgtgatt ccatgtgaac    180
cagggtagcc agaaacctgt gaatgagtaa ggaggcaagg taatgttcaa ctataacatc    240
tgcacagttc tgctt                                                     255
```

<210> SEQ ID NO 460
<211> LENGTH: 196
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 460

```
ctaccccaaa agcgctaaat aataaaataa cacagtttat atctgtaatg actggcatac      60
ctggtaatga ttggtttgta ccatgtgctg tgggctggga taaatccttc gctggacct     120 cggactggga taacccggtc tgctgggctg taaaatcaag agagcatcat atgaatgaac    180
cttttgattt tgacaa                                                    196
```

<210> SEQ ID NO 461
<211> LENGTH: 206

```
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 461
tcttgaaagt tagtaagagt aacccccaaag ttggggtggg gactgtagct accttgggcg    60
gtgcttcatc agaccctccg gagtcccagg acactgtggc ctgtcttctg gactccatcc   120
tcatgcgctc ttcttgctga gccttctctt cctccaggat tgtgctagag agacaacaca   180
ttgtcttagg ggagctgaca acccag                                         206

<210> SEQ ID NO 462
<211> LENGTH: 184
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 462
gcacctgaac aagcaatgga tgttttaaat ataaaaacag aagtattcaa aaggtggcaa    60
aggagtaatt ctctctttcg gggcagggtt gattaggaag ccttcctgaa gcaggtaaca   120
tctgagctgg gttctgaaaa ctgaataaaa gtttataggt ggcaaaggtc aggaaaggga   180
tttc                                                                 184

<210> SEQ ID NO 463
<211> LENGTH: 306
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 463
gagaagcagc ataatctgcc cccaccccca ggccctctct cccgccaact cctacctgag    60
ctgagcttta agttcagtaa acctgggccg cctgctgggg tcataggccc agcatttcgt   120
cataaggctg tagagggtag gaggacaatt tggaggcatt ggtaatcttt ccccattttc   180
aattcgaccg attacatcat tgttcttcac tccttgaaaa ggcttcacac catgcatcag   240
tatctcccac atacacacac ctgtcaagtg ggaatgaaaa cacaacagtg agctcagtat   300
gaagaa                                                               306

<210> SEQ ID NO 464
<211> LENGTH: 247
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 464
gaaggcaaat caacctacat attccaaaaa gagataattt ttttttgtat aacatatgaa    60
atataatttt taaagaatac aaaactttta agagtactca ccaaacatcc atacgtcact   120
agctgaggta aaacgtcgaa aattgattga ctctggagcc atccatttaa taggcaattt   180
tcctttggaa gctagaagat taattttaga aaataaattt tccttgttat ctgcttaaga   240
atctaac                                                              247
```

<210> SEQ ID NO 465
<211> LENGTH: 218
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 465
aatacgttaa agattccaag cctatttctt aggtactact ctgatttctt accttttgtag     60 taagtactat cttccatata tcgggataat ccaaagtctc ctaattttac acaatcattt    120
gaggacacca gaacattccg agcagcaatg tccctgataa agaagaattt gagacaataa    180
gacttaaaat aagaaaaaca aacatacaag ctcatata                            218

<210> SEQ ID NO 466
<211> LENGTH: 226
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 466
gatcactact tttcagaagg gaacttaaca gctttatgac tgtatcttac ctgtgtacaa     60
atcttttgct ctctagatat gcaagagctg tactaagctg ataggcatac aggatcaaag    120
atgctagatc caaactgtat ttccttactt gcaaaaatga cctcagcttt tggaacaatg    180
accaaaagaa aaaaaaaaaa aaagaattaa gtggcagtga atcgaa                   226

<210> SEQ ID NO 467
<211> LENGTH: 185
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 467
tagtctatga gctccatcag ggcagggact gtgtgtgtca tgctcacctc tgcattcctg     60
gggtctgggc agcatcaaca ttaggatcac ttatatatct gcaccaattc cagtgcaaag    120
atgtgtaatg gcctaagtac caaagtataa agtaaatgca catcaatcta cctttacaca    180
taaaa                                                                 185

<210> SEQ ID NO 468
<211> LENGTH: 186
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 468
gatttcacag atagaaagtc aaatggagtt ccacagaaat ttctagacac ttacaggctt     60
cttgaagaaa tttctctctc acgctgtccg aagtacagtt tttacatgtt ttaattgcaa    120
ccgccaaagc tggattctcc tgtgttaggg aaattataga atcacacaca catgcaaaaa    180
ggtttg                                                                186

<210> SEQ ID NO 469
<211> LENGTH: 166

```
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 469
gaggcatctg tcaagtctga gcaagaacaa aatcagaagt ttacttactt gagggcatgg      60
tgtaagtatc ttcttcatct ataatctcag cataatcatc tgtttctgca ggaaaagaaa     120
cagatatgtt gaaagaggtt aaacatctga cctcctggta tttcat                    166

<210> SEQ ID NO 470
<211> LENGTH: 156
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 470
tctatgatcg tcttacccca tgagagtgct tttcgaggtc tgctacctag agccccttac      60
ctgacacaga gacggcgtgt gtccgcatgc cttgcttttc gctgttggcc aacctgtgac     120
agacaagagc aaagctgtaa gccctgcaat ttcccc                               156

<210> SEQ ID NO 471
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 471
aatttcctta aactttccaa caaaacaaaa taacagtaca aaaaaagcag tacttacttt      60
ggtattgatg gcaaagcccg ttcaccttct gcggggaaaa agaaaagaga tgcataaggc     120
tcttttcact ccttttgaaa agatggtgcc tagaatcagg gaggaa                    166

<210> SEQ ID NO 472
<211> LENGTH: 216
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 472
ttggtagaag cgcaattggg aatgctcaga acagcacct caccttctg aggtctgatg       60 ataaatgact gcgaggttcc attcaccagc cggcagtacc catctattag gtcagccata    120
ttctccgcaa tggttaggga tggtgccgtc actgtcagag gctaacggag aaaagatcaa    180 gaaacagac ttcattgttc ttcccagtaa gcaaag                               216

<210> SEQ ID NO 473
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 473
acatccctat ttaaccattt tcccttaatg atgaacgtaa cagttcctta cctcgggtgc      60
```

```
acctgctatt tttagttgta gcattccttt tctgtccttg tcttcactgt ttgaatactg    120
aatggtttgc acttgagtga agtcagcaag atgtgtgggc tataaaaagg aaaggtaaaa    180
tctttagact acggataaaa aactcatttc acagagtctg taaatgttct gtgaaatcct    240
cgttgt                                                                246

<210> SEQ ID NO 474
<211> LENGTH: 163
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 474
tctttgtgta acgccaagtt cccgaaaggt cagagcagac ttacattgca gcccttgtcc    60
gttaggtaac tgattccttc ttctgggccg attgccagtt ccactgaaat aatccagctt    120
gacttttgaa ggtgaaacaa gtgagaacag aggtggcaga agg                      163

<210> SEQ ID NO 475
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 475
agaaaaagta aaatcaaact agcccactat ttcccatatt cccatactta caccaagagc    60
acacttgaag cattccttat caaatctgta gactggagac aggatctcaa agaatttcag    120
aatactttct tctctattaa ggttggcaaa ttgtctaaat gtttgttgga tcagttttct    180
tagtgttttg gcctgcatga caaaattacc aaaacatctt gtaaaaatca gcaatgagta    240
aagacc                                                                246

<210> SEQ ID NO 476
<211> LENGTH: 167
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 476
ctggggaaaa ggtcttggca taattttgtt attttattat gataaaggag actctaatta    60
ccttgacaga atccagtaaa ctcttaggaa aaaatcgctt taaaccaaca tcttttctga    120
aatataaaaa gaagcgtatt aacaaataac accaccaaat caattaa                  167

<210> SEQ ID NO 477
<211> LENGTH: 227
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 477
agaaatagca gtgtttcaga atcagtattt aattttaaaa taaactaaga atttagttct    60
gcatatttgc aggtatagat tgtaagtaca atacttactc taatacttca tagttagact    120
```

```
tcttttctag tgcattgccc cgcatctccc agtatgatcg cctaaaatca gggaagacat    180
acatttatat gtatatataa ggaatgtttg tgttgttaag tgataaa                 227

<210> SEQ ID NO 478
<211> LENGTH: 195
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 478
aaataggatt caaagaaaca aacaaaaaag tatatgaaag cagtctctaa tacctgttga    60
tagaagaaat tcaaagttgg cttatcttca gtaaactggt ttagaaatcc ttttggcaaa   120
taacgaattc tcaattcata tctaaaaata attcacaaaa cagaacaatt agaaatcagt   180
cattttctca attta                                                   195

<210> SEQ ID NO 479
<211> LENGTH: 368
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 479
gttgtaatga caagcagtgt gaaaattaaa catatacatt tgttatcttg tgcatgtttt    60
taaaaagcaa agaaatcaa gtgtgcatca caccaaagca ggtttgtatc ttacttccac   120
tcctctggtg ggtgagcaag ctcatacttc tccctcacac tggagacgcc catatccacg   180
tgaagccagt gaacctcctc tgaccgcagg tgactgaggc ggaatccata gcaggccaca   240
tgctttactt tgtgactgtc cactatcttc tgaatgatgc cctaaaacat accccccaca   300
agaatgactg ttataaactg aaaaaaaaaa aaaaaaaaa aaaaaccaaa acaaaacaaa   360
aacaaaac                                                           368

<210> SEQ ID NO 480
<211> LENGTH: 358
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 480
catacatgcc attacatttt aacctaaata aacattaaag atgtctcatg gaaaaacgta    60
cttaccctga catcagtagc atctccatgc ctgataatac tggcccaggt ggttggctca   120
ctattgcttt caaaataatg aaagaccttt aatactcgct ccattgcacc aggagaacgt   180
tccataccag tacccaggtg agtcttagta ctcgaatttg gtgtgtgatt caagttgggg   240
tcaaggtaag cagctgccat tatttgcta gatgctaggt atctgtcata ttctgttaaa   300
agaacaaaat aatttttgt gtataatact tgaaatctac caattacaat gtgatatg     358

<210> SEQ ID NO 481
<211> LENGTH: 193
<212> TYPE: DNA
<213> ORGANISM: Artificial Sequence
<220> FEATURE:
<223> OTHER INFORMATION: Description of Artificial Sequence: Synthetic
      nucleotide construct
```

```
<400> SEQUENCE: 481
cccagctatt cgggaggctg aggcagggca attgcttgaa cctgggaggc agaggttgca      60
gtcagccgag atcatgccac tccactccag cctggcagcc tgggtgacac agcaagactc     120
tgtctcaaaa aaaaacaaaa aaaaaagact aagcattaca taatcatgta gtacaatcac     180
atgccacaca agg                                                        193

<210> SEQ ID NO 482
<211> LENGTH: 325
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 482
ccgctgcaca gaaggagccc gcccagcccc cgacccgcgc ccgcgcccg gcgccccgca       60 ctcactcgga ccgcggctcg gcgccgtgaa gcgaaggcag acgacgacgg ggcggcgctg     120
ggcgacagca gccgcgcttc ctcccacgcc tcacgccgcg ggctcacagt ggtccgggac     180
cggcggcggc ggcggcggcg cgggctcgcg ccctcgaggc cgtgctgcgt cggcgcgggc     240
ccgcgcgcgt gcgcggcagc cggctgaggc gcgcgtcctc tctcggcagc gcacgcccga    300
cccggtctca gtccggagtt cccgc                                          325

<210> SEQ ID NO 483
<211> LENGTH: 177
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 483
gttttctgtt gcagttcgtg ccctcgtgag gctggcatgc aggatggcag acagcccgg       60 ccacatgccc catggaggga gttccaacaa cctctgccac accctggggc ctgtgcatcc     120
tcctgaccca caggtaagcc ccttaccttt gtctgcagca cactgaagag ttcccaa        177

<210> SEQ ID NO 484
<211> LENGTH: 285
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 484
ccttagaggg tgctgttggg gtgctgggcc tctagggtc gtccccaggc ctctgctgca       60
gcctggctgc tcacggaggc cctctgtccc ccgttccaga ggcatcccaa cacgctgtct     120
tttcgctgct cgctggcgga cttccagatc gaaaagaaga taggccgagg acagttcagc    180
gaggtgtaca aggccacctg cctgctggac aggaagacag tggctctgaa gaaggtgcag     240
gtgagctgac aacccgtggg gtcaaacctg catctcggga ggtgg                    285

<210> SEQ ID NO 485
<211> LENGTH: 195
<212> TYPE: DNA
<213> ORGANISM: Artificial Sequence
<220> FEATURE:
<223> OTHER INFORMATION: Description of Artificial Sequence: Synthetic
```

-continued nucleotide construct

<400> SEQUENCE: 485
cactggacac agattgtaac cactctattt ctcttttcc tcccgcccaa gatctttgag      60
atgatggacg ccaaggcgag gcaggactgt gtcaaggaga tcggcctctt gaaggtgagc     120
accctgggcc gagcgggagc tttgcctcct cggggaggtt ctggggccgc ggctgggcca     180
catcatgtcc atcac                                                     195

<210> SEQ ID NO 486
<211> LENGTH: 226
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 486
gtcccgtctt cacttggtgc cccttccct ctttccctcc tcatgcagca actgaaccac       60
ccaaatatca tcaagtattt ggactcgttt atcgaagaca acgagctgaa cattgtgctg     120
gagttggctg acgcagggga cctctcgcag atgatcaagg tgagcgcctg gcggggtggg     180
ggtgctgggg gctgcgcaga tctggagcca aaggtggcag tcttcc                    226

<210> SEQ ID NO 487
<211> LENGTH: 272
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 487
actggggaaa ggacagaggc agtgccctgt ggccacccac ctccaagccc gctcacccgg      60
gcctatccct ctgcttgtct cccccactgc agtactttaa gaagcagaag cggctcatcc     120
cggagaggac agtatggaag tactttgtgc agctgtgcag cgccgtggag cacatgcatt     180
cacgccgggt gatgcaccga ggtacgtgcc acccgccagg agccgcccgg agccacctgg     240
agcccaggaa gacacttcct catggctcct cc                                   272

<210> SEQ ID NO 488
<211> LENGTH: 235
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 488
cacctacccc aagcctccta ccccacacca atctccttct cctcgccctg cagacatcaa      60
gcctgccaac gtgttcatca cagccacggg cgtcgtgaag ctcggtgacc ttggtctggg     120
ccgcttcttc agctctgaga ccaccgcagc ccactcccta ggtaaggggg acctgtctgt     180
gccccagcag cccccagcgg tcctggtgac catgcaggga gacgcaaaca ttctc          235

<210> SEQ ID NO 489
<211> LENGTH: 185
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 489
ccctacatgg agcataagca gccccgcccc ttgctgtgtt gcagtgggga cgccctacta    60
catgtcaccg gagaggatcc atgagaacgg ctacaacttc aagtccgaca tctggtccct   120
gggctgtctg ctgtacgagg tgagtctctg tccgtggctc agcagcattt ggtgggacat   180
gcatg                                                               185

<210> SEQ ID NO 490
<211> LENGTH: 233
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 490
cttctgagcc ttgaggccga aagcttatct tcgttgttcc cgtcccttgc agatggcagc    60
cctccagagc cccttctatg gagataagat gaatctcttc tccctgtgcc agaagatcga   120
gcagtgtgac tacccccac tccccgggga gcactactcc gagaaggtga gtttgcagga   180
gccggaggcc tcgccagccc caggaggcca ccgaggctta tgagggccgc tcc          233

<210> SEQ ID NO 491
<211> LENGTH: 204
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 491
cctcagtaag actgctttct tgagaataac acaccattct ctcccctgca gttacgagaa    60
ctggtcagca tgtgcatctg ccctgacccc caccagagac ctgacatcgg atacgtgcac   120
caggtggcca agcagatgca catctggatg tccagcacct gagcgtggat gcaccgtgcc   180
ttatcaaagc cagcaccact ttgc                                          204

<210> SEQ ID NO 492
<211> LENGTH: 207
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 492
taggcttggg acctgattgc ttattttaac aaagtcactt tgagagcccc actcaccagc    60
caatatagca ctggcagagg ttttcatggg atgtcgcttg tttgatgagc agctcaactt   120
gcgttggaac atccaaagtg tcatcatgag agaagtcccg acctagcaca ggaggaacaa   180
aaacatttca ctctcttcct ggcaatc                                       207

<210> SEQ ID NO 493
<211> LENGTH: 176
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 493

```
gtgtgctcag attttatgtc cctttaagt aaacacatga cacactcacc agtgagctta    60
tctcgaaccc tgttaataat ctggatagct ttcttattta gggcctctgg tttcaccaaa   120
ccgtctccaa ctggaataca caaaagtaga ataactgta agaatgggag caatac        176

<210> SEQ ID NO 494
<211> LENGTH: 177
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 494
ttaatgagct agtcactggt gcggttcctc agaggctgaa cttactgaaa gaatgaatag    60
attctggcac tgtggtcccc gttttcttat gggctggctc tccaagttcc acccgtcca   120 aaatttctat gggaaaagaa atcaattaac agaaaattca acaccaaaa agccact      177

<210> SEQ ID NO 495
<211> LENGTH: 177
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 495
gcacaagggg gagagccttt gcgacctccc gtggatgcac ctaccgactg actggccagc    60
agagtaggaa tccgtcctcg ttcgggatcg cttgttgcct ttggtatttg ctagggagag   120
aaataaagag tattgaaaca tgcttcaaat tttgacttga agaaacttg gttattt      177

<210> SEQ ID NO 496
<211> LENGTH: 250
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 496
ggattacagg tgtgagccac tgagctcagc tcccaggcac ttgatgatac tcactgtcca    60
tcagcctcca gttcagcaag gggtcataga caaaggcttc cagcacgcc atgacactgt   120 ccttgtgctc tcgcagcacc tccatcactg tgtggcatgt gattctgtag ttgccatcca   180
ggcctgtaac ctagaaatgg gacagagcca ctcaccacag gagttactaa ctctccaccc   240
aaagcaagcc                                                          250

<210> SEQ ID NO 497
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 497
cctgatccca tttggaagca gctcgttccc gatatccact cacctccata gcattggtca    60
acattcttgt tagtctaaat ggaatcttct ctggaaactt ctctcgggtc atagcaacct   120
acagaataat aaatgggaaa agccaaatca atgtttattt tcttta                  166
```

```
<210> SEQ ID NO 498
<211> LENGTH: 166
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 498
agtgatcacc cgggaagatg aggttggggt tctagaacat gtgttcacct caaagcagtc      60
cccaaagtca atgtgcagga tcttcccact cagacggtcc agcatcaggt tggatgggtg     120
tctttgagaa acagaagaca gatcagggag ggatcaacag agataa                    166

<210> SEQ ID NO 499
<211> LENGTH: 188
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 499
cattcaggaa aactacaatg gagaaagaag actaaaaaaa ccaaattaaa ttactcacct      60
atctcccagg cctaaaatat acccaaccat tgacatgacc gctaaagaac gggtataatt     120
ggttcttcgg tcaaaccaca cctagaacac aggagtgcat gtgaactacg gttctggaaa     180
ctttaatt                                                              188

<210> SEQ ID NO 500
<211> LENGTH: 214
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 500
gggttccagg agagcgcagg tctgcagggc ccagtggcct acctcggagc tggggctttt      60
cagccacagc agcttggcca ggtcgtcccc agctgtatta ttgacggcat gctcaaacac     120
ctccaccttc tgcatcagag tcaagtggtc atagtccgga gccatctgca tcaggacaca     180
actgttcagt aagagagcag cctaagacat gtag                                 214

<210> SEQ ID NO 501
<211> LENGTH: 236
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 501
gccacggaag gggcactagc tctcgtggcc gcatcacata cccgcaacat gatgcgatgc      60
tcgatgttga gaaggatctt cttcttctcc ctgtagtccc ggatgagggc gtgcagtgtg     120
tcacagtggg gaacccagcc aatgaggccc gagttggtcg ataaagggat gacagcgtat     180
ctctggatgc tggcgcccac agaaaagcag ggttagtgta ccgtaaagag agtata        236

<210> SEQ ID NO 502
<211> LENGTH: 266
<212> TYPE: DNA
<213> ORGANISM: Artificial Sequence
<220> FEATURE:
```

<223> OTHER INFORMATION: Description of Artificial Sequence: Synthetic
nucleotide construct

<400> SEQUENCE: 502

```
acatgactac acgagacaaa tgtaggaaaa aaccagaaga cttctcaaat tgttgccatt      60
tcagggtttc tgaatacctg aggttttcc gaagagatgt tgggtcattg gccagaaggg     120
tgttaaccag gccgaagagc tgcatcacac gctcatcctg gcgcagatct tcatggcctt    180
ttagaaggaa aacaaactca tgtccgttgc tgcctgtaag gaacagtggg agcggtgagt    240
gtacatcaga ggtcctcagc tcttca                                          266
```

<210> SEQ ID NO 503
<211> LENGTH: 266
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 503

```
gtgtaggagg gagaagtggg tgacagaagt gcacaatggt ccttacccat aagtgtcaat      60
ttccggggcc tctgcttgga tgtgatgact tgcaaagacg gtgctatgga ctgaatgcga    120
atgattggct ggttggggtc atatgttcct ggcacagcca attcaaggtc ccggcacatc    180
agaagttttg gggaaacata ttgcagctct aaggatgtga gctgtaaata attaccaaag    240
gatttagtgt tctgcctcca gggaag                                          266
```

<210> SEQ ID NO 504
<211> LENGTH: 236
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 504

```
cagaaaggac tataatgaca gttaaccctg ccaggagcct gaagatccta cctgaggcag      60
ctgctttgag attcgtcgga acacatgata atagaggtcc caggcttggg tgaggtcctt    120
gacattccct gatttcatgt acttcctgca ccactcttgg gcctccatta aatctcgacc    180
ataggcctga gagagaaagc aggcacgttt tcaagttatc aaagtctcaa ccaacc         236
```

<210> SEQ ID NO 505
<211> LENGTH: 282
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 505

```
tagtggcaga atatttctac agggttatgt cctttcgtgt tttttacccc atacctgatt      60
aaaggatgtt tccttcagag tctggggggcc ccgttccatc atagcatgca agggctccag    120
cacctcaaac atgcctttca cgttcctttc cccaaagtac aaacgagatg cctcttccag    180
gccttcatgc cacatctcat gccagaggat ggccactcgg atcagctcct cgctcacctg    240
aagccaagag aagaaggaga gaagcatcaa gaatcagcta ac                        282
```

<210> SEQ ID NO 506
<211> LENGTH: 216

```
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 506
aagggaccag ggtctatgaa gccccacagt ggctccgacc caccatcatg gcctgctgga      60
ccagggtgtt gctgtgctca cacatgttct tcagaatctt gttggctgca ttgtgccggg    120
ctgtcgtggt agacttagaa gccactgtca gtgggtagat gagggcctga gggaaaaaca    180
gaagaaacat ctataaagga aatgtgggtt ggggaa                              216

<210> SEQ ID NO 507
<211> LENGTH: 215
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 507
ggaaaggctg accaccaaac cagtggttag atgagaaact gcccagagtc tccacatacc     60
tgggggtggt accgaccaat gtctgtgaga agctggtgaa tgagacgtcc caccaagggt    120
ctgggcgtat caattcttgc aatgagctga ggtataacct ggtattcaaa agacacagt    180 atgtagcata tgagacttga aacaactagt tattc                               215

<210> SEQ ID NO 508
<211> LENGTH: 186
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 508
agagagactt ggagccacct tcacctgtaa ccaagtatcc tcacctgtag ccaggtatca     60
atctggatgg ctttcacccc ctccactaag gcctcattga catctggcca gtgaccataa    120
tcaaaccata aggtgagaac tctgaaaaag aaatgagaaa gtcacagaaa atttagtttc    180
ccagtt                                                               186

<210> SEQ ID NO 509
<211> LENGTH: 194
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 509
cttgccatta acatggccta ccagagttgc atccttccct tctctgatac ctgagtgtat     60
cctggaggtt gttgcctcgt gacaaggaga tggaacggaa gaagccctgg acggcaggca    120
ccgtgtacat caggagggtt ttggacagat cctgttggaa cacacacgtg ttagcgacac    180
tcttgcctct gctt                                                      194

<210> SEQ ID NO 510
<211> LENGTH: 343
<212> TYPE: DNA
<213> ORGANISM: Artificial Sequence
<220> FEATURE:
```

```
<223> OTHER INFORMATION: Description of Artificial Sequence: Synthetic
      nucleotide construct

<400> SEQUENCE: 510
cctggcacct tggttggttg ttaataagga agaagggaag ggtacctcag tgaccttctt      60
ctgcagcggc gatggggtgg ggctgttctc ggtgctctcg gcctcgctct cactgttgct     120
gccctcggtg ctggcagtgg tggtggcagt ggcggccgtg gtggcggcag tggtggcgtt     180
ggtgatgttg gccccgctgg catgacgcag tttcttcttc tcatcgcggg cttggttctg     240
atgtttgtag tgtagcacag cttcgaagtt catcactgcc cacgcatgcc aggcctggtt     300
ggggagaaag gcaaggacag acactggagc tgtgaccaac agc                       343

<210> SEQ ID NO 511
<211> LENGTH: 194
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 511
gacagggctg gaatatgact tgccccaggt cagtggggac ctcaccgggc catgagcttg      60
tgcagttcct gcttatgctg ctggtcctca gtagcgatgg catgctgggc ctgttgctgc     120
atggtctgga caaatgctg catgtgctgg aaggcatcga tctgtaacag gacaaaggca     180
cagagagcca cttg                                                      194

<210> SEQ ID NO 512
<211> LENGTH: 157
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 512
gctgcatggt ctggacaaaa tgctgcatgt gctggaaggc atcgatctgt aacaggacaa      60
aggcacagag agccacttgg cttgtggccc agcttcagag gaagggagct accgttcatc     120
tgataggcat gagtcaaccc ctctccaaac agaatac                             157

<210> SEQ ID NO 513
<211> LENGTH: 225
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 513
cattctggag aaggtggtct gttctggatg cattgggata cagaccttgc gggcactctt      60
ccacatgttt tcatgtagg cataggtcac ctgagggtga actgttggca gaggatggtc     120
aagttgccga gacggatcaa ctcccaggag caacactaaa gttttatgag caagagcctt     180
aaaaataaga gaaactgggt tatagacaga actggacagc ccagg                    225

<210> SEQ ID NO 514
<211> LENGTH: 235
<212> TYPE: DNA
<213> ORGANISM: Artificial Sequence
<220> FEATURE:
<223> OTHER INFORMATION: Description of Artificial Sequence: Synthetic
``` nucleotide construct

<400> SEQUENCE: 514
ggacaccatg gggccctacc tgcccatgtg ggtgggtggt tgtcactcac cagcctgcca    60
ctcttgccgc acaggcttgc atacttgagc caggttctca tgtcttcatg agggctgacc    120
acaagggacc gcaccataag gatttctgc cagtcctcta cgatacgctg gcagccctgg    180
aacattcaga agtgaagatt agatatgtct tctgatacat tgttttttgtg gcaga    235

<210> SEQ ID NO 515
<211> LENGTH: 195
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 515
ggtaggggta ggtgggtgaa ctggggcttt ctaccaagct cacctgcagt ctctcccacc    60
agatctggcg gatgatctct cgtcgctcgg ggacaagttt gtactggata acctcctcca    120
gctcggacag catgtggcaa gaaaccatgg cctgatggaa gcaaatcgca ttccaaacta    180
attactgcac gaaca    195

<210> SEQ ID NO 516
<211> LENGTH: 165
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 516
ggaaataagc tcaaaaatg acaatgtgca gaatagttga cacttacccc atatgcccga    60
ctgtaactct ctcctgccat cgcagttaat tcagcatcca gcaggtccct ggccttgtca    120
atgcactaga agagaaacaa cccttgggac tgagctctgg acttg    165

<210> SEQ ID NO 517
<211> LENGTH: 211
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 517
gaagcactac aatctttcc tcactgagag atctgggtgc atgtaggttt ttacctgttg    60
tgccaaggag aagaggtcct gatgcagtgc cagcacagct ctataaatg ccccatcatg    120 ggtgtcccga gggatcatac aggtgtattc ttccatgctg tcccactgac ctatacacac    180
acacatagac agaaagcatc aaggggggttg g    211

<210> SEQ ID NO 518
<211> LENGTH: 204
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 518
ctcactcacc ccatccttca cagggtgcct gtgagggaag ctttacctaa accccatgca    60

```
gctgcagcag ccatccgggc catcttggct tgggtctcat cattaaccag ggtccacttt      120
tcacagcact gctggtggag ttgacccctg aagaaaatga attatatagt cagattaatc      180
caaatctcct taaactacca atct                                             204
```

<210> SEQ ID NO 519
<211> LENGTH: 235
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 519

```
aagagacgaa gtctcttgca gccacacatg ccatcattct aggaagctca ccattccccc      60
aaggcctcga ggcagcgcat gcggcccagc atcagctctg ggtcgtcctt gttggtgtcc     120
attttcttgt cataggccac aagggcatcc tcccactcgt gcagtttctc ataccaggta     180
gcctggatct cctgttacat gggaaagaaa gactgctgtg aggtacacag aagaa          235
```

<210> SEQ ID NO 520
<211> LENGTH: 175
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 520

```
ctagccaagt ctctacctcc tgcttttcca aaaagaatga ggtgcttacc agctctccaa      60
agtgtttcat ggcatattct aacactccgg ccgctgcctc cggctgctgt agcttattat     120
taatgctgag aaaacaaagg gaaaggtag ttacactcaa caggtctgag ggtag           175
```

<210> SEQ ID NO 521
<211> LENGTH: 241
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 521

```
aagagaggtc attttgcatg aaggcagcaa ttaaaagggg tttatggcct acctgatgag      60
agattctaga atggcagggg tggggccttt ctggaactcc agttctttgt agtgtagtgc     120
tttggcatat gctcggcact tggcagctct ctcacccagc agaacaatgc cattgtcatc     180
tctcagtggc aggggccct ggagaagagc aaaacctcac agcacaggaa aatggcagat      240
g                                                                      241
```

<210> SEQ ID NO 522
<211> LENGTH: 234
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 522

```
cgttttctat gtgctgatct tctccacccg ccctgacaca ctatacctgg ccatcgggtt      60
gtaggcctgt gccagggccc agcaggagcg cagggagggc gatgatgagt ccttcagcag     120
```

```
ctccaggctc agccgtctca gccattccag ccagtcatct ttggagaccc tcctggcagc    180
gccccaggcc tgtgatccca caggtgacaa tggaaaacaa tcagtttcaa gggc          234
```

<210> SEQ ID NO 523
<211> LENGTH: 265
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 523

```
gttaaaagtt ttgagtaagt gagaagagca gagctctcct ttcccagtca cctgaaacaa    60
tggacttgcc ttttggaggt tgatggtgct gacgtgcagt ttcttcatgg gtcctgtttc   120
cactggtcca ctagccaatg catccccttg gccactccta agcatccgat gctggtaaat   180
caaaggatcc tcctcttcat cagcaagtgt gtatccctac aaccaaagat ttataggaaa   240
cacctataac tctactagat gcttc                                         265
```

<210> SEQ ID NO 524
<211> LENGTH: 193
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 524

```
gtagtaaaga caacagggac ttcagaacag aaaagaagta tagttcacct tgacaattct    60
gcagatgagc acatcatagc gctgatgatt gattcggtgt cgcaccagaa ctttattcac   120
cattggaatg aaaatttggt actaaaacag gaggggaag agatgagaaa ctatcatttt    180
ggagagtgga gaa                                                      193
```

<210> SEQ ID NO 525
<211> LENGTH: 267
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 525

```
aaataaggca gaagagcacc tgtctgtcca gactcccatc ttaccttctt ccccagctga    60 aaacaagtg aagacagcgt gtccatggct gtggagcgca gttctgggct ctggtccagt   120
gttcgaacaa tagggtgaat gatccgggag gcatagtcag tgaaatccag ggactccgtc   180
aggcggtcca cagtctctag cgctgcccta caacaatcac taacatacag taactgctaa   240
catacaatct ccaaggaaga gacgtga                                       267
```

<210> SEQ ID NO 526
<211> LENGTH: 228
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 526

```
aaatgaacat ttcaacaaa acattaaagc ttaaagattg ctagtcccaa agaggaggtg     60
ctcactttcg agatggcagt ggagcttcag gggcatcaaa caacttaaca ataggaggca   120
```

```
gcagtaaatg caggtagtca tccaggttgg cgccaaacag ctggattgca gccagtaact      180
gcaaaaggga gcaaaagcat ggtgatgaat agtcaggtcc caagtatc                  228

<210> SEQ ID NO 527
<211> LENGTH: 185
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 527
cttccttgac ccaaacatgg aagaggccaa agcattaact tctactcact ctcatgaggg      60
tgactatttc atccatataa ggtctgatgt ggctcttcac aaaggacacc aacattccca     120
gctgctggaa caaaaactga aatggacaag aggtcaacca gctggtatca tgaaggacat     180
tgaac                                                                 185

<210> SEQ ID NO 528
<211> LENGTH: 346
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 528
tgtggtgcag aggagaaaga gaaggattgg ggtttgaggt acttacttcc cggatggccc      60
catcacagac tcgaatgacg ttaaggaacg tgggcatgac ctggggcagg aactgcacac     120
atttgagtcc cagggacttg aagatgaagg tgatggcctg acaaccatg gtgtgatgat      180 gagagagtga ctggtctcgg aagatccgca tcagggccac catggacaca gctgggtaga     240
actcatccag aggcaagttt cccatgttga ccagcatttc actagtgcta tagtcagcta     300
ggacaaaaca acagagagtg ttagagctac acatggcatg acgtga                    346

<210> SEQ ID NO 529
<211> LENGTH: 232
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 529
gctctgtgag tgagaacttg gcaagtcttt catggctacc cccaacttac aggaatcctg      60
acttgacttg gattctgaca ggctgacagc agaggcatcc cgggactggt ctatcatgcc     120
aatgttcact ttgtgcttgt aaggatccaa agcccctaaa agccctaaca cacgatggc     180 ctgcgtggga aaggggaggg aaaaaagaaa acattcatca caacatgatt ac             232

<210> SEQ ID NO 530
<211> LENGTH: 227
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 530
gccatcgtcc cagcaaagtc tttaaagacc aagtttgcca cgtcccctac ctctctgcgt      60
```

```
gtaccctggt tctgctcagt cttcagaaaa ttcagtagca cctcaagcaa agtagggtac      120
ttcctgtagg gctctactac atagccagtg ctggccacca actgtcccag ggtccacaga      180
gccacctgga taggcacaag aacacgattc aatgagccag tacgaga                   227

<210> SEQ ID NO 531
<211> LENGTH: 225
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 531
gatgacaacg cacagagaaa gcaccagcct ctcggtttgt gttaccttca gaataggctc      60
catgtagggg cggatgagtc ggggggcatt ggagaccagg tgccccagca tgcgggcact     120
ctgctctttg attcttccaa tcccactgtg ctccaactct gtcaaaatct gtagggaaga     180
aaggctcata tgttctctat ggcagaagac attctagaga gagac                    225

<210> SEQ ID NO 532
<211> LENGTH: 315
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 532
ttgtcctaag ctccttaact cccctagatt ccttctgtct ggcaagcctt accaggatct      60
gttatcccaa ctacgagcag tttgctaagc acatctgcca ccacttgcac tgcggtctgg    120
ctaaccacat gagcatggcc actgatgagg tggatggagg gtgtgagcag gcgggagcag    180
gtgcgggcag cctccatgcg gatctccttg tgctcactgt tcaggaaatg atccgcacag    240
tggcgaacaa attgggtcag agagtggcct ggatagaaag gcagagagaa aacagaataa    300
acactgctgc tgtag                                                      315

<210> SEQ ID NO 533
<211> LENGTH: 335
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 533
ttccagcatc tctcactatc ttggcaagag ccgttgtaat ttcttacctt caaattcaaa      60
gctgccaagc gttcggaggg caagagtgat gctgcccaca tcgctggcct cagggagggt    120
cgtgaggcca ggagaggcca gctgatgggc caggcccttg gcatgcctg ggtggcgaag     180 gggtttgtgc ataaggacca gggacagcat tttcagtagc ccatcttgaa tgtccttctt    240
tagctgtgga atctgacggc tcaggtcgta gagcactgca gtgagggcag ggctgagggg    300
aaggaaacaa gtcacataag ggctgggcac atgac                              335

<210> SEQ ID NO 534
<211> LENGTH: 224
<212> TYPE: DNA
<213> ORGANISM: Artificial Sequence
<220> FEATURE:
<223> OTHER INFORMATION: Description of Artificial Sequence: Synthetic
      nucleotide construct
```

<400> SEQUENCE: 534

```
ccaagcctca cgctgataca gggcaagctc aggtttctga cacccacctt agtcccactg    60
ccagcatggg ctccagcagc tccttgatat cctgctggat gcctggcccc attgctcgag   120
ccagcatgct gatgcaagtg aagactgtgg catccacctg cattgccttc tgcctcctgt   180
agagaaatgg agagtggcta gttgagacat aatgacattc ttta                    224
```

<210> SEQ ID NO 535
<211> LENGTH: 277
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 535

```
ccaaccaaat ggagtggaag gtgaaatcat aacagaggtg cttacttatg ggcgaagtcc    60 tttggggca gggccgctcg gatgatgtcc agcacgcgag gcaaatagac cttaaactca    120
gacctcacag ccacagaaag tagccccagg gcttggaagg ccgctgtacg ttccttctcc   180
ttcttgacac agcttaggac atggttcatg gtatcttgga gatactgggt atctgagcac   240
agaaaagaca agtagatag ctccaggtca gggttag                              277
```

<210> SEQ ID NO 536
<211> LENGTH: 196
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 536

```
tgtttaccct gagatgggta atgatgtctt ccatggacat cctcacctgt gaaggcagaa    60
ggtcggaatg cagccaagcg gggcaacaaa ttaaggattg tcatttggat cagcgagttc   120
ttgctattcc tgcatttcag cacccactgg cacacctgag agaggaagga taaagggttg   180 gcagggaaa agtgag                                                    196
```

<210> SEQ ID NO 537
<211> LENGTH: 373
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 537

```
gtgtggagct taggaaaaga gggaaagggc ctctcaccac ttacctgatc aaatttctcc    60
tccatcaagt ctctgcaaca ccggctctcc accaggtgg acttagctgg actgggggag   120
gtcccaaatc ccatgaggcc ttggtgagag ctgtacccca gcagcccac caaggcattt   180 gactgctggg gctgtacagc ctggaaactg gtgaaggggg taatgtgacg aggttttgtt   240
ccgaagccca tgagatcttt gcagtacttg tcgtgtacca gctgctgctg tgtgatttct   300
tccatttctt ctctcagacg ctatatatat gaggaggaaa aaaatcatct ttacttatga   360
ctggcattca aac                                                      373
```

<210> SEQ ID NO 538
<211> LENGTH: 224

```
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 538
ggtacacggg gagcctggac tcccctctgc cgtggcttct cacctctccc tccatgctgc    60
tgattcggac cagctcgtta aggatcaaca aggctccatg gatccgatca tcccgattca   120
tgcccttctc tttggccaag gtctcatcaa atcccttctc tgcttcttca aatgtgtgct   180
atgtagagag acagggtgcc ttcattagag acagagtaca aacc                    224

<210> SEQ ID NO 539
<211> LENGTH: 295
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 539
gcagatgtgc tttgctagtg gtgggaatgg agccatctcc ttaccctgta ccactgaggc    60
ttctgcatct ccttcggctc acgctgggtt gtgagaatca gacaggcacg aagggcggct   120
acagctccct cacggatggc ctgtttgggg tcccacacgg ccacaaaaat gttgtcaaag   180
aagggttgca cttgctggaa gaagaaggta gggacgctga tggccagctc acggagaacc   240
aggacctgga gaaaaagca aaccgagaac tctcattggt accagagttt tgttc         295

<210> SEQ ID NO 540
<211> LENGTH: 332
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 540
ccccatgaca ccatcgttcc ccaagcctgg ctgtgctcct ccctgtagac actcacagct    60
gcatgtctcc ggccctcatt gcggtcagca cccagccatt ccagggctcg cttcacctca   120
aattccacgt actcagcggt aaaagtgtcc cctgccatgg caagacggcc aatgggcttg   180
gatgccattt ccatgacaac tgggtcattg gaggggagga ggttccgaag atagttggca   240
aatctgccaa ttcgggtggc attcccacct tccactccta tgaggctagc tgcaaaagag   300
aggaaggcaa aaggtgatga tggggcgtat gc                                 332

<210> SEQ ID NO 541
<211> LENGTH: 216
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 541
cacaaaggtg agtgtgttgt ttttgtgacc agagactctg tccttaccta tggccaagat    60
gccacctttc ctctcattgg catctgagct ggaaaccaat tcaaaaatgt gatggttcag   120
ttggtcatag aagcgagtag actcctcttg actcatctgc aaaagaagat ataatcagaa   180
caatttctaa taattctcta actgtggtgg tgggag                              216
```

<210> SEQ ID NO 542
<211> LENGTH: 255
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 542
gcccacacat cccacaatga ctggccccag atcccagaag cacctctcgg agttccatgg    60
tgacatagtg ctggagctcc ttggcggctt tggccctggt ttcctcattc cggctcttta   120
ggccactggc aaactgctgc aggacgctca cattgctaga tgtggtggca gcggtggtgg   180
cggcggcagg tccggttcca agcatcttgc cctgaggttc tttagagaga gtttcctttt   240
aatattctgg ataag                                                    255

<210> SEQ ID NO 543
<211> LENGTH: 296
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 543
gcacgtttat aactgttcat gcttccaaag ctcaaacatt cactagttta caagtatgtt    60
gccgcagtca gctgatacca tttaaccgtc tctttgctca agttgaaatc tttcaaaggc   120
agggttactc cacccaagaa aaaattctcc cgcagagatt ctgcactgag tacacttagt   180
tgaagttctc gctgtcttag ggtttctttg ctatatccac tgtatacaag ctacaacaaa   240
ggaaaaaaga acagtaaatc acaaattaaa gtttgtttgg tttcttggaa catttc       296

<210> SEQ ID NO 544
<211> LENGTH: 446
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 544
gcacgtcaga acttaaaaat gaaaattaaa aaaataataa accaaggaaa cttctagaaa    60
tgattttaac ttaccatttc attgaatgtc ggattcctcg ttttcgtga aattttggtt    120 ttacgtttgg atgttttgtg gttatctgga agtaggtatg ttttgacata tggatttggg   180
tcagctccat cttcagtaac ctaaaaagaa aagcagtccc ttaatagtaa tgcttcctac   240
caaggtaagg gtttcctcta caaccatcat tctttgtaat cactcacaag atctttgata   300
tgcatcacca tgatgaaaag agtaccattt cggtaagaga tggataattt cacagctcct   360
cctatttggc ctggagtagg actgaaggaa cctgcatctg aaaatacaaa tattttcatc   420
tttatttact ggttgtagtg gttcaa                                        446

<210> SEQ ID NO 545
<211> LENGTH: 377
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 545

```
gacttgcaga tcatgagtta ccaataaaga gaaaaaaaat aatctcacct gcagacctag      60
ctatcccttc agctttctca tcacgaagta aagggtggaa gaaagtacaa acaagatcac     120
actaagaata aagagaaagc aattcattag tttaaatatt atgtaacaca aaaggtataa     180
gatgttatta cttctcattt agtaaggtta cctctgctac atccgttgaa gcattcatca     240
aactctgtaa gtaactgttt aactcaattt cctttttggc tgctacatct tttatgtgtg     300
ttcttcctag aaccatccta ttaggaaagc tacaaaagaa aaacaaaaac aagtgggatt     360
taaataagta caatatt                                                    377

<210> SEQ ID NO 546
<211> LENGTH: 239
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 546
ataacaagtt gtttcctaca aaaggattta atgtacaagg atgaatacat accctggtaa      60
cttccaaagt ggaaaaataa tactgagctt attgtgaagt tcctgaaatt cgtcaaatgt     120
tcggaagaca aatgatggtt caatctgtcc ttccctcaaa attcggacta cataaatctg     180
aaagaaaatc acaccacaaa cacataaaat ttatatttaa aaccttcttt ccaggccgg      239

<210> SEQ ID NO 547
<211> LENGTH: 336
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 547
gaatcagcaa aggaagtaga aaggacaaca ataatacatg catgattgtt tatgaatatt      60
gaaatcaaac ttacataatg tttatctggg ttgtatttct tatgatatgt aaaaacagag     120
acttccttga ttcgaccatc ttgtctaaag gagtatgttt taggtgaaaa tgaaggatg     180 ggctcatcat tagaaggaag accagaaaaa cgaagctgag caaggttgtg aatgaagaag     240
ttaaactttg tggcaatgct tcccaaactt gattcaataa gcctacaaaa taatcagaaa     300
attcgttaac agtaaatgag aacacatggt aaattc                               336

<210> SEQ ID NO 548
<211> LENGTH: 234
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 548
tcaaagcaat atttttatgtt ccttctgcaa tatacttaaa tatgctttac ctagtaaaga    60
aaattgtagc ttctgcgtct gtagtttggg gttgaagtgc atctctaacg tatttcaaat    120
cttgaatact tgtaagttct ggtaaccctg aaggaatcat ctgtagaaga aaacaaaaag    180
ttctgtgagt taaattttttt aaaacatttg ttcctcactc cttcctgtgg gctg          234

<210> SEQ ID NO 549
<211> LENGTH: 321
```

<212> TYPE: DNA
<213> ORGANISM: Artificial Sequence
<220> FEATURE:
<223> OTHER INFORMATION: Description of Artificial Sequence: Synthetic
       nucleotide construct

<400> SEQUENCE: 549
taaagcaaat tttattccaa atcacaaaa taatctttt taagtattga acatagatg    60 cattaatata aaactaatta agtgcttata aagaatagtt accagtgaaa ggaggttaag   120
aaaaaggttt gtctgctttc ttatcaagtt gtaggcctga cagcagaggt ccacaaacaa   180
ctgaaaacga atggtgggct tttcaccccc attaatgaca tatgccatat cagaggtcag   240
cacaaaagga gcccgatccc tatttaaaat gaaagtacat acaaaatatt atttacagaa   300
gatactccaa tagtgctatt a                                            321

<210> SEQ ID NO 550
<211> LENGTH: 276
<212> TYPE: DNA
<213> ORGANISM: Artificial Sequence
<220> FEATURE:
<223> OTHER INFORMATION: Description of Artificial Sequence: Synthetic
       nucleotide construct

<400> SEQUENCE: 550
aacaggaagt gcctcatttc tttggcaaca gcaataacat tatccttt gaagctgcca     60 aacatctgtg catgtcccaa aaactttcca aagtcaatgt gaaacatgtg tcccgtgctt   120
cgaagcatta tattgtcatt gtgtcgatca cagatgccta aaacataggt ggctacacag   180
catccagcac aggaatagat aaagttctct gaagcctata aaaacatac acaattattt    240 tagaaaatga attattttta aaagaggcag agttta                            276

<210> SEQ ID NO 551
<211> LENGTH: 241
<212> TYPE: DNA
<213> ORGANISM: Artificial Sequence
<220> FEATURE:
<223> OTHER INFORMATION: Description of Artificial Sequence: Synthetic
       nucleotide construct

<400> SEQUENCE: 551
cctctgtaac acattttga caaagcttt tagaatgagg agacatgcta attacctttt      60
catattcttc ttcagaggga ttgtatttcc ttagccactc tgcaagtggt ttatctttaa   120
aggatcctgt cacaccatat tccacttgga ttttcctgag ggtatcggaa gcaggaacca   180
gctccaccat gcctttaatg ataaaatatt aagctatgta aaactgtctc tccaaagtaa   240
g                                                                  241

<210> SEQ ID NO 552
<211> LENGTH: 240
<212> TYPE: DNA
<213> ORGANISM: Artificial Sequence
<220> FEATURE:
<223> OTHER INFORMATION: Description of Artificial Sequence: Synthetic
       nucleotide construct

<400> SEQUENCE: 552
gtacacttta agctaagttc aaggaaaaaa ataagacatc aagacacagc taataaactt    60
acctcgatct ctgccagttg agagacattt gaaaattacc atcctcagat ctagtccttc   120
tttaagccag atcttatcca taatctttat catctgtaaa gctaacatat cttgccgaag   180

```
atcttcacca accttgaaat caaggaaaca aaatgaaact tgtacatctc caaaagactt    240
```

<210> SEQ ID NO 553
<211> LENGTH: 228
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 553

```
caaaatcacc tttgcaattt tgggaaagta atttgataaa aaaatttcta aattgccatt     60
aaaaaacagt aacattattt actcacctta aacatgacat taatttcttc tcccataggg    120
tcagcattca ccattgtgac ttttaggggg acagcattag aactgaagaa ggaacacgac    180
tgcaaataca acatgttaag cattagaaag ataaatgaaa atggattt                 228
```

<210> SEQ ID NO 554
<211> LENGTH: 246
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 554

```
ccatttgcct tcttcctatt attttcaaat gtaatatgaa cttataagta ttttatgtgt     60
caccttaata tttaattctt ttgccactag acttggcttg agagggagac ggcatttatt    120
tttctgaaaa aaggactgta ctcgttccat acttctttgg agaacaacct atagaaagag    180
atgtgatact gtaagtacat aatgaaaatg aagatctatt tttcagacaa gttatgctgt    240
ggatac                                                               246
```

<210> SEQ ID NO 555
<211> LENGTH: 317
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 555

```
cataaagatc cttcctttaa cattaacaca tttatattac cttttatggg tacatacctg     60
tctggctgat ccactagcct gccttacttt ttctgctact cctcctaaaa gctgtacaag    120
tttcgtctgt tttagaagtt cttctctaag tcgttttcct cctactgaca ggagagcacc    180
caaaacatgt tcgtatcggg tactaaactg tacatcatgc agggcatctt tgagaagcct    240
aatacagcaa atatttatg ttagtcacgt cttggttttt ttttttttt ttttttttg      300 agacggagcc tcactcg                                                   317
```

<210> SEQ ID NO 556
<211> LENGTH: 207
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 556

```
ctataaattc taggaatgga aatacggtaa tcaataaaat ttaaatctta ccaatataaa     60
ttgtgtgcta tctggatatt tcccaatgcc ctggacaaaa ggaattgcac taatgaacta    120
```

```
ttcaagtaaa tttcatattt caaagcctac agtaaaagaa aataagaatt attagtggtc    180
taacccatac taaattgttc caataaa                                       207

<210> SEQ ID NO 557
<211> LENGTH: 215
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 557
gggatccctt agcaagttcc cataaaaaac tagagtgaaa gtataaaggg aggtaatcta    60
gtaaaaaact cacttgtaca aactgtggaa gaagatctgt tagctcatca tcactaatgg   120
cctcaatcca ggtcacagct agggatctta cttcctgatc agcaaatcta gaagattacc   180
ataaaaccaa gattggacag tgatttcttt ccagt                              215

<210> SEQ ID NO 558
<211> LENGTH: 354
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 558
tactggaaaa actgacaata aacaagagc aaataaatgt atttgactta ctttgaatca     60
agaagttcca atgcaattag tgggtacaat gcaggccact ggtgaagcaa tgagtaagtt   120
ttggcaagat taacccattt ccagtttggg gcgcttgcta atattttagg aagacaattt   180
gggtgtttga agcaataata acgtttctcc cataaaaaag ctttatcttc tttagaaagt   240
ctgcatatat aatagaatta aattacttct cagtgataac ataatgatat aatctcaatg   300
attaaaaata caaagaagaa atttatttat ttgggacagc tacttcttca taaa         354

<210> SEQ ID NO 559
<211> LENGTH: 258
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 559
tttacattac aggagatact tagcccaaaa cagaataaac agaacatacc caagtgatga    60
gtctttatga agaatatcaa gaagtttccc tttatatca ttctctagtg tttctaagtt    120
atgttgctgt ataatgcttc tgtcaacttg aggagttgta taaataatat caaatgcagg   180
agaaggaaaa tcaaccttta aaatttaaca gaaattgatc aaattacagt ctacgtattt   240
gccacattaa cctctttg                                                 258

<210> SEQ ID NO 560
<211> LENGTH: 257
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 560
```

```
tcatggtata cacacacaca ttttatgaag aaatttaaat gtacacctct ctacatgtca    60
agaagtacca ttacctgtag cactattctt tccatgacat atccttttt ggtaactgtt    120 ccaggaacag aatttgtatg tgatgaagtc caaagatata gaagtttagt tccacatgtt    180
aaaaaccttc acggatgtaa aaataataat gtgattttca ttttaaaaat caattcaaaa    240
tttacaacac atgtaat                                                   257

<210> SEQ ID NO 561
<211> LENGTH: 267
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 561
gtaaacaaca ggacacactg aaagaataaa aagccagaaa tttcacttac agttcatccc    60
atttaataag atagaagaaa ttcttgtaag tgccaacctt ctttgattga ataggtttaa    120
aaagatcctt tccattgtga gacagtgaac atatcaagta gtattttca taactgagaa    180 aagaaagttt aacttgattt ctatcatgat aatacaaatt agttaactaa tacaaataca    240
ttagcagttc ttcctccaaa gagacta                                        267

<210> SEQ ID NO 562
<211> LENGTH: 311
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 562
gattacaggt gcaagccacc atgcctggct gcttaaacag ttacttactt tgatacccaa    60
ttacttgaaa ttccatgagc agcaaaaata gtaaactgga gctgctctgt tgtagtccat   120
gcttccttga cactcttgct actttgggca cagtctgtag gactcctacc agaatttgca   180
tggagtctga aagatcata aattgctgca gttaattggt ttatgcttac ttgaacagga   240
ttttcaggat taagtgagcc tagattaaag aaaaaaaaag ttaatagatt ctctgaaaag   300
gcgatgatta t                                                         311

<210> SEQ ID NO 563
<211> LENGTH: 158
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 563
agattctctg aaaaggcgat gattattgct aaaatttaaa gatttaaaca catacccta    60 gttgaactcc tgctagtgtc ttctcctcca acaaagaag tcacctacac atgcacacac   120
acacacaata gtcagaaaac tgcctatgac ataatata                            158

<210> SEQ ID NO 564
<211> LENGTH: 254
<212> TYPE: DNA
<213> ORGANISM: Artificial Sequence
<220> FEATURE:
<223> OTHER INFORMATION: Description of Artificial Sequence: Synthetic
      nucleotide construct
```

<400> SEQUENCE: 564

```
atctcctgtt taagtacata tttgcatgta ataaaatcct agttaccaaa aatactcaca      60
tcagcagttt tactccttgg aagattaact gctctcttta gcttctttac tgattctgta     120
atggcaagag tctcgacacc atctaaagca ctacagattt ttcttacagc tttaattact     180
tgatctactg ctcggtgttg gttctttaaa aataaaaaat aaaataaaaa taggtaggtg     240
aaatttaaag gacc                                                        254
```

<210> SEQ ID NO 565
<211> LENGTH: 376
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 565

```
aagaagcagc aagaatcttt aagtcattat gccaaaatgt gaattaagac ttacttcaat      60
ttgaagagcc agttctactt ggttgtgata agaatctaag agttcttcaa cagggtgtct     120
gaaagaaaca acagttattg tggctgaagg atgctacaca caaaatgatt gttttcatca     180
ccaaaataag tgtatttgca tccaaaaaca aagtctgaaa acctgcaatt aatgctttag     240
atgatatacc tcgtcatggc ttcttttgcaa ggttttttcta tttgatacag gtgtttgttt     300
aaatccacgg gtgtttcatc atcttctgcc taaacaaaca catatacaca aaaaaatcac     360
atccactctt tggtct                                                      376
```

<210> SEQ ID NO 566
<211> LENGTH: 235
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 566

```
gaattattca gattcaaaca aatggaattc agttatgagg tacacactta ctgttcgggc      60
cagattttga cacattgcac tgaaggtcaa gagttgtagt ctaatttctg tgtcccattt     120
tcgacagttt tgaatatgct catgacttcc aaggcaatga ttactgttaa gatatattaa     180
ttattcacta ttctattcaa attagaaatt ataaggtga gggtaaaatt taaat          235
```

<210> SEQ ID NO 567
<211> LENGTH: 223
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 567

```
ttaaaaatga aatttccaag gatgttgctc agtagttaaa taaacttact tctgcagcac      60
ttcctcttga ccacaaactt ttagaacata gctgccaaca tctacttgat tcaagtcatc     120
atgtacccag caaagggctt gcattataat gatttctaca gtagaactca ctgtaaaaga     180
gttagtcatt attttcactt tgctcattta tatttattca aga                       223
```

<210> SEQ ID NO 568
<211> LENGTH: 265

<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 568

| | | |
|---|---|---|
| cccctaaca gagcaaaacg agaggcttga ggaaccataa acctaccatc acacgtaaaa | 60 |
| gtaactggta gctgaaatcc ttcaatgtca atggagacct tcacactagc attttctccg | 120 |
| catatgtttc tttgtgctgt gactggactt aacaaatagc ctgggtttgt gcggtgattg | 180 |
| gtatatggaa atttggtctt caatctgttc acaagaaaga agaaattaaa ttcttttta | 240 |
| aaaaaacttc atttgagggc tctga | 265 |

<210> SEQ ID NO 569
<211> LENGTH: 213
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 569

| | | |
|---|---|---|
| aactggtttt caagtgaatt tttcaaatga acatttataa agaaaaattc cttactttgt | 60 |
| aatggatcga caaaaagctg ccatctcctc attctgtact tcaacttctt gaagaagaga | 120 |
| acttccagtt ggcaaactac tggtcccatt tgggtctttc tgtaattaaa aaagtgtttt | 180 |
| tattttaaaa gtggaagatc cacaaaatgc tac | 213 |

<210> SEQ ID NO 570
<211> LENGTH: 355
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 570

| | | |
|---|---|---|
| attatccacc ttaggcttac ttagaggatc caagtctaac cagtcaaatt tactgatatc | 60 |
| ctcagacttt ggagatacct gtagattgct gacttttgaa tctgttatct ccaaatcagt | 120 |
| ccttgctttc ccattttta aaaattctga tgtactagct attttgtcaa atagttttgc | 180 |
| catgtcagta ctgactactg gacgatagat aggtaagctt ccttgtggat gaaagggtgt | 240 |
| ggcaggtgtc aaaggatatg agaaatatgg agattgtccc ggaagactta aatatatagg | 300 |
| ttctgtagat ggaaaagtgg gcattcttgg attgaagcca ttttggaatg cagcc | 355 |

<210> SEQ ID NO 571
<211> LENGTH: 367
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 571

| | | |
|---|---|---|
| ggagattgtc ccggaagact aaatatata ggttctgtag atggaaaagt gggcattctt | 60 |
| ggattgaagc catttggaa tgcagcctgt ttactgtaag tagaaggata aatagaaggt | 120 |
| aaagcataag tggaaggccc aggtaatcca ggtggccact gtcctctctg aatagtaggt | 180 |
| ctaaaataga gctgtgctga aaaggaaggg ctcagaatag gagtaactgg taatacaggt | 240 |

```
gtttttttag tctcgaaact gtcatccagc aatagtttct caagttcagc ttgggtgagc    300
ttttctacat caatatctaa tgctcttttt tgggaatctg attcaggaaa caccatgaga    360
tcataat                                                              367
```

<210> SEQ ID NO 572
<211> LENGTH: 366
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 572

```
tcagcttggg tgagcttttc tacatcaata tctaatgctc ttttttggga atctgattca     60
ggaaacacca tgagatcata atcctgcttg ttataaacct gtgcttttt tctggtgctg    120 cttgacaact caaagcctct ctgattgtca gtcacttgtc tatccttttg cagttttgct   180
aaagcctctg cttccatctg taatgcttct tctttgtcca catcttttgc tcttgttggt   240
tccggatgtg aagatggaca ttctttaaat ccgctgttgc tagatatctg agccatgtcc   300
actaaaaaga ccaaaccttc cttcctctat tttttcttg tagcttccaa aatagcaagg    360
cctata                                                              366
```

<210> SEQ ID NO 573
<211> LENGTH: 409
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 573

```
gccctgcctg ttccagtgtc ttctctctct cctgccagga ccatgggtag caacaagagc     60
aagcccaagg atgccagcca gcggcgccgc agcctggagc ccgccgagaa cgtgcacggc   120
gctggcgggg gcgctttccc cgcctcgcag accccccagca agccagcctc ggccgacggc   180
caccgcggcc ccagcgcggc cttcgccccc gcggccgccg agcccaagct gttcggaggc   240
ttcaactcct cggacaccgt cacctccccg cagagggcgg gcccgctggc cggtcagtgc   300
gcgggcggcg cggggtcctc gcccacctgg ggccacggcg gggaggcggc ggggctgtgt   360
gcccggggtc gcccccctctg cgcaggccct tcctctcgcc aggggtagc              409
```

<210> SEQ ID NO 574
<211> LENGTH: 242
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 574

```
ccactcctcc tgggtacagg gccatcctgc ccatgccttc cctggctgtg gccccactgt     60
tctgacacac cccaccccctc tctgcaggtg gagtgaccac ctttgtggcc ctctatgact   120
atgagtctag gacggagaca gacctgtcct tcaagaaagg cgagcggctc cagattgtca   180
acaacacgtg agtgccccct tccctattgc ccctcagggc tgggtggtgg gacttcaaag   240
cg                                                                  242
```

<210> SEQ ID NO 575

```
<211> LENGTH: 193
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 575
gctgacggct cccttctcct ttcctccctc cttctgtccc tgctcagaga gggagactgg    60
tggctggccc actcgctcag cacaggacag acaggctaca tccccagcaa ctacgtggcg   120
ccctccgact ccatccaggc tgaggagtga gtaccgtctc tggctgcctc tacccgtcgt   180
ccctggacac tgc                                                     193

<210> SEQ ID NO 576
<211> LENGTH: 290
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 576
gggcagaaga cccgcctaac tgctcctcct gcctcctcct cagaacacgc cgatggcctg    60
tgccaccgcc tcaccaccgt gtgccccacg tccaagccgc agactcaggg cctggccaag   120
gatgcctggg agatccctcg ggagtcgctg cggctggagg tcaagctggg ccagggctgc   180
tttggcgagg tgtggatggg taaggcctgg cccctgccct cgggagaggc atccacccc    240 caccccgtgt ggcagctccg ggctcccttg gtccctttgc ctttagctgc                290

<210> SEQ ID NO 577
<211> LENGTH: 312
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 577
ggatccctgt gtggtaggag ttgggggggct ccactgagtc agcctgcatc cctcctcaac    60
agggacctgg aacggtacca ccagggtggc catcaaaacc ctgaagcctg cacgatgtc   120 tccagaggcc ttcctgcagg aggcccaggt catgaagaag ctgaggcatg agaagctggt   180
gcagttgtat gctgtggttt cagaggagcc catttacatc gtcacggagt acatgagcaa   240
gggtgagtcc tgggcggccg gggcagggggg caggggcact ccggacaggg caggagcat   300 gagcctcatt tc                                                       312

<210> SEQ ID NO 578
<211> LENGTH: 186
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 578
ggaatcactg catcctggca gagggacagg gcaggagctg gagctgggtc tctctctgcc    60
cagggagttt gctggacttt ctcaagggg agacaggcaa gtacctgcgg ctgcctcagc   120
tggtggacat ggctgctcag gtgagtcagc ccctcccgcc tccccacacc cttggtcctc   180
aagcac                                                              186
```

<210> SEQ ID NO 579
<211> LENGTH: 322
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 579
ccagagtgct ctgtggccct gggagggcat gggtggcacc tgagccaggc tcccacggtt      60
ccgcctgcag atcgcctcag gcatggcgta cgtggagcgg atgaactacg tccaccggga     120
ccttcgtgca gccaacatcc tggtgggaga gaacctggtg tgcaaagtgg cggactttgg     180
gctggctcgg ctcattgaag acaatgagta cacggcgcgg caaggtgggc aggggctgtg     240
tggtatgtcg cgcttggcct gggacaggtc acgtcccgct ctgagcccca gttttttcct     300
cagctgtcat tcctcatggt gc                                              322

<210> SEQ ID NO 580
<211> LENGTH: 224
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 580
cggtcatgac aggaggtcag agctgccctg acctttctcg ttcctgcagg tgccaaattc      60
cccatcaagt ggacggctcc agaagctgcc ctctatggcc gcttcaccat caagtcggac     120
gtgtggtcct tcgggatcct gctgactgag ctcaccacaa agggacgggt gccctaccct     180
ggtaagaagg tcctcatggc ctgtctgtgg tccctgaatc cctc                      224

<210> SEQ ID NO 581
<211> LENGTH: 372
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 581
cttatctatg gtcactccca acctgtccta ggcaggaagc cctcgctgcc ctccccatca      60 gcttcccca ccccactttc ctcaccggag ccgggctccc catgcctcgc tctgcccaca     120
gggatggtga accgcgaggt gctggaccag gtggagcggg gctaccggat gccctgcccg     180
ccggagtgtc ccgagtccct gcacgacctc atgtgccagt gctggcggaa ggagcctgag     240
gagcggccca ccttcgagta cctgcaggcc ttcctggagg actacttcac gtccaccgag     300
ccccagtacc agcccgggga gaacctctag gcacaggcgg gcccagaccg gcttctcggc     360
ttggatcctg gg                                                         372

<210> SEQ ID NO 582
<211> LENGTH: 287
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 582

```
cacagattca taccaaatgc attactttta gattattaac atattctttt acataatttc    60
atttcacata tatggagtcc aaccaagata catctggcat agtaagtttt catcagtagc   120
ttcctgtata aggtaatgca catgtccttc aatagataac ggcagtcctg tcactctatt   180
tcgagtcttg attacacctt gtagtcgctg ctcaatgtca agaacatggg tcttggccta   240 aaagaagaa acataaaacc aaaaacagat gttaataatt tggaatt                287
```

<210> SEQ ID NO 583
<211> LENGTH: 203
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 583

```
tgtagagatg aggactacag cccatatcaa gctatacctt ctactaacct tttcattgac    60
aacttctcca gtttcattca gtggcgcttt ggaatgccct ttcactggtt tactccattc   120
cacaagagga tcatgtagaa aagtctttaa gacactaaaa ttgaaacaaa tattatggta   180
tgatgttatc tttgcaagaa gaa                                          203
```

<210> SEQ ID NO 584
<211> LENGTH: 294
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 584

```
tagggggccaa taattatatt cgaggttact gttaaattat ttacaaagta taggtgatta    60
cctcattaaa ggctctcgct gatcacgcat cagcctcatt gtaacttcac atgctcttcg   120
aaaaagaccc tctgttccca taggacccat tccattaacc atattatgag tcaggcgaaa   180
tggcacaatt tctggaactt caaaggtttc tcccttagaa acaatacatt ttattacaaa   240
ctaacaatgt tagaatttaa aaatctttac tcaaagaact tcatgtccag attc         294
```

<210> SEQ ID NO 585
<211> LENGTH: 306
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 585

```
gagaaaagga aattgagaga aaacacaatt agtaagagta actcatatca cataccttat    60
tgaaaagaca attgaaatct acatgtacgc attcaccagt caaagaatca aagagaatat   120
tttcaccatg acggtctcca gccccagaa tataaccaac cattgacatt actgcagtgg   180
aacggcagta agctgatcta ctactgtacc taaaagaaac acaatgccta tgaaatatcc   240
atatacatat gaggccaata taaatctaaa atattaaaaa taaacattca accataacaa   300
cgtatt                                                             306
```

<210> SEQ ID NO 586
<211> LENGTH: 257
<212> TYPE: DNA
<213> ORGANISM: Artificial Sequence
<220> FEATURE:

<223> OTHER INFORMATION: Description of Artificial Sequence: Synthetic
nucleotide construct

<400> SEQUENCE: 586

```
taaaaataaa cattcaacca taacaacgta ttatattctt ggtaacttac catgatgtag      60
gatcagggaa tgttctcaga aaccactcat gaaaaatagg aggatgcctg ggcaggagaa     120
attctcggaa tactttgagt ttttcagata aagctgctga ctttggtagc atacactggc    180
gaagttcttt tcctgtcata tacactcctg caaggaagag tgatatccat taatcacatc    240
agccaaatga aaaaagg                                                    257
```

<210> SEQ ID NO 587
<211> LENGTH: 416
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 587

```
ggaaggaagg gatggaaaca cttaagtgtt tctgtatata aaatctagaa atttcactat      60
agcttatatc aaaaaacata tgctagcata tattaatacc aattataccc atattatata    120
acttagtacc cacactgtat atgtataaga attaatttta gtacccttt ctttatatag     180 tttggtcaga ataggtctca aaccagcagt gttgttcacc cattcaataa tcccacattc    240
atcatttagt ggataactg catatgttcg aatatgaagt tctcttctac gagactctgc     300
atcttttctt aagcactgtt aaaaaataca cataaattta aaaacaagat agaactcaaa    360
atttctaaat gttatatcaa atatatttaa agattgttca tttcataacc aaagaa         416
```

<210> SEQ ID NO 588
<211> LENGTH: 277
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 588

```
aataaaagca atctggtttt ataatagtca aaaattttt taaaataaaa aataaataaa       60
taaaataaaa gcaaactatc tcccaacctt attaatcaag gaattgaatt ccattagtct    120
acaatccttt ctcaggtcat cttttggctt acacatcatg atgtagaact ttccatctga    180
gccttttaaa gaaatcttct ttggtttctg aagagaagca agaatttcca cctaaaagat    240
gatgagttat atatgaatta gggccaaaaa tttctgt                             277
```

<210> SEQ ID NO 589
<211> LENGTH: 357
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 589

```
tcacgtagat tttgtgaaat acactttta tcttaatttg aagtttttaa caactaaatt       60
ttaaaatcat agtcatataa aactgaagtt taccatatca tcaaaccctg caatataggc    120
ccaatgtcca ggaaatggtt catggctagc atgttagca tgggtaccca gaattgatgg     180
aagtgtaggt atcatgactg attgtagagg aatgaggatt tcactaaatg ttgcttcttc    240
```

```
taccagcttt ttaagcattt taaaatgagt gctcatgctt aatgtggaac tacttccatc    300
aacctgaaaa aataaatagt gcattttaat ttgtttttac cttaaattcc actataa      357
```

<210> SEQ ID NO 590
<211> LENGTH: 457
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 590

```
tattaaaaac tgctttatta agacaaatca tacataatta aaatatacat tttgatatat    60
gtgtacacct atagttagaa ttttaatttta attaatcaaa tgaaaaaatc tgctcaaatt  120
atatacataa ttacccaaca tcagtttata agcactaaga ttatgatagt accggtttat   180
tgcacaattc tagaagctta tctgttaggc gagttgcatc tccaacaaac ttctctaagg   240 atttttcat atgaatagct ttattgagga tttccttgca tctgttcaca cgcatgggat    300
aagatgactg tcataaaaaa gagttaaatg tcataaaaaa gagtttatac aggattttta   360
aaagataaat ttttgcttg acaaaaaact taaaaagtat tcatgatgag agtttatatg    420
atacaaattt tctgaaaatt tatttggcaa tgctatc                           457
```

<210> SEQ ID NO 591
<211> LENGTH: 386
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 591

```
agacgccctg gaacttgtat ctacatatta gtattacata atcaagttca tataaaatgg    60
taaaagatct tttcatataa aaaggtaaaa gacccttta cctttgacac agctgtcatc   120
atccacattg cttgttgagg ataggctaga aatactttgg ctattatttc catcaagaca   180
acaaaaactt catcgtgaga atgacaaatt cgagagatca attgtgaaaa agcagtcaaa   240
aattgatatg gagctaaata gtttgtatgc tctgtgataa ccttgtttat tttacccaaa   300
tcattcctca tttgtacacg atcggagcgg ccagctgggg gaagaaataa gtttaaaaaa   360
caataaagga aagagaaaaa tcagta                                       386
```

<210> SEQ ID NO 592
<211> LENGTH: 228
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 592

```
attagactgt ccagccaaat ctgactttat accaaagtta taattcctag tcctttaaaa    60
cttttacgtg aagagttata ccttttttccc attcatatgc ctttgtacca taatcaagcc  120
atagagttaa cattcgtggc attgactgat atatgaactg atttccatat tgtagagatc   180
tgcaattata tagacaagaa acactattag catagctgtc atttttat               228
```

<210> SEQ ID NO 593
<211> LENGTH: 306

```
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 593
gaatcagtca taagccagaa atacctaga atatgctaag acatgtgata acagtttcaa      60
tattaatagt catccttaca tatttaatct gcaaacatgc agttctcata ctcacctgcc    120
aaaatgaaga actatatacc ggatgagatc accttgcttt tccattttgt tgtctgtgac    180
catgggcatc aatttgtcat agtacttggc aaggtaaaaa tgcccatcct cccattctgg    240
caggcacgcg gtcacatcct ataaaaaga acataggata cctacctaag gaaatcccac    300
gctatg                                                               306

<210> SEQ ID NO 594
<211> LENGTH: 362
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 594
gacttaagtc attttacgta gtcaacagag ttaactgaaa ctgcattata catatacttg     60
ccttatattt tttcataatt gcattgcttt caaagttagc tgtttcttcc ataaatcggc    120
ccactagtag catagctcga ccatggatta acatgttctt accctcaggt ggggtttcat    180
tttcaggaaa acataattca cacctttttt gaagaacaat tagtgcctgg tgaacatcac    240
cctaaaagaa aaaaggcaac aataagcctt ttaatttaaa aacatacttc tattttctgc    300
aaaagtatta gttcattatg tttttgtaca aatccatttg taatttcatg tttatctttt    360
ac                                                                   362

<210> SEQ ID NO 595
<211> LENGTH: 368
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 595
atatccaaat accaaattca agataagtga cattttaaa aaaagtagtg tgagaaacct      60
tttgttgagg cttagtaaag ccctccggag agccaggata ggctccttgg ctctgtagga    120
attctgggtc atttctagtc gagctaccca gttagagaa tcttcttgag aactgtcacc    180
tggagaatgc tggaaaagtg gtttgatgct atgctccaac tcacataaca tgtgcaatct    240
gaagatagat agagcctatg ttaaaatgtt atcatattca gccttattaa tctcatatat    300
aaagcaagta cttaaatca gaaataaaga atttaaaata cacagttgtc tttggtagaa    360
ctttaata                                                             368

<210> SEQ ID NO 596
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct
```

<400> SEQUENCE: 596

```
ctgtcaggtg acatttatag gccagaaata taaaaatgga aattccaaaa tacctcacaa        60
tatattcata tcctcgttgg taggagcctc tttcaaagct tgcagctgaa agaggtacaa       120
tttgttctgc tctcactagt ttcagtgagt cataaaaagc tgtgtatatct cttttttgg       180
ctgataataa tagctgtccc agtctgacac tccatgttgt agattttcca tctgaaaaac       240
aaatgaagag tcaagaaatg tcacggtagc tgggtc                                 276
```

<210> SEQ ID NO 597
<211> LENGTH: 205
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 597

```
ccgcacccat cctaaaactg cttatatttt aagaagtaat tttacctgct gccaaatagt        60
tttccaccaa atcccactgt gacaatttcc aagctgcttc cactctgtac gtgtttaatt       120
catctgtcca ctcggaccta ttaaaagaaa cccatatcaa ctaaacttta atttatttaa       180
ggtgacattc agagattttt cattg                                             205
```

<210> SEQ ID NO 598
<211> LENGTH: 205
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 598

```
ttctccattc agatgcaata acaaaagaaa atcattttat aaaatattac ctgttagcat        60
gcactccatt cacctgagtg ataacagtag acagctgacc aagacctaac atggacttta       120
ctacaccatg ataatgaatg atctagaaat ttaaaaatat ttaaaatagc aattatcact       180
tcaataatag cttggggacc aaaaa                                             205
```

<210> SEQ ID NO 599
<211> LENGTH: 285
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 599

```
ctattcaggg ctattttcat tacagttgcc tttcaattat tatcttacct ggtctggttc        60
tagctgaata gccctgtcat aacaagcagt ggcatccctc agcaagccaa ggctttcatg       120
ttcaaggatc tgttctttta gagatggttc tgcctttcta attgcactga ctccggccac       180
tccatcaggt tcatgcatag cagcatacaa tttctttgtt caatgattaa aaacaatca       240
aaacaagaa aaaacacaa ctggaaataa aactataaaa ccacc                         285
```

<210> SEQ ID NO 600
<211> LENGTH: 392
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 600

```
ataaaagact ggccacatta attttcatta ttaaattcac tatattaact tcagacctgt    60
aaaaatccaa gatgttcctg aatattttgc ttcttttctg taataaatga ttcaaagtgc   120
attacagctc gtgtgtatgc tttggagcga aaggaagcta ctgccagagt atcctggggt   180
atgaggtcta gaaaacgggt tacactctga tagtcttcat aatccacagt agatactaga   240
tcataaaaaa agttgagtaa ttaaagactt ataagataaa atttaaaagt gtcaatttaa   300
gtatttaagt tcaatttatt tcactaaaca aattaatctg aatatattag gatatcatat   360
ttagaatgta actaacaaca gaacaattgt tc                                 392
```

<210> SEQ ID NO 601
<211> LENGTH: 367
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 601

```
taaagggaag agctaattgg tgaatagcta aaaaaaaaaa aaaaaaagaa acagaagtga    60
taactcaccc attgagtcta ccttatttct gtttgatttg ctgtgtggac atttctcagc   120
tttcagtgcc tgaaatttgt gccttgccca ctgtgtgaga tggtcaagca tggagaacac   180
agtctgtgta ctgagttgac acagatcaga tgcaatgtct tgggtattta tggtatgctg   240
atcgtcatgc tttagaactg ccataatttc tgcataaacc tatgagaatc atttataatt   300
aataataata tctatataat accatttaac tattatatga catctaaagc taaccattct   360
aaggcaa                                                             367
```

<210> SEQ ID NO 602
<211> LENGTH: 265
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 602

```
agaaagtaag tttcacatgt tcaaaaacca agtaagatga tttatctcac ctcctgctga    60
tcttcttgat tacaacccag taagacatac accagaatat gtggaagaag atagatggtc   120
actttgaaat catgcttcat cataatgcta cagcaggtga aaattttact ggcaagatca   180
tgtcgaacct gtaaatgcaa aatgtgtaga cagtaacaca ctttcacata ttgattaaat   240
gtcaaagagt agcatgtgag ataat                                         265
```

<210> SEQ ID NO 603
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(5)
<223> OTHER INFORMATION: a, c, g, t, unknown or other

<400> SEQUENCE: 603

```
nnnnngagac c                                                         11
```

```
<210> SEQ ID NO 604
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, g, t, unknown or other

<400> SEQUENCE: 604 gagtcnnnnn                                                           10

<210> SEQ ID NO 605
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, g, t, unknown or other

<400> SEQUENCE: 605 nnnnncactc                                                           10

<210> SEQ ID NO 606
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
cgtcacatta tttaggtgac actatag                                        27

<210> SEQ ID NO 607
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
gcgtactatt aaccctcact aaagg                                          25
```

METHOD TO PRODUCE DNA OF DEFINED LENGTH AND SEQUENCE AND DNA PROBES PRODUCED THEREBY

CROSS-REFERENCE TO RELATED APPLICATIONS

This application is a divisional application of application Ser. No. 11/805,676 filed on May 24, 2007 and claims priority from U.S. Provisional Patent Application No. 60/808,490 filed on May 25, 2006, both of which are hereby incorporated by reference in their entirety.

FEDERALLY-SPONSORED RESEARCH OR DEVELOPMENT

This invention was made with Government support under contracts HG000205 and GM062119 awarded by the National Institutes of Health. The Government has certain rights in this invention.

REFERENCE TO SEQUENCE LISTING, COMPUTER PROGRAM, OR COMPACT DISK

The present application includes sequences to be included in a Sequence Listing in computer readable form found on an accompanying computer file. The present application further includes a lengthy table submitted in electronic form.

LENGTHY TABLES

The patent contains a lengthy table section. A copy of the table is available in electronic form from the USPTO web site (http://seqdata.uspto.gov/?pageRequest=docDetail&DocID=US08795968B2). An electronic copy of the table will also be available from the USPTO upon request and payment of the fee set forth in 37 CFR 1.19(b)(3).

BACKGROUND OF THE INVENTION

1. Field of the Invention

The present invention relates to the field of nucleic acid synthesis and analysis, and particularly to the field of preparing single stranded DNA probes or primers of defined sequence and length.

2. Related Art

The generation of single-stranded DNA has a large number of applications in understanding biological functions of gene expression and function, treatment of diseases in plants and animals, and in applications to diagnostics and forensics. There are currently several applications that rely on the use of long oligonucleotides as probes. These include molecular inversion probes (Willis et al., 2000 U.S. Pat. No. 6,858,412), wherein probes termed "pre-circle" probes are hybridized at either end to a target, then circularized by filling the gap between the ends. It is said that the gap may be between 1 and 2000 nucleotides (Col. 14 1.35), but the examples are directed to single nucleotide gaps. This method is based on the fact that the two targeting domains of a pre-circle probe can be preferentially ligated together, if they are hybridized to a target strand such that they abut and if perfect complementarity exists at the two bases being ligated together. Perfect complementarity at the termini allows the formation of a ligation substrate such that the two termini can be ligated together to form a closed circular probe. If this complementarity does not exist, no ligation substrate is formed and the probes are not ligated together to an appreciable degree. Once the precircle probes have been ligated, the unligated precircle probes and/or target sequences are optionally removed or inactivated. The closed circular probe is then linearized by cleavage at the cleavage site, resulting in a cleaved probe comprising the universal priming sites at the new termini of the cleaved probe. The patent further states that, due to the length of the precircle probes, it is preferred that each target domain range in size from about 5 bases to about 100 bases, with from about 5 to about 40 being especially preferred.

Padlock probes are described in Landegren et al., U.S. Pat. No. 6,235,472, and Landegren et al., 2001). The term "padlock probe" refers to a probe designed to be circularized in the presence of a target sequence, so that it may be caused to close around the target-containing nucleic acid strand such that the cyclic probe will interlock with and thereby be efficiently linked to the target nucleic acid to be detected. In other words, because of the helical nature of double-stranded nucleic acids, such as DNA, circularized probes will be wound around the target strand, topologically connecting probes to target molecules through catenation, in a manner similar to "padlocks". Such covalent catenation of probe molecules to target sequences results in the formation of a hybrid that resists extreme washing conditions, serving to reduce non-specific signals in genetic assays. Any probes hybridizing in a non-specific manner may therefore be efficiently removed by subjecting the target to non-hybridizing conditions and/or exonuclease activity. Further, the novel method may be performed with even very short synthetic probes since only part of the probe molecule needs to form a rigid double-stranded DNA molecule with the target molecule, whereas the rest of the probe molecule may be highly flexible, optionally branched single-stranded DNA or any other spacer material. In this system, a probe is hybridized to a target nucleic acid sequence, such as a DNA strand, via two end segments of the detecting reagent, designated Probe 1 and Probe 3, the latter being complementary to two respective non-contiguous sequences of the target molecule. An additional probe, designated Probe 2, is hybridized to the intermediate segment of the target molecule with the probe ends in juxtaposition to Probe 1 and Probe 3, respectively, and then ligated to the two ends.

Another application of single stranded DNA molecules is described in Fredriksson S., et al., "Protein detection using proximity-dependent DNA ligation assays," Nat Biotechnol, 2002 May; 20 (5):473-7. This paper describes a technique for protein detection, in which the coordinated and proximal binding of a target protein by two DNA aptamers promotes ligation of oligonucleotides linked to each aptamer affinity probe. The ligation of two such proximity probes gives rise to an amplifiable DNA sequence that reflects the identity and amount of the target protein.

Another method for nucleic acid formation is strand displacement amplification (SDA), which is generally described in U.S. Pat. Nos. 5,455,166 and 5,130,238. A single stranded target nucleic acid, usually a DNA target sequence, is contacted with an SDA primer. An "SDA primer" generally has a length of 25-100 nucleotides and is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease", which is chosen to cleave a strand either at the recognition site, or either 3' or 5' to it, without cleaving the complementary sequence, either because the enzyme only cleaves one strand or because of the incorporation of the substituted nucleotides.

For many of the assays described above, single stranded DNA probes are synthesized chemically. Currently, these probes are very expensive to manufacture to the required specificity and purity that these applications demand.

Various attempts have been made to produce defined single-stranded DNA. Nikiforov and Knapp (U.S. Pat. No. 5,518,900) describe a method for producing single-stranded DNA from a PCR fragment where one of the primers used for amplification has a modification that makes that strand resistant to exonuclease digestion. This method suffers from the drawback that every probe requires the synthesis of oligonucleotides with chemically modified nucleotides, which is not economically feasible in large-scale genomic studies.

Higuchi et al., (1989) describe a method for producing single-stranded DNA from PCR fragments where one of the amplification primers is phosphorylated and the corresponding strand with the phosphorylated primers is a preferential substrate for nuclease digestion. The drawback of this method is that the non-phosphorylated strand from a blunt-end DNA molecule (as in a PCR product) acts as a substrate, though with reduced efficiency.

Binkowski, et al., "Correcting errors in synthetic DNA through consensus shuffling," *Nucleic Acids Res*, Mar. 30, 2005; 33 (6): e55, describe a method termed consensus shuffling and demonstrate its use to significantly reduce random errors in synthetic DNA. In this method, errors are revealed as mismatches by re-hybridization of the population. The DNA is fragmented, and mismatched fragments are removed upon binding to an immobilized mismatch binding protein (MutS).

BRIEF SUMMARY OF THE INVENTION

The following brief summary is not intended to include all features and aspects of the present invention, nor does it imply that the invention must include all features and aspects discussed in this summary. The present methods are useful for producing any single stranded DNA molecule where sequence exactness, including exact beginning and ending of all molecules, is needed. The DNA thus produced need not therefore be a probe. In general, the present synthetic methods involving cleavage and digestion of dsDNA permit creation of ssDNA of greater lengths than previously possible, e.g., lengths of 100 to 1000 or even higher nt.

The present invention, in one aspect, comprises a polynucleic acid probe, having a defined length between two ends and a defined sequence, for hybridization to a target polynucleic acid sequence, comprising specified subsequences which are designed to allow the probe to hybridize to relatively widely spaced target regions, have the gap between the target regions filed, and then be circularized, and, finally, be amplified in circular form. The probe will contain the following subsequences: (a) a first target sequence, at one end of the probe, complementary to a first target region of the target polynucleic acid, for specifically binding thereto (the target region being, e.g., human genomic DNA); (b) a second target sequence, at an opposite end of the probe, complementary to a second target region of the target polynucleic acid for specifically binding thereto, where said first and second target regions are separated on the target polynucleic acid by a gap of at least 25-250 nt of target sequence, more preferably between 250 and 1000 nt; (c) at least one amplification primer site, adjacent the target sequence, and connected to a backbone sequence, for specifically binding a PCR primer, said primer oriented in a direction for amplification of target sequences only when nucleic acids are joined to the target sequences as complementary to the target polynucleic acid and further oriented to not amplify the backbone sequence; and (d) a backbone sequence of at least 25 nt, preferably 125-400 nt chosen to be non-complementary to the target polynucleic acid.

The probe will typically be DNA, but can include modified nucleic acids or hybrids. The probe may comprise two amplification primer sites, one adjacent the first target sequence and one adjacent the second target sequence, oriented towards each other, whereby the circularized probe is selectively amplified after linear nucleic acids are digested with an endonuclease. The probe is circularized by gap filling and ligating between the target sequences of the probe, thereby forming a circular probe.

The probe may be formed with different sizes, but contain the afore-mentioned sequences, wherein the backbone region is from a non-human organism and the target sequences hybridize to human genetic sequences.

In one aspect of the invention, the target sequences are adjacent to a 5' end and a 3' end of an exon of a eukaryotic gene, so that an entire exon sequence is obtained and amplified for further study. In certain aspects the invention comprises a primer for performing PCR amplification comprising a homology region for hybridization to a target under annealing conditions and a non-homologous restriction endonuclease recognition sequence. The probe may further comprise a non-homologous region for forming a primer-binding site to another primer.

DETAILED DESCRIPTION OF THE PREFERRED EMBODIMENT

Definitions

Figure 1:
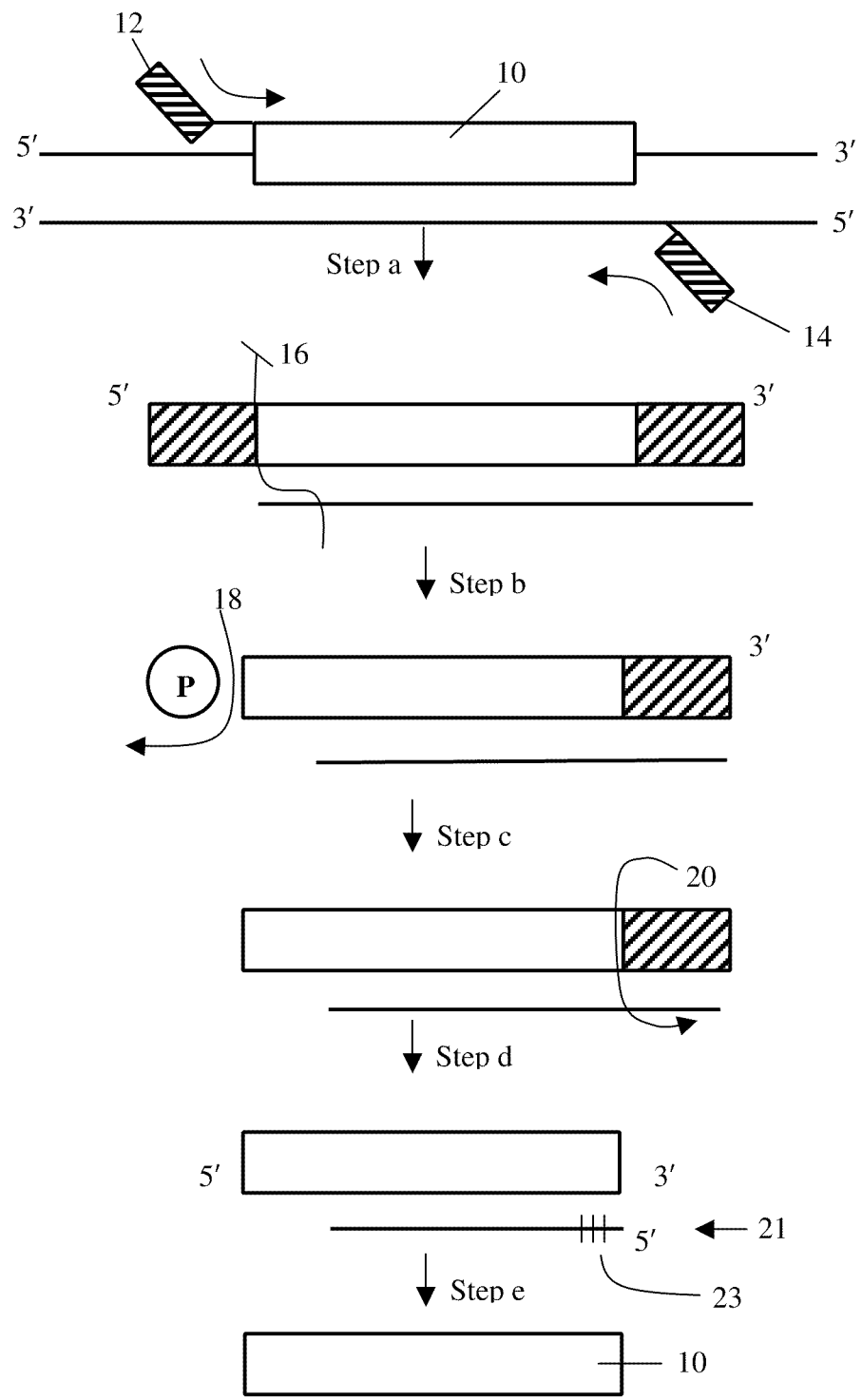
FIG. 1 is a diagram representing the creation of a single stranded polynucleotide (e.g., DNA) probe having a defined length and sequence.

The term "probe" refers to a polynucleic acid that contains target regions that specifically bind to a target, complementary thereto. As is known, in order to be specific the target region must be at least 10 bases long, and should be between 10 and 50, or even longer, bases long. The present probes preferably comprise two target regions, and the regions should be selected to be non-complementary, i.e. not bind to each other. The present probes include nucleic acid sequences that are used to detect identical, allelic or related nucleic acid sequences. The probes are isolated oligonucleotides or polynucleotides and may or may not be attached to a detectable label or reporter molecule. Typical labels include radioactive isotopes, ligands, chemiluminescent agents, and enzymes.

The term "target nucleic acid" refers to the polynucleic acids to be analyzed in the presently preferred method of using the probes to be synthesized. In most cases, the DNA will be human DNA, preferably genomic DNA. However, the present probes may be adapted for use with any sample, including bacteria, viruses, and, particularly in the case of viruses, may include RNA targets. Hybridization of DNA to RNA targets is described in Schwille et al., "Quantitative Hybridization Kinetics of DNA Probes to RNA in Solution Followed by Diffusional Fluorescence Correlation Analysis," *Biochemistry*, 1996, 35, 10182-10193. A polymerase may be used to extend the probe bound to the target nucleic acid by inserting bases complementary to the target.

The term "restriction enzyme" is used in its conventional sense. Restriction enzymes are traditionally classified into three types on the basis of subunit composition, cleavage position, sequence-specificity and cofactor-requirements. Of particular interest are Type II enzymes, which cut DNA at defined positions close to or within their recognition sequences. They produce discrete restriction fragments and distinct gel banding patterns, and they are the only class used in the laboratory for DNA analysis and gene cloning. Rather then forming a single family of related proteins, type II enzymes are a collection of unrelated proteins of many different sorts. Type II enzymes frequently differ so utterly in amino acid sequence from one another, and indeed from every other known protein, that they likely arose independently in the course of evolution rather than diverging from common ancestors.

The most common type II enzymes are those like Hha I, Hind III and Not I that cleave DNA within their recognition sequences. Enzymes of this kind are the principle ones available commercially. Most recognize DNA sequences that are symmetric because they bind to DNA as homodimers, but a few (e.g., BbvC I: CCTCAGC) (SEQ ID NO: 1) recognize asymmetric DNA sequences because they bind as heterodimers. Some enzymes recognize continuous sequences (e.g., EcoR I: GAATTC) (SEQ ID NO: 2) in which the two half-sites of the recognition sequence are adjacent, while others recognize discontinuous sequences (e.g., Bgl I: GCCNNNNNGGC) (SEQ ID NO: 3) in which the half-sites are separated. Cleavage leaves a 3'-hydroxyl on one side of each cut and a 5'-phosphate on the other. They require only magnesium for activity and the corresponding modification enzymes require only S-adenosylmethionine. They tend to be small, with subunits in the 200-350 amino acid range.

The next most common type II enzymes, usually referred to as 'type IIs" are those like Fok I and Alw I that cleave outside of their recognition sequence to one side. These enzymes are intermediate in size, 400-650 amino acids in length, and they recognize sequences that are continuous and asymmetric. They comprise two distinct domains, one for DNA binding, and the other for DNA cleavage. They are thought to bind to DNA as monomers for the most part, but to cleave DNA cooperatively, through dimerization of the cleavage domains of adjacent enzyme molecules. For this reason, some type IIs enzymes are much more active on DNA molecules that contain multiple recognition sites.

The third major kind of type II enzyme, more properly referred to as "type IV" are large, combination restriction-and-modification enzymes, 850-1250 amino acids in length, in which the two enzymatic activities reside in the same protein chain. These enzymes cleave outside of their recognition sequences; those that recognize continuous sequences (e.g., Eco57 I: CTGAAG) (SEQ ID NO: 4) cleave on just one side; those that recognize discontinuous sequences (e.g., Bcg I: CGANNNNNNTGC) (SEQ ID NO: 5) cleave on both sides releasing a small fragment containing the recognition sequence. The amino acid sequences of these enzymes are varied but their organization is consistent. They comprise an N-terminal DNA-cleavage domain joined to a DNA-modification domain and one or two DNA sequence-specificity domains forming the C-terminus, or present as a separate subunit. When these enzymes bind to their substrates, they switch into either restriction mode to cleave the DNA, or modification mode to methylate it.

Type III enzymes are also large combination restriction-and-modification enzymes. They cleave outside of their recognition sequences and require two such sequences in opposite orientations within the same DNA molecule to accomplish cleavage; they rarely give complete digests. No laboratory uses have been devised for them, and none are available commercially.

The terms "complementary" and "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acid strands, in the design and use of peptide nucleic acid (PNA) molecules, and in the design of the present primers for adding restriction sites.

"Hybridization" refers to the process by which a polynucleotide strand anneals with a complementary strand through base pairing under defined hybridization conditions. Specific hybridization is an indication that two nucleic acid sequences share a high degree of identity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml denatured salmon sperm DNA.

Generally, stringency of hybridization is expressed, in part, with reference to the temperature under which the wash step is carried out. Generally, such wash temperatures are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook et al., 1989, Molecular Cloning: A Laboratory Manual, $2^{nd}$ ed., vol. 1 3, Cold Spring Harbor Press, Plainview N.Y.; specifically see volume 2, chapter 9. As described below, a primer that does not entirely match the target is used with appropriate stringency. The "stringency" here is achieved by varying the temperature, magnesium concentration, or both, in the annealing steps where primer and target bind to each other in PCR, or probe and target bind to each other in the SMART reaction. The important point here is that the annealing take place under the buffer conditions of the enzymatic reaction.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"PCR" refers to the polymerase chain reaction, as originally developed and covered by U.S. Pat. Nos. 4,683,195, 4,683,202 and 4,965,188, as well as variations on polymerase chain reaction. In this method, primers complementary to opposite end portions of the selected sequence(s) are used to promote, in conjunction with thermal cycling, successive rounds of primer-initiated replication. The amplified sequence(s) may be readily identified by a variety of techniques.

"Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 10 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Overview

1. Preparation of Probe Using Particular Restriction Endonuclease Reactions

The present method to produce single-stranded DNA molecules of defined length and sequence uses a double stranded DNA molecule as the template. To generate the desired single-stranded DNA molecule from the double stranded DNA template, we employ a series of enzymatic reactions that involves restriction endonucleases, a phosphatase, and an exonuclease. The DNA template can be either a PCR product or any other DNA molecule such as plasmid, viral, genomic DNA, or synthetic DNA.

Referring now to FIG. 1, the starting double stranded DNA is illustrated at the top. Within that molecule, the final, desired final strand is shown as box 10 on the top strand. In a PCR reaction, first shown as "step a," primers 12, 14 are hybridized to the strands and standard PCR amplification is carried out for the number of cycles desired, typically 10-30 cycles. The PCR products will have added sequences, shown with hatching, as non-complementary, containing restriction sites for yielding the defined ends. By using PCR primers having non-complementary portions, PCR products are obtained which have any predetermined 5' and 3' ends. This feature is exploited to engineer specific restriction enzyme sites where the cut site can precisely define any end of the final product. Furthermore, in the creation of SMART probes, as described below, the non-complementary portions of the PCR primers can be designed to include target sequences and primer sequences.

After the PCR product is obtained, in step b, shown in FIG. 1, the amplified double stranded material from step a is reacted with a first restriction endonuclease to create a cut 16 to create the desired sequence at the 5' end of desired top strand 10 of the molecule and create a 5' overhang whereby the desired 5' end overhangs the 3' complementary strand. The cut site should be at the nucleotide that is the desired 5' end, typically next to the first mismatch with the target sequence in the primer. That is, the desired 5' end is assumed to be present in the starting material, although it can be tailored by adding nucleotides in the primer.

After the step b digestion with the first restriction endonuclease (to create the desired 5' end), in step the phosphate group on the overhang is removed by a phosphatase (e.g., shrimp alkaline phosphatase) as shown at 18. Removal of this phosphate makes the top strand (containing the desired product) resistant to exonuclease digestion. After the phosphatase reaction, the double stranded DNA molecule is digested with the second restriction enzyme that creates the desired sequence at other end (3' end) of the molecule in step d.

The second restriction endonuclease is used as shown at 20 to create the desired sequence at the 3' end of the molecule. This should be a blunt end, but may also result in a 3' overhang of the desired strand, as shown at 23. We prefer to use restriction enzymes that generate a blunt-ended molecule in step d, but this is not the only option since there are other ways of generating a blunt end molecule that has a phosphate group. This series of digestions results in the generation a double-stranded DNA molecule with a blunt end that has a 5' phosphate group, and an overhang on the opposite end that has no phosphate group on the 5' end.

After restriction endonuclease and phosphatase treatment, the double-stranded molecule is converted to single strand by digestion with lambda exonuclease, as shown at 21. This generates the final 5' molecule 10, as shown in step e. The exonuclease (e.g., lambda exonuclease, exonucleases I-III from E. coli, nuclease Bal-31, exoribonucleases, and the exonuclease activities of DNA polymerases) will selectively degrade the strand with the phosphorylated 5' end and will keep the other strand intact. The method we have described requires the sequential digestions with restriction enzymes and a phosphatase step in between that allow the formation of a suitable substrate for an enzymatic exonuclease digestion. It does not rely on chemical modification of the primers to generate this molecule.

It is possible to carry out the above described steps with several different dsDNA starting materials and produce multiple, different ssDNAs. In this case the restriction enzymes used require a unique recognition site that is common to all the molecules. To achieve the goal to generating defined ends with shared restriction enzyme recognition sequences, the examples below describe two enzymes that cut in a sequence independent manner. That is, the cut site is outside of the recognition site. There are a few enzymes that have this flexibility of cutting in a sequence independent manner, and we chose two for purposes of illustration—BsaI and MlyI, discussed further below.

The order of the steps in certain respects is important. The amplification must be carried out first in order to generate a large number of final product molecules of the desired sequence, and to add the tailored ends for restriction cleavage. The first cleavage of step b must be done prior to phosphate removal in order to create the desired 5' nucleoside. The 3' cleavage of step d must follow this because a 5' phosphate on the bottom strand (to be removed) is needed for exonuclease digestion.

2. Selection of Restriction Enzymes

Restriction enzymes are chosen based on the desired 5' and 3' ends of the sequence. The most flexibility is obtained with restriction enzymes that cut outside the recognition site, and the recognition site is outside the desired sequence. Thus, there will be one enzyme where the cut is 5' of the recognition site, and one enzyme where the cut is 3' of the recognition site.

BsaI

Digestion with BsaI generates a 5' overhang five bases inward from the recognition site. The recognition site is GGTCTC, (SEQ ID NO: 6) however the cut site is outside the recognition sequence. It cuts in a sequence independent manner to generate a molecule with a 5' overhang that has a phosphate group.

Before Digestion:

```
5' GGTCTCN ↓ NNNNN            (SEQ ID NO: 7)

3' CCAGAGNNNNN ↑ NNNNN         (SEQ ID NO: 8)
```

After Digestion:

```
   5' GGTCTCN  P5'NNNNN

3' CCAGAGNNNNN  3'NNNNN     (SEQ ID NO: 603)
```

MlyI

The recognition sequence of MlyI is GAGTC, but the cut site is 5 bases inward, and it generates a blunt ended molecule with a 5' phosphate group. The cut site is not dependent on the sequence between the recognition site and the cut site. The cut site is marked with arrows.

Before Digestion

```
5' GAGTCNNNNN ↓ NNNNN          (SEQ ID NO: 9)

3' CTCACNNNNN ↑ NNNN           (SEQ ID NO: 10)
```

After Digestion

```
   3' GAGTCNNNNN↓ 5'P NNNN    (SEQ ID NO: 604)

3' CTCACNNNNN↑ 3' NNNN     (SEQ ID NO: 605)
```

The advantage of using restriction enzymes that digest a DNA molecule outside their recognition sequence is the fact that the restriction enzyme digests the DNA molecule in a position that is independent from the sequence constraints of the recognition site. In our methodology we have appropriately placed the position of the recognition sequences for the two restriction enzymes used in the method outside the sequence of the single stranded molecule we want to generate (see Table 1). For some applications, restriction enzymes that digest the DNA molecule within the recognition sequence of the enzyme also can be used. That is, if the desired end corresponds to the recognition/cut site of a restriction enzyme to be used. Also, the restriction enzyme used in the first digestion should produce a 5' overhang (recessed 3' hydroxyl end) even though this is not absolutely necessary.

Any restriction enzyme that produces a 5' overhang at the desired 5' end of the probe may be used (See FIG. 1, cut 16). Below is a representative list of suitable restriction enzymes. This information is adapted from information provided by New England BioLabs, Inc. at their web site. All recognition sequences are written 5' to 3' using the single letter code nomenclature with the point of cleavage indicated by a "/". Numbers in parentheses indicate point of cleavage for non-palindromic enzymes. Isoschizomers with alternative cleavage sites are indicated with a "^". Enzymes that are not currently commercially available are indicated with a "x". The New England BioLabs® Catalog number is shown in the center column.

TABLE 1

| Restriction enzymes producing 5' overhang | | | | | |
|---|---|---|---|---|---|
| Enzyme | Sequence | NEB Enzyme | Catalog # | Sequence | Other Isoschizomers |
| Aar I | CACCTGC (4/8) SEQ ID NO: 11 | | | | |
| Acc36 I | ACCTGC (4/8) SEQ ID NO: 12 | BfuA I | R0701 | ACCTGC (4/8) SEQ ID NO: 12 | BfuA I, BspM I, Bve I |
| Ace IIIx | CAGCTC (7/11) SEQ ID NO: 13 | | | | |
| AclW I | GGATC (4/5) SEQ ID NO: 14 | Alw I | R0513 | GGATC (4/5) SEQ ID NO: 14 | Alw I, BspP I |
| Alw I | GGATC (4/5) SEQ ID NO: 14 | Alw I | R0513 | GGATC (4/5) SEQ ID NO: 14 | AclW I, BspP I |
| Alw26 I | GTCTC (1/5) SEQ ID NO: 15 | BsmA I | R0529 | GTCTC (1/5) SEQ ID NO: 15 | BsmA I, BsoMA I |
| Bbs I | GAAGAC (2/6) SEQ ID NO: 16 | Bbs I | R0539 | GAAGAC (2/6) SEQ ID NO: 16 | Bpi I, BpuA I, BstV2 I |
| Bbv I | GCAGC (8/12) SEQ ID NO: 17 | Bbv I | R0173 | GCAGC (8/12) SEQ ID NO: 17 | BseX I, BstV1 I |

TABLE 1-continued

Restriction enzymes producing 5' overhang

| Enzyme | Sequence | NEB Enzyme | Catalog # | Sequence | Other Isoschizomers |
|---|---|---|---|---|---|
| Bbv IIx | GAAGAC (2/6) SEQ ID NO: 18 | Bbs I | R0539 | GAAGAC (2/6) SEQ ID NO: 18 | Bbs I, Bpi I, BpuA I, BstV2 I |
| BceA I | ACGGC (12/14) SEQ ID NO: 19 | BceA I | R0623 | ACGGC (12/14) SEQ ID NO: 19 | |
| BfuA I | ACCTGC (4/8) SEQ ID NO: 12 | BfuA I | R0701 | ACCTGC (4/8) SEQ ID NO: 12 | Acc36 I, BspM I, Bve I |
| Bpi I | GAAGAC (2/6) SEQ ID NO: 20 | Bbs I | R0539 | GAAGAC (2/6) SEQ ID NO: 20 | Bbs I, BpuA I, BstV2 I |
| BpuA I | GAAGAC (2/6) SEQ ID NO: 20 | Bbs I | R0539 | GAAGAC (2/6) SEQ ID NO: 20 | Bbs I, Bpi I, BstV2 I |
| Bsa I | GGTCTC (1/5) SEQ ID NO: 21 | Bsa I | R0535 | GGTCTC (1/5) SEQ ID NO: 21 | Bso31 I, BspTN I, Eco31 I |
| BsmA I | GTCTC (1/5) SEQ ID NO: 15 | BsmA I | R0529 | GTCTC (1/5) SEQ ID NO: 15 | Alw26 I, BsoMA I |
| BsmB I | CGTCTC (1/5) SEQ ID NO: 22 | BsmB I | R0580 | CGTCTC (1/5) SEQ ID NO: 22 | Esp3 I |
| BsmF I | GGGAC (10/14) SEQ ID NO: 23 | BsmF I | R0572 | GGGAC (10/14) SEQ ID NO: 23 | BslF I |
| Bso31 I | GGTCTC (1/5) SEQ ID NO: 21 | Bsa I | R0535 | GGTCTC (1/5) SEQ ID NO: 21 | Bsa I, BspTN I, Eco31 I |
| BsoMA I | GTCTC (1/5) SEQ ID NO: 15 | BsmA I | R0529 | GTCTC (1/5) SEQ ID NO: 15 | Alw26 I, BsmA I |
| BspM I | ACCTGC (4/8) SEQ ID NO: 12 | BfuA I | R0701 | ACCTGC (4/8) SEQ ID NO: 12 | Acc36 I, BfuA I, Bve I |
| BspP I | GGATC (4/5) SEQ ID NO: 14 | Alw I | R0513 | GGATC (4/5) SEQ ID NO: 14 | AclW I, Alw I |
| BspTN I | GGTCTC (1/5) SEQ ID NO: 21 | Bsa I | R0535 | GGTCTC (1/5) SEQ ID NO: 21 | Bsa I, Bso31 I, Eco31 I |
| Bst6 I | CTCTTC (1/4) SEQ ID NO: 15 | Ear I | R0528 | CTCTTC (1/4) SEQ ID NO: 15 | Eam1104 I, Ear I, Ksp632 I |
| Eam1104 I | CTCTTC (1/4) SEQ ID NO: 15 | Ear I | R0528 | CTCTTC (1/4) SEQ ID NO: 15 | Bst6 I, Ear I, Ksp632 I |
| Ear I | CTCTTC (1/4) SEQ ID NO: 15 | Ear I | R0528 | CTCTTC (1/4) SEQ ID NO: 15 | Bst6 I, Eam1104 I, Ksp632 I |
| Eco31 I | GGTCTC (1/5) SEQ ID NO: 21 | Bsa I | R0535 | GGTCTC (1/5) SEQ ID NO: 21 | Bsa I, Bso31 I, BspTN I |
| Esp3 I | CGTCTC (1/5) SEQ ID NO: 22 | BsmB I | R0580 | CGTCTC (1/5) SEQ ID NO: 22 | BsmB I |
| Fau I | CCCGC (4/6) SEQ ID NO: 24 | Fau I | V0209 | CCCGC (4/6) SEQ ID NO: 24 | Smu I |
| Fok I | GGATG (9/13) SEQ ID NO: 25 | BstF5 I^ | V0031 | GGATG (2/0) SEQ ID NO: 25 | BseG I^, BstF5 I^ |
| Hga I | GACGC (5/10) SEQ ID NO: 26 | Hga I | R0154 | GACGC (5/10) SEQ ID NO: 26 | |
| Ksp632 I | CTCTTC (1/4) SEQ ID NO: 15 | Ear I | R0528 | CTCTTC (1/4) SEQ ID NO: 15 | Bst6 I, Eam1104 I, Ear I |
| Lwe I | GCATC (5/9) SEQ ID NO: 27 | SfaN I | R0172 | GCATC (5/9) SEQ ID NO: 27 | SfaN I |
| Ple I | GAGTC (4/5) SEQ ID NO: 28 | Mly I^ | R0610 | GAGTC (5/5) SEQ ID NO: 28 | Mly I^, Pps I, Sch I^ |

TABLE 1-continued

Restriction enzymes producing 5' overhang

| Enzyme | Sequence | NEB Enzyme | Catalog # | Sequence | Other Isoschizomers |
|---|---|---|---|---|---|
| Pps I | GAGTC (4/5) SEQ ID NO: 28 | Mly I^ | R0610 | GAGTC (5/5) SEQ ID NO: 28 | Mly I^, Ple I, Sch I^ |
| Sap I | GCTCTTC (1/4) SEQ ID NO: 29 | Sap I | R0569 | GCTCTTC (1/4) SEQ ID NO: 29 | |
| SfaN I | GCATC (5/9) SEQ ID NO: 27 | SfaN I | R0172 | GCATC (5/9) SEQ ID NO: 27 | Lwe I |
| Smu I | CCCGC (4/6) SEQ ID NO: 28 | Fau I | V0209 | CCCGC (4/6) SEQ ID NO: 28 | Fau I |
| Sth132 Ix | CCCG (4/8) SEQ ID NO: 29 | | | | |

TABLE 2

Restriction enzymes producing 3' overhang (see 23, step d, FIG. 1)

| Enzyme | Sequence | NEB Enzyme | Catalog # | Sequence | Other Isoschizomers | Enzyme |
|---|---|---|---|---|---|---|
| Acu I | CTGAAG (16/14) SEQ ID NO: 30 | Acu I | R0641 | CTGAAG (16/14) SEQ ID NO: 30 | Eco57 I | |
| AsuHP I | GGTGA (8/7) SEQ ID NO: 31 | Hph I | R0158 | GGTGA (8/7) SEQ ID NO: 31 | Hph I | |
| BciV I | GTATCC (6/5) SEQ ID NO: 32 | BciV I | R0596 | GTATCC (6/5) SEQ ID NO: 32 | Bfu I | |
| Bfi I | ACTGGG (5/4) SEQ ID NO: 33 | Bmr I | R0600 | ACTGGG (5/4) SEQ ID NO: 33 | Bmr I | |
| Bfu I | GTATCC (6/5) SEQ ID NO: 32 | BciV I | R0596 | GTATCC (6/5) SEQ ID NO: 32 | BciV I | |
| Bmr I | ACTGGG (5/4) SEQ ID NO: 33 | Bmr I | R0600 | ACTGGG (5/4) SEQ ID NO: 33 | Bfi I | |
| Bpm I | CTGGAG (16/14) SEQ ID NO: 34 | Bpm I | R0565 | CTGGAG (16/14) SEQ ID NO: 34 | Gsu I | |
| Bse3D I | GCAATG (2/0) SEQ ID NO: 35 | BsrI I | R0574 | GCAATG (2/0) SEQ ID NO: 35 | BseM I, BsrD I | |
| BseG I | GGATG (2/0) SEQ ID NO: 36 | BstF5 I | V0031 | GGATG (2/0) SEQ ID NO: 36 | BstF5 I, Fok I^ | |
| BseM I | GCAATG (2/0) SEQ ID NO: 35 | BsrD I | R0574 | GCAATG (2/0) SEQ ID NO: 35 | Bse3D I, BsrD I | |
| BseM II | CTCAG (10/8) SEQ ID NO: 37 | BspCN I^ | R0624 | CTCAG (9/7) SEQ ID NO: 37 | BspCN I^ | |
| BseR I | GAGGAG (10/8) SEQ ID NO: 38 | BseR I | R0581 | GAGGAG (10/8) SEQ ID NO: 38 | | |
| BsrD I | GCAATG (2/0) SEQ ID NO: 39 | BsrD I | R0574 | GCAATG (2/0) SEQ ID NO: 39 | Bse3D I, BseM I | |
| BstF5 I | GGATG (2/0) SEQ ID NO: 40 | BstF5 I | V0031 | GGATG (2/0) SEQ ID NO: 40 | BtsC I, BseG I, Fok I^ | |
| Eci I | GGCGGA (11/9) SEQ ID NO: 41 | Eci I | R0590 | GGCGGA (11/9) SEQ ID NO: 41 | | |
| Eco57 I | CTGAAG (16/14) SEQ ID NO: 42 | Acu I | R0641 | CTGAAG (16/14) SEQ ID NO: 42 | Acu I | |

TABLE 2-continued

Restriction enzymes producing 3' overhang (see 23, step d, FIG. 1)

| Enzyme | Sequence | NEB Enzyme | Catalog # | Sequence | Other Isoschizomers | Enzyme |
|---|---|---|---|---|---|---|
| Eco57M I | CTGRAG (16/14) SEQ ID NO: 43 | | | | | |
| Gsu I | CTGGAG (16/14) SEQ ID NO: 34 | Bpm I | R0565 | CTGGAG (16/14) SEQ ID NO: 34 | | Bpm I |
| Hph I | GGTGA (8/7) SEQ ID NO: 31 | Hph I | R0158 | GGTGA (8/7) SEQ ID NO: 31 | AsuHP I | |
| Mly I | GAGTC (5/5) SEQ ID NO: 28 | Mly I | R0610 | GAGTC (5/5) SEQ ID NO: 28 | Ple I^, Pps I^, Sch I | |
| Mme I | TCCRAC (20/18) SEQ ID NO: 44 | Mme I | R0637 | TCCRAC (20/18) SEQ ID NO: 44 | | |
| RleA Ix | CCCACA (12/9) SEQ ID NO: 45 | | | | | |
| Sch I | GAGTC (5/5) SEQ ID NO: 28 | Mly I | R0610 | GAGTC (5/5) SEQ ID NO: 28 | Mly I, Ple I^, Pps I^ | |
| TspDT I | ATGAA (11/9) SEQ ID NO: 46 | | | | | |
| TspGW I | ACGGA (11/9) SEQ ID NO: 46 | | | | | |
| Tth111 IIx | CAARCA (11/9) SEQ ID NO: 47 | | | | | |

The enzymes in Table 2 are useful if a recessed 5' end, which is also a suitable target for exonuclease digestion (as is a blunt end) is desired in the second digestion 3. Design of Probes for Multiplex Amplification (a) Introduction The polymerase chain reaction (PCR) is one of the most commonly used techniques in genomics. This method of amplifying DNA from a limited amount of template material has been used extensively in DNA sequencing, SNP genotyping, molecular diagnostics etc., and has become one of the most routine protocols in molecular biology. One of the challenges facing high-throughput genomics is expanding the scale of PCR while keeping costs low. Considerable efforts have been made during the past several years to increase the throughput of PCR by "multiplexing" the reactions. The goal of multiplex PCR is to amplify a large number of targets in the same reaction vessel. This has been a challenge because of the large number of spurious reaction products that arise when a mixture of oligonucleotides are used in the same PCR reaction. Cho et al., (1999) were successfully able to multiplex 50 primer pairs, but this is not the scale that is sufficient for high-throughput genomics.

The present methodology is useful for other "gap fill" techniques. For example, probe ligation methods have been reported. U.S. Pat. No. 4,883,750 to N. M. Whiteley, et al., D. Y. Wu, et al., *Genomics* 4:560 (1989), U. Landegren, et al., *Science* 241:1077 (1988), and E. Winn-Deen, et al., *Clin. Chem.* 37:1522 (1991). In one approach, known as oligonucleotide ligation assay ("OLA"), two probes or probe elements that span a target region of interest are hybridized to the target region. Where the probe element bases pair with adjacent target bases, the confronting ends of the probe elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, hybridization, and ligation in the presence of pairs of probe elements, the target sequence is amplified linearly, allowing very small amounts of target sequence to be detected and/or amplified. This approach is referred to as ligase detection reaction.

Another technique requiring "gap fill" is molecular inversion probe (MIP) technology (U.S. Pat. No. 6,858,412, described above). Using this technology, several thousand probes have been hybridized to genomic DNA in one reaction vessel. Both padlock probes and MIP technology use single-stranded "pre-circles" to hybridize to target DNA. These pre-circles contain sequences on the 3' and 5' ends that are complementary to the target DNA. The DNA in between the complementary target sequences in the probe does not hybridize with the target, and forms a loop between the two hybridized target sequences (HTS). In the presence of DNA polymerase and ligase, the molecule extends from the 3' end of the annealed probe and synthesizes a complement of the target until it reaches the 5' end of the annealed probe. This is the "gap-fill" reaction. The molecule is circularized at that point by DNA ligase. This molecule is then freed from genomic DNA by exonucleases. In the MIP protocol, the closed circle is linearized, and the target sequences amplified with primer sequences present in the loop. The circles are not opened in the padlock probes, and the sequences are amplified by the rolling circle method. Currently the MIP technology is extensively used in SNP genotyping where the hybridized target sequences are very close to each other with a gap length of just one base pair, and the "gap-fill" reaction is the polymerization of one nucleotide before the ligation reaction. The MIP technology can conceivably be used in multiplex PCR reactions where the HTS (hybridized target sequences)

are far apart and the "gap-fill" reaction can involve the polymerization of several nucleotides.

Meng Li (2006) et al., have used the padlock probe method to perform a "gap-fill" reaction where the HTS were 20 bases apart, and rolling circle amplification was used to amplify the DNA.

In all of the above cases, as the distance between the HTS (hybridized target sequences) becomes farther apart, the "gap-fill" reactions are also longer. To our knowledge, there are no publications that perform these large gap-fill reactions extending hundreds of bases, and ligations using the padlock method. We hypothesize that the rate-limiting step to perform a padlock or MIP methodology where the HTS are few hundred base bases apart might reside in the physical constraints of the corresponding sequences present on the probe to find the appropriate target sequences in the template DNA. We hypothesize optimizing the length of the spacer molecule in the probe will improve the chances of the corresponding sequences on the probe of finding their counterparts on the template DNA more efficiently. Thus will facilitate a more efficient gap-fill reaction and the downstream steps of the MIP or padlock protocol.

The present gap filling protocols are similar to others in that the gap fill reaction mixture contains a polymerase and a mixture of all four deoxynucleoside-triphosphates (also called deoxynucleotides or dNTPs, i.e. dATP, dTTP, dCTP and dGTP) in a manner similar to the MIP reaction and other polymerizations. Suitable enzymes include the Stoffel fragment of Taq polymerase (Applied Biosystems) or T4 DNA polymerase or any other enzyme that has no strand displacement activity or 5' exonuclease activity. It is important that the gap fill reaction be carried out with an enzyme that has a lack of 5 prime exonuclease activity and a lack of strand displacement activity.

Modified or substituted dNTPs may be also used, such as 2' deoxyadenosine 5'-O-(1-thiotriphosphate), 5-methyldeoxycytidine 5'-triphosphate, 2'-deoxyuridine 5'-triphosphate, and 7-deaza-2'-deoxyguanosine 5'-triphosphate. In addition, the substitution of the dNTP may occur after incorporation into a newly synthesized strand; for example, a methylase may be used to add methyl groups to the synthesized strand. Peptidenucleic acid residues may be incorporated, as described in US PGPUB 2005/0053944 "Methods and kit for hybridization analysis using peptide nucleic acid probes," hereby incorporated by reference.

(b) Design of Spacer Probes—Spacer Multiplex Amplification ReacTion (SMART)

A procedure which solves the problem of performing gap-fill reaction and ligation where the HTS (hybridized target sequences) are few hundred bases apart on the template DNA has been developed. We call the new methodology Spacer Multiplex Amplification ReacTion (SMART) because the success of the method is based on the optimization of the length of spacer backbone sequence on the probe. SMART probes are single-stranded molecules that have target (corresponding) sequences to genomic DNA or other target to be analyzed on either end of the of the probe sequence. An amplification primer AP1 and AP2 that was common to all the probes flanked each target. To test the hypothesis that the length of the spacer would determine the efficiency of longer extensions, we used probes where the length between the two common amplification primers was either 221 bases, or 38 bases as in conventional MIP probes. The SMART probes synthesized by the method we describe above, and the conventional MIP-size probes were synthesized chemically. The final configuration of the SMART probes, made according to FIG. 1, is shown in FIG. 2.

That is, the length of the spacer backbone should be at least 50% of the length of the HTS (hybridized target sequence) gap to be filled.

We reasoned that we could create molecules with varying spacer lengths by using the method of probe synthesis that we have developed and is described above. We designed smaller sized probes that approximated the conventional MIP) sizes, and the larger probes for the corresponding targets to test our hypothesis.

Figure 2:
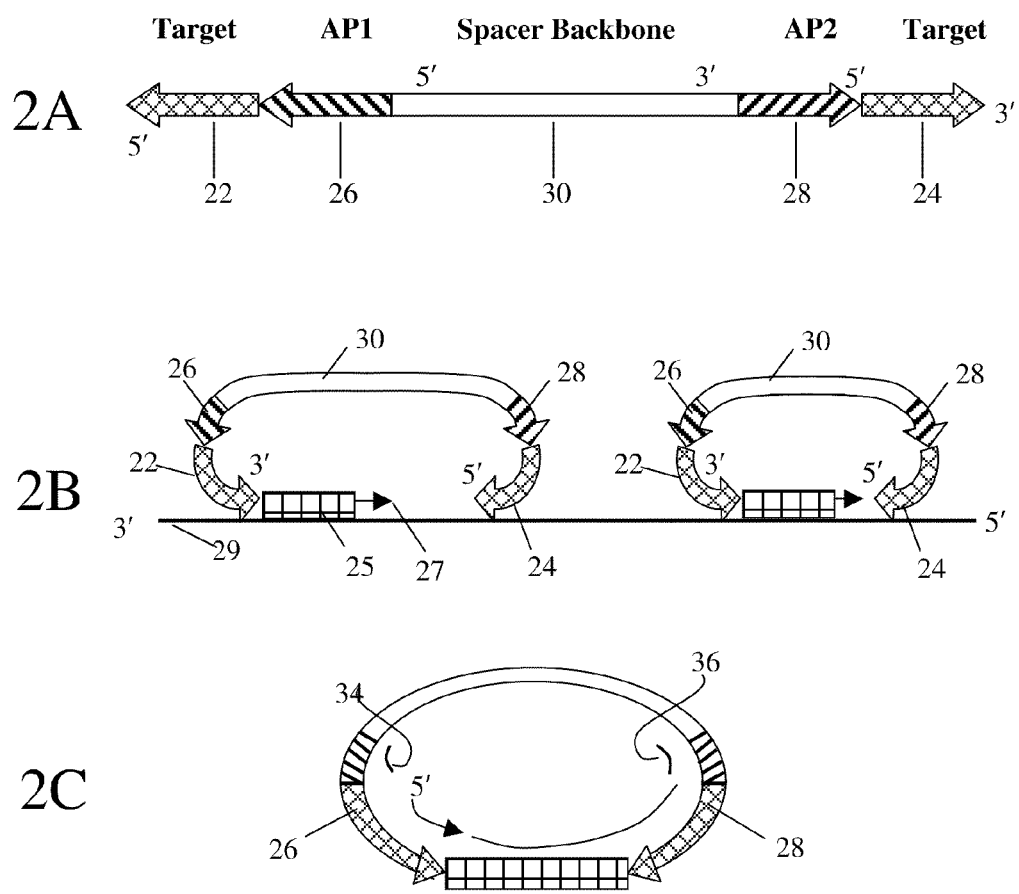
FIG. 2 is a diagram (2A) of a probe having common amplification primer regions and a spacer backbone, a diagram showing binding of a probe (2B) and a diagram of a circularized probe being amplified while still in a circle (2C)

As shown in FIG. 2, the present probes, as prepared by the present method, comprise target sequences 22, 24, which are exactly complementary to and bind to targets such as genomic DNA 29. The arrowheads 27 indicate the direction of polymerization on a single stranded target molecule 29 shown in 2B. As is conventionally known, all polymerases have 5' to 3' polymerization activity and require a template strand and either a DNA or RNA primer having a 3' end to which newly added bases are joined. AP1 and AP2 (26, 28) are common amplification primer sites for later amplification. Each probe comprises target sequences 22,24, one on each end, primer sites 26,28 next to each target sequence, and a spacer backbone 30 in between. The spacer backbones 30 are of variable length depending on the application. They are random DNA sequences that do not hybridize to target sequences. They may include peptide nucleic acids or other polymers.

As shown in FIG. 2B, multiple probes may be used on a target sequence, having unique target sequences 22, 24, but having common primer amplification sites 26, 28. Thus, in the amplification step shown in FIG. 2C, common primers binding to sites 26 and 28 will be used to amplify all hybridized, ligated probes. FIG. 2B shows one probe shown in FIG. 2A in contact with one region of single stranded target DNA 29 with a gap filling reaction catalyzed by DNA polymerase adding residues 25 and continuing as shown at 27 until the newly added region is complete up to the 5' end of probe target region 24. For purposes of illustration, another probe having a smaller spacer backbone and a smaller gap is targeted to a different sequence. The probes have different targeting regions, differing in size and sequence, but identical primer regions AP1 and AP2. This permits a high degree of multiplexing in the final amplification reaction. Gap filling reactions adding nucleotides 25 are carried out by DNA polymerase, preferably lacking 3'-5' exonuclease activity and the strand displacement activity, such as T4 polymerase, Taq, PolI (stofffel fragment). It is not necessary that the polymerase be thermostable.

Then, as shown in FIG. 2C, the probes are circularized by joining the newly added nucleotides to the end of the opposite target sequence. DNA ligase such as Ampligase, which functions at a high temperature, or any other DNA ligase such as T4 or *E. coli* DNA ligase may be used once the gap is filled. Then, an exonuclease is used to digest unreacted probes—which are linear—and target DNA. The circular probes that remain are then amplified as circles, as shown in 2C, using amplification primers 34, 36 targeted to primer sites API and AP2. Multiple copies of the target sequences in the target DNA, including the filled in gaps, are then prepared for further analysis.

EXAMPLES

Example 1

Probe Synthesis

The desired single-stranded probe we want to create is 298 bp. and the sequence of the molecule is SEQ ID NO: 48

```
5'TTGTTTTCTCCGTCGCCGTATCCCTTTAGTGAGGGTTAATAGTACGCT

TACTTCCGCGAAACGTCAGCGGAAGCACCACTATCTGGCGATCAAAAGGA

TGGTCATCGGTCACGGTGACAGTACGGGTACCTGACGGCCAGTCCACACT

GCTTTCACGCTGGCGCGGAAAAGCCGCGCTCG1CCGCCTTTACAATGTCC

CCGACGATTTTTTCCGCCCTCAGCGTACCGTTTATCGTACAGTTTTCAGC

TATCGTCACATTATTTAGGTGACACTATAGCCACAAATCAAGATCCGAAT

T3'
```

The underlined portions of the sequence represent the amplification primer sites described in Example 2, it being understood that the 5' primer is the reverse complement of the underlined sequence. The probe sequence of SEQ ID NO: 48 above is derived from a double stranded DNA product, and it may be present in any organism or vector, as part of a larger The first step in the procedure is to incorporate the two restrictions sites at the appropriate position of the double stranded molecule. To achieve that, we amplified a double-stranded PCR product with PCR primers that had an MlyI sequence engineered into the one primer, and the BsaI sequence engineered into the other primer.

```
Reverse primer (MlyI_Target)
                                    (SEQ ID NO: 50)
CATCGTGAGTCACTCGAATTCGGATCTTGATTTGTGG Forward primer (BsaI_Target)
                                    (SEQ ID NO: 51)
GTACGAGGTCTCACTTGTTTTCTCCGTCGCCGTA
```

Thus, the reverse primer of SEQ ID NO: 50 and the forward primer SEQ ID NO: 51 do not hybridize completely to the target sequence of SEQ ID NO: 48. They will still function to prime PCR amplification, and the amplification product will contain the engineered sequence shown in italics, which need not be complementary to the target sequence.

```
                                                    (SEQ ID NO: 52)
5'GTACGAGGTCTCA↓TTGTTTTCTCCGTCGCCGTATCCCTTTAGTGAGGGTTAATAGTACGC
3'CATGCTCCAGAGTAACA↑AAAGAGGCAGCGGCATAGGGAAATCACTCCCAATTATCATGCG

TTACTTCCGCGAAACGTCAGCGGAAGCACCACTATCTGGCGATCAAAAGGATGGTCATCG
AATGAAGGCGCTTTGCAGTCGCCTTCGTGGTGATAGACCGCTAGTTTTCCTACCAGTAGC

GTCACGGTGACAGTACGGGTACCTGACGGCCAGTCCACACTGCTTTCACGCTGGCGCGGA
CAGTGCCACTGTCATGCCCATGGACTGCCGGTCAGGTGTGACGAAAGTGCGACCGCGCCT

AAAGCCGCGCTCGCCGCCTTTACAATGTCCCCGACGATTTTTTCCGCCCTCAGCGTACCG
TTTCGGCGCGAGCGGCGGAAATGTTACAGGGGCTGCTAAAAAAGGCGGGAGTCGCATGGC

TTTATCGTACAGTTTTCAGCTATCGTCACATTATTTAGGTGACACTATAGCCACAAATCA
AAATAGCATGTCAAAAGTCGATAGCAGTGTAATAAATCCACTGTGATATCGGTGTTTAGT

A G A T C C G A A T T ⇓ G A G T G A C T C A C G A T G 3'
T C T A G G C T T A A ⇑ C T C A C T C A G T G C T A C    5' MlyI
``` sequence, and is set forth below in double stranded form as SEQ ID NO: 49

```
TTGTTTTCTCCGTCGCCGTATCCCTTTAGTGAGGGTTAATAGTACGCTT

ACTTCCGCGAAAACAAAAGAGGCAGCGGCATAGGGAAATCACTCCCAAT

TATCATGCGAATGAAGGCGCTT

ACGTCAGCGGAAGCACCACTATCTGGCGATCAAAAGGATGGTCATCGGT

CACGGTGACAGTGCAGTCGCCTTCGTGGTGATAGACCGCTAGTTTTCCT

ACCAGTAGCCAGTGCCACTGTC

TACGGGTACCTGACGGCCAGTCCACACTGCTTTCACGCTGGCGCGGAAA

AGCCGCGCTCGATGCCCATGGACTGCCGGTCAGGTGTGACGAAAGTGCG

ACCGCGCCTTTTCGGCGCGAGC

CCGCCTTTACAATGTCCCCGACGATTTTTTCCGCCCTCAGCGTACCGTT

TATCGTACAGTGGCGGAAATGTTACAGGGGCTGCTAAAAAAGGCGGGAG

TCGCATGGCAAATAGCATGTCA

TTTCAGCTATCGTCACATTATTTAGGTGACACTATAGCCACAAATCAAG

ATCCGAATTAAAGTCGATAGCAGTGTAATAAATCCACTGTGATATCGGT

GTTTAGTTCTAGGCTTAA
```

Step 1: Incorporation of Restriction Sites at the Ends of Double Stranded Template by PCR Amplification With Engineered Primers Step 2: Digestion at 5' End The first digestion with BsaI generates a 5' overhang five bases inward from the recognition site on the top strand, and 1 base inward on the lower strand. This creates a molecule with a recessed 3' end and a protruding 5' end. The 5' end now has a phosphate group. The molecule will be as in SEQ ID NO: 52, with the portions 5' (top strand) and 3' (bottom strand) of the single bold arrow removed.

Step 3: Phosphatase Treatment

The phosphate group on the 5' overhang of this molecule (shown as double underlined TTGT in SEQ ID NO: 52) is then cleaved with a phosphatase making it resistant to lambda exonuclease cleavage.

Step 4: Second Digestion at 3' End to Create a Blunt End

The molecule is then digested with the enzyme MlyI that cuts 5 bases inward from the recognition site, and generates a blunt-end molecule that has a phosphate group at the 5' end. This can be seen in SEQ ID NO: 52 as removal of the portions 3' of the double arrow (top strand) and 5' of the double arrow (bottom strand). The 5' adenosine on the bottom strand will have a terminal phosphate group after the restriction enzyme cleavage.

Step 5: Digestion of Second Strand

The molecule as shown in SEQ ID NO: 52 now has a 5' phosphate on the adenosine on the blunt end, and a non-phosphorylated 5' overhang (TTGT) on the other. As a result, when it is digested with Lambda exonuclease, the enzyme preferentially cleaves the phosphorylated strand, and generates the desired single-stranded molecule shown in SEQ ID NO: 48.

The desired ssDNA has now been formed. The target sequences, AP1 and AP2 are in bold and italic in SEQ ID NO: 52, above.

Example 2

Multiplex Probe Design

Enzymatic synthesis of the long single-stranded molecule was derived from a double-stranded PCR product following the procedure described above.

1) Generation of Double Stranded Templates Shown in FIG. 3A

Figure 3:
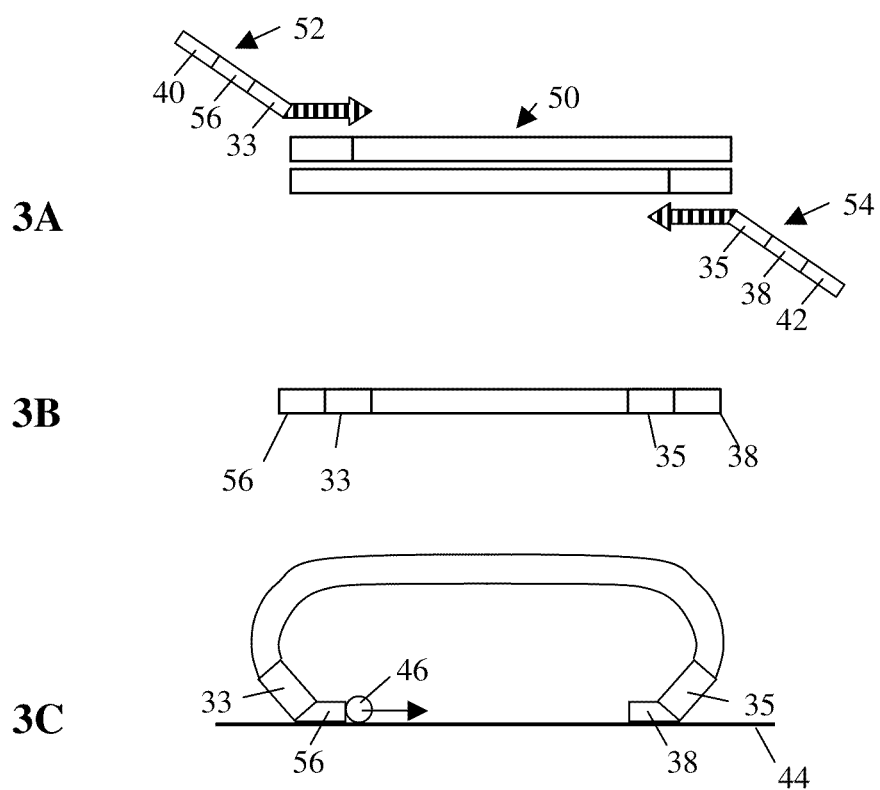
FIG. 3 is a diagram showing a technique for spacer multiplex detection, ("SMART," or Spacer Multiplex Amplification ReacTion) showing a target sequence and probe creation (3A), amplified sequence design (3B), and hybridization of the present probe (3C)

As shown in FIG. 3, double stranded DNA is first amplified using primers 52, 54. A 220 by sequence from bacteriophage lambda, shown at 50, serves as starting point and a backbone for the probe. The phage was selected because its DNA would be non-hybridizable with human target DNA. The PCR amplification primers were synthesized with additional amplification primer 1 (AP1) sequence 33 on the forward primer and amplification primer 2 35 (AP2) sequence on the reverse amplification primers (FIG. 3A). These are common amplification primer targets for PCR using common primers for a multiple of probes in the downstream application. The molecule with the backbone and amplification primers was common for all the probes, except for the target sequences. The probes contain unique target sequences 56, 38.

The common lambda backbone was used as the template to make the template-specific probes (FIG. 3A). The forward primer had recognition sequences for MlyI (40) at the 5' end. The reverse primer had sequences complementary to the target on the genomic DNA that was the desired distance apart from first target, as well as the amplification primer 2 on the target and a BsaI recognition sequence 42 at the 5' end of the reverse primer. The resulting fragment has MlyI and BsaI adaptors flanking the two targets with the spacer DNA in between them (FIG. 3C) when the probe ends hybridize to the target.

2) Generation of Single Stranded Probe of FIG. 3B:

The PCR fragment generated as shown in FIG. 3A was digested with BsaI to generate the 5' overhang. The molecule was then dephosphorylated with Shrimp alkaline phosphatase to remove the 5' phosphate. It was then digested with MlyI to generate a specific 5' end opposite the specific end created with the BsaI digestion. This molecule then was digested with lambda exonuclease. The final probe configuration is shown in FIG. 3B, wherein the target sequences 56 and 38 were targeted to human genomic DNA 44. The single-stranded probe was subsequently phosphorylated with T4 polynucleotide kinase prior to being hybridized to the genomic DNA. Ligation requires a 5' phosphate group, added by this phoshporylation step, because it was removed earlier to protect from exonuclease digestion.

3. Amplification of Target 100 attomoles probe was annealed with 500 ng human genomic DNA. This was done by denaturation at 95° C. and annealing overnight at 58° C. As illustrated in FIG. 3C, the single stranded probe hybridized to the target, and was extended by polymerase as shown at 46. It was then ligated to form a circular probe.

The spacer backbone is illustrated in FIG. 3C as forming a loop between the hybridized targets. The DNA polymerase catalyzed the polymerization of DNA from the 3' end to fill the gap between the two targets. The ampligase enzyme closes the circle by ligating the two ends of the probe when the enzyme reaches the 5' end of the other target. The probes were extended and circularized using Stoffel polymerase and Ampligase in ampligase buffer (Epicenter). Following circularization, unreacted probe and genomic DNA were digested using Exonuclease I and III.

The exonuclease digestion freed the circles from genomic DNA. The circles were then amplified. It should be noted that, unlike the MIPS protocol, the molecules were not linearized, and amplification was performed using primer sequences present in the loop of probe that does not hybridize with the target. Specific amplification of probes that had hybridized was demonstrated by sequencing. The entire contents of the extension and ligation reactions were used for PCR amplification in a cocktail containing 10 mM tris-HCL (ph8.3), 50 mM Potassium Chloride, 0.2.5 mM Magnesium Chloride, and 2 units Amplitaq Gold. The primers used for amplification were done using the forward primer CGTCACATTATT-TAGGTGACACTATAG (SEQ ID No: 606) and GCGTAC-TATTAACCCTCACTAAAGG (SEQ ID No: 607) as the reverse primer. The cycling parameters were 10 mins of heat inactivation at 95° C. followed by 40 cycles of 95° C. for 30 sec, 63° C. for 30 sec, and 72° C. for 30 sec.

Example 3

Probe Target Annealing

We compared the ability of the conventional sized MIPS that were chemically synthesized, and the SMART probes that we generated, in their ability to extend from the annealed target. The SMART probes had a spacer of 280 nucleotides in between the target sequences and the MIPS probe had a spacer of 80 nucleotides. This would typically be part of an overall SMART probe of a length of about 320 nucleotides. We discovered that the SMART probes we tested were able to amplify target molecules with gaps up to about 400 nt long. These gaps are filled in as part of the present process, and the content of the filled gap provides analytical information. The longest extension tested in Table 1 was 330, with the longest success at 175, but it is expected, based on DNA polymerization in other techniques, that the present methods and materials would work for longer extensions by varying the size of the spacer. The MIPs probes on the other hand were unable to extend molecules in the ranges that we routinely observed with the SMART probes. (Table 3).

We have shown that the SMART probes synthesized by the method described above are able to function robustly by extending over larger distances than the conventional-sized MIP probes. We believe that the optimal backbone length will depend on the target size being amplified, and that having the ability to vary this spacer length will be important to be able to efficiently multiplex PCR from thousands of exons in a single reaction. These probes have application not only in multiplex PCR, but also to generate the constructs necessary for Mismatch repair detection (MRD) assay.

TABLE 3

Comparison of MIP and SMART probes in amplification of identical genomic targets.

| Length of gap-fill (bases) | outcome of MIPS (80 base spacer) | outcome of SMARTS (280 base spacer) |
|---|---|---|
| 1 | successful | successful |
| 161 | successful | successful |
| 186 | successful | successful |
| 141 | successful | successful |
| 175 | successful | successful |
| 244 | failed | successful |

TABLE 3-continued

Comparison of MIP and SMART probes in amplification of identical genomic targets.

| Length of gap-fill (bases) | outcome of MIPS (80 base spacer) | outcome of SMARTS (280 base spacer) |
|---|---|---|
| 249 | failed | successful |
| 290 | failed | successful |
| 330 | failed | successful |

The above Table 3 shows that a MIPS probe with an 80 base space (region between target sequences) would not amplify when the gap between the ends of the probe was 244 nucleotides (nt). On the other hand, the SMART probes were successful at all gap distances tested, even those longer than the spacer. The SMART probes may be made to any length. It is very hard to synthesize a ss DNA molecule bigger than 120-140 base pair total and at the same time accurate and reliable for high through put molecular biology analysis. The present method enables the convenient synthesis of large ssDNA molecules and provides the opportunity for the discovery of novel methodologies, such as long-gapped circular probes.

Example 4

Preparation of Single Stranded Probe

Step 1: Creation of the Lambda Backbone Common to all Probes

The template used was Lambda DNA, shown at 30 in FIG. 3. Lambda DNA is commonly used as a substrate in restriction enzyme activity assays and for preparation of DNA molecular weight standards. The phage is isolated from a heat-inducible lysogenic *E. coli* W3110 (cI857 Sam7) strain. Primers (52 and 54 in FIG. 3) were prepared by the addition of Amplification 1 (AP1) and Amplification 2 (AP2) sequences to backbone from bacteriophage lambda.

```
Primer 1 (SK51 has AP1)
                                            SEQ ID NO: 53
TGTCTATAGTGTCACCTAAATTAATGTGACGATAGCTG Primer 2 (SK52 has AP2seq)
                                            SEQ ID NO: 54
TGTCCCTTTAGTGAGGGTTAATAGTACGCTTACTTCCGCG
```

The sequence after amplification is

```
                                            SEQ ID NO: 55
5' TGTCTATAGTGTCACCTAAATTAATGTGACGATAGCTGAAAACTGTAC
GATAAACGGTACGCTGAGGGCGGAAAAAATCGTCGGGGACATTGTAAAGG
CGGCGAGCGCGGCTTTTCCGCGCCAGCGTGAAAGCAGTGTGGACTGGCCG
TCAGGTACCCGTACTGTCACCGTGACCGATGACCATCCTTTTGATCGCCA
GATAGTGGTGCTTCCGCTGACGTTTCGCGGAAGTAAGCGTACTA
TTAACCCTCACTAAAGGGACA
```

The added sequences, from the primers, are bold and italicized.

Reaction Conditions 2.5 µl PCRII 10× buffer (ABI)

2.5 µl 25 mM MgCl₂

2.5 µl 1.25 mM dNTP 1.25 µl 5 uM SK51

1.25 µl 5 uMSK52

2.5 µl 10 ng/µl Bacteriophage lambda DNA 12.5 µl dH₂0

1.25 units amplitaq Gold (Applied Biosystems)

TABLE 4

| PCR conditions | |
|---|---|
| Hold: | 94° C. 10 mins |
| Cycle Touch down in 0.5° C. decrements 14 cycles. | 94° C. 20 secs, 64° C. 30 sec 72° C. 30 sec. |
| Cycle 25 cycles | 94° C. 20 sec, 56° C. 30 sec 72° C. 30 sec |
| Hold | 72° C. 5 mins |
| Hold | 4° C. o/n |

Step 2: Addition of MLYI and BSAI Adaptor Sequences and Probe Specific Sequences to Backbone

```
SK302_Probe_F:
                                            SEQ ID NO: 56
GTACGAGGTCTCA*GAAATGACAAATATAGATGGCAAAAGCCATCCCTTT
AGTGAGGGTTAAT SK302_Probe_R:
                                            SEQ ID NO: 57
CGTGAGTCACTCGTCACAGATAGGCATGGTGTCAAAGTCATCTATAG
TGTCACCTAAAT 3'
```

Figure 4:
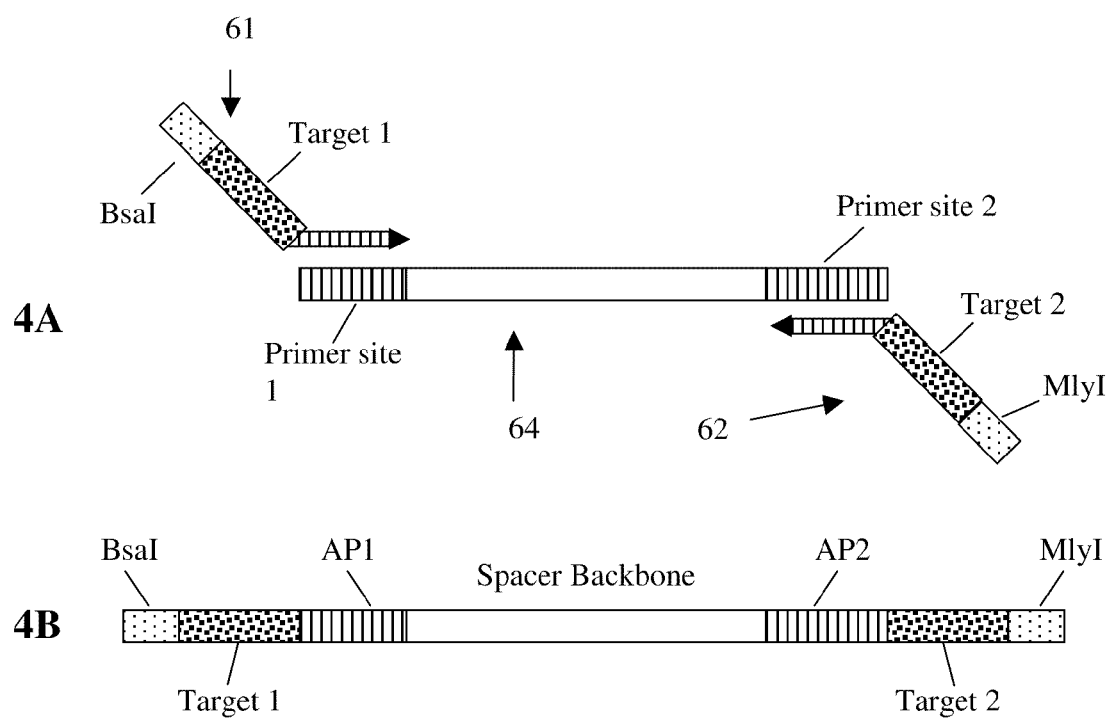
FIG. 4 is a diagram showing a probe having a spacer backbone and adapter sequences.

These adaptor sequences are analogous to those shown at 40 and 42 in FIG. 3, but used in a second amplification as shown in FIG. 4. The bold residues adjacent the * will represent the final 5' end and will be seen in the amplified sequence below. The 5' sequence TAC and reverse probe sequence CAT are in shaded text to show the correlation between the target and the probe.

```
Target 2 BsaI
                                            SEQ ID NO 58
GTACGAGGTCTCA*GAAATGACAAATATAGATGGCAAAAGCCATCCCTTTAGTGAGGGTTA
CATGCTCCAGAGTCTTT*ACTGTTTATATCTACCGTTTTCGGTAGGGAAATCACTCCCAAT ATAGTACGCTTACTTCCGCGAAACGTCAGCGGAAGCACCACTATCTGGCGATCAAAGGA
TATCATGCGAATGAAGGCGCTTTGCAGTCGCCTTCGTGGTGATAGACCGCTAGTTTTCCT
```

-continued

```
TGGTCATCGGTCACGGTGACAGTACGGGTACCTGACGGCCAGTCCACACTGCTTTCACGC
ACCAGTAGCCAGTGCCACTGTCATGCCCATGGACTGCCGGTCAGGTGTGACGAAAGTGCG

TGGCGCGGAAAAGCCGCGCTCGCCGCCTTTACAATGTCCCCGACGATTTTTTCCGCCCTC
ACCGCGCCTTTTCGGCGCGAGCGGCGGAAATGTTACAGGGGCTGCTAAAAAAGGCGGGAG

AGCGTACCGTTTATCGTACAGTTTTCAGCTATCGTCACATTAATTTAGGTGACACTATAG
TCGCATGGCAAATAGCATGTCAAAAGTCGATAGCAGTGTAATTAAATCCACTGTGATATC

ATGACTTTGACACCATGCCTATCTGTGA**CGAGTGACTCACGATG   3'
TACTGAAACTGTGGTACGGATAGACACT**GCTCACTGAGTGC░░░   5'
```

As can be seen in the amplified sequence above, the final 5' end is bolded to the right of the *. The bolded region to the left of the * can be seen to be complementary to the bolded sequence of probe R, with the final, added pairs of residues indicated by shading. The ** indicates where the final 3' end will be.

2.5 µl PCRII 10× buffer (ABI)
2.5 µl 25 mM MgCl$_2$
2.5 µl 1.25 mM dNTP
1.25 µl 5 µM SK302_Probe_F
1.25 µl 5 µM SK302_Probe_R
2.5 µl 1:10,000 dil of Step 1 PCR
12.5 µl dH$_2$0
1.25 units amplitaq Gold (ABI)

TABLE 5

PCR conditions

| | |
|---|---|
| Hold: | 94° C. 10 mins |
| Cycle | 94° C. 20 secs, 64° C. 30 sec 72° C. 30 sec. |
| Touch down in 0.5° C. decrements 14 cycles. | |
| Cycle 25 cycles | 94° C. 20 sec, 56° C. 30 sec 72° C. 30 sec |
| Hold | 72° C. 5 mins |
| Hold | 4° C. o/n |

Step 3: Digestion With BsaI

The first digestion with BsaI cuts 1 base inward from the recognition site on the top strand, and 5 bases inward on the lower strand. This creates a molecule with a recessed 3' end and a protruding 5' end. The 5' end (G in the sequence GAA adjacent *) now has a phosphate group. The sequence is shown at SEQ ID NO: 58, where the asterisks indicate cut sites.

Procedure:
Clean up the PCR product on a Micro Biospin P-30 column (Bio-Rad).
Spin the column at 1000 g for 2 min.
Add 50 µl PCR product (approx 200 ng) and spin 1000 g 4 min.
Use 45 µl of eluate for BsaI digestion
Add 5 µl NEB3 buffer and 3 µl BsaI (New England Biolabs)
Incubate at 50° C. for 2 hrs followed by 65° C. heat inactivation.

Step 4: Dephosphorylation

The phosphate group on the 5' overhang of this molecule (G in the sequence GAA) is then cleaved with a phosphatase making it resistant to lambda exonuclease cleavage.
Add 3 µl Shrimp Alkaline Phosphatase (1 unit/ul United States Biochemical)
Incubate 37° C. for 60 min followed by heat inactivation at 80° C. 15 min Step 5: Digestion with MlyI The molecule is then digested with the enzyme MlyI that cuts 5 bases inward from the recognition site, and generates a blunt-end molecule that has a phosphate group at the 5' end. The reaction was cleaned up as in Step 3 on the Micro Bio-Spin P-30 columns as described above:
To 45 µl of the eluate add 5 µl NEB buffer I and 3 µl MlyI (NEB).
Incubate at 37° C. for 60 min followed by heat inactivation for 15 min at 65° C.
After this step, the molecule has the sequence shown in SEQ ID NO: 58, with the portions 5' of the * and 3' of the ** (with reference to the top strand) removed.

Step 6: Digestion with Lambda Exonuclease

This enzyme preferentially cleaves the phosphorylated strand, and generates the desired single-stranded molecule. The resulting sequence is the top strand of STEP 5.
To achieve this, we added 0.2 units Lambda Exonuclease (NEB) to the MlyI digested DNA. Incubate at 37° C. for 15 min followed by heat inactivation for 15 min at 80° C.

Step 7: Phosphorylation of 5' End:
Use 10 µl of the exonuclease digested DNA, 5 µl T4DNA ligase buffer (NEB), 1 µl T4 Polynucleotide kinase. Incubate 37° C. 60 min followed by heat inactivation for 15 min at 65° C.

Example 5

Spacer Multiplex Amplification ReacTion (SMART) Using the Above ssDNA Probe

Dilute kinased probe to 10 fmole/µl. Use this as the stock. Make a fresh 1:200 dilution to make a 50 amol/µl working solution.

TABLE 6

Hybridization of Probe to Target DNA

| | |
|---|---|
| Probe | 2 µl |
| Human Genomic DNA | 2 µl (500 ng) |
| Water | 3 µl |
| 10x Ampligase buffer (Epicenter Technologies) | 0.7 µl |
| Mix well by pipetting. | |

Hold at 95° C. for 5 mins.
Gradually decrease temperature by 1° C. decrements to 58° holding at 1 min at each temperature. Hold overnight at 58° C.
The target DNA is TLR10 (toll like receptor) of human genomic DNA2. Extension of hybridized probe and ligation
Place tubes on a cold metal block on ice.
After 2 mins add a 6.5 µl of a master mix containing
0.8 µl 10× Ampligase buffer
5 units Ampligase Epicenter)
0.5 units Stoffel fragment of Taq polymerase (Applied Biosystems)

5.2 µl dH20
Incubate 58° C. for 2 mins.
Place on ice block
Add 1.5 µl of Cold dNTP mix (1.25 mM)
Mix well by pipetting.
Incubate 58° C. for 15 mins and hold at 37° C.
2. Exonuclease Digestion of Linear Probes/Template:
Add 10 units Exonuclease I (Ecpicenter Technologies) and 10 units Exonuclease III (Ecpicenter Technologies). Incubate at 37° C. for 15 mins and heat inactivate at 80° C. for 15 mins.
3. PCR Using Common Primers on Released Probes
5 µl PCRII 10× buffer (ABI)
5 µl 25 mM MgCl$_2$
5 µl 1.25 mM dNTP
5 µl 1 µM Amplification Primer 1
5 µl 1 µM Amplification Primer 2
5 µl 10 ng/µl extension and Ligation mix
20 µl dH$_2$0
2 units amplitaq Gold (ABI)
PCR conditions
95° C. 10 min.
Cycle 40 times 94° C. 30 sec
   63° C. 30 sec
   72° C. 30 sec
72° C. 5 mins
hold 4° C.

The PCR step described above is carried out after the probe made by exonuclease digestion (i.e. after STEP 7) is hybridized to a target sequence, e.g., human genomic DNA. The hybridized DNA is detected and amplified by the PCR reaction described immediately above. The target sequence that is amplified after extension from the annealed probe is shown below,

```
                                      SEQ ID NO: 59
ATGACTTTGACACCATGCCTATCTGTGA*GGAAGCTGGCAACATGTCACA

CCTGGAAATCCTAGGTTTGAGTGGGGCAAAAATACAAAAATCAGATTTCC

AGAAAATTGCTCATCTGCATCTAAATACTGTCTTCTTAGGATTCAGAACT

CTTCCTCATTATGAAGAAGGTAGCCTGCCCATCTTAAACACAACAAAACT

GCACATTGTTTTACCAATGGACACAAATTTCTGGGTTCTTTTGCGTGATG

GAATCAAGACTTCAAAAATATTA*GAAATGACAAATATAGATGGCAAAAG

CCA
```

In the above representation, the bold sequences can be seen to correspond to those underlined in SEQ ID NO: 58 (amplified sequence) and the remainder of the sequence is that which is filled in. The human DNA sequence is based on Homo sapiens toll-like receptor 10 (TLR10), transcript, which can be found in GenBank as, e.g. NM_001017388. In the sequences below, the target sequences are also shown in bold.

Example 6

Multiplex PCR Amplification

In this example, 3 different probes were mixed in the same tube to amplify products that are of three different lengths in the same tube. The present example includes three probes that bound to human genomic DNA. To prepare the probes we used 3 sets of primers. Each primer is identified with reference to the probe for which it is used, e.g. SK302-Probe_F is the forward primer for what will be the SK302 probe.
Probe 1—Extends 328 Bases
SK302_Probe_F:

```
                                      SEQ ID NO: 56
GTACGAGGTCTCA*GAAATGACAAATATAGATGGCAAAAGCCATCCCTTT

AGTGAGGGTTAAT
```

It can be seen that the bolded bases of Probe F correspond to the bolded residues at the 3' end of SEQ ID NO: 59.
SK302_Probe_R: This sequence is given above as SEQ ID NO: 57. Probe SK302 is also disclosed in Step 2 of Example 4.
The Target genomic sequence is as given in Example 5, SEQ ID NO: 59.
Probe 2—Extends 244 Bases
SK298_Probe_F and SK298_Probe_R sequences are given in Example 4
Their target genomic sequence 2 is

```
                                      SEQ ID NO: 60
TTCTAGACATGCCCTTCATGTGATTCTTATG*AGAAAAAACCACCCAAAG

AATTCCTAGAAAGATTCAAATCACTTCTCCAAAAGGTATCTACCTTAAGT

TTCATTTGATTTTCTGCTTTATCTTTACCTATCCAGATTTGCTTCTTAGT

TACTCACGGTATACTATTTCCACAGATGATTCATCAGCATCTGTCCTCTA

GAACACACGGAAGTGAAGATTCCTGAGGATCTAACTTGCAGTTGGACACT

ATGTTACATACTCTAATATAGTAGTGAAAGTCATTTCTTTGTATTCCAAG

TGGAGGAGTACAATATATTAGCGATGGGAAAAAAAAACTCATAAGTGTGC

AAAGTCAGGA**TTATTTCCCCATAATCACTATACAATAGTCT
```

This target sequence is from the human IL21 gene
SK298_Probe_F bolded residues can be seen to be the reverse complement of the 5' end of Target genomic sequence 2 and can be visually matched at the asterisk. Similarly, for SK298_Probe_R, the bolded sequence can be found at the double asterisk in genomic sequence 2.
Probe 3 Extends 251 Bases SK303_Probe_F:
```
                                      SEQ ID NO: 61
CATCGTGAGTCACTCG*TAGGCATGGTGTCAAAGTCATTAAAAGAAAGAC TATAGTGTCACCTAAAT
```
SK303_Probe_R:
```
                                      SEQ ID NO: 62
GTACGAGGTCTCA**GAAATGACAAATATAGATGGCAAAAGCCAATTTCC

CTTTAGTGAGGGTTAAT
```

Target genomic sequence 3, also from TLR10

```
                                      SEQ ID NO: 63
TCTTTCTTTTAATGACTTTGACACCATGCCTA*TCTGTGAGGAAGCTGGC

AACATGTCACACCTGGAAATCCTAGGTTTGAGTGGGGCAAAAATACAAAA

ATCAGATTTCCAGAAAATTGCTCATCTGCATCTAAATACTGTCTTCTTAG

GATTCAGAACTCTTCCTCATTATGAAGAAGGTAGCCTGCCCATCTTAAAC

ACAACAAAACTGCACATTGTTTTACCAATGGACACAAATTTCTGGGTTCT
```

-continued

TTTGCGTGATGGAATCAAGACTTCAAAAATATTA**GAAATGACAAATAT

AGATGGCAAAAGCCAATT

These three sets of primers (SK302 Probe F, SK302 Probe R; SK298 Probe F, SK298 ProbeR; and SK303 ProbeF and SK303 ProbeR) were used in each of three PCR amplifications with the template used in STEP 2 of the example where we describe preparation of the double stranded PCR product prior to digestion with MlyI (Example 2). All subsequent steps were performed exactly as in the example. After the single-stranded probes were phosphorylated using T4 polynucleotide kinase, the three single stranded probes were then mixed together such that their final concentration was 100 attomoles/µl. 2 µl of the mixed probe set was used in the SMART reaction exactly as described in the example. After amplification using the common PCR primers, we were able to identify the 3 discrete products that were the result of the three extensions and circularization of the three probes.

This example demonstrates that we can perform a multiplex PCR using the SMART probes.

Example 7

Multiplex PCR Amplification Using Over 500 Different Probes, which are Described in Accompanying CD We designed probes to amplify exons from human genomic DNA in a multiplex fashion. To achieve this goal, we identified targets in the introns adjacent to the exons. For each exon, we designed two targets, one on each side of the exon, in the flanking intronic sequence. The distance between the targets varied based on the size of the exon. To connect the two targets we made a spacer backbone (see FIG. 4) from lambda DNA that was common to all the probes. To construct each exon probe, we designed a pair of primers (FIGS. 4, 61,62) that amplified a double-stranded PCR product using the backbone template. One primer for each exon had a BsaI site, a target sequence for the exon, followed by a region of homology to the backbone DNA (shown by vertical stripes in FIG. 4). The other primer for the exon probe had an MlyI site, the second target exon, followed by the homology to the backbone. The double-stranded probes for each exon were then converted into single-stranded probes. It should be noted that exons are about 150 to 400 nt long, so that the probes must obtain such information (gap filling) for the sequencing purpose described here. That is, one will obtain on the order of $10^6$ amplified probes containing the exon sequence (30-40 PCR cycles), which is sufficient to determine the exon sequence in the gap. Another aspect of the present multiplex methodology is the high number of probes which can be amplified simultaneously, without artifacts. Aspects enabling this are the use of common amplification primers, and the use of a relatively low level of amplification primer (on the order of 100 attomoles).

Step 1. Preparation of the Backbone

The template used was Lambda DNA, shown at 64, FIG. 4, and at 30 in FIG. 2. Primers (52 and 54 in FIGS. 3, 61, 62, FIG. 4) were prepared by the addition of Amplification 1 (AP1) and Amplification 2 (AP2) sequences to backbone from bacteriophage lambda. The Primer SK618 has Amplification primer 1 shown below in bold italics, and the primer SK619 has Amplification primer 2 shown in bold italics. The PCR reaction was performed in 50 mM Potassium Chloride, 10 mM Tris-HCl (pH8.5), 2.5 mM Magnesium Chloride, 2 units Amplitaq gold. The cycling conditions were 10 min heat inactivation at 950 C followed by 25 cycles of 94° C. for 30 sec, 63° C. for 30 sec, and 72° C. for 30 sec per cycle.

Primer 1 (SK618 has AP1)
SEQ ID NO: 64
*GGGGCGCGCCCTATAGTGTCACCTAAAT*TAATGTGACGATAGCTG Primer 2 (SK619 has AP2seq)
SEQ ID NO: 65
▓▓▓*TCGATCCCTTTAGTGAGGGTTAA*TAGTACGCTTACTTCCGCG

The sequence after amplification (see FIG. 4B) is

SEQ ID NO: 66
5' *GGGGCGCGCCCTATAGTGTCACCTAAAT*TAATGTGACGATAGCTGAAA

ACTGTACGATAAACGGTACGCTGAGGGCGGAAAAAATCGTCGGGGACATT

GTAAAGGCGGCGAGCGCGGCTTTTCCGCGCCAGCGTGAAAGCAGTGTGGA

CTGGCCGTCAGGTACCCGTACTGTCACCGTGACCGATGACCATCCTTTTG

ATCGCCAGATAGTGGTGCTTCCGCTGACGTTTCGCGGAAGTAAGCGTACT

*ATTAACCCTCACTAAAGGGATCGA*▓▓▓

For the convenience of the reader, three corresponding nucleotides are shaded to show correspondence between primer 2 and the amplified sequence.

Preparation of Single Stranded Probes

For each probe, two primers were used with this backbone as the template for a PCR reaction. One primer had a target sequence to genomic DNA with a BsaI adaptor, and the second primer had the target with a MlyI adaptor. These primers were used in a PCR reaction with the backbone DNA as template analogous to that shown in FIG. 4.

As an example:

Primer 292361_Bsa
GTACGAGGTCTCActgtaagccctgcaatttccccCCATCGATTCCCTTTAG    SEQ ID NO: 67

Primer 292361_Mly
CATCGTGAGTCACTCGtcatggggtaagacgatcatagaGGGGCGCGCCCTATAGTGT SEQ ID NO: 68

The sequence of the double-stranded probe after amplification is shown below.

BsaI
SEQ ID NO: 69
5'GTACGAGGTCTCA*<u>ctgtaagccctgcaatttcccc</u>CCATCGATTCCCTTTAGGGTTAATA
CATGCTCCAGAGTGACAT*TCGGGACGTTAAAGGGGGTAGCTAAGGGAAATCCCAATTAT -continued
```
GTACGCTTACTTCCGCGAAACGTCAGCGGAAGCACCACTATCTGGCGATCAAAAGGATGG
CATGCGAATGAAGGCGCTTTGCAGTCGCCTTCGTGGTGATAGACCGCTAGTTTTCGTACC TCATCGGTCACGGTGACAGTACGGGTACCTGACGGCCAGTCCACACTGCTTTCACGCTGG
AGTAGCCAGTGCCACTGTCATGCCCATGGACTGCCGGTCAGGTGTGACGAAAGTGCGACC CGCGGAAAAGCCGCGCTCGCCGCCTTTACAATGTCCCCGACGATTTTTTCCGCCCTCAGC
GCGCCTTTTCGGCGCGAGCGGCGGAAATGTTACAGGGGCTGCTAAAAAAGGCGGGAGTCG GTACCGTTTATCGTACAGTTTTCAGCTATCGTCACATTAATTTAGGTGACACTATAGGGC
CATGGCAAATAGCATGTCAAAAGTCGATAGCAGTGTAATTAAATCCACTGTGATATCCCG GCGCCCCtctatgatcgtcttaccccatga**CGAGTGACTCACGATG 3'
CGCGGGGAGATACTAGCAGAATGGGGTACT**GCTCACTGAGTGCTAC MlyI
```

It will be apparent that the "tga" at the 3' end adjacent the ** corresponds to the reverse complement of the "tca" at the beginning of Primer 292361_Mly shown in bold. The target sequences that hybridize to genomic DNA are shown in lower case and underlined. The restriction cut sites for BsaI and MlyI are shown with an asterisk. As can be seen in the amplified sequence above, the final 5' end is bolded to the right of the *.

After the double-stranded probe was amplified, the PCR products were digested with 10 units of BsaI in NEB4 (New England Biolabs) at 50° C., followed by digestion with 3 units Shrimp Alkaline Phosphatase (United States Biochemicals) at 37° C. in the same buffer for 60 min. The reaction volume was increased to 100 µl, and the MlyI digestion was carried out in NEB buffer 4 at 37° C. using 20 units MlyI (New England Biolabs). 20 µl of this reaction was digested with 0.5 units of Lambda Exonuclease (NEB) at 37° C. for 10 mins. The reaction products were phosphorylated using 5 units of Polynucleotide Kinase in T4DNA ligase buffer (NEB).

Hybridization of Probes, Extension, Multiplex PCR 100 attomoles of each probe was hybridized to 500 ng of human genomic DNA in 7 µl of 1× ampligase buffer containing 20 mM tris-HCl (pH8.3), 25 mM KCl, and 10 mM magnesium chloride. The hybridization was carried out in a single tube in a thermal cycler by raising the temperature of the mix to 98° C. for 2 min, and gradually bringing the temperature to 58° C. by decreasing the temperature by 1° C. per minute. The reaction was held at 58° C. overnight. The extension reaction was carried out by adding 1.6 µl of 5×GC buffer (NEB) that was supplied with Phusion™ High-Fidelity DNA Polymerase, 100 nM dNTP, 0.4 units Phusion™ High-Fidelity DNA Polymerase (NEB), and 0.5 units ampligase (Epicenter). The reaction was incubated for 20 min at 58° C. and 10 min at 72° C. The excess probe and genomic DMA was digested with 1 unit Exonuclease I and 0.2 units Exonuclease III for 310 min at 37° C. followed by heat inactivation for 20 min at 80° C. The reaction volume was raised to 50 µl and the PCR reaction was carried out in 1×GC buffer (NEB), 200 mM dNTP, and 0.2 units Phusion™ High-Fidelity DNA Polymerase after addition of the two amplification primers AP1 and AP2. The reactions were cycled 40 times at 98° C. for 30 sec, 62° C. 30 sec, and 72° C. 30 sec per cycle.

Determining Success of Multiplex PCR 1.5 micrograms of the PCR products were digested with 0.04 units DnaseI (NEB) for 5 min. After a column cleanup on a Biorad P-30 chromatography column, the products were end-labeled with followed by end-labeling at 37° C. for 10 min with 1 nmole of Bio-N6-ddATP in 1×NEBuffer 4 (NEB) supplemented with 2.5 mM cobalt chloride using 1 unit Terminal Transferase (NEB).

The labeled products were hybridized to a DNA microarray chip containing tiling probes to all the exon targets under interrogation. Tiling probes are complementary to various subsequences within a DNA sequence set (here, the human genome). They are further described in European Patent EP1479782. The success of the multiplex PCR was determined by whether a sequence for each exon could be determined by analyzing the re-sequencing array.

TABLE 7

Success of multiplex PCR

| Size of amplicon(bp) | Percent GC 35-50% | | Percent GC >50% | | Total |
|---|---|---|---|---|---|
| | Success | Failures | Success | FAILURES | |
| 150-200 | 78 | 1 | 27 | 7 | 113 |
| 200-300 | 187 | 2 | 67 | 46 | 302 |
| 300-400 | 57 | 0 | 25 | 14 | 96 |
| 400-500 | 9 | 0 | 5 | 8 | 22 |
| Total | 331 | 3 | 124 | 75 | 533 |

The above results show that overall, 331 probes out of 533 were amplified in the multiplex reaction, as evidenced by sufficient quantity of probe to show a signal when the amplicon, containing the target sequence, was hybridized to a DNA microarray containing human gene sequences. If the probes are designed to contain less than 50% GC content in the amplicon and target and primer sequences, the failure rate is 3/331 or less than 1%.

A Lengthy Table is submitted herewith on CD describing all 500 probes, SEQ ID NOs 70-601. Each entry on the CD ROM is organized as follows: an arbitrary probe ID NO (e.g. 29190), SEQ ID NO; the size of the amplified sequence in by (e.g. 235), including the target sequence, and the actual sequence filled in and amplified with the target sequences set off by slashes. These sequences represent human gene exon sequences obtained with the probes and are presented for purposes of exemplification of a large scale multiplex reaction with relatively large gaps filled in and amplified using the present SMART probes.

CONCLUSION

Other Embodiments

The present specific description is meant to exemplify and illustrate the invention and should in no way be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but would be understood by workers in the field Such patents or publications are hereby incorporated by reference to the same extent as if each was specifically and individually incorporated by reference for the purpose of describing and enabling the method or material referred to.

Alternative embodiments may be carried out, given the present teachings. For example, US PGPUB 2005/0053990 to Roberts et al., published Mar. 10, 2005 entitled "Cleavage of RNA by restriction endonucleases," hereby incorporated by reference, teaches that a number of restriction endonucleases have been shown to be capable of cleaving RNA in RNA/DNA duplexes although this property is not inherent in the universe of restriction endonucleases. It is taught there that restriction endonuclease cleavage of RNA/DNA duplexes have precise ends corresponding to the cleavage site of the restriction endonuclease. RNA is expected to be size limited only at the lower end of the range, typically 2-8 nucleotides longer than the length of the recognition sequence of the restriction enzyme. Given this teaching, one may prepare cDNA-RNA duplexes from RNA using reverse transcriptase and prepare ssDNA probes from cDNA according to the present teachings.

REFERENCES

Cho R J, Mindrinos M N, Richards D R, Sapolsky R J, Anderson M, Drenkard E, Dewdney J, Reuber T L, Stammers M, Federspiel N, Theologis A, Yang W H, Hubbell E, Lashkari D, Lemieux B, Dean C, Lipshutz R J, Ausubel F M, Davis R W and Oefner P J. Genome-Wide Mapping with Biallelic Markers in *Arabidopsis thaliana*. *Nature Genetics*, 1999, 23:203-207.

Crothers et al., Amplification of DNA to produce single-stranded product of defined sequence and length U.S. Pat. No. 6,815,167 (Nov. 9, 2004).

Hardenbol P, Baner J, Jain M, Nilsson M, Namsaraev E A, Karlin-Neumann G A, Fakhrai-Rad H, Ronaghi M, Willis T D, Landegren U, Davis R W. Multiplexed genotyping with sequence-tagged molecular inversion probes. *Nat Biotechnol*. (2003) June; 21 (6):673-8.

Higuchi, R and Ochman, H. Production of single-stranded DNA templates by exonuclease digestion following the polymerase chain reaction. *Nucleic Acids Research*, Vol 17, No. 14, 5865 (1989).

Landegren et al., Rolling circle replication of padlock probes U.S. Pat. No. 6,558,928 (May 6, 2003).

Landegren et al., Nucleic acid detecting reagent U.S. Pat. No. 6,235,472 (May 22, 2001).

Li M, Diehl F. Dressman D, Vogelstein B, Kinzler K. BEAMing up for detection and quantification of rare sequence variants. *Nature Methods* 3, 95-97 (2006).

Lizardi. Rolling Circle reporter Systems. U.S. Pat. No. 5,854,033. (1998).

Multiplex amplification enabled by selective circularization of large sets of genomic DNA fragments Fredrik Dahl, Mats Gullberg, Johan Stenberg, Ulf Landegren and Mats Nilsson *Nucleic Acids Research* (2005) 33 (8):e71.

Nikiforov et al., U.S. Pat. No. 5,518,900 Method for generating single-stranded DNA molecules (May 1996).

Nilsson, M., et al., "Padlock Probes: Circularizing Oligonucleotides for Localized DNA Detection," *Science*, 285: 2085-2088 (1994).

Willis et al., Direct multiplex characterization of genomic DNA U.S. Pat. No. 6,858,412, (February 2005).

What is claimed is:

1. A method for preparing a molecule for sequencing, comprising the step of hybridizing to said molecule for sequencing a probe molecule of defined sequence and length, having a non-human sequence, a predefined 5' end, a predefined 3' end and a portion of a double stranded precursor molecule, said probe molecule further being prepared from said double stranded precursor molecule by a method comprising the steps of:
(a) amplifying the double stranded precursor molecule with primers each containing a sequence homologous to a portion of the double stranded molecule and a sequence not homologous to the double stranded precursor molecule, said primers also containing a sequence comprising one of said predefined 5' end or said predefined 3' end, said primers further containing restriction enzyme cleavage sites to obtain an amplified double stranded molecule having cleavage sites at the 3' and 5' ends, said primers further comprising a first target sequence and a second, different, target sequence, wherein the first target sequence and the second target sequence hybridize to human genetic sequences;
(b) cleaving the amplified double stranded molecule at the 5' end with a first restriction enzyme;
(c) cleaving the amplified double stranded probe molecule at the 3' end with a second, different restriction enzyme to prepare the probe molecule of defined sequence and length; and (d) hybridizing said double stranded probe molecule of step (c) through said first target sequence and said second target sequence to said molecule for sequencing, thereby preparing said molecule for sequencing.

2. The method of claim 1 wherein a cleaving step is done with a type IIs restriction enzyme.

3. The method of claim 2 further comprising the step of digesting with BsaI to generate a 5' overhang outside of BsaI's recognition site.

4. The method of claim 1 wherein the cleaving with a restriction enzyme at the desired predetermined 3' end is done with a restriction enzyme to create a 3' blunt end or no 5' overhang.

5. The method of claim 1 wherein the predefined 5' end and predefined 3' end are separated by at least 125 nucleotides of spacer backbone from the precursor molecule.

6. The method of claim 1 wherein the nonhuman organism is a microorganism.

7. The method of claim 1 wherein said molecule for sequencing spans an exon.

8. The method of claim 1 further comprising the step of sequencing said molecule after said hybridizing of step (d).

9. The method of claim 1 wherein said hybridizing is done at an elevated temperature.

\* \* \* \* \*